US009452990B2

(12) United States Patent
Dechantsreiter et al.

(10) Patent No.: US 9,452,990 B2
(45) Date of Patent: Sep. 27, 2016

(54) COMPLEMENT PATHWAY MODULATORS AND USES THEREOF

(71) Applicants: Michael Dechantsreiter, Chestnut Hill, MA (US); Jonathan E. Grob, Sharon, MA (US); Aengus Macsweeney, Basel (CH); Wolfgang Miltz, Basel (CH); Stefan Andreas Randl, Frankfurt am Main (DE); Richard Sedrani, Basel (CH); Holger Sellner, Buchs (CH); Finton Sirockin, Blotzheim (FR); Eric Valeur, Vieux Ferrette (FR)

(72) Inventors: Michael Dechantsreiter, Chestnut Hill, MA (US); Jonathan E. Grob, Sharon, MA (US); Aengus Macsweeney, Basel (CH); Wolfgang Miltz, Basel (CH); Stefan Andreas Randl, Frankfurt am Main (DE); Richard Sedrani, Basel (CH); Holger Sellner, Buchs (CH); Finton Sirockin, Blotzheim (FR); Eric Valeur, Vieux Ferrette (FR)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/408,216

(22) PCT Filed: Jun. 19, 2013

(86) PCT No.: PCT/US2013/046644
§ 371 (c)(1),
(2) Date: Dec. 15, 2014

(87) PCT Pub. No.: WO2013/192345
PCT Pub. Date: Dec. 27, 2013

(65) Prior Publication Data

US 2015/0126492 A1 May 7, 2015

Related U.S. Application Data

(60) Provisional application No. 61/662,002, filed on Jun. 20, 2012, provisional application No. 61/776,244, filed on Mar. 11, 2013.

(51) Int. Cl.

| | |
|---|---|
| ***C07D 239/95*** | (2006.01) |
| ***C07D 403/12*** | (2006.01) |
| ***C07D 401/14*** | (2006.01) |
| ***C07D 413/14*** | (2006.01) |
| ***C07D 401/12*** | (2006.01) |
| ***C07D 403/04*** | (2006.01) |
| ***C07D 403/14*** | (2006.01) |
| ***C07D 405/12*** | (2006.01) |
| ***C07D 409/12*** | (2006.01) |
| ***A61K 31/517*** | (2006.01) |
| ***A61K 31/5377*** | (2006.01) |

(52) U.S. Cl.
CPC .......... *C07D 239/95* (2013.01); *A61K 31/517* (2013.01); *A61K 31/5377* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 409/12* (2013.01); *C07D 413/14* (2013.01)

(58) Field of Classification Search
CPC .................................................. C07D 403/12
See application file for complete search history.

(56) References Cited

FOREIGN PATENT DOCUMENTS

| | | |
|---|---|---|
| BE | 871821 | 5/1979 |
| DE | 3906920 | 9/1989 |
| EP | 0100200 | 2/1984 |
| EP | 0624584 | 11/1994 |
| EP | 2133334 | 12/2009 |
| GB | 2068961 | 8/1981 |
| GB | 2295387 | 5/1996 |
| JP | 10007572 | 1/1998 |
| JP | 2000281660 | 10/2000 |
| WO | 95/25726 | 9/1995 |
| WO | 96/09824 | 4/1996 |
| WO | 97/20820 | 6/1997 |
| WO | 99/43682 | 9/1999 |
| WO | 00/52134 | 9/2000 |
| WO | 00/78716 | 12/2000 |
| WO | 2009/005671 | 1/2001 |
| WO | 01/44193 | 6/2001 |
| WO | 01/62750 | 8/2001 |
| WO | 0162750 | 8/2001 |
| WO | 01/68615 | 9/2001 |
| WO | 02/08221 | 1/2002 |
| WO | 02/102381 | 12/2002 |
| WO | 2004/002960 | 1/2004 |

(Continued)

OTHER PUBLICATIONS

Sarma et al., Expert Opinion on Therapeutic Patents, 15(10):1333-1351 (2005).

*Primary Examiner* — Paul V Ward
(74) *Attorney, Agent, or Firm* — John B. Alexander

(57) ABSTRACT

The present invention provides a compound of formula I a method for manufacturing the compounds of the invention, and its therapeutic uses as inhibitor of the complement alternative pathway and particularly as inhibitor of Factor B for the treatment of e.g. age-related macular degeneration and diabetic retinopathy. The present invention further provides a combination of pharmacologically active agents and a pharmaceutical composition.

(I)

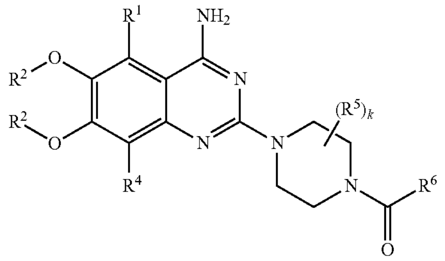

15 Claims, No Drawings

(56) References Cited

FOREIGN PATENT DOCUMENTS

| | | |
|---|---|---|
| WO | 2004/010942 | 2/2004 |
| WO | 2005005397 | 1/2005 |
| WO | 2005/040136 | 5/2005 |
| WO | 2005/051304 | 6/2005 |
| WO | 2005/056524 | 6/2005 |
| WO | 2005/056550 | 6/2005 |
| WO | 2005/058823 | 6/2005 |
| WO | 2005056015 | 6/2005 |
| WO | 2005123697 | 12/2005 |
| WO | 2006/124862 | 11/2006 |
| WO | 2007/003964 | 1/2007 |
| WO | 2007/037187 | 4/2007 |
| WO | 2008026034 | 10/2008 |
| WO | 2008126034 | 10/2008 |
| WO | 2008140198 | 11/2008 |
| WO | 2009/005671 | 1/2009 |
| WO | 2009/006567 | 1/2009 |

COMPLEMENT PATHWAY MODULATORS AND USES THEREOF

This application is a U.S. National Phase filing of International Application No. PCT/US2013/046644 filed 19 Jun. 2013, which claims priority to U.S. Application No. 61/662,002 filed 20 Jun. 2012 and 61/776,244 filed 11 Mar. 2013, the contents of which are incorporated herein by reference in their entirety.

FIELD OF THE INVENTION

The invention relates to the inhibition of the complement alternative pathway and particularly to inhibition of Factor B, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor B may be a suitable target for the inhibition of this amplification of the complement pathways because its plasma concentration in humans is typically about 200 μg/mL (or about 2 μM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H (CFH) (Edwards A O, et al. Complement factor H polymorphism and age-related macular degeneration. Science. 2005 Apr. 15; 308(5720):421-4; Hageman G S, et al Acommon haplotype in the complement regulatory gene factor H (HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol V is Sci. 2006 August; 47(8):3242-6; Simonelli F, et al. Polymorphism p. 402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement C2 (Gold B, et al. Variation in factor B (BF) and complement component 2 (C2) genes is associated with age-related macular degeneration. Nat. Genet. 2006 April; 38(4):458-62 and Jakobsdottir J, et al. C2 and CFB genes image-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Mailer J B, et al Variation in complement factor 3 is associated with risk of age-related macular degeneration. Nat. Genet. 2007 October; 39(10):1200-1 and Park K H, et al Complement component 3 (C3) haplotypes and risk of advanced age-related macular degeneration. Invest Ophthalmol V is Sci. 2009 July; 50(7):3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor B activity and/or Factor B mediated complement pathway activation. Such Factor B modulators are preferably high affinity Factor B inhibitors that inhibit the catalytic activity of complement Factor B, such as primate Factor B and particularly human Factor B.

The compounds of the present invention inhibit or suppress the amplification of the complement system caused by C3 activation irrespective of the initial mechanism of activation (including for example activation of the classical, lectin or alternative pathways).

Various embodiments of the invention are described herein. It will be recognized that features specified in each embodiment may be combined with other specified features to provide further embodiments.

Within certain aspects, Factor B modulators provided herein are compounds of Formula I and salts and tautomers thereof:

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more additional therapeutically active agents.

The invention further provides methods of treating or preventing complement mediated diseases, the method comprising the steps of identifying a patient in need of complement modulation therapy and administering a compound of Formula (I) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor B activation and/or Factor B-mediated signal transduction of the complement system. Such compounds may be used in vitro or in vivo to modulate (preferably inhibit) Factor B activity in a variety of contexts.

In a first embodiment, the invention provides compounds of Formula I and salts and tautomers thereof, which modulate the alternative pathway of the complement system. Compounds of Formula I are represented by the structure:

(I)

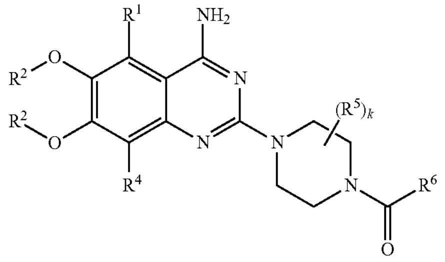

or salt or stereoisomer thereof, wherein $R^1$ is hydrogen or halogen $R^2$ is $C_1$-$C_4$alkyl;

$R^3$ is hydrogen, $C_1$-$C_6$alkyl, $C_1$-$C_4$alkoxy$C_1$-$C_4$alkyl, or halo$C_1$-$C_4$alkyl;

$R^4$ is halogen, cyano or hydrogen, wherein at least one of $R^1$ and $R^4$ is not hydrogen;

$R^5$ is independently selected at each occurrence from hydrogen, $C_1$-$C_6$alkyl, $C_1$-$C_4$alkoxy$C_1$-$C_4$alkyl, phenyl, and $C_3$-$C_6$cycloalkyl;

k is 0-3;

$R^6$ is $CH_2CHR^7R^8$, or $R^6$ is $CH{=}CHR^9$, wherein $R^9$ is $C_3$-$C_6$cycloalkyl or phenyl optionally substituted with 0, 1, or 2 groups independently selected from halogen, $C_1$-$C_4$alkyl, $C_1$-$C_4$alkoxy, halo $C_1$-$C_4$alkyl, cyano or hydroxy, or $R^6$ is bicyclic heteroaryl having 1 or 2 ring heteroatoms independently selected from N, O or S, partially unsaturated carbocycle or partially unsaturated heterocycle having 1 or 2 ring heteroatoms independently selected from N, O or S, each of which is optionally substituted with 0 to 3 substituents independently selected from amino, halogen, cyano, hydroxy, $C_1$-$C_4$alkyl or $C_1$-$C_4$alkoxy; or $R^6$ is $CH_2$heterocycle having 4 to 7 ring atoms and 1 or 2 ring heteroatoms selected from N, O or S, which is optionally substituted with 0, 1, or 2 groups independently selected from phenyl, halogen and $C_1$-$C_6$alkyl, or two substituents, taken in combination form a benzo ring optionally substituted with halogen or cyano;

$R^7$ is $(CH_2)_pNR^{10}R^{11}$ or $C(O)NR^A{}_2$, wherein $R^A$ is independently selected at each occurrence from hydrogen and $C_1$-$C_4$alkyl, or $NR^A{}_2$ taken in combination form a 4-6 member azacycle;

p is 0 or 1;

$R^8$ is $C_1$-$C_6$alkyl, $C_3$-$C_6$cycloalkyl; or $R^8$ is phenyl optionally substituted with 0-2 $R^{12}$; or $R^8$ is a 5 or 6 member heteroaryl having 1 or 2 ring heteroatoms selected from N, O and S and optionally substituted with 0-2 $R^{13}$ groups;

$R^{10}$ is hydrogen or $C_1$-$C_4$alkyl;

$R^{11}$ is hydrogen, optionally substituted $C_1$-$C_6$alkyl or $C_1$-$C_6$haloalkyl, wherein the optional substituents are selected from $C_1$-$C_4$alkoxy, $C_3$-$C_6$cycloalkyl and 4-6 member heterocycle having 1-2 ring heteroatoms selected from N, O and S; or $NR^{10}R^{11}$, taken in combination form a 4 to 7 member saturated azacycle optionally substituted with 0, 1, or 2 $C_1$-$C_4$alkyl groups;

$R^{12}$ is independently selected at each occurrence from hydrogen, cyano, hydroxy, halogen, $C_1$-$C_4$alkyl, $C_2$-$C_4$alkenyl, $C_2$-$C_4$alkynyl, $C_1$-$C_4$haloalkyl or $C_1$-$C_4$alkoxy;

$R^{13}$ is independently selected at each occurrence from hydrogen, $C_1$-$C_4$alkyl, or halogen.

In a second embodiment, compounds of embodiment 1 are provided which are represented by formula (II):

(II)

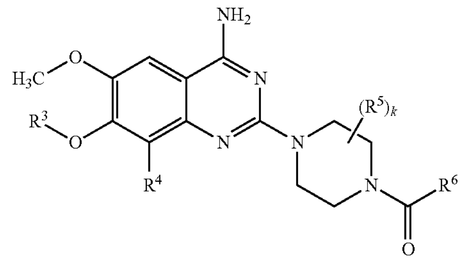

or a salt thereof.

In a third embodiment, compounds of embodiment 1 or 2 are provided which are represented by formula (III):

(III)

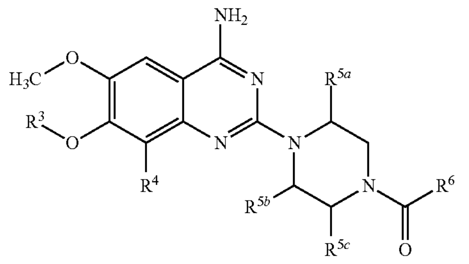

or salt thereof, wherein $R^{5a}$ is hydrogen, phenyl, $C_1$-$C_4$alkyl, $C_3$-$C_6$cycloalkyl, or methoxy$C_1$-$C_4$alkyl;

$R^{5b}$ is hydrogen or $C_1$-$C_4$alkyl; and $R^{5c}$ is hydrogen or $C_1$-$C_4$alkyl. Certain preferred compounds of the third embodiment include compounds in which $R^{5a}$ hydrogen, phenyl, $C_1$-$C_4$alkyl, or methoxy$C_1$-$C_4$alkyl.

In a fourth embodiment, compounds of any one of embodiments one to three are provided which are represented by formula (IV):

(IV)

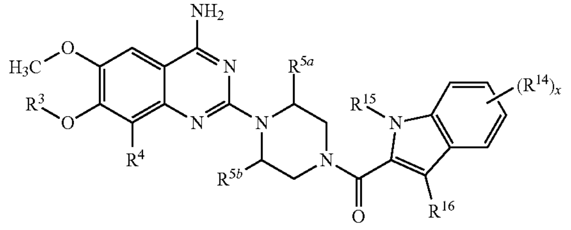

or salt thereof, wherein $R^{5a}$ is hydrogen, methyl, ethyl, propyl or phenyl;

$R^{5b}$ is hydrogen or methyl;

x is 0, 1, or 2;

$R^{14}$ is independently selected at each occurrence from fluoro, chloro, hydroxy, methoxy and cyano;

$R^{15}$ is hydrogen or $C_1$-$C_4$alkyl; and $R^{16}$ is hydrogen or amino.

In a fifth embodiment, compounds of any one of embodiments one to three are provided which are represented by formula (V):

(V)

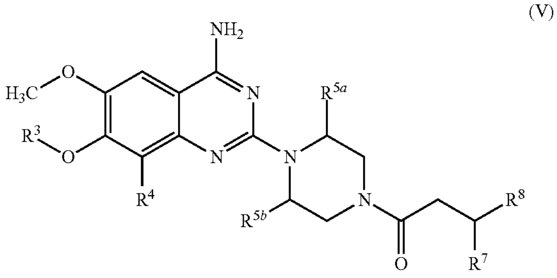

or salt thereof, wherein $R^{5a}$ is hydrogen, methyl, ethyl, propyl or phenyl; and $R^{5b}$ is hydrogen or methyl.

In a sixth embodiment, compounds of embodiment five are provided in which $R^7$ is $NR^{10}R^{11}$;

$R^8$ is furyl, $C_3$-$C_6$cycloalkyl, $C_1$-$C_4$alkyl, pyridyl optionally substituted by fluoro, thienyl optionally substituted by chloro or $C_1$-$C_4$alkyl, or phenyl optionally substituted by cyano, halogen, mono- di- and trifluoromethyl, $C_1$-$C_4$alkyl, vinyl or ethynyl;

$R^{10}$ is hydrogen or methyl; and $R^{11}$ is hydrogen, $C_1$-$C_6$haloalkyl or $C_1$-$C_6$alkyl optionally substituted with cyclopropyl, $C_1$-$C_4$alkoxy or 4-6 member heterocycle having 1 ring heteroatom selected from N, O and S; or $NR^{10}R^{11}$, taken in combination, form a 4-6 member saturated azacycle.

In certain compounds of the sixth embodiment, at least one of $R^{10}$ and $R^{11}$ is not hydrogen.

In a seventh embodiment, compounds of any one of embodiments one to three are provided which are represented by formula (VI):

(VI)

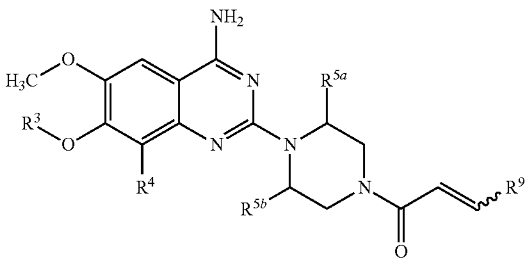

or salt thereof, wherein $R^9$ is selected from $C_3$-$C_6$cycloalkyl or phenyl, wherein the phenyl is unsubstituted or substituted with halogen or cyano. In certain compounds of the seventh embodiment, $R^9$ is selected from $C_3$-$C_6$cycloalkyl or phenyl, wherein the phenyl is unsubstituted or substituted with cyano. In certain other compounds of the seventh embodiment, $R^9$ is phenyl, 4-fluorophenyl or 4-cyanophenyl.

In a eighth embodiment, compounds of any one of embodiments one to three are provided which are represented by formula (VII):

(VII)

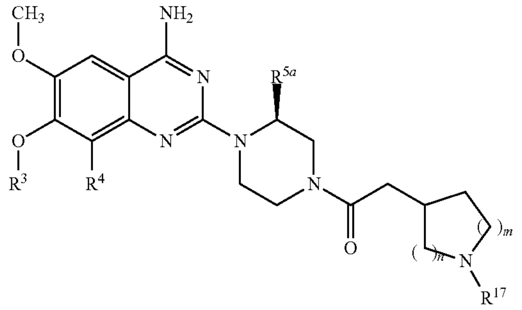

wherein $R^{17}$ is $C_1$-$C_4$alkyl; and n is 0 or 1;

m is 0, 1, or 2, wherein n+m is 1, 2, or 3; or a salt thereof.

In a ninth embodiment, compounds of any one of embodiments one to eight are provided in which $R^4$ is fluoro.

In a tenth embodiment, compounds of any one of embodiments one to nine are provided in which $R^3$ is methyl optionally substituted with 0, 1, 2 or 3 fluoro substitutents; or $R^3$ is methoxy$C_1$-$C_4$alkyl. In certain aspects of the invention $R^3$ is methyl or methoxyethyl.

In a eleventh embodiment, compounds of any one of embodiments one to ten are provided in which $R^{5a}$ is hydrogen, methyl, ethyl, propyl or phenyl; and $R^{5b}$ and $R^{5c}$ are each independently hydrogen or methyl.

In a twelfth embodiment, individual compounds according to the invention are those listed in the Examples section below. In certain aspects the compound is selected from the group consisting of:

1-[4-(4-Amino-8-fluoro-6,7-dimethoxy-quinazolin-2-yl)-piperazin-1-yl]-3-cyclopropyl-propenone;

4-{3-[4-(4-Amino-8-fluoro-6,7-dimethoxy-quinazolin-2-yl)-piperazin-1-yl]-3-oxo-propenyl}-benzonitrile;

(1-[4-(4-Amino-8-fluoro-6,7-dimethoxy-quinazolin-2-yl)-3-methoxymethyl-piperazin-1-yl]-3-cyclopropyl-propenone;

1-[4-(4-Amino-8-fluoro-6,7-dimethoxy-quinazolin-2-yl)-3-(2-methoxy-ethyl)-piperazin-1-yl]-3-cyclopropyl-propenone;

4-Amino-2-[4-(3-cyclopropyl-acryloyl)-piperazin-1-yl]-6,7-dimethoxy-quinazoline-8-carbonitrile;

1-[4-(4-Amino-8-fluoro-6,7-dimethoxy-quinazolin-2-yl)-3-methyl-piperazin-1-yl]-3-cyclobutyl-propenone;

4-{3-[4-(4-Amino-8-fluoro-6,7-dimethoxy-quinazolin-2-yl)-3-methyl-piperazin-1-yl]-3-oxo-propenyl}-benzonitrile;

4-{3-[4-(4-Amino-8-fluoro-6,7-dimethoxy-quinazolin-2-yl)-3-ethyl-piperazin-1-yl]-3-oxo-propenyl}-benzonitrile;

4-{3-[4-(4-Amino-8-fluoro-6,7-dimethoxy-quinazolin-2-yl)-3-propyl-piperazin-1-yl]-3-oxo-propenyl}-benzonitrile;

4-{3-[4-(4-Amino-8-fluoro-6,7-dimethoxy-quinazolin-2-yl)-3-phenyl-piperazin-1-yl]-3-oxo-propenyl}-benzonitrile;

4-(3-{4-[4-Amino-8-fluoro-6-methoxy-7-(2-methoxy-ethoxy)-quinazolin-2-yl]-piperazin-1-yl}-3-oxo-propenylybenzonitrile;

1-[4-(4-Amino-5-fluoro-6,7-dimethoxy-quinazolin-2-yl)-piperazin-1-yl]-3-cyclopropyl-propenone;

[4-(4-Amino-8-fluoro-6,7-dimethoxy-quinazolin-2-yl)-piperazin-1-yl]-(1H-indol-2-yl)-methanone;

2-[4-(4-Amino-8-fluoro-6,7-dimethoxy-quinazolin-2-yl)-piperazine-1-carbonyl]-1H-indole-5-carbonitrile;

[4-(4-Amino-8-fluoro-6,7-dimethoxy-quinazolin-2-yl)-piperazin-1-yl]-(5-hydroxy-1H-indol-2-yl)-methanone;

[4-(4-Amino-8-fluoro-6,7-dimethoxy-quinazolin-2-yl)-piperazin-1-yl]-(4-methoxy-1H-indol-2-yl)-methanone;

[4-(4-Amino-8-fluoro-6,7-dimethoxy-quinazolin-2-yl)-piperazin-1-yl]-(5-fluoro-1H-indol-2-yl)-methanone;

[4-(4-Amino-8-fluoro-6,7-dimethoxy-quinazolin-2-yl)-piperazin-1-yl]-(5,7-difluoro-1H-indol-2-yl)-methanone;

2-[4-(4-Amino-8-fluoro-6,7-dimethoxy-quinazolin-2-yl)-3-methyl-piperazine-1-carbonyl]-1H-indole-5-carbonitrile;

[4-(4-Amino-8-fluoro-6,7-dimethoxy-quinazolin-2-yl)-3-methyl-piperazin-1-yl]-(5-fluoro-1H-indol-2-yl)-methanone;

2-[4-(4-Amino-8-fluoro-6,7-dimethoxy-quinazolin-2-yl)-3-ethyl-piperazine-1-carbonyl]-1H-indole-5-carbonitrile;

2-[4-(4-Amino-8-fluoro-6,7-dimethoxy-quinazolin-2-yl)-3-propyl-piperazine-1-carbonyl]-1H-indole-5-carbonitrile;

[4-(4-Amino-8-fluoro-6,7-dimethoxy-quinazolin-2-yl)-3-propyl-piperazin-1-yl]-(5-fluoro-1H-indol-2-yl)-methanone;

2-[4-(4-Amino-8-fluoro-6,7-dimethoxy-quinazolin-2-yl)-3-phenyl-piperazine-1-carbonyl]-1H-indole-5-carbonitrile;

(4-(4-amino-8-fluoro-6,7-dimethoxyquinazolin-2-yl)-3-phenylpiperazin-1-yl)(5-fluoro-1H-indol-2-yl)methanone;

{4-[4-Amino-8-fluoro-6-methoxy-7-(2-methoxy-ethoxy)-quinazolin-2-yl]-3-methyl-piperazin-1-yl}-(5-chloro-1H-indol-2-yl)-methanone;

3-Amino-1-[4-(4-amino-8-fluoro-6,7-dimethoxy-quinazolin-2-yl)-piperazin-1-yl]-hex-5-yn-1-one;

3-Amino-1-[4-(4-amino-8-fluoro-6,7-dimethoxy-quinazolin-2-yl)-piperazin-1-yl]-3-cyclopentyl-propan-1-one;

3-Amino-1-[4-(4-amino-8-fluoro-6,7-dimethoxy-quinazolin-2-yl)-piperazin-1-yl]-5-methyl-hexan-1-one;

3-Amino-1-[4-(4-amino-8-fluoro-6,7-dimethoxy-quinazolin-2-yl)-piperazin-1-yl]-3-furan-2-yl-propan-1-one hydrochloride;

3-Amino-1-[4-(4-amino-8-fluoro-6,7-dimethoxy-quinazolin-2-yl)-piperazin-1-yl]-3-furan-3-yl-propan-1-one;

3-Amino-1-[4-(4-amino-8-fluoro-6,7-dimethoxy-quinazolin-2-yl)-piperazin-1-yl]-3-thiophen-2-yl-propan-1-one;

3-Amino-1-[4-(4-amino-8-fluoro-6,7-dimethoxy-quinazolin-2-yl)-piperazin-1-yl]-3-thiophen-3-yl-propan-1-one;

3-Amino-1-[4-(4-amino-8-fluoro-6,7-dimethoxy-quinazolin-2-yl)-piperazin-1-yl]-3-(5-methyl-thiophen-2-yl)-propan-1-one (R1=H, R2=5-methyl-thiophen-2-yl);

3-Amino-1-[4-(4-amino-8-fluoro-6,7-dimethoxy-quinazolin-2-yl)-piperazin-1-yl]-3-phenyl-propan-1-one;

3-Amino-1-[4-(4-amino-8-fluoro-6,7-dimethoxy-quinazolin-2-yl)-piperazin-1-yl]-3-m-tolyl-propan-1-one;

3-Amino-1-[4-(4-amino-8-fluoro-6,7-dimethoxy-quinazolin-2-yl)-piperazin-1-yl]-3-p-tolyl-propan-1-one;

3-Amino-1-[4-(4-amino-8-fluoro-6,7-dimethoxy-quinazolin-2-yl)-piperazin-1-yl]-3-(4-ethynyl-phenyl)-propan-1-one;

3-{1-Amino-3-[4-(4-amino-8-fluoro-6,7-dimethoxy-quinazolin-2-yl)-piperazin-1-yl]-3-oxo-propyl}-benzonitrile;

4-{1-Amino-3-[4-(4-amino-8-fluoro-6,7-dimethoxy-quinazolin-2-yl)-piperazin-1-yl]-3-oxo-propyl}-benzonitrile;

3-Amino-1-[4-(4-amino-8-fluoro-6,7-dimethoxy-quinazolin-2-yl)-piperazin-1-yl]-3-(3-fluoro-phenyl)-propan-1-one;

3-Amino-1-[4-(4-amino-8-fluoro-6,7-dimethoxy-quinazolin-2-yl)-piperazin-1-yl]-3-(4-fluoro-phenyl)-propan-1-one;

3-Amino-1-[4-(4-amino-8-fluoro-6,7-dimethoxy-quinazolin-2-yl)-piperazin-1-yl]-3-(3-chloro-phenyl)-propan-1-one;

3-Amino-1-[4-(4-amino-8-fluoro-6,7-dimethoxy-quinazolin-2-yl)-piperazin-1-yl]-3-(4-chloro-phenyl)-propan-1-one;

3-Amino-1-[4-(4-amino-8-fluoro-6,7-dimethoxy-quinazolin-2-yl)-piperazin-1-yl]-3-(4-bromo-phenyl)-propan-1-one;

3-Amino-1-[4-(4-amino-8-fluoro-6,7-dimethoxy-quinazolin-2-yl)-piperazin-1-yl]-3-(2,4-difluoro-phenyl)-propan-1-one;

3-Amino-1-[4-(4-amino-8-fluoro-6,7-dimethoxy-quinazolin-2-yl)-piperazin-1-yl]-3-(3-chloro-4-fluoro-phenyl)-propan-1-one;

3-Amino-1-[4-(4-amino-8-fluoro-6,7-dimethoxy-quinazolin-2-yl)-piperazin-1-yl]-3-(4-difluoromethyl-phenyl)-propan-1-one;

3-Amino-1-[4-(4-amino-8-fluoro-6,7-dimethoxy-quinazolin-2-yl)-piperazin-1-yl]-3-(3-trifluoromethyl-phenyl)-propan-1-one;

3-Amino-1-[4-(4-amino-8-fluoro-6,7-dimethoxy-quinazolin-2-yl)-piperazin-1-yl]-3-(4-trifluoromethyl-phenyl)-propan-1-one;

3-Amino-1-[4-(4-amino-8-fluoro-6,7-dimethoxy-quinazolin-2-yl)-3-methyl-piperazin-1-yl]-5-methyl-hexan-1-one;

3-Amino-1-[4-(4-amino-8-fluoro-6,7-dimethoxy-quinazolin-2-yl)-3-methyl-piperazin-1-yl]-3-phenyl-propan-1-one hydrochloride;

4-{1-Amino-3-[4-(4-amino-8-fluoro-6,7-dimethoxy-quinazolin-2-yl)-3-methyl-piperazin-1-yl]-3-oxo-propyl}-benzonitrile;

3-Amino-1-[4-(4-amino-8-fluoro-6,7-dimethoxy-quinazolin-2-yl)-3-methyl-piperazin-1-yl]-3-(2-fluoro-phenyl)-propan-1-one;

3-Amino-1-[4-(4-amino-8-fluoro-6,7-dimethoxy-quinazolin-2-yl)-3-methyl-piperazin-1-yl]-3-(4-fluoro-phenyl)-propan-1-one;

3-Amino-1-[4-(4-amino-8-fluoro-6,7-dimethoxy-quinazolin-2-yl)-3-methyl-piperazin-1-yl]-3-(4-trifluoromethyl-phenyl)-propan-1-one;

3-Amino-1-[4-(4-amino-8-fluoro-6,7-dimethoxy-quinazolin-2-yl)-3-methyl-piperazin-1-yl]-4-phenyl-butan-1-one;

3-Amino-1-[4-(4-amino-8-fluoro-6,7-dimethoxy-quinazolin-2-yl)-3-methyl-piperazin-1-yl]-4-pyridin-4-yl-butan-1-one;

4-{1-Amino-3-[4-(4-amino-8-fluoro-6,7-dimethoxy-quinazolin-2-yl)-3-ethyl-piperazin-1-yl]-3-oxo-propyl}-benzonitrile;

3-Amino-1-[4-(4-amino-8-fluoro-6,7-dimethoxy-quinazolin-2-yl)-3-ethyl-piperazin-1-yl]-3-(4-fluoro-phenyl)-propan-1-one;

3-Amino-1-[4-(4-amino-8-fluoro-6,7-dimethoxy-quinazolin-2-yl)-3-ethyl-piperazin-1-yl]-3-(4-trifluoromethyl-phenyl)-propan-1-one;

4-{1-Amino-3-[4-(4-amino-8-fluoro-6,7-dimethoxy-quinazolin-2-yl)-3-propyl-piperazin-1-yl]-3-oxo-propyl}-benzonitrile;

3-Amino-1-[4-(4-amino-8-fluoro-6,7-dimethoxy-quinazolin-2-yl)-3-propyl-piperazin-1-yl]-3-(4-trifluoromethyl-phenyl)-propan-1-one;

3-Amino-1-[4-(4-amino-8-fluoro-6,7-dimethoxy-quinazolin-2-yl)-3-phenyl-piperazin-1-yl]-3-(4-fluoro-phenyl)-propan-1-one;

4-(1-Amino-3-{4-[4-amino-8-fluoro-6-methoxy-7-(2-methoxy-ethoxy)-quinazolin-2-yl]-piperazin-1-yl}-3-oxo-propylybenzonitrile;

4-(1-Amino-3-{4-[4-amino-8-fluoro-6-methoxy-7-(2-methoxy-ethoxy)-quinazolin-2-yl]-3-methyl-piperazin-1-yl}-3-oxo-propylybenzonitrile;

1-[4-(4-Amino-8-fluoro-6,7-dimethoxy-quinazolin-2-yl)-piperazin-1-yl]-3-methylamino-3-phenyl-propan-1-one;

3-Amino-1-[4-(4-amino-8-fluoro-6,7-dimethoxy-quinazolin-2-yl)-2,5-dimethyl-piperazin-1-yl]-3-phenyl-propan-1-one;

3-amino-1-[4-(4-amino-8-fluoro-6,7-dimethoxy-quinazolin-2-yl)-2,5-dimethyl-piperazin-1-yl]-3-(4-fluorophenyl)-propan-1-one;

4-Amino-2-[4-(3-amino-3-phenyl-propionyl)-piperazin-1-yl]-6,7-dimethoxy-quinazoline-8-carbonitrile;

4-Amino-2-{4-[3-amino-3-(4-fluoro-phenyl)-propionyl]-piperazin-1-yl}-6,7-dimethoxy-quinazoline-8-carbonitrile;

4-(3-(4-(4-amino-8-fluoro-6,7-dimethoxyquinazolin-2-yl)piperazin-1-yl)-1-(methylamino)-3-oxopropyl)benzonitrile;

1-(4-(4-amino-8-fluoro-6,7-dimethoxyquinazolin-2-yl)piperazin-1-yl)-3-cyclohexyl-3-(methylamino)propan-1-one;

3-Amino-1-[4-(4-amino-5-fluoro-6,7-dimethoxy-quinazolin-2-yl)-piperazin-1-yl]-3-(4-fluoro-phenyl)-propan-1-one;

1-[4-(4-Amino-8-fluoro-6,7-dimethoxy-quinazolin-2-yl)-piperazin-1-yl]-3-ethylamino-3-(4-fluoro-phenyl)-propan-1-one;

1-[4-(4-Amino-8-fluoro-6,7-dimethoxy-quinazolin-2-yl)-piperazin-1-yl]-3-dimethylamino-3-phenyl-propan-1-one;

1-[4-(4-Amino-8-fluoro-6,7-dimethoxy-quinazolin-2-yl)-piperazin-1-yl]-3-dimethylamino-3-phenyl-propan-1-one;

1-(4-(4-amino-8-fluoro-6,7-dimethoxyquinazolin-2-yl)piperazin-1-yl)-3-(1,3-difluoropropan-2-ylamino)-3-(4-fluorophenyl)propan-1-one;

1-[4-(4-Amino-8-fluoro-6,7-dimethoxy-quinazolin-2-yl)-piperazin-1-yl]-3-(4-fluoro-phenyl)-3-(2,2,2-trifluoro-ethylamino)-propan-1-one;

1-[4-(4-Amino-8-fluoro-6,7-dimethoxy-quinazolin-2-yl)-piperazin-1-yl]-3-(4-fluoro-phenyl)-3-isopropylamino-propan-1-one;

4-(3-(4-(4-amino-8-fluoro-6,7-dimethoxyquinazolin-2-yl)piperazin-1-yl)-1-(ethylamino)-3-oxopropyl)benzonitrile;

5-(3-(4-(4-amino-8-fluoro-6,7-dimethoxyquinazolin-2-yl)piperazin-1-yl)-1-(isopropylamino)-3-oxopropyl)-2-fluorobenzonitrile;

1-(4-(4-amino-8-fluoro-6,7-dimethoxyquinazolin-2-yl)piperazin-1-yl)-3-(5-chlorothiophen-2-yl)-3-(propylamino)propan-1-one;

1-(4-(4-amino-8-fluoro-6,7-dimethoxyquinazolin-2-yl)piperazin-1-yl)-3-(cyclopropylmethylamino)-3-(thiophen-3-yl)propan-1-one;

1-(4-(4-amino-8-fluoro-6,7-dimethoxyquinazolin-2-yl)piperazin-1-yl)-3-(4-fluorophenyl)-3-(3-methoxypropylamino)propan-1-one;

4-(3-(4-(4-amino-8-fluoro-6,7-dimethoxyquinazolin-2-yl)piperazin-1-yl)-1-(isopropylamino)-3-oxopropyl)benzonitrile;

1-(4-(4-amino-8-fluoro-6,7-dimethoxyquinazolin-2-yl)piperazin-1-yl)-3-(azetidin-1-yl)-3-(4-fluorophenyl)propan-1-one;

4-(3-(4-(4-amino-8-fluoro-6,7-dimethoxyquinazolin-2-yl)-3,5-dimethylpiperazin-1-yl)-1-(isopropylamino)-3-oxopropyl)benzonitrile;

(1-[4-(4-Amino-8-fluoro-6,7-dimethoxy-quinazolin-2-yl)-piperazin-1-yl]-3-(2-fluoro-ethylamino)-3-(4-fluoro-phenyl)-propan-1-one;

1-[4-(4-Amino-8-fluoro-6,7-dimethoxy-quinazolin-2-yl)-piperazin-1-yl]-3-(4-fluoro-phenyl)-3-piperidin-1-yl-propan-1-one;

1-[4-(4-Amino-8-fluoro-6,7-dimethoxy-quinazolin-2-yl)-piperazin-1-yl]-3-(4-fluoro-phenyl)-3-(2-methoxy-ethylamino)-propan-1-one;

1-[4-(4-Amino-8-fluoro-6,7-dimethoxy-quinazolin-2-yl)-piperazin-1-yl]-3-(5-fluoro-pyridin-2-yl)-3-isopropylamino-propan-1-one;

(4-{3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

(4-{3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

[4-(4-Amino-8-fluoro-6,7-dimethoxy-quinazolin-2-yl)-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-methyl-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-ethyl-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-phenyl-piperazin-1-yl]-(1-amino-1,2,3,4-tetrahydro-naphthalen-2-yl)-methanone;

1-(4-(4-amino-8-fluoro-6,7-dimethoxyquinazolin-2-yl)piperazin-1-yl)-2-(1-isobutylpyrrolidin-2-yl)ethanone;

1-[4-(4-Amino-8-fluoro-6,7-dimethoxy-quinazolin-2-yl)-piperazin-1-yl]-2-azetidin-2-yl-ethanone;

1-[4-(4-Amino-8-fluoro-6,7-dimethoxy-quinazolin-2-yl)-piperazin-1-yl]-2-pyrrolidin-2-yl-ethanone;

1-[4-(4-Amino-8-fluoro-6,7-dimethoxy-quinazolin-2-yl)-piperazin-1-yl]-2-(5-phenyl-pyrrolidin-2-yl)-ethanone;

1-[4-(4-Amino-8-fluoro-6,7-dimethoxy-quinazolin-2-yl)-piperazin-1-yl]-2-(2,3-dihydro-1H-isoindol-1-yl)-ethanone;

1-[4-(4-Amino-8-fluoro-6,7-dimethoxy-quinazolin-2-yl)-piperazin-1-yl]-2-piperidin-2-yl-ethanone;

1-[4-(4-Amino-8-fluoro-6,7-dimethoxy-quinazolin-2-yl)-piperazin-1-yl]-2-piperidin-3-yl-ethanone;

1-[4-(4-Amino-8-fluoro-6,7-dimethoxy-quinazolin-2-yl)-3-methyl-piperazin-1-yl]-2-pyrrolidin-2-yl-ethanone;

1-[4-(4-Amino-8-fluoro-6,7-dimethoxy-quinazolin-2-yl)-3-ethyl-piperazin-1-yl]-2-pyrrolidin-2-yl-ethanone;

1-[4-(4-Amino-8-fluoro-6,7-dimethoxy-quinazolin-2-yl)-3-ethyl-piperazin-1-yl]-2-piperidin-2-yl-ethanone;

1-[4-(4-Amino-8-fluoro-6,7-dimethoxy-quinazolin-2-yl)-3-propyl-piperazin-1-yl]-2-pyrrolidin-2-yl-ethanone;

1-[4-(4-Amino-8-fluoro-6,7-dimethoxy-quinazolin-2-yl)-3-phenyl-piperazin-1-yl]-2-azetidin-2-yl-ethanone hydrochloride;

1-[4-(4-Amino-8-fluoro-6,7-dimethoxy-quinazolin-2-yl)-3-phenyl-piperazin-1-yl]-2-pyrrolidin-2-yl-ethanone;

1-[4-(4-Amino-8-fluoro-6,7-dimethoxy-quinazolin-2-yl)-3-phenyl-piperazin-1-yl]-2-piperidin-2-yl-ethanone;

1-[4-(4-Amino-8-fluoro-6,7-dimethoxy-quinazolin-2-yl)-3-phenyl-piperazin-1-yl]-2-piperidin-3-yl-ethanone;

1-[4-(4-Amino-8-fluoro-6,7-dimethoxy-quinazolin-2-yl)-3-phenyl-piperazin-1-yl]-2-morpholin-2-yl-ethanone;

1-{4-[4-Amino-8-fluoro-6-methoxy-7-(2-methoxy-ethoxy)-quinazolin-2-yl]-piperazin-1-yl}-2-pyrrolidin-2-yl-ethanone;

1-{4-[4-Amino-8-fluoro-6-methoxy-7-(2-methoxy-ethoxy)-quinazolin-2-yl]-piperazin-1-yl}-2-piperidin-2-yl-ethanone;

1-[4-(4-Amino-8-fluoro-6,7-dimethoxy-quinazolin-2-yl)-piperazin-1-yl]-2-1,2,3,4-tetrahydro-isoquinolin-1-yl-ethanone;

1-[4-(4-Amino-8-fluoro-6,7-dimethoxy-quinazolin-2-yl)-piperazin-1-yl]-2-(6-fluoro-1,2,3,4-tetrahydro-isoquinolin-1-yl)-ethanone;

1-[4-(4-Amino-8-fluoro-6,7-dimethoxy-quinazolin-2-yl)-piperazin-1-yl]-3-$d^3$-methylamino-3-phenyl-propan-1-one;

1-(4-(4-amino-8-fluoro-6,7-dimethoxyquinazolin-2-yl)piperazin-1-yl)-3-(4-fluorophenyl)-3-($d^3$-methylamino)propan-1-one hydrochloride;

1-(4-(4-amino-8-fluoro-6,7-dimethoxyquinazolin-2-yl)piperazin-1-yl)-3-(1,1,2,2,2-$d^5$ ethylamino)-3-(4-fluorophenyl)propan-1-one;

1-(4-(4-Amino-8-chloro-6,7-dimethoxyquinazolin-2-yl)piperazin-1-yl)-3-cyclopropylprop-2-en-1-one;

1-(4-(4-Amino-5-chloro-6,7-dimethoxyquinazolin-2-yl)piperazin-1-yl)-3-cyclopropylprop-2-en-1-one;

1-(4-(4-Amino-8-bromo-6,7-dimethoxyquinazolin-2-yl)piperazin-1-yl)-3-cyclopropylprop-2-en-1-one;

1-(4-(4-Amino-8-chloro-6,7-dimethoxyquinazolin-2-yl)piperazin-1-yl)-3-(4-fluorophenyl)prop-2-en-1-one;

3-amino-1-(4-(4-Amino-8-bromo-6,7-dimethoxyquinazolin-2-yl)piperazin-1-yl)-3-phenylpropan-1-one;

3-Amino-1-(4-(4-amino-8-chloro-6,7-dimethoxyquinazolin-2-yl)piperazin-1-yl)-3-(4-fluorophenyl)propan-1-one;

4-Amino-6,7-dimethoxy-2-(4-(2-(piperidin-2-yl)acetyl)piperazin-1-yl)quinazoline-8-carbonitrile;

4-Amino-1-[4-(4-amino-8-fluoro-6,7-dimethoxy-quinazolin-2-yl)-piperazin-1-yl]-3-phenyl-butan-1-one; and 4-[4-(4-Amino-8-fluoro-6,7-dimethoxy-quinazolin-2-yl)-piperazin-1-yl]-2-(4-fluoro-phenyl)-4-oxo-butyramide.

In a thirteenth embodiment, compounds of embodiment one are provided which have a specific regiochemistry or stereochemistry. Thus, compounds are provided which are selected from the group consisting of:

(E)-1-[4-(4-Amino-8-fluoro-6,7-dimethoxy-quinazolin-2-yl)-piperazin-1-yl]-3-cyclopropyl-propenone;

4-{(E)-3-[4-(4-Amino-8-fluoro-6,7-dimethoxy-quinazolin-2-yl)-piperazin-1-yl]-3-oxo-propenyl}-benzonitrile;

((E)-1-[(R)-4-(4-Amino-8-fluoro-6,7-dimethoxy-quinazolin-2-yl)-3-methoxymethyl-piperazin-1-yl]-3-cyclopropyl-propenone;

(E)-1-[4-(4-Amino-8-fluoro-6,7-dimethoxy-quinazolin-2-yl)-3-(2-methoxy-ethyl)-piperazin-1-yl]-3-cyclopropyl-propenone;

4-Amino-2-[4-((E)-3-cyclopropyl-acryloyl)-piperazin-1-yl]-6,7-dimethoxy-quinazoline-8-carbonitrile;

(E)-1-[(S)-4-(4-Amino-8-fluoro-6,7-dimethoxy-quinazolin-2-yl)-3-methyl-piperazin-1-yl]-3-cyclobutyl-propenone;

4-{(E)-3-[(S)-4-(4-Amino-8-fluoro-6,7-dimethoxy-quinazolin-2-yl)-3-methyl-piperazin-1-yl]-3-oxo-propenyl}-benzonitrile;

4-{(E)-3-[(S)-4-(4-Amino-8-fluoro-6,7-dimethoxy-quinazolin-2-yl)-3-ethyl-piperazin-1-yl]-3-oxo-propenyl}-benzonitrile;

4-{(E)-3-[(S)-4-(4-Amino-8-fluoro-6,7-dimethoxy-quinazolin-2-yl)-3-propyl-piperazin-1-yl]-3-oxo-propenyl}-benzonitrile;

4-{(E)-3-[(S)-4-(4-Amino-8-fluoro-6,7-dimethoxy-quinazolin-2-yl)-3-phenyl-piperazin-1-yl]-3-oxo-propenyl}-benzonitrile;

4-((E)-3-{4-[4-Amino-8-fluoro-6-methoxy-7-(2-methoxy-ethoxy)-quinazolin-2-yl]-piperazin-1-yl}-3-oxo-propenylbenzonitrile;

(E)-1-[4-(4-Amino-5-fluoro-6,7-dimethoxy-quinazolin-2-yl)-piperazin-1-yl]-3-cyclopropyl-propenone;

[4-(4-Amino-8-fluoro-6,7-dimethoxy-quinazolin-2-yl)-piperazin-1-yl]-(1H-indol-2-yl)-methanone;

2-[4-(4-Amino-8-fluoro-6,7-dimethoxy-quinazolin-2-yl)-piperazine-1-carbonyl]-1H-indole-5-carbonitrile;

[4-(4-Amino-8-fluoro-6,7-dimethoxy-quinazolin-2-yl)-piperazin-1-yl]-(5-hydroxy-1H-indol-2-yl)-methanone;

[4-(4-Amino-8-fluoro-6,7-dimethoxy-quinazolin-2-yl)-piperazin-1-yl]-(4-methoxy-1H-indol-2-yl)-methanone;

[4-(4-Amino-8-fluoro-6,7-dimethoxy-quinazolin-2-yl)-piperazin-1-yl]-(5-fluoro-1H-indol-2-yl)-methanone;

[4-(4-Amino-8-fluoro-6,7-dimethoxy-quinazolin-2-yl)-piperazin-1-yl]-(5,7-difluoro-1H-indol-2-yl)-methanone;

2-[(S)-4-(4-Amino-8-fluoro-6,7-dimethoxy-quinazolin-2-yl)-3-methyl-piperazine-1-carbonyl]-1H-indole-5-carbonitrile;

[(S)-4-(4-Amino-8-fluoro-6,7-dimethoxy-quinazolin-2-yl)-3-methyl-piperazin-1-yl]-(5-fluoro-1H-indol-2-yl)-methanone;

2-[(S)-4-(4-Amino-8-fluoro-6,7-dimethoxy-quinazolin-2-yl)-3-ethyl-piperazine-1-carbonyl]-1H-indole-5-carbonitrile;

2-[(S)-4-(4-Amino-8-fluoro-6,7-dimethoxy-quinazolin-2-yl)-3-propyl-piperazine-1-carbonyl]-1H-indole-5-carbonitrile;

[(S)-4-(4-Amino-8-fluoro-6,7-dimethoxy-quinazolin-2-yl)-3-propyl-piperazin-1-yl]-(5-fluoro-1H-indol-2-yl)-methanone;

2-[(S)-4-(4-Amino-8-fluoro-6,7-dimethoxy-quinazolin-2-yl)-3-phenyl-piperazine-1-carbonyl]-1H-indole-5-carbonitrile;

(S)-(4-(4-amino-8-fluoro-6,7-dimethoxyquinazolin-2-yl)-3-phenylpiperazin-1-yl)(5-fluoro-1H-indol-2-yl)methanone;

{(S)-4-[4-Amino-8-fluoro-6-methoxy-7-(2-methoxy-ethoxy)-quinazolin-2-yl]-3-methyl-piperazin-1-yl}-(5-chloro-1H-indol-2-yl)-methanone;

(S)-3-Amino-1-[4-(4-amino-8-fluoro-6,7-dimethoxy-quinazolin-2-yl)-piperazin-1-yl]-hex-5-yn-1-one;

(R)-3-Amino-1-[4-(4-amino-8-fluoro-6,7-dimethoxy-quinazolin-2-yl)-piperazin-1-yl]-3-cyclopentyl-propan-1-one;

(S)-3-Amino-1-[4-(4-amino-8-fluoro-6,7-dimethoxy-quinazolin-2-yl)-piperazin-1-yl]-5-methyl-hexan-1-one;

(R)-3-Amino-1-[4-(4-amino-8-fluoro-6,7-dimethoxy-quinazolin-2-yl)-piperazin-1-yl]-3-furan-2-yl-propan-1-one hydrochloride;

(R)-3-Amino-1-[4-(4-amino-8-fluoro-6,7-dimethoxy-quinazolin-2-yl)-piperazin-1-yl]-3-furan-3-yl-propan-1-one;

(R)-3-Amino-1-[4-(4-amino-8-fluoro-6,7-dimethoxy-quinazolin-2-yl)-piperazin-1-yl]-3-thiophen-2-yl-propan-1-one;

(R)-3-Amino-1-[4-(4-amino-8-fluoro-6,7-dimethoxy-quinazolin-2-yl)-piperazin-1-yl]-3-thiophen-3-yl-propan-1-one;

(R)-3-Amino-1-[4-(4-amino-8-fluoro-6,7-dimethoxy-quinazolin-2-yl)-piperazin-1-yl]-3-(5-methyl-thiophen-2-yl)-propan-1-one (R1=H, R2=5-methyl-thiophen-2-yl);

(R)-3-Amino-1-[4-(4-amino-8-fluoro-6,7-dimethoxy-quinazolin-2-yl)-piperazin-1-yl]-3-phenyl-propan-1-one;

(R)-3-Amino-1-[4-(4-amino-8-fluoro-6,7-dimethoxy-quinazolin-2-yl)-piperazin-1-yl]-3-m-tolyl-propan-1-one;

(R)-3-Amino-1-[4-(4-amino-8-fluoro-6,7-dimethoxy-quinazolin-2-yl)-piperazin-1-yl]-3-p-tolyl-propan-1-one;

(R)-3-Amino-1-[4-(4-amino-8-fluoro-6,7-dimethoxy-quinazolin-2-yl)-piperazin-1-yl]-3-(4-ethynyl-phenyl)-propan-1-one;

3-{(R)-1-Amino-3-[4-(4-amino-8-fluoro-6,7-dimethoxy-quinazolin-2-yl)-piperazin-1-yl]-3-oxo-propyl}-benzonitrile;

4-{(R)-1-Amino-3-[4-(4-amino-8-fluoro-6,7-dimethoxy-quinazolin-2-yl)-piperazin-1-yl]-3-oxo-propyl}-benzonitrile;

(R)-3-Amino-1-[4-(4-amino-8-fluoro-6,7-dimethoxy-quinazolin-2-yl)-piperazin-1-yl]-3-(3-fluoro-phenyl)-propan-1-one;

(R)-3-Amino-1-[4-(4-amino-8-fluoro-6,7-dimethoxy-quinazolin-2-yl)-piperazin-1-yl]-3-(4-fluoro-phenyl)-propan-1-one;

(R)-3-Amino-1-[4-(4-amino-8-fluoro-6,7-dimethoxy-quinazolin-2-yl)-piperazin-1-yl]-3-(3-chloro-phenyl)-propan-1-one;

(R)-3-Amino-1-[4-(4-amino-8-fluoro-6,7-dimethoxy-quinazolin-2-yl)-piperazin-1-yl]-3-(4-chloro-phenyl)-propan-1-one;

(R)-3-Amino-1-[4-(4-amino-8-fluoro-6,7-dimethoxy-quinazolin-2-yl)-piperazin-1-yl]-3-(4-bromo-phenyl)-propan-1-one;

(R)-3-Amino-1-[4-(4-amino-8-fluoro-6,7-dimethoxy-quinazolin-2-yl)-piperazin-1-yl]-3-(2,4-difluoro-phenyl)-propan-1-one;

(R)-3-Amino-1-[4-(4-amino-8-fluoro-6,7-dimethoxy-quinazolin-2-yl)-piperazin-1-yl]-3-(3-chloro-4-fluoro-phenyl)-propan-1-one;

(R)-3-Amino-1-[4-(4-amino-8-fluoro-6,7-dimethoxy-quinazolin-2-yl)-piperazin-1-yl]-3-(4-difluoromethyl-phenyl)-propan-1-one;

(R)-3-Amino-1-[4-(4-amino-8-fluoro-6,7-dimethoxy-quinazolin-2-yl)-piperazin-1-yl]-3-(3-trifluoromethyl-phenyl)-propan-1-one;

(R)-3-Amino-1-[4-(4-amino-8-fluoro-6,7-dimethoxy-quinazolin-2-yl)-piperazin-1-yl]-3-(4-trifluoromethyl-phenyl)-propan-1-one;

(S)-3-Amino-1-[(S)-4-(4-amino-8-fluoro-6,7-dimethoxy-quinazolin-2-yl)-3-methyl-piperazin-1-yl]-5-methyl-hexan-1-one;

(R)-3-Amino-1-[(S)-4-(4-amino-8-fluoro-6,7-dimethoxy-quinazolin-2-yl)-3-methyl-piperazin-1-yl]-3-phenyl-propan-1-one hydrochloride;

4-{(R)-1-Amino-3-[(S)-4-(4-amino-8-fluoro-6,7-dimethoxy-quinazolin-2-yl)-3-methyl-piperazin-1-yl]-3-oxo-propyl}-benzonitrile;

(R)-3-Amino-1-[(S)-4-(4-amino-8-fluoro-6,7-dimethoxy-quinazolin-2-yl)-3-methyl-piperazin-1-yl]-3-(2-fluoro-phenyl)-propan-1-one;

(R)-3-Amino-1-[(S)-4-(4-amino-8-fluoro-6,7-dimethoxy-quinazolin-2-yl)-3-methyl-piperazin-1-yl]-3-(4-fluoro-phenyl)-propan-1-one;

(R)-3-Amino-1-[(S)-4-(4-amino-8-fluoro-6,7-dimethoxy-quinazolin-2-yl)-3-methyl-piperazin-1-yl]-3-(4-trifluoromethyl-phenyl)-propan-1-one;

(S)-3-Amino-1-[(S)-4-(4-amino-8-fluoro-6,7-dimethoxy-quinazolin-2-yl)-3-methyl-piperazin-1-yl]-4-phenyl-butan-1-one;

(S)-3-Amino-1-[(S)-4-(4-amino-8-fluoro-6,7-dimethoxy-quinazolin-2-yl)-3-methyl-piperazin-1-yl]-4-pyridin-4-yl-butan-1-one;

4-{(R)-1-Amino-3-[(S)-4-(4-amino-8-fluoro-6,7-dimethoxy-quinazolin-2-yl)-3-ethyl-piperazin-1-yl]-3-oxo-propyl}-benzonitrile;

(R)-3-Amino-1-[(S)-4-(4-amino-8-fluoro-6,7-dimethoxy-quinazolin-2-yl)-3-ethyl-piperazin-1-yl]-3-(4-fluoro-phenyl)-propan-1-one;

(R)-3-Amino-1-[(S)-4-(4-amino-8-fluoro-6,7-dimethoxy-quinazolin-2-yl)-3-ethyl-piperazin-1-yl]-3-(4-trifluoromethyl-phenyl)-propan-1-one;

4-{(R)-1-Amino-3-[(S)-4-(4-amino-8-fluoro-6,7-dimethoxy-quinazolin-2-yl)-3-propyl-piperazin-1-yl]-3-oxo-propyl}-benzonitrile;

(R)-3-Amino-1-[(S)-4-(4-amino-8-fluoro-6,7-dimethoxy-quinazolin-2-yl)-3-propyl-piperazin-1-yl]-3-(4-trifluoromethyl-phenyl)-propan-1-one;

(R)-3-Amino-1-[(S)-4-(4-amino-8-fluoro-6,7-dimethoxy-quinazolin-2-yl)-3-phenyl-piperazin-1-yl]-3-(4-fluoro-phenyl)-propan-1-one;

4-((R)-1-Amino-3-{4-[4-amino-8-fluoro-6-methoxy-7-(2-methoxy-ethoxy)-quinazolin-2-yl]-piperazin-1-yl}-3-oxo-propyl)benzonitrile;

4-((R)-1-Amino-3-{(S)-4-[4-amino-8-fluoro-6-methoxy-7-(2-methoxy-ethoxy)-quinazolin-2-yl]-3-methyl-piperazin-1-yl}-3-oxo-propylybenzonitrile;

(R)-1-[4-(4-Amino-8-fluoro-6,7-dimethoxy-quinazolin-2-yl)-piperazin-1-yl]-3-methylamino-3-phenyl-propan-1-one;

(R)-3-Amino-1-[(2R,5S)-4-(4-amino-8-fluoro-6,7-dimethoxy-quinazolin-2-yl)-2,5-dimethyl-piperazin-1-yl]-3-phenyl-propan-1-one;

(R)-3-amino-1-[(2R,5S)-4-(4-amino-8-fluoro-6,7-dimethoxy-quinazolin-2-yl)-2,5-dimethyl-piperazin-1-yl]-3-(4-fluorophenyl)-propan-1-one;

4-Amino-2-[4-((R)-3-amino-3-phenyl-propionyl)-piperazin-1-yl]-6,7-dimethoxy-quinazoline-8-carbonitrile;

4-Amino-2-{4-[(R)-3-amino-3-(4-fluoro-phenyl)-propionyl]-piperazin-1-yl}-6,7-dimethoxy-quinazoline-8-carbonitrile;

(R)-4-(3-(4-(4-amino-8-fluoro-6,7-dimethoxyquinazolin-2-yl)piperazin-1-yl)-1-(methylamino)-3-oxopropyl)benzonitrile;

(R)-1-(4-(4-amino-8-fluoro-6,7-dimethoxyquinazolin-2-yl)piperazin-1-yl)-3-cyclohexyl-3-(methylamino)propan-1-one;

(R)-3-Amino-1-[4-(4-amino-5-fluoro-6,7-dimethoxy-quinazolin-2-yl)-piperazin-1-yl]-3-(4-fluoro-phenyl)-propan-1-one;

(R)-1-[4-(4-Amino-8-fluoro-6,7-dimethoxy-quinazolin-2-yl)-piperazin-1-yl]-3-ethylamino-3-(4-fluoro-phenyl)-propan-1-one;

(R)-1-[4-(4-Amino-8-fluoro-6,7-dimethoxy-quinazolin-2-yl)-piperazin-1-yl]-3-dimethylamino-3-phenyl-propan-1-one;

(R)-1-[4-(4-Amino-8-fluoro-6,7-dimethoxy-quinazolin-2-yl)-piperazin-1-yl]-3-dimethylamino-3-phenyl-propan-1-one;

(R)-1-(4-(4-amino-8-fluoro-6,7-dimethoxyquinazolin-2-yl)piperazin-1-yl)-3-(1,3-difluoropropan-2-ylamino)-3-(4-fluorophenyl)propan-1-one;

(R)-1-[4-(4-Amino-8-fluoro-6,7-dimethoxy-quinazolin-2-yl)-piperazin-1-yl]-3-(4-fluoro-phenyl)-3-(2,2,2-trifluoro-ethylamino)-propan-1-one;

(R)-1-[4-(4-Amino-8-fluoro-6,7-dimethoxy-quinazolin-2-yl)-piperazin-1-yl]-3-(4-fluoro-phenyl)-3-isopropylamino-propan-1-one;

(R)-4-(3-(4-(4-amino-8-fluoro-6,7-dimethoxyquinazolin-2-yl)piperazin-1-yl)-1-(ethylamino)-3-oxopropyl)benzonitrile;

(R)-5-(3-(4-(4-amino-8-fluoro-6,7-dimethoxyquinazolin-2-yl)piperazin-1-yl)-1-(isopropylamino)-3-oxopropyl)-2-fluorobenzonitrile;

(R)-1-(4-(4-amino-8-fluoro-6,7-dimethoxyquinazolin-2-yl)piperazin-1-yl)-3-(5-chlorothiophen-2-yl)-3-(propylamino)propan-1-one;

(R)-1-(4-(4-amino-8-fluoro-6,7-dimethoxyquinazolin-2-yl)piperazin-1-yl)-3-(cyclopropylmethylamino)-3-(thiophen-3-yl)propan-1-one;

(R)-1-(4-(4-amino-8-fluoro-6,7-dimethoxyquinazolin-2-yl)piperazin-1-yl)-3-(4-fluorophenyl)-3-(3-methoxypropylamino)propan-1-one;

(R)-4-(3-(4-(4-amino-8-fluoro-6,7-dimethoxyquinazolin-2-yl)piperazin-1-yl)-1-(isopropylamino)-3-oxopropyl)benzonitrile;

(R)-1-(4-(4-amino-8-fluoro-6,7-dimethoxyquinazolin-2-yl)piperazin-1-yl)-3-(azetidin-1-yl)-3-(4-fluorophenyl)propan-1-one;

4-((R)-3-((3R,5S)-4-(4-amino-8-fluoro-6,7-dimethoxyquinazolin-2-yl)-3,5-dimethylpiperazin-1-yl)-1-(isopropylamino)-3-oxopropyl)benzonitrile;

((R)-1-[4-(4-Amino-8-fluoro-6,7-dimethoxy-quinazolin-2-yl)-piperazin-1-yl]-3-(2-fluoro-ethylamino)-3-(4-fluoro-phenyl)-propan-1-one;

(R)-1-[4-(4-Amino-8-fluoro-6,7-dimethoxy-quinazolin-2-yl)-piperazin-1-yl]-3-(4-fluoro-phenyl)-3-piperidin-1-yl-propan-1-one;

(R)-1-[4-(4-Amino-8-fluoro-6,7-dimethoxy-quinazolin-2-yl)-piperazin-1-yl]-3-(4-fluoro-phenyl)-3-(2-methoxy-ethylamino)-propan-1-one;

(R)-1-[4-(4-Amino-8-fluoro-6,7-dimethoxy-quinazolin-2-yl)-piperazin-1-yl]-3-(5-fluoro-pyridin-2-yl)-3-isopropylamino-propan-1-one;

(4-{(R)-3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

(4-{(R)-3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

[4-(4-Amino-8-fluoro-6,7-dimethoxy-quinazolin-2-yl)-piperazin-1-yl]-((1R,2R)-1-amino-1,2,3,4-tetrahydro-naphthalen-2-yl)-methanone;

[(S)-4-(4-Amino-8-fluoro-6,7-dimethoxy-quinazolin-2-yl)-3-methyl-piperazin-1-yl]-((1R,2R)-1-amino-1,2,3,4-tetrahydro-naphthalen-2-yl)-methanone;

[(S)-4-(4-Amino-8-fluoro-6,7-dimethoxy-quinazolin-2-yl)-3-ethyl-piperazin-1-yl]-((1R,2R)-1-amino-1,2,3,4-tetrahydro-naphthalen-2-yl)-methanone;

[(S)-4-(4-Amino-8-fluoro-6,7-dimethoxy-quinazolin-2-yl)-3-phenyl-piperazin-1-yl]-((1R,2R)-1-amino-1,2,3,4-tetrahydro-naphthalen-2-yl)-methanone;

(S)-1-(4-(4-amino-8-fluoro-6,7-dimethoxyquinazolin-2-yl) piperazin-1-yl)-2-(1-isobutylpyrrolidin-2-yl)ethanone;

1-[4-(4-Amino-8-fluoro-6,7-dimethoxy-quinazolin-2-yl)-piperazin-1-yl]-2-(S)-azetidin-2-yl-ethanone;

1-[4-(4-Amino-8-fluoro-6,7-dimethoxy-quinazolin-2-yl)-piperazin-1-yl]-2-(S)-pyrrolidin-2-yl-ethanone;

1-[4-(4-Amino-8-fluoro-6,7-dimethoxy-quinazolin-2-yl)-piperazin-1-yl]-2-((2S,5R)-5-phenyl-pyrrolidin-2-yl)-ethanone;

1-[4-(4-Amino-8-fluoro-6,7-dimethoxy-quinazolin-2-yl)-piperazin-1-yl]-2-(2,3-dihydro-1H-isoindol-1-yl)-ethanone;

1-[4-(4-Amino-8-fluoro-6,7-dimethoxy-quinazolin-2-yl)-piperazin-1-yl]-2-(S)-piperidin-2-yl-ethanone;

1-[4-(4-Amino-8-fluoro-6,7-dimethoxy-quinazolin-2-yl)-piperazin-1-yl]-2-(S)-piperidin-3-yl-ethanone;

1-[(S)-4-(4-Amino-8-fluoro-6,7-dimethoxy-quinazolin-2-yl)-3-methyl-piperazin-1-yl]-2-(S)-pyrrolidin-2-yl-ethanone;

1-[(S)-4-(4-Amino-8-fluoro-6,7-dimethoxy-quinazolin-2-yl)-3-ethyl-piperazin-1-yl]-2-(S)-pyrrolidin-2-yl-ethanone;

1-[(S)-4-(4-Amino-8-fluoro-6,7-dimethoxy-quinazolin-2-yl)-3-ethyl-piperazin-1-yl]-2-(S)-piperidin-2-yl-ethanone;

1-[(S)-4-(4-Amino-8-fluoro-6,7-dimethoxy-quinazolin-2-yl)-3-propyl-piperazin-1-yl]-2-(S)-pyrrolidin-2-yl-ethanone;

1-[(S)-4-(4-Amino-8-fluoro-6,7-dimethoxy-quinazolin-2-yl)-3-phenyl-piperazin-1-yl]-2-(S)-azetidin-2-yl-ethanone hydrochloride;

1-[(S)-4-(4-Amino-8-fluoro-6,7-dimethoxy-quinazolin-2-yl)-3-phenyl-piperazin-1-yl]-2-(S)-pyrrolidin-2-yl-ethanone;

1-[(S)-4-(4-Amino-8-fluoro-6,7-dimethoxy-quinazolin-2-yl)-3-phenyl-piperazin-1-yl]-2-(S)-piperidin-2-yl-ethanone;

1-[(S)-4-(4-Amino-8-fluoro-6,7-dimethoxy-quinazolin-2-yl)-3-phenyl-piperazin-1-yl]-2-(S)-piperidin-3-yl-ethanone;

1-[(S)-4-(4-Amino-8-fluoro-6,7-dimethoxy-quinazolin-2-yl)-3-phenyl-piperazin-1-yl]-2-morpholin-2-yl-ethanone;

1-{4-[4-Amino-8-fluoro-6-methoxy-7-(2-methoxy-ethoxy)-quinazolin-2-yl]-piperazin-1-yl}-2-(S)-pyrrolidin-2-yl-ethanone;

1-{4-[4-Amino-8-fluoro-6-methoxy-7-(2-methoxy-ethoxy)-quinazolin-2-yl]-piperazin-1-yl}-2-(S)-piperidin-2-yl-ethanone;

1-[4-(4-Amino-8-fluoro-6,7-dimethoxy-quinazolin-2-yl)-piperazin-1-yl]-2-(R)-1,2,3,4-tetrahydro-isoquinolin-1-yl-ethanone;

1-[4-(4-Amino-8-fluoro-6,7-dimethoxy-quinazolin-2-yl)-piperazin-1-yl]-2-(6-fluoro-1,2,3,4-tetrahydro-isoquinolin-1-yl)-ethanone;

(R)-1-[4-(4-Amino-8-fluoro-6,7-dimethoxy-quinazolin-2-yl)-piperazin-1-yl]-3-$d^3$-methylamino-3-phenyl-propan-1-one hydrochloride;

(R)-1-(4-(4-Amino-8-fluoro-6,7-dimethoxyquinazolin-2-yl) piperazin-1-yl)-3-(4-fluorophenyl)-3-($d^3$-methylamino) propan-1-one hydrochloride;

(R)-1-(4-(4-Amino-8-fluoro-6,7-dimethoxyquinazolin-2-yl) piperazin-1-yl)-3-(1,1,2,2,2-$d^5$ ethylamino)-3-(4-fluorophenyl)propan-1-one;

(E)-1-(4-(4-Amino-8-chloro-6,7-dimethoxyquinazolin-2-yl) piperazin-1-yl)-3-cyclopropylprop-2-en-1-one;

(E)-1-(4-(4-Amino-5-chloro-6,7-dimethoxyquinazolin-2-yl) piperazin-1-yl)-3-cyclopropylprop-2-en-1-one;

(E)-1-(4-(4-Amino-8-bromo-6,7-dimethoxyquinazolin-2-yl)piperazin-1-yl)-3-cyclopropylprop-2-en-1-one;

(E)-1-(4-(4-Amino-8-chloro-6,7-dimethoxyquinazolin-2-yl) piperazin-1-yl)-3-(4-fluorophenyl)prop-2-en-1-one;

(R)-3-amino-1-(4-(4-Amino-8-bromo-6,7-dimethoxyquinazolin-2-yl)piperazin-1-yl)-3-phenylpropan-1-one;

(R)-3-Amino-1-(4-(4-amino-8-chloro-6,7-dimethoxyquinazolin-2-yl)piperazin-1-yl)-3-(4-fluorophenyl)propan-1-one;

(S)-4-Amino-6,7-dimethoxy-2-(4-(2-(piperidin-2-yl)acetyl) piperazin-1-yl)quinazoline-8-carbonitrile;

(R)-4-Amino-1-[4-(4-amino-8-fluoro-6,7-dimethoxy-quinazolin-2-yl)-piperazin-1-yl]-3-phenyl-butan-1-one; and (R)-4-[4-(4-Amino-8-fluoro-6,7-dimethoxy-quinazolin-2-yl)-piperazin-1-yl]-2-(4-fluoro-phenyl)-4-oxo-butyramide, and salts thereof.

In another embodiment, pharmaceutical compositions are provided which comprise one or more pharmaceutically acceptable carriers and a therapeutically effective amount of a compound of any one of formulae (I), (II), (III), (IV), (V), (VI) and (VII), or a subformulae thereof.

In another embodiment, combinations, in particular pharmaceutical combinations, are provided which comprise a therapeutically effective amount of the compound of any one of formulae (I), (II), (III), (IV), (V), (VI) and (VII), or a subformulae thereof.

In another embodiment, methods of modulating complement alternative pathway activity in a subject are provided which methods comprise administering to the subject a therapeutically effective amount of the compound of any one of formulae (I), (II), (III), (IV), (V), (VI) and (VII), or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae (I), (II), (III), (IV), (V), (VI) and (VII), or a subformulae thereof.

In another embodiment, methods of treating age related macular degeneration in a subject are provided which methods comprise administering to the subject a therapeutically effective amount of the compound of any one of formulae (I), (II), (III), (IV), (V), (VI) and (VII), or a subformulae thereof.

In another aspect, the invention provides for the use of compounds of any one of formulae (I), (II), (III), (IV), (V), (VI) and (VII), or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according to any one of formulae (I), (II), (III), (IV), (V), (VI) and (VII), or a subformulae thereof in the treatment of age-related macular degeneration.

In one embodiment, the invention provides a combination, in particular a pharmaceutical combination, comprising a therapeutically effective amount of the compound according to the definition of formula (I), (II), (III), (IV), (V), (VI), (VII), or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(O) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, $(alkyl)_2N$—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an 0-O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In one aspect, the present invention provides (R)-4-(3-(4-(4-amino-8-fluoro-6,7-dimethoxyquinazol in-2-yl)piperazin-1-yl)-1-(ethylamino)-3-oxopropyl)benzonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (R)-1-[4-(4-Amino-8-fluoro-6,7-dimethoxy-quinazolin-2-yl)-piperazin-1-yl]-3-ethylamino-3-(4-fluoro-phenyl)-propan-1-one in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (R)-1-[4-(4-Amino-8-fluoro-6,7-dimethoxy-quinazolin-2-yl)-piperazin-1-yl]-3-(5-fluoro-pyridin-2-yl)-3-isopropylamino-propan-1-one in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (R)-1-[4-(4-Amino-8-fluoro-6,7-dimethoxy-quinazolin-2-yl)-piperazin-1-yl]-3-(4-fluoro-phenyl)-3-piperidin-1-yl-propan-1-one in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (R)-1-[4-(4-Amino-8-fluoro-6,7-dimethoxy-quinazolin-2-yl)-piperazin-1-yl]-3-(4-fluoro-phenyl)-3-isopropylamino-propan-1-one in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (S)-1-(4-(4-amino-8-fluoro-6,7-dimethoxyquinazol in-2-yl)piperazin-1-yl)-2-(1-isobutylpyrrolidin-2-yl)ethanone in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

In another aspect, the present invention provides a pharmaceutical composition comprising a compound of the present invention and a pharmaceutically acceptable carrier. The pharmaceutical composition can be formulated for particular routes of administration such as oral administration, parenteral administration, and ophthalmic administration, etc. In addition, the pharmaceutical compositions of the present invention can be made up in a solid form (including without limitation capsules, tablets, pills, granules, powders or suppositories), or in a liquid form (including without limitation solutions, suspensions, emulsions, each of which may be suitable for ophthalmic administration). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ophthalmic application, e.g., for the treatment of eye diseases e.g., for therapeutic or prophylactic use in treating age related macular degeneration and other complement mediated ophthalmic disorders. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor B modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing compelment mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, anca vasculitis, cryoglobulinemia, systemic lupus, lupus erythematosus, psoriasis, multiple sclerosis, transplantation, diseases of the central nervous system such as Alzheimer's disease and other neurodegenerative conditions, atypically hemolytic uremic syndrome (aHUS), glomerulonephritis (including membrane proliferative glomerulonephritis), dense deposit disease, blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In one embodiment of the present invention, there is provided (R)-4-(3-(4-(4-amino-8-fluoro-6,7-dimethoxyquinazolin-2-yl)piperazin-1-yl)-1-(ethylamino)-3-oxopropyl) benzonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is provided (R)-1-[4-(4-Amino-8-fluoro-6,7-dimethoxy-quinazolin-2-yl)-piperazin-1-yl]-3-ethylamino-3-(4-fluoro-phenyl)-propan-1-one for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is provided (R)-1-[4-(4-Amino-8-fluoro-6,7-dimethoxy-quinazolin-2-yl)-piperazin-1-yl]-3-(5-fluoro-pyridin-2-yl)-3-isopropylamino-propan-1-one for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is provided (R)-1-[4-(4-Amino-8-fluoro-6,7-dimethoxy-quinazolin-2-yl)-piperazin-1-yl]-3-(4-fluoro-phenyl)-3-piperidin-1-yl-propan-1-one for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is provided (R)-1-[4-(4-Amino-8-fluoro-6,7-dimethoxy-quinazolin-2-yl)-piperazin-1-yl]-3-(4-fluoro-phenyl)-3-isopropylamino-propan-1-one for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is provided (S)-1-(4-(4-amino-8-fluoro-6,7-dimethoxyquinazolin-2-yl)piperazin-1-yl)-2-(1-isobutylpyrrolidin-2-yl) ethanone for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor B, wherein the other therapeutic agent is prepared for administration with a compound of formula (I). The invention also provides a compound of formula (I) for use in a method of treating a disease or condition mediated by the complement alternative pathway and/or Factor B, wherein the compound of formula (I) is administered with another therapeutic agent. The invention also provides another therapeutic agent for use in a method of treating a disease or condition mediated by the complement alternative pathway and/or Factor B, wherein the other therapeutic agent is administered with a compound of formula (I).

The invention also provides the use of a compound of formula (I) for treating a disease or condition mediated by the complement alternative pathway and/or Factor B, wherein the patient has previously (e.g. within 24 hours) been treated with another therapeutic agent. The invention also provides the use of another therapeutic agent for treating a disease or condition mediated by the complement alternative pathway and/or Factor B wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include complement inhibitors (such as inhibitors of Factor D, C5a receptor and antibody or Fabs against C5, C3, properidin, factor H, and the like), anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor B, wherein the method comprises administering to the subject a therapeutically effective amount of the compound according to the definition of Formula (I).

In one embodiment, the invention provides a compound according to the definition of formula (I), (II), (III), (IV), (V), (VI), (VII) or any subformulae thereof, for use as a medicament.

In one embodiment, the invention provides the use of a compound according to the definition of formula (I), (II), (III), (IV), (V), (VI), (VII) or any subformulae thereof, for the treatment of a disorder or disease in a subject mediated by complement activation. In particular, the invention provides the use of a compound according to the definition of formula (I), (II), (III), (IV), (V), (VI), (VII) or any subformulae thereof, for the treatment of a disorder or disease mediated by activation of the complement alternative pathway.

In one embodiment, the invention provides the use of a compound according to the definition of formula (I), (II), (III), (IV), (V), (VI) or (VII) in the manufacture of a medicament for the treatment of a disorder or disease in a subject characterized by activation of the complement system. More particularly in the manufacture of a medicament for the treatment of a disease or disorder in a subject characterized by over activation of the complement alternative pathway.

In one embodiment, the invention provides the use of a compound according to the definition of formula (I), (II), (III), (IV), (V), (VI), (VII) or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing compelment mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypically hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

The following examples are intended to illustrate the invention and are not to be construed as being limitations thereon. Temperatures are given in degrees centrigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the following in vitro tests may be used

Biological Example 1

Human Complement Factor B ELISA Assay

CVF-Bb complex prepared from purified cobra venom factor (1 μM), recombinant human complement factor B (expressed in *drosophila* cells and purified using standard methods) and human complement factor D (expressed in *E. Coli*, refolded and purified using standard methods). CVF-Bb complex at 3 nM concentration was incubated with test compound at various concentrations for 1 hour at room temperature in PBS pH 7.4 containing 10 mM $MgCl_2$ and 0.05% (w/v) CHAPS. Human complement C3 substrate purified from plasma was added to a final concentration of 1 μM. After 1 hour incubation at room temperature, the enzyme reaction was stopped by addition of a cocktail of concentrated pan-protease inhibitors. The product of the reaction, C3a, was quantified by means of an enzyme-linked-immunosorbent assay. $IC_{50}$ values were calculated from percentage of inhibition of CVF-Bb activity as a function of test compound concentration.

Factor B $IC_{50}$ values for the individual examples:

| Example number | $IC_{50}$ [nM] |
|---|---|
| 1 | 500 |
| 2 | 16 |
| 3 | 2060 |
| 4 | 16460 |
| 5 | 440 |
| 6 | 190 |
| 7 | 20 |
| 8 | 11 |
| 9 | 20 |
| 10 | 6 |
| 11 | 230 |
| 12 | 140 |
| 13 | 1050 |
| 14 | 3290 |
| 15 | 1280 |
| 16 | 1440 |
| 17 | 340 |
| 18 | 20 |
| 19 | 80 |

-continued

| Example number | $IC_{50}$ [nM] |
|---|---|
| 20 | 9630 |
| 21 | 70 |
| 22 | 17 |
| 23 | 15 |
| 24 | 90 |
| 25 | 6 |
| 26 | 11 |
| 27 | 280 |
| 28 | 5 |
| 29 | 14 |
| 30 | 70 |
| 31 | 1040 |
| 32 | 100 |
| 33 | 680 |
| 34 | 90 |
| 35 | 310 |
| 36 | 190 |
| 37 | 40 |
| 38 | 180 |
| 39 | 230 |
| 40 | 220 |
| 41 | 70 |
| 42 | 510 |
| 43 | 40 |
| 44 | 10 |
| 45 | 50 |
| 46 | 40 |
| 47 | 110 |
| 48 | 90 |
| 49 | 60 |
| 50 | 450 |
| 51 | 180 |
| 52 | 110 |
| 53 | 50 |
| 54 | 260 |
| 55 | 160 |
| 56 | 240 |
| 57 | 210 |
| 58 | 9 |
| 59 | 160 |
| 60 | 20 |
| 61 | 40 |
| 62 | 2250 |
| 63 | 7320 |
| 64 | 7 |
| 65 | 30 |
| 66 | 90 |
| 67 | 10 |
| 68 | 60 |
| 69 | 7 |
| 70 | 110 |
| 71 | 70 |
| 72 | 230 |
| 73 | 60 |
| 74 | 50 |
| 75 | 760 |
| 76 | 100 |
| 77 | 4 |
| 78 | 80 |
| 79 | 50 |
| 80 | 6 |
| 81 | 510 |
| 82 | 1020 |
| 83 | 30 |
| 84 | 6 |
| 85 | 80 |
| 86 | 40 |
| 87 | 40 |
| 88 | 30 |
| 89 | 30 |
| 90 | 1 |
| 91 | 12 |
| 92 | 8 |
| 93 | 4 |
| 94 | 6 |
| 95 | 3 |
| 96 | 10 |

-continued

| Example number | $IC_{50}$ [nM] |
|---|---|
| 97 | 11 |
| 98 | 6 |
| 99 | 6 |
| 100 | 20 |
| 101 | 13 |
| 102 | 1 |
| 103 | 15 |
| 104 | 760 |
| 105 | 1070 |
| 106 | 2660 |
| 107 | 240 |
| 108 | 170 |
| 109 | 4270 |
| 110 | 140 |
| 111 | 380 |
| 112 | 350 |
| 113 | 230 |
| 114 | 3870 |
| 115 | 320 |
| 116 | 540 |
| 117 | 780 |
| 118 | 270 |
| 119 | 610 |
| 120 | 80 |
| 121 | 20 |
| 122 | 200 |
| 123 | 890 |
| 124 | 5950 |
| 125 | 9950 |
| 126 | 2900 |
| 127 | 200 |
| 128 | 120 |
| 129 | 710 |
| 130 | 10 |
| 131 | 3 |

The following Examples, while representing preferred embodiments of the invention, serve to illustrate the invention without limiting its scope.

General Synthetic Aspects

The following Examples serve to illustrate the invention without limiting the scope thereof. Typically, the compounds of formula (I) can be prepared according to the Schemes provided below.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art.

EXPERIMENTAL SECTION

Abbreviations

AcOH Acetic acid
Boc tert Butoxy carbonyl
$Boc_2O$ Di-tert butyl dicarbonate
Cbz Carboxybenzyl
CDI 1,1'-Carbonyldiimidazol
DCE 1,2-Dichloroethane
DEAD Diethyl azodicarboxylate
DIPEA Diisopropylethylamine
DMF N,N-Dimethyl formamide
DMSO Dimethylsulfoxide
EDC 1-Ethyl-3-(3-dimethylaminopropyl)carbodiimide EtOAc Acetic acid ethyl ester
$Et_2O$ Diethylether
EtOH Ethanol
HATU 2-(1H-7-Azabenzotriazol-1-yl)-1,1,3,3-tetramethyl-uroniumhexafluorophosphate methanaminium
HBTU O-Benzotriazole-N,N,N',N'-tetramethyl-uronium-hexafluoro-phosphate
HCl Hydrochloric acid
HOBT Hydroxybenzotriazol
HV High vacuum
HPLC High performance liquid chromatography
RT room temperature
TFA Trifluoroacetic acid
THF Tetrahydrofurane
T3P Propylphosphonic anhydride All reagents, starting materials and intermediates utilized in these examples were available from commercial sources or were readily prepared by methods known to those skilled in the art. $^1$H-NMR spectra were recorded on a Varian Gemini 600 MHz or a Bruker 400 MHz NMR spectrometer. Significant peaks were tabulated in the order: multiplicity (s, singlet; d, doublet; t, triplet; q, quartet; m, multiplet; br, broad) and number of protons. Electron Spray Ionization (ESI) mass spectra were recorded on a Waters UPLC Acquity or an Agilent 1100 series LC/MS, see conditions below. Mass spectrometry results were reported as the ratio of mass over charge. Preparative HPLC purifications were performed with a Gilson GX-281 or a Waters HPLC system using the conditions outlined below.

LC/MS Runs:

Method A1:

UPLC-MS Instrument: Waters UPLC Acquity; column: Acquity HSS T3 1.8 μm 2.1×50 mm at 50° C., eluent A: water+0.05% HCOOH+3.75 mM ammonium acetate, B: $CH_3CN$+0.04% HCOOH, Gradient: 10 to 95% B in 1.5 min, flow: 1.2 ml/min.

Method A2:

UPLC-MS Instrument: Waters UPLC Acquity; column: Acquity HSS T3 1.8 μm 2.1*50 mm at 50° C., Eluent A: water+0.05% HCOOH+3.75 mM ammonium acetate, B: $CH_3CN$+0.04% HCOOH, Gradient: 2 to 98% B in 1.4 min, flow: 1.2 ml/min.

Method A3:

LC-MS Instrument: Agilent 1100 series; column: Waters Sunfire C18 2.5 μm 3*30 mm, Eluent A: water+0.1% HCOOH; B: $CH_3CN$+0.1% HCOOH, Gradient: 10 to 98% B in 2.5 min.

Method A4:

LC-MS Instrument: Agilent 1100 series; column: Eclipse, XDB-C18, 1.8 μm, 4.6×50 mm, Eluent A: water+0.1% TFA, B: $CH_3CN$+0.1% TFA, gradient: 5-100% $CH_3CN$ in 6 min, flow: 1 ml/min Method A5:

UPLC-MS Instrument: Waters UPLC Acquity; column: Acquity HSS T3 1.8 μm 2.1×50 mm at 50° C., eluent A: water+0.05% HCOOH+3.75 mM ammonium acetate, B: $CH_3CN$+0.04% HCOOH, Gradient: 5 to 95% B in 1.4 min, flow: 1.2 ml/min.

Method A6:

UPLC-MS Instrument: Waters UPLC Acquity; column: Acquity HSS T3 1.8 μm 2.1×50 mm at 60° C., eluent A: water+0.05% HCOOH+3.75 mM ammonium acetate, B: $CH_3CN$+0.04% HCOOH, Gradient: 5 to 95% B in 1.4 min, flow: 1.0 ml/min.

Preparative HPLC Runs:

Method P1:

column: Waters SunFire C18 ODB, 5 μm, 100×30 mm, Eluent A: water+0.1% TFA, B: $CH_3CN$+0.1% TFA, Gradient: 0 to 2.5 min: 20% B, 2.5 to 22.5 min: 20 to 100% B, 22.5 to 25 min; 100% B, Flow: 40 ml/min.

Method P2:

column: Waters Sunfire C18 ODB, 5 μm, 100×30 mm, Eluent A: water+0.1% HCOOH, B: $CH_3CN$+0.1% HCOOH, Gradient: 0 to 2.5 min: 5% B, 2.5 to 22.5 min: 5 to 100% B, 22.5 to 25 min: 100% B, Flow: 40 ml/min.

Method P3:

column: Waters Sunfire C18 ODB, 5 μm, 100×30 mm, Eluent A: water+0.1% TFA, B: $CH_3CN$+0.1% TFA, Gradient: 0 to 2.5 min: 5% B, 2.5 to 22.5 min: 5 to 100% B, 22.5 to 25 min; 100% B, Flow: 40 ml/min.

Method P4:

column: Waters SunFire C18 ODB, 5 μm, 50×19 mm, Eluent A: water+0.1% TFA, B: $CH_3CN$+0.1% TFA, Gradient: 0 to 2.5 min: 5% B, 2.5 to 22.5 min: 5 to 100% B, 22.5 to 25 min; 100% B, Flow: 20 ml/min.

Method P5:

column: X-Bridge C18 ODB, 5 μm, 100×30 mm, Eluent A: water+7.3 mM $NH_4OH$, B: $CH_3CN$+7.3 mM $NH_4OH$, Gradient: 0 to 12.5 min: 5 to 99% B, 12.5 to 15 min: 99% B, Flow: 45 ml/min.

Method P6:

column: X-Bridge C18 ODB, 5 μm, 100×30 mm, Eluent A: water+7.3 mM $NH_4OH$, B: $CH_3CN$+7.3 mM $NH_4OH$, Gradient: 0 to 9.5 min: 30 to 80% B, 9.5 to 12 min: 80 to 99% B, 12 to 14.5 min: 99% B, Flow: 45 ml/min.

Method P7:

column: Waters Sunfire C18 ODB, 5 μm, 100×30 mm, Eluent A: water+0.1% TFA, B: $CH_3CN$+0.1% TFA, Gradient: 0 to 2.0 min: 5% B, 2.0 to 30 min: 5 to 100% B, Flow: 40 ml/min.

Method P8:

column: Waters SunFire C18 ODB, 5 μm, 100×30 mm, Eluent A: water+0.1% TFA, B: $CH_3CN$+0.1% TFA, Gradient: 0 to 0.5 min: 20% B, Flow: 5 ml/min, 0.5 to 18.5 min: 20 to 100% B, flow 40 ml/min, 18.5 to 20 min: 100% B, Flow: 40 ml/min.

Method P9:

column: Waters SunFire C18 ODB, 5 μm, 100×30 mm, Eluent A: water+0.1% TFA, B: $CH_3CN$+0.1% TFA, Gradient: 0 to 0.5 min: 5% B, Flow: 5 ml/min, 0.5 to 18.5 min: 5 to 100% B, flow 40 ml/min, 18.5 to 20 min: 100% B, Flow: 40 ml/min.

Method P10:

column: Waters SunFire C18 ODB, 5 μm, 100×30 mm, Eluent A: water+0.1% TFA, B: $CH_3CN$+0.1% TFA, Gradient: 0 to 0.5 min: 10% B, Flow: 5 ml/min, 0.5 to 18.5 min: 10 to 100% B, flow 40 ml/min, 18.5 to 20 min: 100% B, Flow: 40 ml/min.

Method P11:

column: X-Bridge C18 ODB, 5 μm, 100×30 mm, Eluent A: water+7.3 mM $NH_4OH$, B: $CH_3CN$+7.3 mM $NH_4OH$, Gradient: 0 to 12 min: 5 to 99% B, 12 to 13.5 min: 99% B, Flow: 45 ml/min.

Reaction Scheme 1: Synthesis of 2-Chloro-8-fluoro-6,7-dimethoxy-quinazolin-4-ylamine (9)

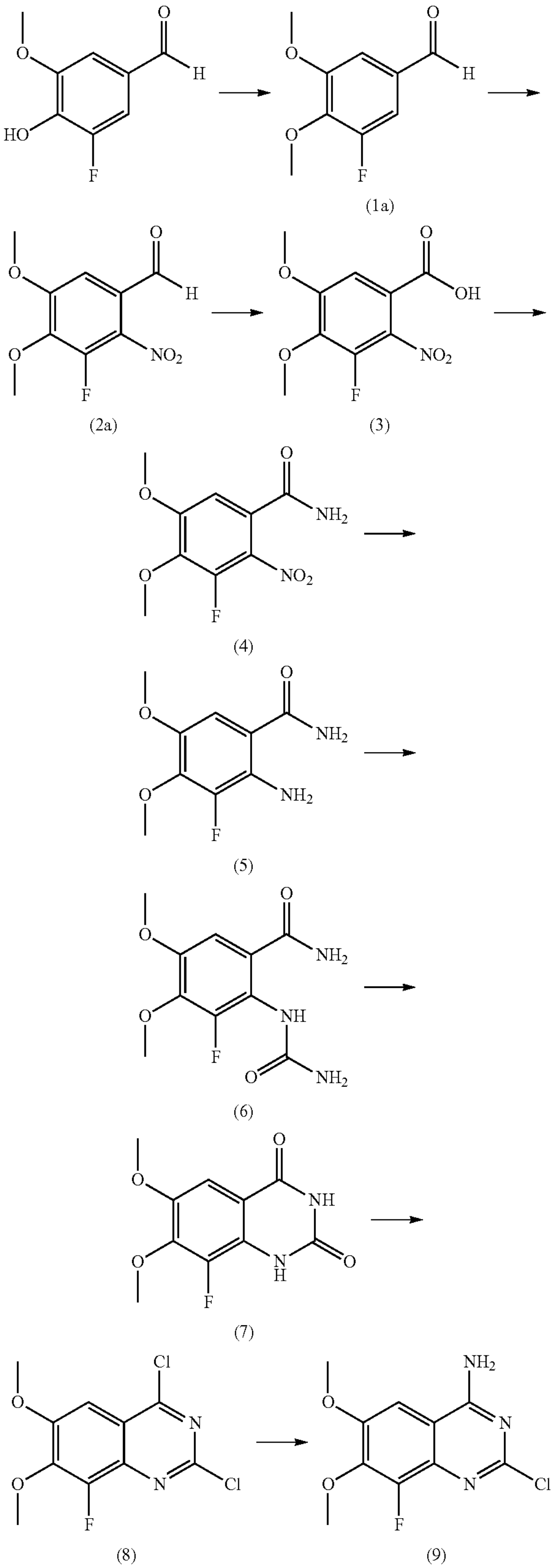

(1a) (2a) (3) (4) (5) (6) (7) (8) (9)

Step A 2-Fluoro-3,4-dimethoxy-benzaldehyde (1a)

To 3-fluoro-4-hydroxy-5-methoxybenzaldehyde (1.0 g, 5.88 mmol) in DMF (50 ml) was added NaH (60% in mineral oil, 0.282 g, 7.05 mmol). After 15 min of stirring, methyl iodide (1.47 ml, 23.5 mmol) was added and the reaction was stirred at RT for 16 h. The reaction was quenched with water, extracted twice with cyclohexane, the organic phase was dried and the solvent was evaporated. The residue was purified by flash chromatography (silica gel, cyclohexane/EtOAc: 9/1 to 2/1). LC MS (ESI): 185.2 $[M+H]^+$, $^1$H-NMR (400 MHz, DMSO-$d^6$) δ (ppm): 9.90 (s, 1H), 7.48 (s, 1H), 7.46 (s, 1H), 3.92 (s, 6H).

Step B 3-Fluoro-4,5-dimethoxy-2-nitro-benzaldehyde (2a)

To 2-Fluoro-3,4-dimethoxy-benzaldehyde (1a) (740 mg, 4.02 mmol) was added nitric acid (9 ml) at RT. The reaction was heated to 65° C. in order to solubilize the starting material and stirring was continued at RT for another 2 h. The reaction mixture was then poured into ice and the resulting mixture was freeze dried. The residue was purified by flash chromatography (silica gel, cyclohexane/EtOAc: 9/1 to 2/1). LC MS (ESI): 228.3 $[M-H]^-$, $^1$H-NMR (400 MHz, DMSO-$d^6$) δ (ppm): 9.97 (s, 1H), 7.59 (s, 1H), 4.02 (m, 6H).

Step C 3-Fluoro-4,5-dimethoxy-2-nitro-benzoic acid (3)

A solution of 3-fluoro-4,5-dimethoxy-2-nitro-benzaldehyde (2a) (533 mg, 2.33 mmol) in acetone (9 ml) was added dropwise to a solution of 10% $KMnO_4$ in water (6 ml) at 60° C. Stirring of the reaction mixture at 70° C. was continued for another 60 min until the violet color had disappeared. The hot suspension was filtered and the precipitate was rinsed with hot acetone and hot water. The filtrate was concentrated to eliminate acetone and the resulting aqueous phase was basified to pH 11-12 with 2N NaOH and extracted with chloroform. The aqueous phase was acidified to pH 3 with conc. HCl, the solid was collected by filtration, rinsed with water and dried under high vacuum. LC MS (ESI): 244.2 $[M-H]^-$, $^1$H-NMR (400 MHz, DMSO-$d^6$) δ (ppm): 14.2 (br s, 1H), 7.38 (s, 1H), 3.96 (s, 6H).

Step D 3-Fluoro-4,5-dimethoxy-2-nitro-benzamide (4)

3-Fluoro-4,5-dimethoxy-2-nitro-benzoic acid (3) (412 mg, 1.68 mmol) was treated with thionyl chloride (4 ml) at 90° C. during 2 h. The volatiles were evaporated and the residue was taken up in THF and evaporated. The obtained acid chloride was dissolved in THF (8 ml) and added dropwise to a 0.5M $NH_3$ solution in THF (16.8 ml, 8.4 mmol) at 0° C. The solution was stirred at RT during 1 h and the solvent was evaporated. The residue was treated with water and the precipitate was collected by filtration, rinsed with water and dried under high vacuum. LC MS (ESI): 289.3 $[M+HCOO]^-$, $^1$H-NMR (400 MHz, DMSO-$d^6$) δ (ppm): 8.25 (s, 1H), 7.83 (s, 1H), 7.25 (s, 1H), 3.98 (s, 3H), 3.91 (s, 3H).

Step E 2-Amino-3-fluoro-4,5-dimethoxy-benzamide (5)

Iron powder (164 mg) was added portionwise to a solution of 3-fluoro-4,5-dimethoxy-2-nitro-benzamide (4) (265 mg, 1.08 mmol) in AcOH (6 ml) at 90° C. The reaction was heated to 105° C. and stirring at this temperature was continued for 15 min. After cooling to RT, the insoluble parts were filtered off over paper and rinsed with AcOH. Evaporation of AcOH yielded a solid which was dissolved in water, frozen and lyophilized. LC MS (ESI): 215.2 $[M+H]^+$; $^1$H-NMR (400 MHz, $CDCl_3$) δ (ppm): 7.82 (br s, 1H), 7.19 (br s, 1H), 7.08 (s, 1H), 6.19 (br s, 2H), 3.84 (s, 3H), 3.75 (s, 3H).

Step F 3-Fluoro-4,5-dimethoxy-2-ureido-benzamide (6)

To a solution of 2-amino-3-fluoro-4,5-dimethoxy-benzamide (5) (365 mg, 1.70 mmol) in AcOH (4 ml) was added a solution of sodium cyanate (222 mg, 3.41 mmol) in water (1.5 ml). The reaction mixture was stirred at RT for 1 h followed by dilution with water (1.5 ml). The resulting precipitate was collected by filtration, rinsed with water and dried under high vacuum. LC MS (ESI): 258.3 $[M+H]^+$; $^1$H-NMR (400 MHz, DMSO-$d^6$) δ (ppm): 8.22 (s, 1H), 7.89 (s, 1H), 7.55 (s, 1H), 7.03 (s, 1H), 6.20 (s, 2H), 3.85 (s, 3H), 3.82 (s, 3H).

Step G 8-Fluoro-6,7-dimethoxy-1H-quinazoline-2,4-dione (7)

A solution of 3-fluoro-4,5-dimethoxy-2-ureido-benzamide (6) (210 mg, 0.82 mmol) in 2M NaOH (6 ml) was stirred at RT for 2 h. The solution was then acidified to pH 1 using conc. HCl leading to precipitation of the desired product which was collected by filtration, rinsed with water and dried under high vacuum. LC MS (ESI): 241.1 $[M+H]^+$; $^1$H-NMR (400 MHz, DMSO-$d^6$) δ (ppm): 11.35 (s, 1H), 11.20 (s, 1H), 7.25 (s, 1H), 3.94 (s, 3H), 3.86 (s, 3H).

Step H 2,4-Dichloro-8-fluoro-6,7-dimethoxy-quinazoline (8)

To a solution of 8-fluoro-6,7-dimethoxy-1H-quinazoline-2,4-dione (7) (161 mg, 0.67 mmol) in $POCl_3$ (2.3 ml) was added N,N-dimethylaniline (81 mg, 0.67 mmol) and the reaction mixture was stirred at 120° C. for another 2 h. Then the solvent was evaporated and the residue was taken up in water. The resulting precipitate was collected by filtration, rinsed with water and dried under high vacuum. LC MS (ESI): 277.1 $[M+H]^+$, $^1$H-NMR (400 MHz, DMSO-$d^6$) δ (ppm): 7.37 (s, 1H), 4.16 (s, 3H), 4.06 (s, 3H).

Step I 2-Chloro-8-fluoro-6,7-dimethoxy-quinazolin-4-ylamine (9)

To a solution of 2,4-dichloro-8-fluoro-6,7-dimethoxy-quinazoline (8) (148 mg, 0.534 mmol) in THF (4 ml) was added a 25% solution of $NH_4OH$ in water (1.66 ml) and stirring of the reaction mixture at 40° C. was continued for 16 h. The solvent was evaporated and the resulting solid was suspended in water, collected by filtration and dried under high vacuum. LC MS (ESI): 258.2 $[M+H]^+$; $^1$H-NMR (400 MHz, DMSO-$d^6$) δ (ppm): 8.27 (s, 2H), 7.57 (s, 1H), 3.97 (s, 3H), 3.92 (s, 3H).

Reaction Scheme 2:

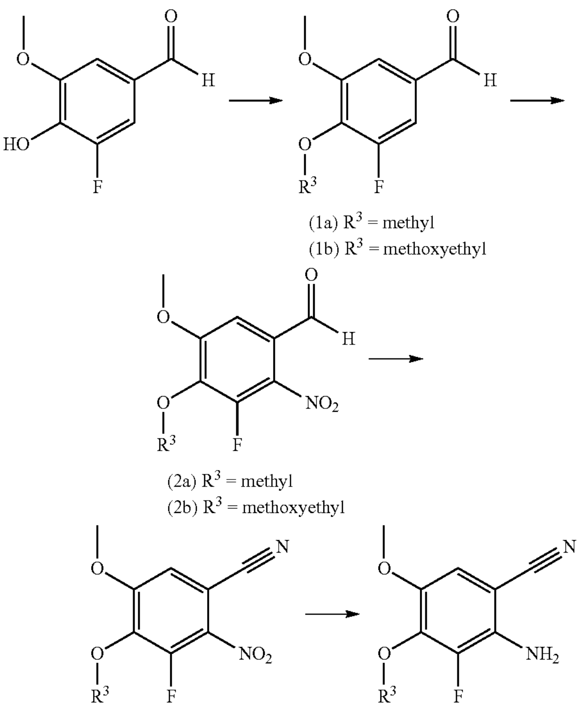

(1a) $R^3$ = methyl
(1b) $R^3$ = methoxyethyl (2a) $R^3$ = methyl
(2b) $R^3$ = methoxyethyl (10a) $R^3$ = methyl
(10b) $R^3$ = methoxyethyl (11a) $R^3$ = methyl
(11b) $R^3$ = methoxyethyl

Synthesis of 2-Amino-3-fluoro-4,5-dimethoxy-benzonitrile (11a, $R^3$=methyl)

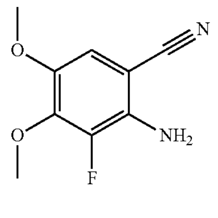

Step A: 3-Fluoro-4,5-dimethoxy-2-nitro-benzonitrile (10a)

3-Fluoro-4,5-dimethoxy-2-nitro-benzaldehyde (2a) (1.25 g, 5.45 mmol) was added to a solution of $NH_2OH$.HCl (0.493 g, 7.09 mmol) and sodium formate (0.589 g, 13.09 mmol) in formic acid (13 ml) and the resulting solution was heated at 100° C. for 3 h. Then the reaction mixture was poured on ice and the resulting suspension was filtered. Evaporation of the solvent afforded a solid which was dried under high vacuum and used in the next step without further purification. LC MS (ESI): 225.0 $[M-H]^-$, $^1$H-NMR (400 MHz, $CDCl_3$) δ (ppm): 7.78 (s, 1H), 4.05 (s, 3H), 4.0 (s, 3H).

Step B: 2-Amino-3-fluoro-4,5-dimethoxy-benzonitrile (11a)

A suspension of 3-fluoro-4,5-dimethoxy-2-nitro-benzonitrile (10a) (2.08 g, 7 mmol) in water (35 ml) was heated to 100° C. before sodium dithionite (2.43 g, 14 mmol) was added. After 5 min a yellow solution was formed and heating at 100° C. was continued for another 60 min. Upon cooling to RT a solid precipitated. The desired product was isolated by filtration followed by drying under high vacuum and used without further purification. LC MS (ESI): 196.9 $[M+H]^+$; $^1$H-NMR (400 MHz, DMSO-$d^6$) δ (ppm): 6.96 (s, 1H), 5.69 (br s, 2H), 3.88 (s, 3H), 3.74 (s, 3H).

Synthesis of 2-Amino-3-fluoro-5-methoxy-4-(2-methoxy-ethoxy)-benzonitrile (11b, $R^3$=methoxyethyl)

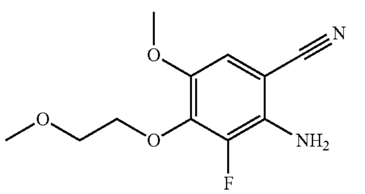 [SMILES: COCCOc1c(OC)cc(C#N)c(N)c1F]

Step A 3-Fluoro-5-methoxy-4-(2-methoxy-ethoxy)-benzaldehyde (1b)

At RT DEAD (45.4 ml, 115 mmol) was added during 10 min to a solution of 3-fluoro-4-hydroxy-5-methoxybenzaldehyde (15 g, 88 mmol), 2-methoxyethanol (8.72 g, 115 mmol) and triphenylphosphine (30.1 g, 115 mmol) in toluene (350 ml) and stirring was continued for 16 h. The reaction mixture was diluted with water and EtOAc, washed with 2M aqueous NaOH and NaCl-solution. The organic phase was separated and dried over $Na_2SO_4$ followed by evaporation of the solvent. The crude product was purified by flash chromatography (silica gel, 0-60% ethylacetate in cyclohexane) to give the title compound. LC MS (ESI): 229.2 $[M+H]^+$; $^1$H-NMR (600 MHz, $CDCl_3$) δ (ppm): 9.88 (s, 1H), 7.42 (m, 2H), 4.23 (t, 2H), 3.91 (s, 3H) 3.60 (t, 2H).

Step B 3-Fluoro-5-methoxy-4-(2-methoxy-ethoxy)-2-nitro-benzaldehyde (2b)

At 0° C. 3-fluoro-5-methoxy-4-(2-methoxy-ethoxy)-benzaldehyde (1b) (10 g, 43.8 mmol) was carefully dissolved in nitric acid (100 ml). The reaction mixture was heated to 150° C. and stirred for another 15 min before it was allowed to cool to RT and stirred for 2 h. The mixture was poured on ice, the water layer was extracted with ethylacetate and the solvent was evaporated. Purification of the crude product by flash chromatography (silica gel, 60-100% methanol/$CH_2Cl_2$) afforded the desired product. LC MS (ESI): 274.2 $[M+H]^+$; $^1$H-NMR (600 MHz, DMSO-$d^6$) δ (ppm): 9.95 (s, 1H), 7.57 (s, 1H), 4.32 (t, 2H), 4.00 (s, 3H), 3.61 (t, 2H), 3.25 (s, 3H).

Step C 3-Fluoro-5-methoxy-4-(2-methoxy-ethoxy)-2-nitro-benzonitrile (10b)

3-Fluoro-5-methoxy-4-(2-methoxy-ethoxy)-2-nitro-benzaldehyde (2b) (900 mg, 3.29 mmol) was added to a solution of $NH_2OH.HCl$ (298 mg, 4.28 mmol) and sodium formate (356 mg, 7.91 mmol) in formic acid (8 ml). The reaction mixture was heated at 100° C. for 16 h before it was poured on ice whereupon a solid precipitated. Filtration and drying under high vacuum afforded the desired product. GC MS (ESI): 270 $[M]^+$; $^1$H-NMR (600 MHz, DMSO-$d^6$) δ (ppm): 7.75 (s, 1H), 4.30 (t, 2H), 4.01 (s, 3H), 3.61 (t, 2H), 3.26 (s, 3H).

Step D 2-Amino-3-fluoro-5-methoxy-4-(2-methoxy-ethoxy)-benzonitrile (11b)

3-Fluoro-5-methoxy-4-(2-methoxy-ethoxy)-2-nitro-benzonitrile (10b) (750 mg, 2.78 mmol) was suspended in water (10 ml) and heated to 100° C. Then sodium dithionite (966 mg, 5.55 mmol) was added portionwise. After 5 min a yellow solution formed and stirring was continued for 24 h at 100° C. For workup EtOAc was added, the organic phase was washed with a saturated solution of $NaHCO_3$ and brine and dried over $Na_2SO_4$. Evaporation of the solvent yielded the crude product which was purified by flash chromatography (silica, 0-50% EtOAc in cyclohexane) to give the title compound. LC MS (ESI): 241.2 $[M+H]^+$; $^1$H-NMR (600 MHz, DMSO-$d^6$) δ (ppm): 6.94 (s, 1H), 5.66 (br s, 2H), 4.20 (t, 2H), 3.72 (s, 3H), 3.55 (t, 2H), 3.27 (s, 3H).

Reaction Scheme 3:

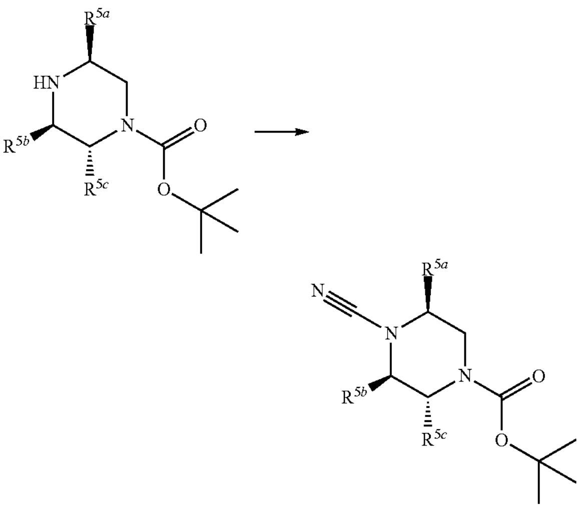

(12)

Synthesis of 4-Cyano-piperazine-1-carboxylic acid tert-butyl ester (12a, $R^{5a}$, $R^{5b}$, $R^{5c}$=H)

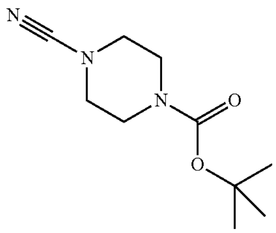

Tert-butyl piperazine-1-carboxylate (1 g, 5.37 mmol) was dissolved in $CH_2Cl_2$ (20 ml) and the solution was cooled to 0° C. Then DIPEA (0.938 ml, 5.37 mmol) was added, followed by cyanic bromide (0.626 g, 5.91 mmol). The reaction mixture was stirred for 2 h at 0° C. For workup water was added and the mixture was extracted with $CH_2Cl_2$. The combined organic layers were washed with water and brine, dried over $Na_2SO_4$, filtered and concentrated to give the desired product which was used without further purification. LC MS (ESI): 212 $[M+H]^+$, $^1H$-NMR (600 MHz, DMSO-$d^6$) δ (ppm): 3.38 (m, 4H), 3.18 (m, 4H), 1.4 (s, 9H).

The following compounds were prepared with similar method ($^1H$ NMR data in supplementary table 1):

| | $R^{5a}$ | $R^{5b}$ | $R^{5c}$ | Structure/Chemical Name | MS (ESI) m/z |
|---|---|---|---|---|---|
| 12b | (S)-methyl | H | H | (S)-4-Cyano-3-methyl-piperazine-1-carboxylic acid tert-butyl ester | 226.2 $[M + H]^+$ |
| 12c | (S)-ethyl | H | H | (S)-4-Cyano-3-ethyl-piperazine-1-carboxylic acid tert-butyl ester | 240.4 $[M + H]^+$ |
| 12d | (S)-propyl | H | H | (S)-4-Cyano-3-propyl-piperazine-1-carboxylic acid tert-butyl ester | 254.4 $[M + H]^+$ |
| 12e | (S)-phenyl | H | H | (S)-4-Cyano-3-phenyl-piperazine-1-carboxylic acid tert-butyl ester | 288.3 $[M + H]^+$ |
| 12f | (S)-methyl | H | (R)-methyl | (2R,5S)-4-Cyano-2,5-dimethyl-piperazine-1-carboxylic acid tert-butyl ester | 240.2 $[M + H]^+$ |
| 12g | (S)-methyl | (R)-methyl | H | (3R,5S)-4-Cyano-3,5-dimethyl-piperazine-1-carboxylic acid tert-butyl ester | 240.3 $[M + H]^+$ |

Synthesis of (R)-4-Cyano-3-methoxymethyl-piperazine-1-carboxylic acid benzyl ester (15)

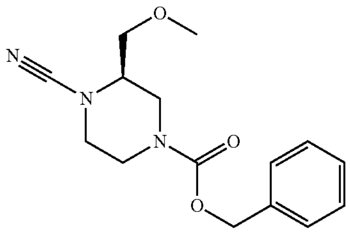 [SMILES: COC[C@H]1CN(C(=O)OCc2ccccc2)CCN1C#N]

Step A (R)-2-Methoxymethyl-piperazine-1,4-dicarboxylic acid 4-benzyl ester 1-tert-butyl ester (13)

At 0° C. triethylamine (0.91 ml, 6.51 mmol) followed by benzyl chloroformate (0.379 ml, 2.66 mmol) were added to a solution of (R)-tert-butyl 2-(methoxymethyl)piperazine-1-carboxylate (600 mg, 2.61 mmol) in $CH_2Cl_2$ (10 ml) and stirring at RT under nitrogen atmosphere was continued for 2 h. For workup a saturated solution of sodium bicarbonate was added and the mixture was extracted with $CH_2Cl_2$. The organic phases were combined, dried and concentrated to give a residue which was purified by preparative HPLC (Method P1). LC MS (ESI): 365.3 $[M+H]^+$.

Step B (R)-3-Methoxymethyl-piperazine-1-carboxylic acid benzyl ester (14)

To a solution of (R)-2-methoxymethyl-piperazine-1,4-dicarboxylic acid 4-benzyl ester 1-tert-butyl ester (13) (960 mg, 2.63 mmol) in dioxane (2 ml) was added a 4N solution of HCl in dioxane (2 ml) and the reaction mixture was stirred at RT for 1 h. Then the mixture was frozen, lyophilized and the resulting solid (hydrochloride salt) used in the following step without further purification. LC MS (ESI): 265.2 $[M+H]^+$.

Step C(R)-4-Cyano-3-methoxymethyl-piperazine-1-carboxylic acid benzyl ester (15)

(R)-3-Methoxymethyl-piperazine-1-carboxylic acid benzyl ester (14) (960 mg, 3.63 mmol) was dissolved in $CH_2Cl_2$ (5 ml) and cooled to 0° C., then DIPEA (1.269 ml, 7.26 mmol) and cyanic bromide (423 mg, 4.00 mmol) were added and the reaction mixture was stirred for 2 h at 0° C. For workup a saturated solution of sodium bicarbonate was added and the mixture was extracted with $CH_2Cl_2$. The organic phases were combined, dried and concentrated to give a residue which was purified by preparative HPLC (Method P1). LC MS (ESI): 290.2 $[M+H]^+$.

Synthesis of 4-Cyano-3-(2-methoxy-ethyl)-piperazine-1-carboxylic acid benzyl ester (19)

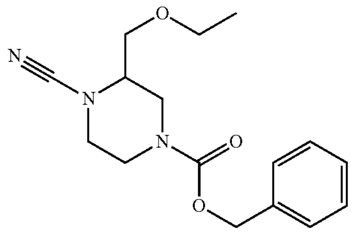 [SMILES: CCOCC1CN(C(=O)OCc2ccccc2)CCN1C#N]

Step A 2-(2-Hydroxy-ethyl)-piperazine-1,4-dicarboxylic acid 4-benzyl ester 1-tert-butyl ester (16)

At 0° C. triethylamine (0.65 ml, 4.69 mmol) and benzyl chloroformate (0.28 ml, 1.97 mmol) were added to a solution of tert-butyl 2-(2-hydroxyethyl)piperazine-1-carboxylate (500 mg, 1.87 mmol) in $CH_2Cl_2$ (18 ml) under a nitrogen atmosphere. After stirring at RT for 2 h $CH_2Cl_2$ followed by 1N HCl were added, the organic phase was separated and washed with a saturated solution of $NaHCO_3$. Drying of the organic phase followed by evaporation of the solvent afforded the desired product which was used without further purification. LC MS (ESI): 365.2 $[M+H]^+$; $^1H$-NMR (400 MHz, DMSO-$d^6$) δ (ppm): 7.37 (m, 5H), 5.11 (dd, 2H), 4.40 (s, 1H), 4.16 (s. 1H), 3.90 (m, 2H), 3.76 (m, 1H), 3.37 (m, 1H), 3.06-2.78 (m, 3H), 1.60 (m, 2H), 1.41 (s, 9H).

Step B 2-(2-Methoxy-ethyl)-piperazine-1,4-dicarboxylic acid 4-benzyl ester 1-tert-butyl ester (17)

At 0° C. sodium hydride (60% in oil, 54 mg, 1.36 mmol) was added to a solution of 2-(2-hydroxy-ethyl)-piperazine-1,4-dicarboxylic acid 4-benzyl ester 1-tert-butyl ester (16) (380 mg, 1.04 mmol) in DMF (9 ml) under a nitrogen atmosphere. After 30 min at 0° methyl iodide (0.085 ml, 1.36 mmol) was added. Stirring was continued at RT for another 16 h. The reaction mixture was then quenched carefully with EtOAc/water at 0° C., the organic phase was separated, dried and the solvent evaporated. The resulting residue was purified by flash chromatography (silica, cyclohexane/EtOAc: 9/1 to 3/1). LC MS (ESI): 379.3 $[M+H]^+$; $^1H$-NMR (400 MHz, DMSO-$d^6$) δ (ppm): 7.37 (m, 5H), 5.10 (m, 2H), 4.14 (s, 1H), 3.89 (m, 2H), 3.77 (m, 1H), 3.25 (m, 2H), 3.19 (s, 3H), 3.08-2.74 (m, 3H), 1.67 (m, 2H), 1.41 (s, 9H).

Step C 3-(2-Methoxy-ethyl)-piperazine-1-carboxylic acid benzyl ester (18)

A 4N HCl solution in dioxane (3 ml) was added to a solution of 2-(2-methoxy-ethyl)-piperazine-1,4-dicarboxylic acid 4-benzyl ester 1-tert-butyl ester (17) (210 mg, 0.55 mmol) in dioxane (0.5 ml) The reaction mixture was stirred at RT for 2 h, frozen and lyphilized to furnish the desired product as a hydrochloride salt. LC MS (ESI): 279.2 $[M+H]^+$; $^1H$-NMR (400 MHz, DMSO-$d^6$) δ (ppm): 9.29 (br s, 1H), 9.24 (br s, 1H), 7.39 (m, 5H), 5.12 (s, 2H), 4.10 (d, 1H), 4.00 (d, 1H), 3.46 (t, 2H), 3.31-2.96 (m, 8H), 1.85 (m, 2H).

Step D 4-Cyano-3-(2-methoxy-ethyl)-piperazine-1-carboxylic acid benzyl ester (19)

At 0° C. DIPEA (0.063 ml, 0.359 mmol) and a solution of cyanic bromide (21 mg, 0.198 mmol) in $CH_2Cl_2$ (0.1 ml) were added to a solution of 3-(2-methoxy-ethyl)-piperazine-1-carboxylic acid benzyl ester (18) (50 mg, 0.18 mmol) in $CH_2Cl_2$ (0.2 ml). The reaction mixture was stirred at 0° C. for 2 h and then quenched with water. The organic phase was separated and washed with a saturated solution of $NaHCO_3$, dried and the solvent was evaporated. The resulting residue was purified by flash chromatography (silica, cyclohexane/EtOAc: 9/1 to 1/1) to afford the title compound. LC MS (ESI): 322.3 [M+H2O+H]$^+$; $^1H$-NMR (400 MHz, DMSO-$d^6$) δ (ppm): 7.38 (m, 5H), 5.10 (s, 2H), 3.81 (dd, 1H), 3.69 (m, 1H), 3.43-3.36 (m, 3H), 3.30-3.14 (m, 7H), 1.78 (m, 2H).

Reaction Scheme 4:

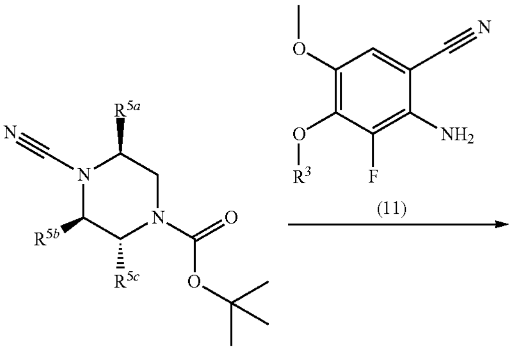

(11)

(12)

-continued

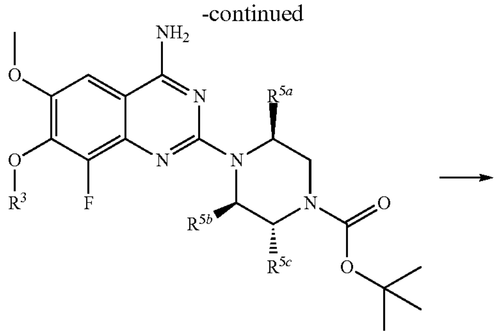

(20)

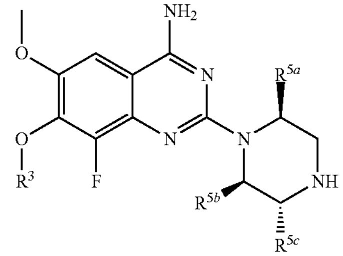

(21)

Synthesis of 8-Fluoro-6,7-dimethoxy-2-piperazin-1-yl-quinazolin-4-ylamine (21a, $R^3$=methyl, $R^{5a}$, $R^{5b}$, $R^{5c}$=H)

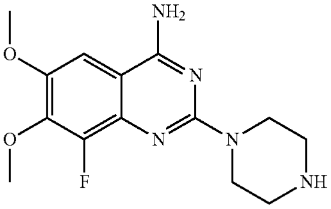 [SMILES: COc1cc2c(N)nc(N3CCNCC3)nc2c(F)c1OC]

Step A 4-(4-Amino-6,7-dimethoxy-quinazolin-2-yl)-piperazine-1-carboxylic acid tert-butyl ester (20a)

At 0° C. NaH (60% in mineral oil, 135 mg, 3.36 mmol) was added to a solution of 2-amino-3-fluoro-4,5-dimethoxy-benzonitrile (11a) (600 mg, 3.06 mmol) in THF (4.5 ml) and the mixture was stirred for 30 min. Then 4-cyano-piperazine-1-carboxylic acid tert-butyl ester (12a) (646 mg, 3.06 mmol) was added and the reaction mixture was stirred at 55° C. for 72 h. The reaction mixture was quenched with water and diluted with EtOAc, washed with saturated aqueous $NaHCO_3$ and NaCl-solutions, dried over $Na_2SO_4$ and the solvent was evaporated under reduced pressure. The crude product was purified by trituration with diethylether. LC MS (ESI): 408.3 $[M+H]^+$; $^1H$-NMR (400 MHz, DMSO-$d^6$) δ (ppm): 7.4 (br, 2H), 7.39 (s, 1H), 3.9 (s, 3H), 3.85 (s, 3H), 3.71 (m, 4H), 3.37 (m, 4H), 1.44 (s, 9H).

Step B 8-Fluoro-6,7-dimethoxy-2-piperazin-1-yl-quinazolin-4-ylamine (21a)

4-(4-Amino-6,7-dimethoxy-quinazolin-2-yl)-piperazine-1-carboxylic acid tert-butyl ester (20a) (990 mg, 2.430 mmol) was dissolved in dioxane (1.0 ml). Then 4M HCl in dioxane (6.07 ml, 24.30 mmol) was added and the mixture was stirred for 2 h at RT. The reaction mixture was concentrated under reduced pressure. The residue was triturated with diethylether and a solid was collected by filtration corresponding to the title compound (as its bis-hydrochloride salt) which was used in the next step without further purification. LC MS (ESI): 308.2 $[M+H]^+$; $^1H$-NMR (400 MHz, DMSO-$d^6$) δ (ppm): 9.5 (br, 2H), 8.3 (br, 1H), 7.61 (s, 1H), 4.02 (m, 2H), 4.00 (m, 2H), 3.97 (s, 3H), 3.89 (s, 3H), 3.20 (m, 4H).

The following compounds were prepared with similar method ($^1H$ NMR data in supplementary table 2)

| | $R^3$ | $R^{5a}$ | $R^{5b}$ | $R^{5c}$ | Chemical Name | MS (ESI) m/z |
|---|---|---|---|---|---|---|
| 21b | methyl | (S)-methyl | H | H | 8-Fluoro-6,7-dimethoxy-2-((S)-2-methyl-piperazin-1-yl)-quinazolin-4-yl amine hydrochloride | 322.4 $[M + H]^+$ |
| 21c | methyl | (S)-ethyl | H | H | 2-((S)-2-Ethyl-piperazin-1-yl)-8-fluoro-6,7-dimethoxy-quinazolin-4-ylamine hydrochloride | 336.2 $[M + H]^+$ |
| 21d | methyl | (S)-propyl | H | H | 8-Fluoro-6,7-dimethoxy-2-((S)-2-propyl-piperazin-1-yl)-quinazolin-4-ylamine hydrochloride | 350.3 $[M + H]^+$ |
| 21e | methyl | (S)-phenyl | H | H | 8-Fluoro-6,7-dimethoxy-2-((S)-2-phenyl-piperazin-1-yl)-quinazolin-4-ylamine hydrochloride | 384.2 $[M + H]^+$ |
| 21f | 2-methoxy ethyl | H | H | H | 8-Fluoro-6-methoxy-7-(2-methoxy-ethoxy)-2-piperazin-1-yl-quinazolin-4-ylamine hydrochloride | 352.3 $[M + H]^+$ |
| 21g | 2-methoxy ethyl | (S)-methyl | H | H | 8-Fluoro-6-methoxy-7-(2-methoxy-ethoxy)-2-((S)-2-methyl-piperazin-1-yl)-quinazolin-4-ylamine hydrochloride | 366.2 $[M + H]^+$ |
| 21h | methyl | (S)-methyl | H | (R)-methyl | 8-Fluoro-6,7-dimethoxy-2-((2S,5R)-2,5-dimethyl-piperazin-1-yl)-quinazolin-4-ylamine | 336.2 $[M + H]^+$ |
| 21i | methyl | (S)-methyl | (R)-methyl | H | 8-Fluoro-6,7-dimethoxy-2-((2S,6R)-2,6-dimethyl-piperazin-1-yl)-quinazolin-4-ylamine hydrochloride | 336.2 $[M + H]^+$ |

Synthesis of 8-Fluoro-6,7-dimethoxy-2-((R)-2-methoxymethyl-piperazin-1-yl)-quinazolin-4-ylamine (21j, $R^3$=methyl, $R^{5a}$=(R)-methoxymethyl, $R^{5b}$, $R^{5c}$=H)

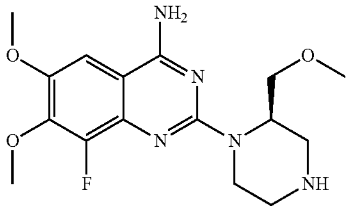 [SMILES: COC[C@H]1CNCCN1c1nc(N)c2cc(OC)c(OC)c(F)c2n1]

This compound was synthesized analogously to 21a from 2-amino-3-fluoro-4,5-dimethoxy-benzonitrile (11a) and (R)-4-cyano-3-methoxymethyl-piperazine-1-carboxylic acid benzyl ester (15) followed by cleavage of the Z-protecting group by hydrogenation which was done in the following way. (R)-4-(4-Amino-8-fluoro-6,7-dimethoxy-quinazolin-2-yl)-3-methoxymethyl-piperazine-1-carboxylic acid benzyl ester (326 mg, 0.671 mmol) was suspended in ethanol (10 ml) and Pd/C (71.5 mg, 0.067 mmol) was added. After stirring under a $H_2$ atmosphere for 2 h at RT chloroform was added, the metal was collected by filtration and the solvent was evaporated. The resulting product (as its free base) was dried under high vacuum and used in the next step without further purification. LC MS (ESI): 352.2 $[M+H]^+$.

Synthesis of 8-fluoro-6,7-dimethoxy-2-[2-(2-methoxy-ethyl)-piperazin-1-yl]-quinazolin-4-ylamine (21k, $R^3$=methyl, $R^{5a}$=methoxyethyl, $R^{5b}$, $R^{5c}$=H)

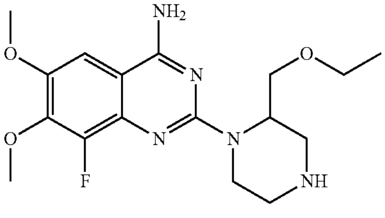 [SMILES: CCOCC1CNCCN1c1nc(N)c2cc(OC)c(OC)c(F)c2n1]

This compound (as its hydrochloride salt) was synthesized analogously to 21a from 2-amino-3-fluoro-4,5-dimethoxy-benzonitrile (11a) and 4-cyano-3-(2-methoxy-ethyl)-piperazine-1-carboxylic acid benzyl ester (19) followed by cleavage of the Z-protecting group by hydrogenation analogously to example 21j using a 4:1 mixture of 1.25 M HCl in methanol/methanol as solvent. LC MS (ESI): 366.2 $[M+H]^+$.

Reaction Scheme 5: Synthesis of 4-Amino-6,7-dimethoxy-2-piperazin-1-yl-quinazoline-8-carbonitrile (32)

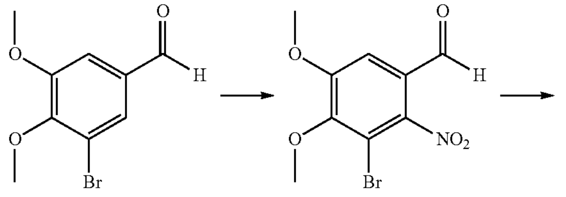
(22)

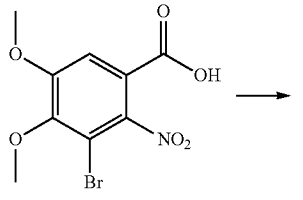
(23)

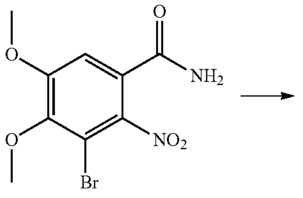
(24)

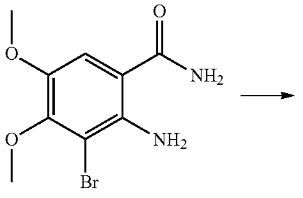
(25)

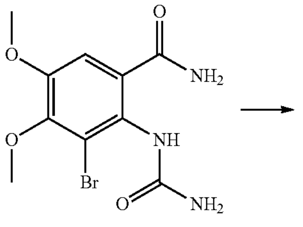
(26)

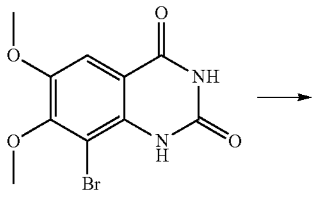
(27)

-continued

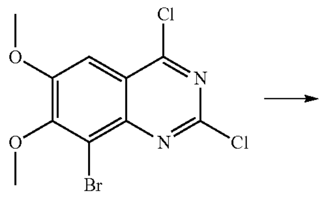
(28)

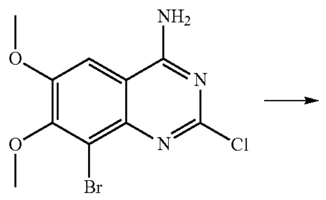
(29)

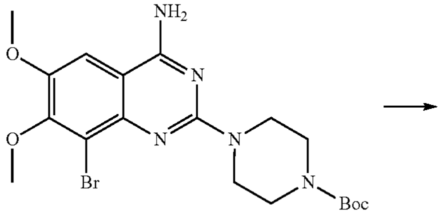
(30)

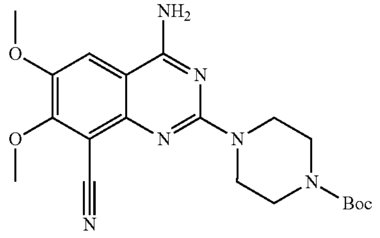
(31)

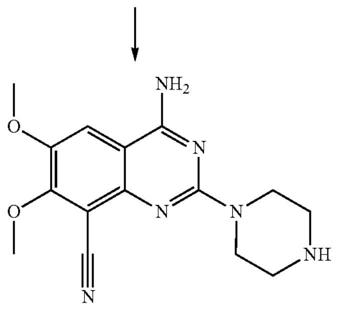
(32)

Step A
3-Bromo-4,5-dimethoxy-2-nitro-benzaldehyde (22)

5-Bromoveratraldehyde (10 g, 40.8 mmol) was suspended in nitric acid (77 ml, 1714 mmol) and the reaction mixture was stirred at 60° C. until the solid was dissolved, then at RT for another 16 h. Water (200 ml) was added to the reaction mixture and the formed precipitate was collected and crystallized from AcOH. LC MS (ESI): 290.1 $[M+H]^+$; $^1$H-NMR (400 MHz, methanol-$d^4$) δ (ppm): 9.82 (s, 1H), 7.70 (s, 1H), 4.08 (s, 3H), 4.02 (s, 3H).

Step B 3-Bromo-4,5-dimethoxy-2-nitro-benzoic acid (23)

Sodium perborate tetrahydrate (4.46 g, 29.0 mmol) was added portionwise during 10 min to a stirred solution of 3-bromo-4,5-dimethoxy-2-nitro-benzaldehyde (22) (5.6 g, 19.31 mmol) in AcOH (100 ml). The reaction mixture was stirred at 50° C. for 16 h. Then the solvent was evaporated and the residue was taken up in $CH_2Cl_2$ and water and extracted with $CH_2Cl_2$. The organic phases were combined, dried and concentrated to yield the title compound. LC MS (ESI): 304.2 $[M-H]^-$; $^1$H-NMR (400 MHz, methanol-d$^4$) δ (ppm): 7.67 (s, 1H), 4.02 (s, 3H), 3.97 (s, 3H).

Step C 3-Bromo-4,5-dimethoxy-2-nitro-benzamide (24)

A solution of 3-bromo-4,5-dimethoxy-2-nitro-benzoic acid (23) (6 g, 19.60 mmol) and CDI (3.81 g, 23.52 mmol) in THF (100 ml) was stirred at RT for 2 h. Then the solution was cooled to 0° C. and a 0.5M solution of ammonia in THF (78 ml, 39.2 mmol) was added slowly to the reaction mixture. Stirring was continued for 16 h at RT. The solvent was concentrated and the residue was taken up in $CH_2Cl_2$. The organic phase was washed with a saturated solution of $NaHCO_3$, dried and concentrated to afford the desired product. LC MS (ESI): 349.2 $[M+HCOO]^-$ Step D 2-Amino-3-bromo-4,5-dimethoxy-benzamide (25)

At 90° C. iron powder (2.08 g, 37.2 mmol) was added portionwise to a solution of 3-bromo-4,5-dimethoxy-2-nitro-benzamide (24) (4.2 g, 13.77 mmol) in AcOH 100 ml). The reaction mixture was heated up to 105° C. and stirred at that temperature for 15 min. The hot solution was then filtered and allowed to cool to RT. Water was added and the mixture was extracted with $CH_2Cl_2$. Drying of the organic phase followed by evaporation of the solvent yielded the desired product. LC MS (ESI): 275.2 $[M+H]^+$ Step E 3-Bromo-4,5-dimethoxy-2-ureido-benzamide (26)

A solution of sodium cyanate (1.42 g, 21.8 mmol) in water (16 ml) was added to a solution of 2-amino-3-bromo-4,5-dimethoxy-benzamide (25) (3 g, 10.91 mmol) in AcOH (50 ml). The reaction mixture was stirred at RT for 1 h. Water was added and the formed precipitate was collected by filtration, rinsed with water and dried under high vacuum. LC MS (ESI): 318.2 $[M+H]^+$ Step F 8-Bromo-6,7-dimethoxy-1H-quinazoline-2,4-dione (27)

3-Bromo-4,5-dimethoxy-2-ureido-benzamide (26) (3.0 g, 9.43 mmol) was dissolved in 2N NaOH (100 ml) and the mixture was stirred at RT for 2 h. The solution was then acidified to pH 1 using concentrated HCl. The formed precipitate was collected by filtration, rinsed with water, frozen and lyophilized. LC MS (ESI): 301.2 $[M+H]^+$ Step G 8-Bromo-2,4-dichloro-6,7-dimethoxy-quinazoline (28)

N—N-dimethylaniline (0.97 ml, 7.64 mmol) was added to a solution of 8-bromo-6,7-dimethoxy-1H-quinazoline-2,4-dione (27) (2.3 g, 7.64 mmol) in $POCl_3$ (30 ml) and the reaction mixture was stirred at 120° C. for 2 h. The solvent was evaporated and water was added to the residue. The formed precipitate was collected by filtration and dried under high vacuum. LC MS (ESI): 337.1 $[M+H]^+$ Step H 8-Bromo-2-chloro-6,7-dimethoxy-quinazolin-4-ylamine (29)

A 25% solution of $NH_4OH$ in water (18.4 ml, 118 mmol) was added to a solution of 8-bromo-2,4-dichloro-6,7-dimethoxy-quinazoline (28) (2 g, 5.92 mmol) in THF (20 ml) and the reaction mixture was stirred at 40° C. for 16 h. The solvent was evaporated and water was added to the residue. The formed precipitate was collected by filtration, frozen and lyophilized. LC MS (ESI): 318.2 $[M+H]^+$; $^1$H-NMR (400 MHz, methanol-d$^4$) δ (ppm): 7.63 (s, 1H), 4.02 (s, 3H), 3.98 (s, 3H).

Step I 4-(4-Amino-8-bromo-6,7-dimethoxy-quinazolin-2-yl)-piperazine-1-carboxylic acid tert-butyl ester (30)

8-Bromo-2-chloro-6,7-dimethoxy-quinazolin-4-ylamine (29) (2 g, 6.28 mmol), triethylamine (1.313 ml, 9.42 mmol) and tert-butyl piperazine-1-carboxylate (2.339 g, 12.56 mmol) were dissolved in isopentyl alcohol (20 ml) and the mixture was stirred at 120° C. for 2 days. The solvent was then evaporated and diethyl ether was added to the residue. The formed precipitate was collected by filtration and dried under vacuum to give the title compound. LC MS (ESI): 512.5 $[M+HCOO]^-$, $^1$H-NMR (400 MHz, DMSO-d$^6$) δ (ppm): 7.61 (s, 1H), 7.46 (br s, 2H), 3.87 (s, 3H), 3.82 (s, 3H), 3.76 (m, 4H), 3.40 (m, 4H), 1.44 (s, 9H).

Step J 4-(4-Amino-8-cyano-6,7-dimethoxy-quinazolin-2-yl)-piperazine-1-carboxylic acid tert-butyl ester (31)

4-(4-Amino-8-bromo-6,7-dimethoxy-quinazolin-2-yl)-piperazine-1-carboxylic acid tert-butyl ester (30) (1 g, 2.135 mmol) and copper cyanide (0.210 g, 2.349 mmol) were added to N.methyl-2-pyrrolidone (5 ml) and the mixture was stirred at 200° C. for 1 h. Water was added and the solution was extracted with $CH_2Cl_2$. The organic phase was washed with water, dried and concentrated to afford the title compound which was used in the following step without further purification. LC MS (ESI): 415.5 $[M+H]^+$ Step K 4-Amino-6,7-dimethoxy-2-piperazin-1-yl-quinazoline-8-carbonitrile (32)

A solution of 4-(4-amino-8-cyano-6,7-dimethoxy-quinazolin-2-yl)-piperazine-1-carboxylic acid tert-butyl ester (31) (5.3 g, 3.84 mmol) in 4N HCl in dioxane (20 ml) was stirred at RT for 1 h. The solution was then frozen and lyophilized. The solid residue was dissolved in methanol and diethylether was added leading to precipitation of the desired product which was collected by filtration, dried under high vacuum and used in the following step without further purification. LC MS (ESI): 315.3 $[M+H]^+$.

Reaction Scheme 6: Synthesis of 8-bromo-6,7-dimethoxy-2-(piperazin-1-yl)quinazolin-4-amine (33)

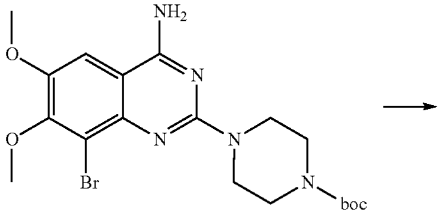

(30)

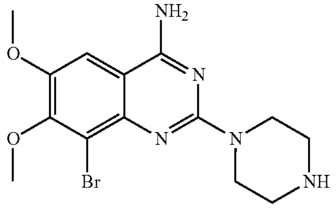

(33)

A solution of 4-(4-amino-8-bromo-6,7-dimethoxy-quinazolin-2-yl)-piperazine-1-carboxylic acid tert-butyl ester (30) (150 mg, 0.32 mmol) in 4N HCl in dioxane (4 ml) was stirred at RT for 1 h. The solution was then frozen and lyophilized to afford the title compound LC MS (ESI): 368.2 $[M+H]^+$.

Synthesis of 2,8-dichloro-6,7-dimethoxyquinazolin-4-amine (34)

(34)

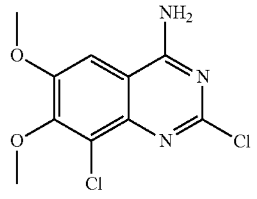

2,8-Dichloro-6,7-dimethoxyquinazolin-4-amine (34) was synthesized as described in *Aust. J. Chem.* 1981, 34, 1561. LC MS (ESI): 274.2 $[M-H]^-$.

Reaction Scheme 7: Synthesis of 8-chloro-6,7-dimethoxy-2-(piperazin-1-yl)quinazolin-4-amine (39)

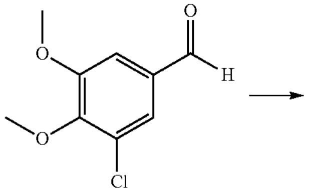

-continued

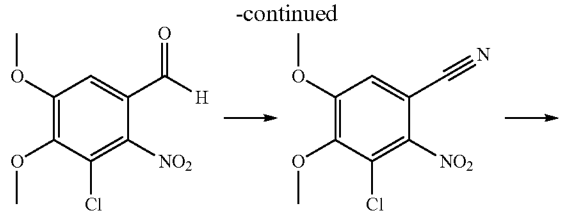

(35) (36)

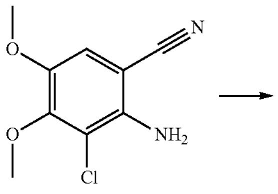

(37)

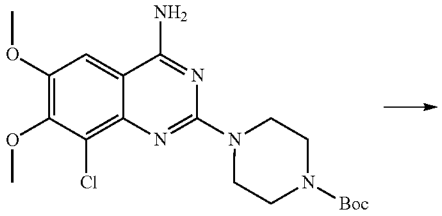

(38)

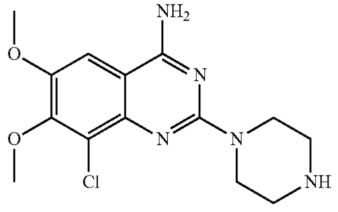

(39)

Step A
3-Chloro-4,5-dimethoxy-2-nitrobenzaldehyde (35)

At RT nitric acid (33.2 ml) was slowly added to 3-chloro-4,5-dimethoxybenzaldehyde (3.1 g, 15.45 mmol). The reaction mixture was heated to 55° C. for 1 h and kept stirring at this temperature for 2.5 h. The mixture was poured on ice and the precipitate was collected by filtration and dried under HV to afford the title compound which was used without further purification. LC MS (ESI): 245.9 $[M+H]^+$.

Step B 3-Chloro-4,5-dimethoxy-2-nitrobenzonitrile (36)

3-Chloro-4,5-dimethoxy-2-nitrobenzaldehyde (35) (3.99 g, 14.62 mmol) was added to a solution of $NH_2OH.HCl$ (1.32 g, 19.0 mmol) and sodium formate (1.58 g, 35.1 mmol) in formic acid (35 ml). The reaction mixture was heated at 100° C. for 16 h before it was poured on ice whereupon a solid precipitated. Filtration and drying under HV afforded the desired product. $^1H$-NMR (400 MHz, DMSO-$d^6$) δ (ppm): 7.10 (s, 1H), 3.94 (s, 3H), 3.93 (s, 3H).

Step C
2-Amino-3-chloro-4,5-dimethoxybenzonitrile (37)

3-Chloro-4,5-dimethoxy-2-nitrobenzonitrile (36) (3.55 g, 14.63 mmol) was dissolved in acetic acid (64 ml) and heated to 90° C. Then iron powder (2.21 g, 39.5 mmol) was added portionwise and the reaction mixture was heated to 105° C. After 50 min the reaction mixture was allowed to cool to RT and filtered. The filtrate was concentrated and the resulting solid was suspended in ethyl acetate and filtered. The crude product was purified by flash column chromatography (120 g silica, 100% cyclohexane for 4 min, 0 to 50% ethyl acetate/cyclohexane in 30 min, flow: 85 ml/min) to afford the desired product. LC MS (ESI): 213.0 $[M+H]^+$.

Step D tert-Butyl 4-(4-amino-8-chloro-6,7-dimethoxyquinazolin-2-yl)piperazine-1-carboxylate (38)

At 0° C. NaH (60% in mineral oil, 155 mg, 3.88 mmol) was added to a solution of 2-amino-3-chloro-4,5-dimethoxybenzonitrile (37) (750 mg, 3.53 mmol) in THF (5 ml) and the mixture was stirred for 30 min. Then 4-cyano-piperazine-1-carboxylic acid tert-butyl ester (12a) (745 mg, 3.53 mmol) was added and the reaction mixture was stirred at 55° C. for 3 h. The reaction mixture was quenched with water and diluted with EtOAc, washed with saturated aqueous $NaHCO_3$ and NaCl solutions, dried over $Na_2SO_4$ and the solvent was evaporated under reduced pressure. The crude product was purified by trituration with diethylether. LC MS (ESI): 424.2 $[M+H]^+$.

Step E 8-Chloro-6,7-dimethoxy-2-(piperazin-1-yl)quinazolin-4-amine (39)

The Boc-deprotection was performed as described for 21a. LC MS (ESI): 324.2 $[M+H]^+$.

Reaction Scheme 8: Synthesis of 2,5-dichloro-6,7-dimethoxyquinazolin-4-amine (46)

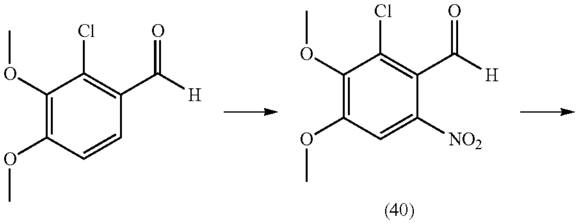

(40)

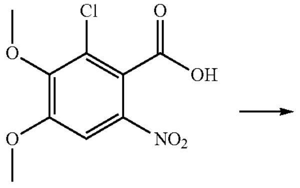

(41)

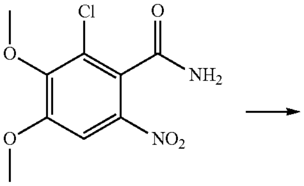

(42)

-continued

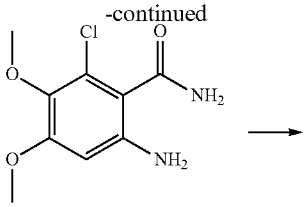

(43)

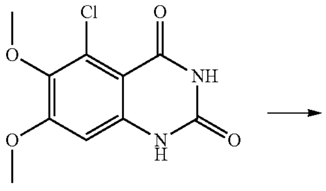

(44)

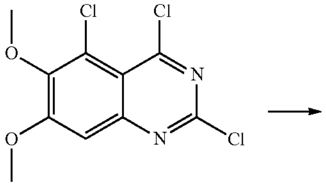

(45)

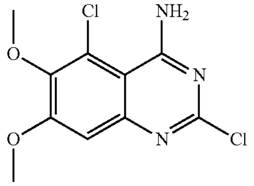

(46)

Step A 2-Chloro-3,4-dimethoxy-6-nitrobenzaldehyde (40)

At 0° C. nitric acid (4.5 ml) was slowly added to 2-chloro-3,4-dimethoxybenzaldehyde (500 mg, 2.49 mmol). The reaction mixture was heated to 65° C. to solubilize the starting material and then allowed to stir at RT for 2 h. The mixture was poured on ice and the precipitate was collected by filtration, rinsed with water and dried under HV to afford the title compound which was used without further purification. LC MS (ESI): 244.1 $[M-H]^-$.

Step B 2-Chloro-3,4-dimethoxy-6-nitrobenzoic acid (41)

At 60° C. a solution of 2-chloro-3,4-dimethoxy-6-nitrobenzaldehyde (40) (520 mg, 2.12 mmol) in acetone (8.5 ml) was added dropwise to a 10% aqueous solution of $KMnO_4$ (5.8 ml). The reaction mixture was stirred at 70° C. for 1 h. The precipitated solid was filtered off and washed with hot water and acetone. The acetone was evaporated and the remaining filtrate was basified to pH 11-12 using 2N NaOH and extracted with chloroform. The aqueous phase was acidified to pH 1 with concentrated HCl leading to precipitation of a solid which was filtered off, rinsed with water and dried under high vacuum to give the desired product. LC MS (ESI): 260.1 $[M-H]^-$.

Step C 2-Chloro-3,4-dimethoxy-6-nitrobenzamide (42)

2-Chloro-3,4-dimethoxy-6-nitrobenzoic acid (41) (293 mg, 1.12 mmol) was treated with thionyl chloride (3 ml) at 90° C. for 2 h. The solvent was evaporated, the residue was dissolved in THF and the solvent was evaporated once again. The resulting acid chloride was dissolved in THF (12 ml) and added dropwise to a 0.5M solution of $NH_3$ in THF (11.2 ml, 5.6 mmol) at 0° C. The reaction mixture was stirred at RT for 1 h before the solvent was evaporated. The resulting solid was dissolved in water, the precipitate was filtered off, rinsed with water and dried under HV to afford the title compound. LC MS (ESI): 261.2 $[M+H]^+$.

Step D 6-Amino-2-chloro-3,4-dimethoxybenzamide (43)

Iron powder (137 mg, 2.45 mmol) was added portionwise to a solution of 2-chloro-3,4-dimethoxy-6-nitrobenzamide (42) (236 mmol, 0.91 mmol) in acetic acid (7 ml) at 90° C. The temperature was increased to 105° C. and the reaction mixture was stirred at this temperature for 15 min. The hot suspension was filtered through Celite and the solid residue was rinsed with hot acetic acid. The filtrate was concentrated to afford the title compound which was used without further purification. LC MS (ESI): 231.1 $[M+H]^+$.

Step E 5-Chloro-6,7-dimethoxyquinazoline-2,4(1H,3H)-dione (44)

At RT a solution of sodium cyanate (338 mg, 5.2 mmol) in water (2 ml) was added to a solution of 6-amino-2-chloro-3,4-dimethoxybenzamide (43) (600 mg, 2.6 mmol) in acetic acid (6 ml) and the reaction mixture was stirred for 1 h. Water was added, the precipitate was filtered off, rinsed with water and the filtrate was concentrated. The resulting residue was treated with 2N NaOH (7 ml) at 100° C. for 1 h. After cooling to RT the reaction solution was acidified to pH 1 using concentrated HCl and the precipitate was filtered off, rinsed with water and dried under HV. LC MS (ESI): 257.1 $[M+H]^+$.

Step F 2,4,5-Trichloro-6,7-dimethoxyquinazoline (45)

N,N-Dimethylaniline (0.064 ml, 0.50 mmol) was added to a solution of 5-chloro-6,7-dimethoxyquinazoline-2,4(1H,3H)-dione (44) (129 mg, 0.50 mmol) in $POCl_3$ (1.8 ml) and the reaction mixture was stirred at 120° C. for 2 h. The solvent was evaporated and the residue was treated with water. The resulting precipitate was rinsed with water and dried under HV to give the title compound which was used without further purification. LC MS (ESI): 293.0 $[M+H]^+$.

Step G 2,5-Dichloro-6,7-dimethoxyquinazolin-4-amine (46)

A 25% aqueous solution of $NH_4OH$ (1.05 ml, 6.75 mmol) was added to a solution of 2,4,5-trichloro-6,7-dimethoxyquinazoline (45) (99 mg, 0.34 mmol) in THF (2.5 ml) and the reaction mixture was stirred at 40° C. for 16 h. The solvent was evaporated and the resulting solid was suspended in water, filtered and dried under HV to afford the title compound which was used without further purification. LC MS (ESI): 274.2 $[M+H]^+$.

Reaction Scheme 9: Synthesis of the 2-Chloro-5-fluoro-6,7-dimethoxyquinazolin-4-ylamine (55)

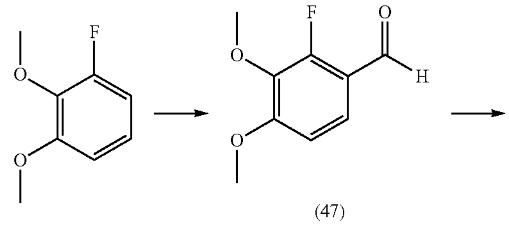

(47)

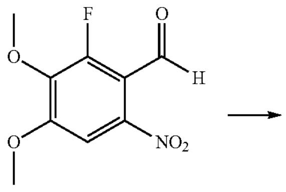

(48)

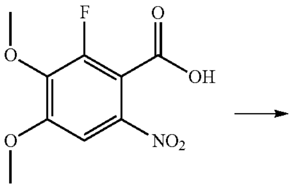

(49)

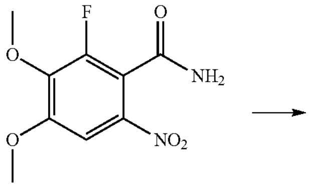

(50)

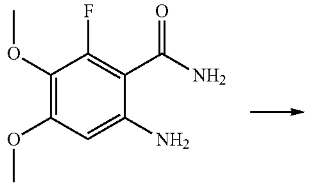

(51)

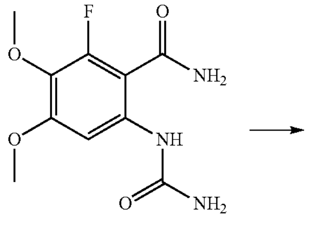

(52)

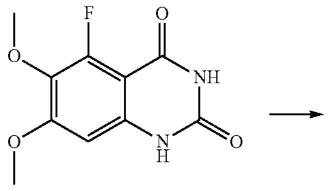

(53)

-continued

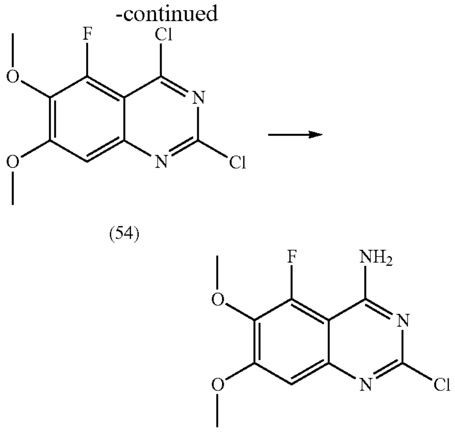

(54)

(55)

Step A 2-Fluoro-3,4-dimethoxy-benzaldehyde (47)

At 0° C. a solution of titanium tetrachloride (5.83 ml, 52.8 mmol) in anhydrous $CH_2Cl_2$ (15 ml) was added dropwise over 30 min to a solution of 1-fluoro-2,3-dimethoxybenzene (5 g, 32.0 mmol) in anhydrous $CH_2Cl_2$ (45 ml) under a nitrogen atmosphere. To the resulting solution was added dropwise over 15 min a solution of dichloromethyl methyl ether (3.19 ml, 35.2 mmol) in anhydrous $CH_2Cl_2$ (10 ml) whereupon the reaction mixture turned red. Stirring at 0° C. was continued for 30 min before the reaction solution was allowed to warm to rt. After stirring for another 5 h the reaction mixture was poured onto 200 g of crushed ice. The organic layer was separated, and the aqueous phase was extracted with $CH_2Cl_2$. The organic phases were combined, dried and concentrated. The residue was purified by preparative HPLC (Method P1). LC MS (ESI): 185.1 $[M+H]^+$; $^1$H-NMR (400 MHz, methanol-$d^4$) δ (ppm): 7.21 (t, 1H), 6.85 (dd, 1H), 3.89 (s, 3H), 3.86 (s, 3H).

Step B 2-Fluoro-3,4-dimethoxy-6-nitro-benzaldehyde (48)

2-Fluoro-3,4-dimethoxy-benzaldehyde (47) (4.85 g, 26.3 mmol) was dissolved in nitric acid (49.4 ml, 1106 mmol) and the mixture was stirred at 60° C. until the solid was dissolved, then at RT for another 16 h. Water (200 ml) was added to the reaction mixture and the formed precipitate was collected by filtration and crystallized from AcOH. LC MS (ESI): 228.2 $[M-H]^-$; $^1$H-NMR (600 MHz, DMSO-$d^6$) δ (ppm): 10.06 (s, 1H), 7.68 (s, 1H), 4.00 (s, 3H), 3.94 (s, 3H).

Step C 2-Fluoro-3,4-dimethoxy-6-nitro-benzoic acid (49)

Sodium perborate tetrahydrate (5.04 g, 32.7 mmol) was added portionwise over 10 min to a stirred solution of 2-fluoro-3,4-dimethoxy-6-nitro-benzaldehyde (48) (5 g, 21.82 mmol) in AcOH (75 ml) The reaction mixture was stirred at 50° C. for another 16 h. The solvent was evaporated and the residue was taken up in $CH_2Cl_2$ and water. The aqueous phase was separated, frozen and lyophilized to afford the title compound. LC MS (ESI): 489.4 $[2M-H]^-$; $^1$H-NMR (400 MHz, methanol-$d^4$) δ (ppm): 7.60 (s, 1H), 4.00 (s, 3H), 3.97 (s, 3H).

Step D 2-Fluoro-3,4-dimethoxy-6-nitro-benzamide (50)

A solution of 2-fluoro-3,4-dimethoxy-6-nitro-benzoic acid (49) (4.81 g, 19.62 mmol) in thionyl chloride (60 ml) was stirred at 90° C. for 2 h. Then the solution was concentrated and the resulting residue was taken up in THF. The solvent was evaporated before THF (30 ml) was added again. The reaction solution was cooled to 0° C. and a 0.5M solution of ammonia in THF (78 ml, 39.2 mmol) was added slowly. Stirring at RT was continued for 2 h before the solvent was evaporated. The residue was taken up in $CH_2Cl_2$, the organic phase was washed with a saturated solution of $NaHCO_3$, dried and concentrated to afford the desired product. LC MS (ESI): 289.4 $[M+HCOO]^-$ Step E 6-Amino-2-fluoro-3,4-dimethoxy-benzamide (51)

At 90° C. iron powder (1.30 g, 23.2 mmol) was added portionwise to a solution of 2-fluoro-3,4-dimethoxy-6-nitro-benzamide (50) (2.1 g, 8.60 mmol) in AcOH. The reaction mixture was stirred at 105° C. for 15 min before the hot solution was filtered. The filtrate was cooled to RT and quenched with water. The mixture was extracted with $CH_2Cl_2$, the organic phase was dried and concentrated to yield the title compound. LC MS (ESI): 215.2 $[M+H]^+$.

Step F 2-Fluoro-3,4-dimethoxy-6-ureido-benzamide (52)

A solution of sodium cyanate (0.850 g, 13.07 mmol) in water (10 ml) was added to a solution of 6-amino-2-fluoro-3,4-dimethoxy-benzamide (51) (1.4 g, 6.54 mmol) in AcOH (25 ml). The reaction mixture was stirred at RT for 1 h. For workup water was added and the mixture was extracted with $CH_2Cl_2$, the combined organic phases were washed with a saturated solution of $NaHCO_3$, dried, and concentrated to yield the title compound. LC MS (ESI): 258.3 $[M+H]^+$ Step G 5-Fluoro-6,7-dimethoxy-1H-quinazoline-2,4-dione (53)

A solution of 2-fluoro-3,4-dimethoxy-6-ureido-benzamide (52) (0.5 g, 1.944 mmol) in 2N aq. NaOH (50 ml) was stirred at RT for 2 h. Acidification to pH 1 using concentrated HCl led to formation of a precipitate which was collected by filtration, rinsed with water and dried under high vacuum. LC MS (ESI): 241.2 $[M+H]^+$; $^1$H-NMR (400 MHz, methanol-$d^4$) δ (ppm): 6.56 (s, 1H), 3.97 (s, 3H), 3.85 (s, 3H).

Step H 2,4-Dichloro-5-fluoro-6,7-dimethoxy-quinazoline (54)

N—N-dimethylaniline (0.158 ml, 1.249 mmol) was added to a solution of 5-fluoro-6,7-dimethoxy-1H-quinazoline-2,4-dione (53) (300 mg, 1.249 mmol) in $POCl_3$ (10 ml) and the reaction mixture was stirred at 120° C. for 2 h. The solvent was evaporated and water was added to the residue which led to the precipitation of a solid which was collected by filtration and dried under high vacuum. LC MS (ESI): 277.2 $[M+H]^+$ Step 12-Chloro-5-fluoro-6,7-dimethoxy-quinazolin-4-ylamine (55)

A 25% $NH_4OH$ solution in water (2.474 ml, 15.88 mmol) was added to a solution of 2,4-dichloro-5-fluoro-6,7-dimethoxy-quinazoline (54) (220 mg, 0.794 mmol) in THF (10 ml) and the reaction mixture was stirred at 40° C. for 3 h. The solvent was evaporated and water was added to the residue. The formed precipitate was collected by filtration, frozen and lyophilized. LC MS (ESI): 258.2 $[M+H]^+$ Reaction Scheme 10: Synthesis of the piperazinyl building blocks

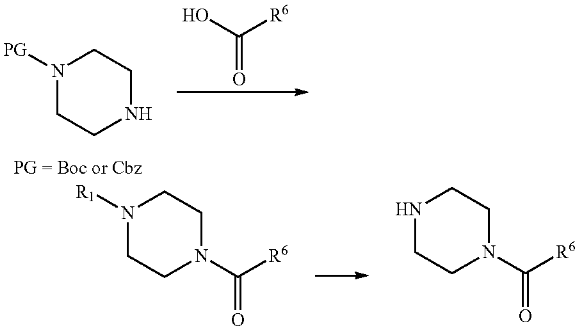

(56) (57)

Synthesis of (E)-3-Cyclopropyl-1-piperazin-1-yl-propenone (57a, $R^6$=—CH═CH-cyclopropyl)

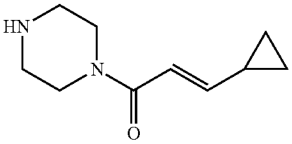 [SMILES: O=C(/C=C/C1CC1)N1CCNCC1]

Step A 4-((E)-3-Cyclopropyl-acryloyl)-piperazine-1-carboxylic acid tert-butyl ester (56a)

At 0° C. triethylamine (5.95 ml, 43.0 mmol) and HBTU (6.11 g, 16.1 mmol) were added to a solution of tert-butyl piperazine-1-carboxylate (2.0 g, 10.7 mmol) and (E)-3-cyclopropylacrylic acid (1.44 g, 12.9 mmol) in $CH_3CN$ (100 ml). The mixture was stirred at RT for 16 h. The solvent was evaporated, and the residue was taken up in $CH_2Cl_2$/1N HCl. The organic phase was separated, washed with a saturated solution of $NaHCO_3$, dried and the solvent was evaporated. The residue was purified by flash chromatography (silica, cyclohexane/EtOAc: 4/1 to 1/2), to give the title compound as a white solid. LC MS (ESI): 281.3 $[M+H]^+$; $^1H$-NMR (400 MHz, DMSO-$d^6$) δ (ppm): 6.56 (d, 1H), 6.21 (dd, 1H), 3.51 (m, 4H), 3.33 (m, 4H), 1.63 (m, 1H), 1.42 (s, 9H), 0.87 (m, 2H), 0.59 (m, 2H).

Step B (E)-3-Cyclopropyl-1-piperazin-1-yl-propenone (57a)

A solution of 4-((E)-3-cyclopropyl-acryloyl)-piperazine-1-carboxylic acid tert-butyl ester (56a) (550 mg, 1.96 mmol) in 4N HCl in dioxane (10 ml) was stirred at RT for 3 h, frozen and lyophilized to give the title compound (as its mono-hydrochloride salt) as a white solid. LC MS (ESI): 181.2 $[M+H]^+$; $^1H$-NMR (400 MHz, DMSO-$d^6$) δ (ppm): 9.43 (br s, 2H), 6.58 (d, 1H), 6.25 (dd, 1H), 3.77 (m, 4H), 3.07 (m, 4H), 1.63 (m, 1H), 0.89 (m, 2H), 0.61 (m, 2H).

Synthesis of [(R)-1-(4-Fluoro-phenyl)-3-oxo-3-piperazin-1-yl-propyl]-carbamic acid tert-butyl ester (57b, $R^6$=(R)—$CH_2$—CHNHBoc-4-F-Ph)

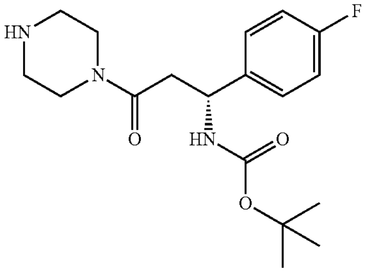 [SMILES: CC(C)(C)OC(=O)N[C@H](CC(=O)N1CCNCC1)c1ccc(F)cc1]

Step A 4-[(R)-3-tert-Butoxycarbonylamino-3-(4-fluoro-phenyl)-propionyl]-piperazine-1-carboxylic acid benzyl ester (56b)

Benzyl piperazine-1-carboxylate (100 mg, 0.454 mmol), (R)-3-(tert-butoxycarbonyl amino)-3-(4-fluorophenyl)propanoic acid (154 mg, 0.545 mmol) and DIPEA (0.16 ml, 0.91 mmol) were dissolved in $CH_2Cl_2$ (10 ml) and stirred at RT for 10 min, then T3P (0.270 ml, 0.454 mmol, 50% wt in EtOAc) was added to the mixture and stirring was continued for 1 h at RT. For workup a saturated solution of $NaHCO_3$ was added and the mixture was extracted with $CH_2Cl_2$. The combined organic phases were dried and the solvent was evaporated to give the title compound which was used without further purification LC MS (ESI): 486.3 $[M+H]^+$ Step B [(R)-1-(4-Fluoro-phenyl)-3-oxo-3-piperazin-1-yl-propyl]-carbamic acid tert-butyl ester (57b)

4-[(R)-3-tert-Butoxycarbonylamino-3-(4-fluoro-phenyl)-propionyl]-piperazine-1-carboxylic acid benzyl ester (56b) (245 mg, 0.505 mmol) was suspended in ethanol (10 ml) and Pd/C (53.7 mg, 0.050 mmol) was added. The suspension was stirred under a $H_2$ atmosphere for 4 h at RT. For workup chloroform was added and the filtrate was collected by filtration. Concentration of the filtrate and drying under high vacuum afforded the desired product (as its free base) which was used without further purification. LC MS (ESI): 352.3 $[M+H]^+$ Reaction Scheme 11: Synthesis of the beta aminoacid derivatives

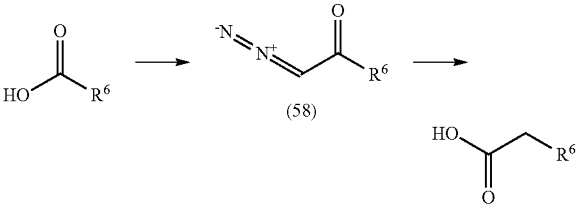

(58)

(59)

Synthesis of (R)-3-tert-Butoxycarbonylamino-3-cyclopentyl-propionic acid (59a)

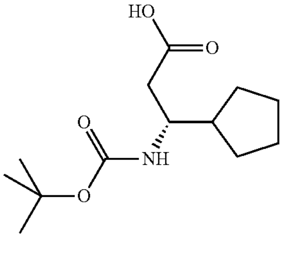 [SMILES: CC(C)(C)OC(=O)N[C@H](CC(=O)O)C1CCCC1]

Step A ((S)-1-Cyclopentyl-3-diazo-2-oxo-propyl)-carbamic acid tert-butyl ester (58a)

A solution of ethylchloroformate (128 μL, 1.336 mmol) in THF (1 ml) was added to a solution of Boc-cyclopentyl-Gly-OH (250 mg, 1.028 mmol) and triethylamine (186 μL, 1.336 mmol) in THF (8 ml) at 0° C. The mixture was stirred at 0° C. for 30 min to allow formation of the corresponding mixed anhydride (m/z=338.0) before a freshly prepared solution of diazomethane in diethylether was added (a solution of diazomethane in diethylether was obtained by addition of N-methyl-N-nitrosourea (371 mg, 3.60 mmol) to 40% KOH/diethylether 1/1 (10 ml) and stirring for 15 min at 0° C. followed by separation of the organic phase). The reaction mixture was stirred overnight at RT. The reaction mixture was diluted with diethylether and quenched with a 10% citric acid solution. The organic layer was separated, washed with a saturated solution of $NaHCO_3$ and brine and dried. Evaporation of the solvent yielded the title compound which was used without further purification. LC MS (ESI): 290.0 $[M+Na]^+$; $^1H$ NMR (400 MHz, DMSO-$d^6$) δ ppm 6.03 (0H, br. s), 3.56-3.65 (1H, m), 1.74-1.81 (1H, m), 1.63-1.71 (1H, m), 1.56 (3H, br. s), 1.43-1.50 (2H, m), 1.39 (9H, s), 1.22-1.32 (2H, m).

Step B (R)-3-tert-Butoxycarbonylamino-3-cyclopentyl-propionic acid (59a)

Silver benzoate (40.3 mg, 0.176 mmol) was added to a solution of ((S)-1-cyclopentyl-3-diazo-2-oxo-propyl)-carbamic acid tert-butyl ester 58a (235 mg, 0.879 mmol) in dioxane and water and heated at 70° C. overnight. The reaction mixture was filtered and concentrated. The residue was dissolved in ethylacetate and the resulting solution was washed with 1N HCl. The organic phase was dried and concentrated to afford the desired product which was used without further purification. LC MS (ESI): 280.0 $[M+Na]^+$; $^1H$ NMR (400 MHz, DMSO-$d^6$) δ ppm 12.28 (1H, br. s), 3.71 (1H, br. s.), 2.21-2.40 (2H, m), 1.50-1.64 (4H, m), 1.42-1.50 (2H, m), 1.37 (9H, s), 1.22-1.33 (2H, m), 1.10-1.21 (1H, m).

Synthesis of (2S,5R)-2-Carboxymethyl-5-phenyl-pyrrolidine-1-carboxylic acid tert-butyl ester (59b)

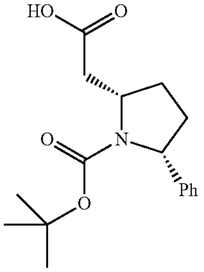 [SMILES: CC(C)(C)OC(=O)N1[C@H](CC(=O)O)CC[C@@H]1c1ccccc1]

Oxalyl chloride (0.05 ml, 0.57 mmol) was added to a solution of (2S,5R)-Boc-5-phenyl-pyrrolidine-2-carboxylic acid (160 mg, 0.55 mmol) and triethylamine (0.08 ml, 0.57 mmol) in THF (5 ml) at 15° C. The reaction mixture was stirred at −15° C. for 30 min before the precipitated triethylammonium chloride salt was filtered off and washed with acetonitrile. At −5° C. TMS-diazomethane (0.55 ml, 1.1 mmol, 2M in hexanes) was added to the solution of the mixed anhydride and stirring was continued for 3 h. For workup the reaction mixture was diluted with diethyl ether and quenched with a 10% citric acid solution. The organic layer was separated, washed with a saturated solution of $NaHCO_3$ and brine and dried. The solvent was evaporated and the crude product was purified by flash column chromatography (12 g silica, 100% cyclohexane to ethyl acetate/cyclohexane 1:1 in 20 min, flow: 30 ml/min) to afford the desired product. LC MS (ESI): 338.0 $[M+Na]^+$.

Rearrangement of the diazoketone to the corresponding carboxylic acid 59b was performed as described for 59'. LC MS (ESI): 328.0 $[M+Na]^+$.

The following compounds were prepared with similar method ($^1H$ NMR data in supplementary table 3):

| | Structure/ | Chemical Name | MS (ESI) m/z |
|---|---|---|---|
| 59c | 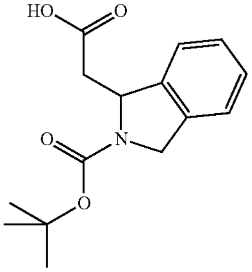 [SMILES: CC(C)(C)OC(=O)N1Cc2ccccc2C1CC(=O)O] | 1-Carboxymethyl-1,3-dihydro-isoindole-2-carboxylic acid tert-butyl ester<br>Synthesis as described for 59a using TMS-diazomethane instead of diazomethane | 300.0 $[M + Na]^+$ |

-continued

| Structure/ | | Chemical Name | MS (ESI) m/z |
|---|---|---|---|
| 59d | 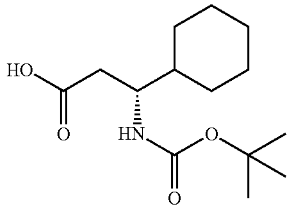 [SMILES: CC(C)(C)OC(=O)N[C@H](CC(=O)O)C1CCCCC1] | (R)-3-(tert-butoxycarbonylamino)-3-cyclohexylpropanoic acid Synthesis as described for 59a using diazomethane | 272.3 $[M + H]^+$ |

Reaction Scheme 12:

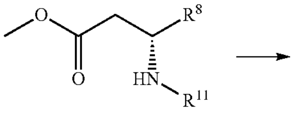

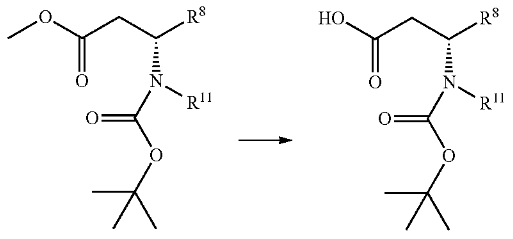

(60) (61)

or

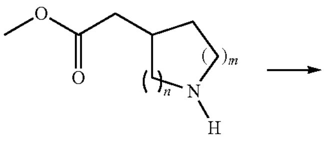

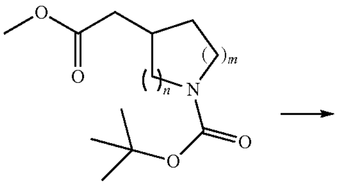

(60)

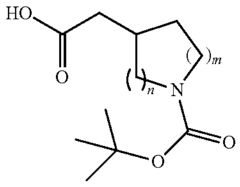

(61)

Synthesis of (R)-3-tert-Butoxycarbonylamino-3-furan-3-yl-propionic acid (61a, $R^8$=3-furyl $R^{11}$=H)

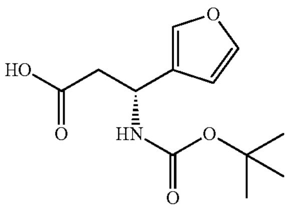 [SMILES: CC(C)(C)OC(=O)N[C@H](CC(=O)O)c1ccoc1]

Step A (R)-3-tert-Butoxycarbonylamino-3-furan-3-yl-propionic acid methyl ester (60a)

$Et_3N$ (0.136 ml, 0.973 mmol) and $Boc_2O$ (0.135 ml, 0.584 mmol) were added to a solution of methyl-(3R)-3-amino-(3-furyl)propanoate HCl (100 mg, 0.486 mmol) in $CH_2Cl_2$ (5 ml) at 0° C. Stirring was continued at 0° C. for 2 hr before the reaction mixture was diluted with $CH_2Cl_2$. The organic phase was washed with 1N HCl and water. The organic layer was dried and the solvent was evaporated to afford a colorless oil. LC MS (ESI): 292.0 $[M+Na]^+$; $^1$H-NMR (400 MHz, DMSO-$d^6$) δ (ppm): 7.57 (s, 1H), 7.50 (s, 1H), 7.24 (d, 1H), 6.45 (s, 1H), 4.89 (m, 1H), 3.58 (s, 3H), 2.70 (m, 2H), 1.38 (s, 9H)

Step B (R)-3-tert-Butoxycarbonylamino-3-furan-3-yl-propionic acid (61a)

LiOH.$H_2O$ (37.4 mg, 0.891 mmol) was added to a solution of (R)-3-tert-butoxycarbonylamino-3-furan-3-yl-propionic acid methyl ester (60a) (120 mg, 0.446 mmol) in DME (3 ml) and water (1.5 ml). The reaction mixture was stirred at RT for 2 h. The solvent was evaporated, the aqueous layer was acidified to pH 1 using 1N HCl and extracted with $CH_2Cl_2$. The combined organic layers were dried and the solvent was evaporated. LC MS (ESI): 227.9 $[M+Na]^+$; 1H-NMR (400 MHz, DMSO-$d^6$) δ (ppm): 12.4 (s, 1H), 7.56 (s, 1H), 7.47 (s, 1H), 7.19 (d, 1H), 6.44 (s, 1H), 4.86 (m, 1H), 2.62 (m, 2H), 1.38 (s, 9H)

The following compounds were prepared with similar method ($^1$H NMR data in supplementary table 4):

| | Structure | Chemical Name | MS (ESI) m/z |
|---|---|---|---|
| 61b | 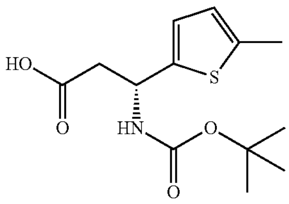 [SMILES: Cc1ccc([C@@H](CC(=O)O)NC(=O)OC(C)(C)C)s1] | 2S,5R)-2-Carboxymethyl-5-phenyl-pyrrolidine-1-carboxylic acid tert-butyl ester | 307.9 $[M + Na]^+$ |
| 61c | 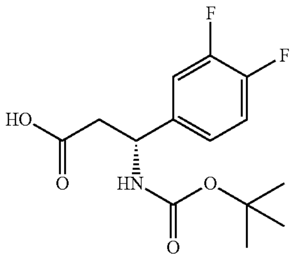 [SMILES: CC(C)(C)OC(=O)N[C@H](CC(=O)O)c1ccc(F)c(F)c1] | (R)-3-tert-Butoxycarbonylamino-3-(3,4-difluoro-phenyl)-propionic acid | 324.0 $[M + Na]^+$ |
| 61d | 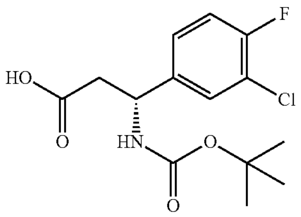 [SMILES: CC(C)(C)OC(=O)N[C@H](CC(=O)O)c1ccc(F)c(Cl)c1] | ((R)-3-tert-Butoxycarbonylamino-3-(3-chloro-4-fluoro-phenyl)-propionic acid | 339.9 $[M + Na]^+$ |
| 61e | 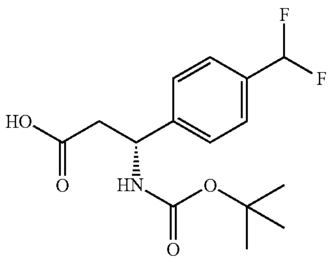 [SMILES: CC(C)(C)OC(=O)N[C@H](CC(=O)O)c1ccc(C(F)F)cc1] | (R)-3-tert-Butoxycarbonylamino-3-(4-difluoromethyl-phenyl)-propionic acid | 314.2 $[M - H]^-$ |
| 61f | 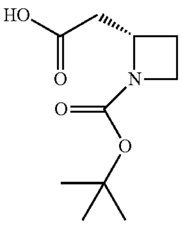 | (S)-2-Carboxymethyl-azetidine-1-carboxylic acid tert-butyl ester | 238.0 $[M + Na]^+$ |

Synthesis of (R)-3-tert-Butoxycarbonylamino-3-(2,4-difluoro-phenyl)-propionic acid (61g, $R^8$=3,4-difluorophenyl, $R^8$=H)

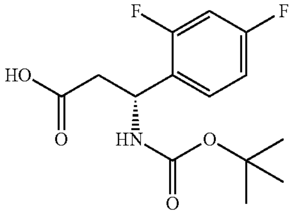 [SMILES: CC(C)(C)OC(=O)N[C@H](CC(=O)O)c1ccc(F)cc1F]

To a stirred solution of (R)-3-amino-3-(2,4-difluorophenyl)propanoic acid (100 mg, 0.497 mmol) in tert-butanol (1 ml) $Boc_2O$ (0.138 ml, 0.597 mmol) was added and the reaction mixture was stirred at RT for 16 h. Since no reaction had taken place 2M NaOH in $H_2O$ (0.249 ml, 0.497 mmol) was added and the mixture was stirred for another 3 h. For workup the reaction mixture was neutralized with 1M HCl and extracted with EtOAc. The combined organic layers were washed with brine, dried over $Na_2SO_4$ and concentrated. The compound was used without further purification. LC MS (ESI): 302.2 [M+H]+

Synthesis of (1R,2R)-1-tert-Butoxycarbonylamino-1,2,3,4-tetrahydro-naphthalene-2-carboxylic acid (61h)

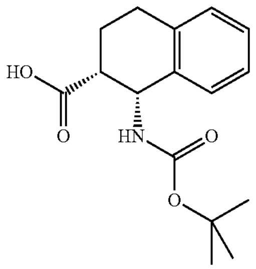 [SMILES: CC(C)(C)OC(=O)N[C@H]1c2ccccc2CC[C@H]1C(=O)O]

This compound was synthesized analogously to 60a from (1R,2R)-1-amino-1,2,3,4-tetrahydronaphtalene-2-carboxylic acid. LC MS (ESI): 313.9 $[M+Na]^+$; $^1$H-NMR (400 MHz, DMSO-$d^6$) δ (ppm): 12.18 (s, 1H), 7.24 (m, 1H), 7.16 (m, 2H), 7.10 (m, 1H), 7.01 (m, 1H), 5.15 (m, 1H), 2.78 (m, 2H), 2.68 (m, 1H), 2.08 (m, 1H), 1.88 (m, 1H), 1.40 (s, 9H)

Synthesis of (R)-4-tert-Butoxycarbonylamino-3-phenyl-butyric acid (61i)

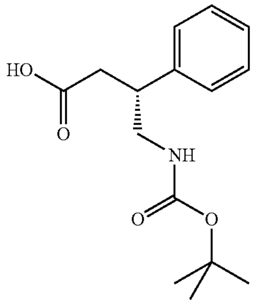 [SMILES: CC(C)(C)OC(=O)NC[C@H](CC(=O)O)c1ccccc1]

(R)-4-Amino-3-phenylbutanoic acid (100 mg, 0.56 mmol) was dissolved in DMF (3 ml). $K_2CO_3$ (231 mg, 1.674 mmol) and $Boc_2O$ (0.143 ml, 0.614 mmol) were added and the reaction mixture was stirred at RT for 16 hr. For workup the solvent was evaporated, the residue was taken up in $H_2O$ and washed with diethylether. The aqueous phase was acidified to pH 2 using 1N HCl, and extracted with EtOAc. The organic phase was dried over $MgSO_4$ and the solvent was evaporated to give the title compound which was used without further purification. LC MS (ESI): 278.2 $[M-H]^-$ Synthesis of (R)-3-tert-Butoxycarbonylamino-3-(4-ethynyl-phenyl)-propionic acid (64)

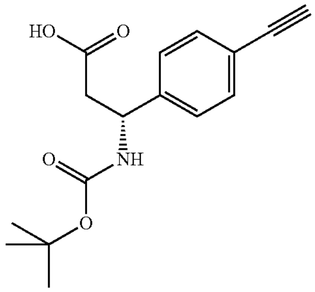 [SMILES: C#Cc1ccc([C@@H](CC(=O)O)NC(=O)OC(C)(C)C)cc1]

Step A (R)-3-tert-Butoxycarbonylamino-3-(4-iodo-phenyl)-propionic acid methyl ester (62)

$Boc_2O$ (0.274 ml, 1.180 mmol) was added to a stirred solution of (R)-methyl 3-amino-3-(4-iodophenyl)propanoate (300 mg, 0.98 mmol) in 3 ml of tert-butanol, and the reaction mixture was stirred at RT for 16 h. Then 2M NaOH in $H_2O$ (0.492 ml, 0.983 mmol) was added and the mixture was stirred for another 3 h. The reaction mixture was neutralized with 1M HCl and extracted with EtOAc. The aqueous layer was extracted with EtOAc. The combined organic layers were washed with brine, dried over $Na_2SO_4$ and concentrated to give the title compound which was used without further purification. LC MS (ESI): 406.1 $[M+H]^+$; $^1$H-NMR (400 MHz, $CDCl_3$) δ (ppm): 7.58 (d, 2H), 6.98 (d, 2H), 5.4 (br, 1H), 4.95 (m, 1H), 3.55 (s, 3H), 2.75 (m, 2H), 1.35 (s, 9H).

Step B (R)-3-tert-Butoxycarbonylamino-3-(4-trimethylsilanylethynyl-phenyl)-propionic acid methyl ester (63)

Under Ar $PdCl_2(PPh_3)_2$ (35.6 mg, 0.051 mmol), copper(I) iodide (9.66 mg, 0.051 mmol), $Et_3N$ (0.562 ml, 4.05 mmol) and ethynyltrimethylsilane (0.287 ml, 2.028 mmol) were added to a solution of (R)-3-tert-butoxycarbonylamino-3-(4-iodo-phenyl)-propionic acid methyl ester (62) (411 mg, 1.014 mmol) in methanol (8.25 ml). The reaction mixture was stirred for 2 h. Then $K_2CO_3$ (14.02 mg, 0.101 mmol) was added and the mixture was stirred for another 3 h at RT. The reaction mixture was filtered over hyflo and concentrated. Then the mixture was diluted with EtOAc and washed with a saturated $NaHCO_3$ solution and brine. The organic phase was dried over $Na_2SO_4$ and the organic solvent was evaporated to afford the title compound which was used in the next step without further purification. LC MS (ESI): 376.3 $[M+H]^+$.

Step C(R)-3-tert-Butoxycarbonylamino-3-(4-ethynyl-phenyl)-propionic acid (64)

(R)-3-tert-Butoxycarbonylamino-3-(4-trimethylsilanyl-ethynyl-phenyl)-propionic acid methyl ester (63) (380 mg, 1.012 mmol) was dissolved in methanol (4.64 ml), then a solution of $LiOH.H_2O$ (48.5 mg, 2.024 mmol) in $H_2O$ (4.64 ml) was added. The reaction mixture was stirred for 16 h at RT. Methanol was removed under reduced pressure before EtOAc and water were added. The organic phase was separated and the aqueous phase was extracted with EtOAc. The combined organic layers were dried over $Na_2SO_4$ and the solvent was evaporated. The product was used without further purification. LC MS (ESI): 288.3 $[M-H]^-$.

Reaction Scheme 13:

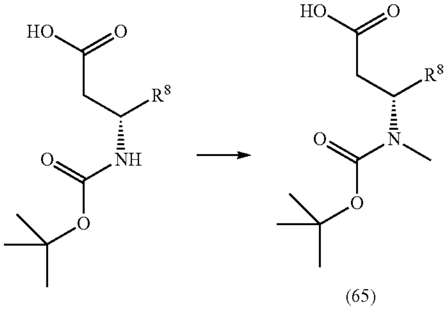

(65)

Synthesis of (R)-3-(tert-Butoxycarbonyl-methyl-amino)-3-phenyl-propionic acid (65a, $R^8$=phenyl)

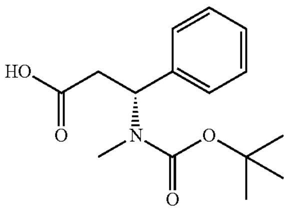 [SMILES: CN(C(=O)OC(C)(C)C)[C@H](CC(=O)O)c1ccccc1]

At 0° C. sodium hydride (90 mg, 3.77 mmol) was added to a solution of Boc-Beta-Phe-OH (100 mg, 0.377 mmol) in THF (3 ml) under an Ar atmosphere. After 30 minutes methyl iodide (0.141 ml, 2.262 mmol) was added and stirring was continued for 20 h at RT. The reaction mixture was quenched with water in an ice bath and extracted with EtOAc. The organic phase was washed with 1N HCl and brine, dried and concentrated under reduced pressure. The crude product was purified by flash chromatography (silica, 0-10% methanol in dichloromethane). LC MS (ESI): 302.0 $[M+Na]^+$; $^1H$ NMR (400 MHz, DMSO-$d^6$) δ ppm 7.34-7.40 (2H, m), 7.25-7.33 (3H, m), 5.39-5.72 (1H, m), 2.94-3.06 (1H, m), 2.83 (1H, br. s), 2.58 (3H, s), 1.41 (9H, s).

The following compounds were prepared with similar method ($^1H$ NMR data in supplementary table 5):

| | Structure | Chemical Name | MS (ESI) m/z |
|---|---|---|---|
| 65b | 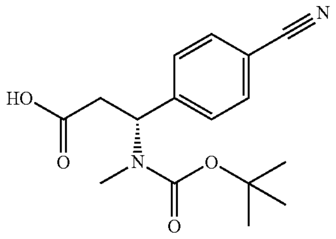 [SMILES: CN(C(=O)OC(C)(C)C)[C@H](CC(=O)O)c1ccc(C#N)cc1] | (R)-3-(tert-butoxycarbonyl(methyl)amino)-3-(4-cyanophenyl)propanoic acid | 327.0 $[M + Na]^+$ |
| 65c | 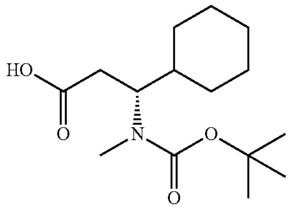 [SMILES: CN(C(=O)OC(C)(C)C)[C@H](CC(=O)O)C1CCCCC1] | (R)-3-(tert-butoxycarbonyl(methyl)amino)-3-cyclohexylpropanoic acid | 286.4 $[M + H]^+$ |
| 65d | 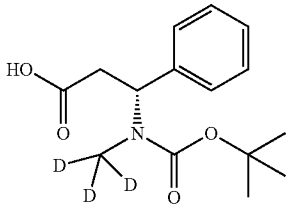 [SMILES: [2H]C([2H])([2H])N(C(=O)OC(C)(C)C)[C@H](CC(=O)O)c1ccccc1] | (R)-3-(tert-butoxycarbonyl($d^3$-methyl)amino)-3-phenyl propanoic acid | 283.4 $[M + H]^+$ |

-continued

| Structure | | Chemical Name | MS (ESI) m/z |
|---|---|---|---|
| 65e | 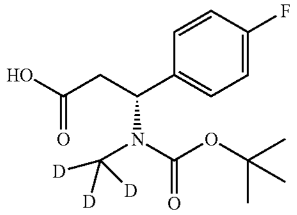 [SMILES: [2H]C([2H])([2H])N(C(=O)OC(C)(C)C)[C@H](CC(=O)O)c1ccc(F)cc1] | (R)-3-(tert-butoxycarbonyl(d3-methyl)amino)-3-(4-fluorophenyl)propanoic acid | 301.0 $[M + H]^+$ |

Reaction Scheme 14:

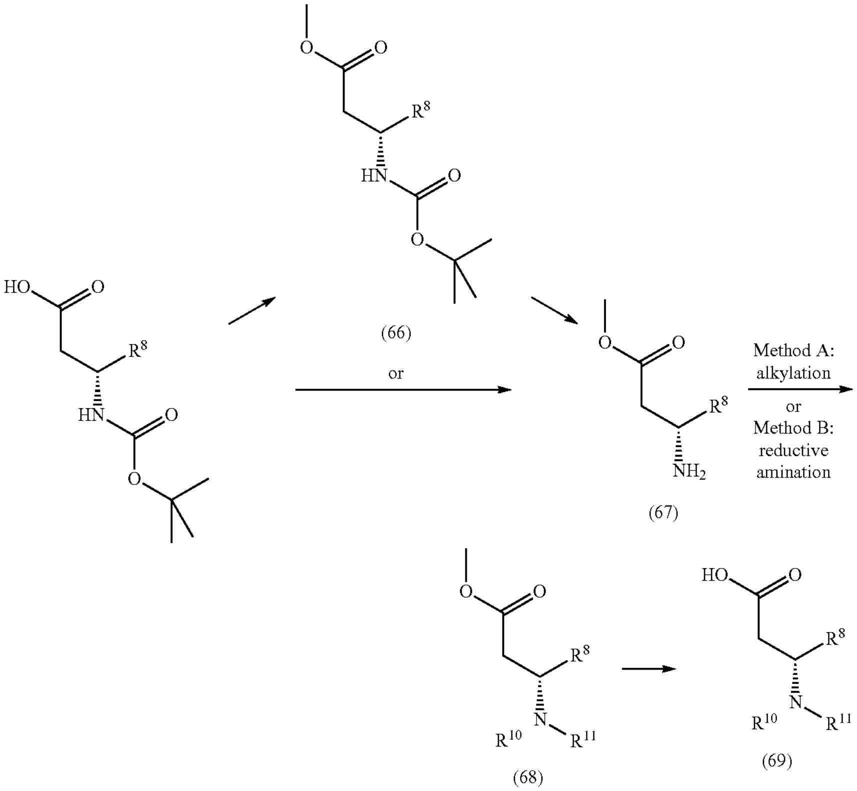

Examples for Method A

Synthesis of (R)-3-(4-Fluoro-phenyl)-3-(2,2,2-trifluoro-ethylamino)-propionic acid (69a, $R^8$=4-fluorophenyl, $R^{10}$=H, $R^{11}$=trifluoro-ethyl)

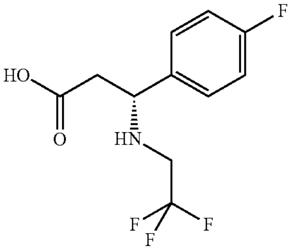 [SMILES: O=C(O)C[C@@H](NCC(F)(F)F)c1ccc(F)cc1]

Step A (R)-3-tert-Butoxycarbonylamino-3-(4-fluoro-phenyl)-propionic acid methyl ester (66a)

At 0° C. TMS-diazomethane (2.65 ml, 5.29 mmol) was added to a solution of (R)-3-(tert-butoxycarbonylamino)-3-(4-fluorophenyl)propanoic acid (1.0 g, 3.53 mmol) in THF/methanol (2:1, 10.5 ml) under a nitrogen atmosphere. Stirring of the reaction mixture was continued at RT for 2 h. The solvents were evaporated and the residue was purified by flash chromatography (silica, cyclohexane/EtOAc: 9/1 to 1/1). to give the title compound. LC MS (ESI): 298.2 $[M+H]^+$; $^1H$-NMR (400 MHz, DMSO-$d^6$) δ (ppm): 7.49 (d, 1H), 7.35 (dd, 2H), 7.15 (dd, 2H), 4.91 (m, 1H), 3.57 (s, 3H), 2.74 (m, 2H), 1.36 (s, 9H).

Step B ((R)-Methyl 3-amino-3-(4-fluorophenyl) propanoate (67a)

To a solution of (R)-3-tert-butoxycarbonylamino-3-(4-fluoro-phenyl)-propionic acid methyl ester (66a) (896 mg, 3.01 mmol) in dioxane (5 ml) was added a 4N HCl solution in dioxane (15 ml). The reaction mixture was stirred at RT for 2 h. The mixture was frozen and lyophilized to afford the title compound as hydrochloride salt. LC MS (ESI): 198.1 $[M+H]^+$; $^1$H-NMR (400 MHz, DMSO-$d^6$) δ (ppm): 8.65 (br s, 3H), 7.60 (dd, 1H), 7.28 (dd, 2H), 4.64 (dd, 1H), 3.56 (s, 3H), 3.19 (dd, 1H), 3.01 (dd, 1H).

Step C(R)-3-(4-Fluoro-phenyl)-3-(2,2,2-trifluoro-ethylamino)-propionic acid methyl ester (68a)

$Na_2CO_3$ (2.25 g, 21.2 mmol) was added to a solution of (R)-3-amino-3-(4-fluoro-phenyl)-propionic acid methyl ester (67a) (709 mg, 3.03 mmol) in $CH_2Cl_2$ (20 ml) and water (20 ml). The mixture was stirred at RT for 30 min, the organic phase was separated, dried and the solvent was evaporated. The residue was taken up in DMF (40 ml) and DIPEA (1.59 ml, 9.10 mmol) as well as 2,2,2-trifluoroethyltrifluoromethane sulfonate (0.48 ml, 3.34 mmol) were added. The reaction mixture was stirred at RT for 16 h. The solution was then diluted with diethyl ether and quenched with water. The organic phase was separated, washed with brine, dried and the solvent was evaporated. The residue was purified by flash chromatography (silica, cyclohexane/EtOAc: 9/1 to 4/1). LC MS (ESI): 280.1 $[M+H]^+$; $^1$H-NMR (400 MHz, DMSO-$d^6$) δ (ppm): 7.40 (dd, 1H), 7.17 (dd, 2H), 4.09 (dd, 1H), 3.53 (s, 3H), 3.12 (m, 1H), 2.98 (m, 2H), 2.77 (dd, 1H), 2.58 (dd, 1H).

Step D (R)-3-(4-Fluoro-phenyl)-3-(2,2,2-trifluoro-ethylamino)-propionic acid (69a)

A solution of $LiOH.H_2O$ (147 mg, 3.51 mmol) in water (2 ml) was added to a solution of (R)-3-(4-fluoro-phenyl)-3-(2,2,2-trifluoro-ethylamino)-propionic acid methyl ester (68a) (490 mg, 1.75 mmol) in THF (4 ml) and the reaction mixture was stirred at 65° C. for 2 h. The solvents were evaporated and the resulting solid was used in the following step without further purification. LC MS (ESI): 266.1 $[M+H]^+$; $^1$H-NMR (400 MHz, DMSO-$d^6$) δ (ppm): 7.35 (dd, 1H), 7.11 (dd, 2H), 3.98 (m, 1H), 3.90 (m, 1H), 3.05 (m, 1H), 2.84 (m, 1H), 2.12 (m, 2H).

Synthesis of (R)-3-Ethylamino-3-(4-fluoro-phenyl)-propionic acid (69b, $R^8$=4-fluorophenyl, $R^{10}$=H, $R^{11}$=ethyl)

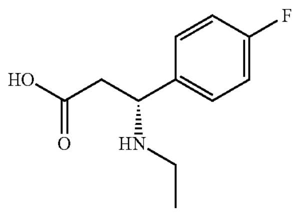

Step A (R)-methyl 3-amino-3-(4-fluorophenyl)propanoate (67a)

To (R)-3-(tert-butoxycarbonylamino)-3-(4-fluorophenyl) propanoic acid (1 g, 3.53 mmol) in methanol (18 ml) was added dropwise chlorotrimethylsilane (2.26 ml, 17.7 mmol) and the reaction mixture was stirred at RT for 15 h. The solvent was evaporated. The resulting residue was dissolved in $CH_2Cl_2$ and washed with a saturated solution of $NaHCO_3$. The organic layer was dried and the solvent was evaporated to afford the title compound which was used in the next step without further purification. LC MS (ESI): 198.1 $[M+H]^+$; $^1$H NMR (400 MHz, DMSO-$d^6$) δ (ppm): 7.41 (dd, 2H), 7.12 (t, 2H), 4.21 (t, 1H), 3.55 (s, 3H), 2.58 (dd, 2H), 1.97 (br, 2H).

Step B (R)-methyl 3-(4-fluoroophenyl)-3-(ethylamino)propanoate (68b)

A solution of (R)-methyl 3-amino-3-(4-fluorophenyl)propanoate (67a) (100 mg, 0.51 mmol) in EtOAc (1.1 ml) was added to a mixture of ethyl trifluoromethanesulfonate (0.079 ml, 0.609 mmol) and $NaHCO_3$ in water (3 ml) and EtOAc (1.1 ml). The mixture was stirred at RT for 30 min. For workup a saturated solution of $NaHCO_3$ was added and the mixture was extracted with EtOAc. The combined organic extracts were dried and the solvent was evaporated. The crude product was purified by flash chromatography (silica, $CH_2Cl_2$ 100% to $CH_2Cl_2$/methanol 94/6 in 20 min, flow=30 mL/min) to yield the title compound. LC MS (ESI): 226.2 $[M+H]^+$, $^1$H NMR (400 MHz, DMSO-$d^6$) δ (ppm): 7.30-7.39 (m, 2H), 7.11-7.14 (m, 2H), 3.96 (t, 1H), 3.53 (s, 3H), 2.70 (dd, 1H), 2.50 (m, 1H), 2.25-2.35 (m, 2H), 2.14-2.20 (m, 1H), 0.94 (t, 3H).

Step C(R)-3-Ethylamino-3-(4-fluoro-phenyl)-propionic acid (69b)

This compound was synthesized analogously to 69a, step D from (R)-methyl 3-(4-fluoroophenyl)-3-(ethylamino)propanoate (68b). LC MS (ESI): 212.1 $[M+H]^+$, $^1$H NMR (400 MHz, DMSO-$d^6$) δ (ppm): 7.74 (dd, 2H), 7.52 (d, 1H), 7.36 (d, 1H), 3.89-3.72 (m, 1H), 2.40-2.27 (m, 1H), 2.27-2.13 (m, 1H), 2.13-1.96 (m, 2H), 0.95 (t, 3H). Synthesis of (R)-3-(4-cyanophenyl)-3-(ethylamino)propanoic acid (69c, $R^8$=4-cyanophenyl, $R^{10}$=H, $R^{11}$=ethyl)

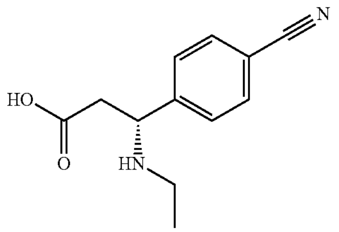 [SMILES: CCN[C@H](CC(=O)O)c1ccc(C#N)cc1]

Step A (R)-methyl 3-amino-3-(4-cyanophenyl)propanoate (67c)

To (R)-3-(tert-butoxycarbonylamino)-3-(4-cyanophenyl) propanoic acid (2 g, 6.89 mmol) in methanol (20 ml) was added dropwise chlorotrimethylsilane (4.40 ml, 34.4 mmol) and the reaction mixture was stirred at RT for 2 h. The solvent was evaporated. The resulting gum was treated with ether and the solvent was evaporated to give the title compound. LC MS (ESI): 205.1 $[M+H]^+$; $^1$H NMR (400 MHz, DMSO-$d^6$) δ (ppm): 8.79 (br, 3H), 7.94 (d, 2H), 7.77 (d, 2H), 4.74 (br s, 1H), 3.58 (s, 3H), 3.22 (dd, 1H), 3.06 (dd, 1H).

Step B (R)-methyl 3-(4-cyanophenyl)-3-(ethylamino)propanoate (68c)

$Na_2CO_3$ (308 mg, 2.91 mmol) was added to a solution of (R)-methyl 3-amino-3-(4-cyanophenyl)propanoate (67c)

(100 mg, 0.415 mmol) in $CH_2Cl_2$ (3 ml) and water (3 ml). The mixture was stirred at RT for 30 min, the organic phase was separated, dried and the solvent was evaporated. At RT a solution of $NaHCO_3$ (175 mg, 2.077 mmol) in water (800 uL) was added to a mixture of the resulting residue in EtOAc (800 uL) followed by dropwise addition of a solution of ethyl trifluoromethanesulfonate (0.065 ml, 0.499 mmol) in EtOAc (600 uL). The reaction mixture was stirred at RT for 2 h. The reaction mixture was extracted with EtOAc and a saturated solution of $NaHCO_3$, the organic phase was dried and the solvent was evaporated. The residue was purified by preparative HPLC (Method P1). Pure fractions were poured into a saturated solution of $NaHCO_3$ and extracted with $CH_2Cl_2$. The combined organic phases were dried and the solvent was evaporated. LC MS (ESI): 233 $[M+H]^+$, $^1H$ NMR (400 MHz, DMSO-$d^6$) δ (ppm): 7.79 (m, 2H), 7.56 (m, 2H), 4.04 (t, 1H), 3.53 (s, 3H), 2.73 (m, 1H), 2.54 (m, 1H), 2.39-2.18 (m, 2H), 0.94 (t, 3H).

Step C(R)-3-(4-cyanophenyl)-3-(ethylamino)propanoic acid (69c)

This compound was synthesized analogously to 69a, step D from (R)-methyl 3-(4-cyanophenyl)-3-(ethylamino)propanoate (68c). LC MS (ESI): 219 $[M+H]^+$, $^1H$ NMR (400 MHz, DMSO-$d^6$) δ (ppm): 7.74 (dd, 2H), 7.52 (d, 1H), 7.36 (d, 1H), 3.89-3.72 (m, 1H), 2.40-2.27 (m, 1H), 2.27-2.13 (m, 1H), 2.13-1.96 (m, 2H), 0.95 (t, 3H).

The following compounds ($R^8$=4-fluorophenyl, $R^{10}$=H) were prepared analogously to 69c:

| | Structure | Chemical Name | MS (ESI) m/z |
|---|---|---|---|
| 69d | 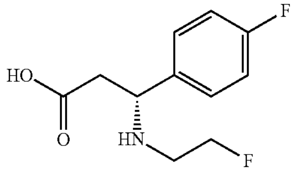 [SMILES: O=C(O)C[C@@H](NCCF)c1ccc(F)cc1] | (R)-3-(2-Fluoro-ethylamino)-3-(4-fluoro-phenyl)-propionic acid | 244.1 $[M + H]^+$ |
| 69e | 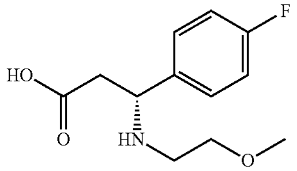 | (R)-3-(4-Fluoro-phenyl)-3-(2-methoxy-ethylamino)-propionic acid | 256.2 $[M + H]^+$ |

2-Fluoroethyl trifluoromethanesulfonate was prepared in the following way:

At −78° C. trifluoromethanesulfonic anhydride (0.22 ml, 1.3 mmol) was added dropwise to a solution of 2-fluoroethanol (75 mg, 1.17 mmol) and triethylamine (0.18 ml, 1.3 mmol) in $CH_2Cl_2$ (1.4 ml). The reaction mixture was allowed to warm to RT and stirred for an additional hour. The reaction mixture was quenched with water, the organic phase was separated and washed with a saturated solution of. $NaHCO_3$ and brine. Drying of the organic layer and concentration afforded the title compound which was used without further purification. $^1H$ NMR (400 MHz, DMSO-$d^6$) δ (ppm): 4.75 (m, 1H), 4.64 (m, 1H), 4.61 (m, 1H), 4.54 (m, 1H).

2-Methoxyethyl trifluoromethanesulfonate was prepared analogously as 2-fluoroethyl trifluoromethanesulfonate from 2-methoxyethanol and trifluoromethanesulfonic anhydride. $^1H$ NMR (400 MHz, DMSO-$d^6$) δ (ppm): 4.43 (m, 2H), 3.62 (m, 2H), 3.36 (s, 3H).

Synthesis of (R)-3-(azetidin-1-yl)-3-(4-fluorophenyl)propanoic acid (69f, $R^8$=4-fluorophenyl, $R^{10}$-$R^{11}$=$(CH_2)_3$)

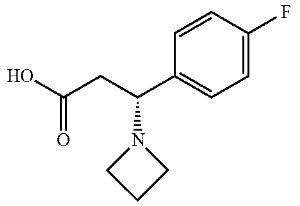 [SMILES: O=C(O)C[C@H](c1ccc(F)cc1)N1CCC1]

Step A (R)-Methyl 3-(azetidin-1-yl)-3-(4-fluorophenyl)propanoate (68f)

Triethylamine (1.4 ml, 10.1 mmol) and 1,3-dibromopropane (362 μL, 3.55 mmol) were added to a solution of (R)-methyl 3-amino-3-(4-fluorophenyl)propanoate (67a) (200 mg, 1.014 mmol) in DMF (5 ml). The reaction mixture was heated at 65° C. for 15 h. After cooling to RT and quenching with water, the mixture was extracted with diethylether. The combined organic phases were dried and the solvent was evaporated. The residue was purified by preparative HPLC (Method P3). Pure fractions were poured into saturated solution of. $NaHCO_3$ and extracted with $CH_2Cl_2$. The combined organic phases were dried, filtered and concentrated to afford the title compound. LC MS (ESI): 238.1 $[M+H]^+$.

Step B (R)-3-(Azetidin-1-yl)-3-(4-fluorophenyl) propanoic acid (69f)

The title compound was obtained by saponification of (R)-methyl 3-(azetidin-1-yl)-3-(4-fluorophenyl)propanoate (68f) as described for 69a, step D, and used in the next step without purification. LC MS (ESI): 224.1 $[M+H]^+$, $^1H$ NMR (400 MHz, DMSO-$d^6$) δ (ppm): 7.30 (dd, 2H), 7.02 (dd, 2H), 3.56 3.60 (m, 1H), 2.91-2.98 (m, 4H), 2.19 (dd, 1H), 1.75-1.85 (m, 3H).

The following compounds ($R^8$=4-fluorophenyl) were prepared analogously to 69f:

| | Structure | Chemical Name | MS (ESI) m/z |
|---|---|---|---|
| 69g | 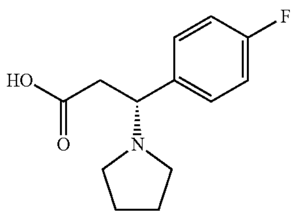 [SMILES: O=C(O)C[C@H](c1ccc(F)cc1)N1CCCC1] | (R)-3-(4-Fluoro-phenyl)-3-pyrrolidin-1-yl-propionic acid | 252.2 $[M + H]^+$ |
| 69h | 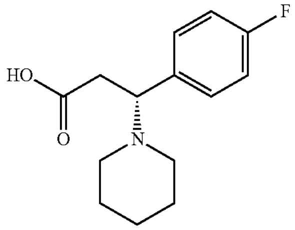 [SMILES: O=C(O)C[C@H](c1ccc(F)cc1)N1CCCCC1] | (R)-3-(4-Fluoro-phenyl)-3-piperidin-1-yl-propionic acid | 266.2 $[M + H]^+$ |

Examples for Method B

Synthesis of (R)-3-(4-Fluoro-phenyl)-3-isopropylamino-propionic acid (69i, $R^8$=4-fluorophenyl, $R^{10}$=H, $R^{11}$=isopropyl)

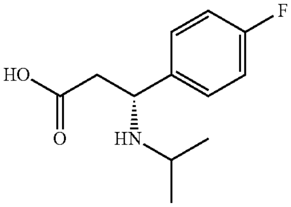 [SMILES: CC(C)N[C@H](CC(=O)O)c1ccc(F)cc1]

Step A ((R)-3-(4-Fluoro-phenyl)-3-isopropylamino-propionic acid methyl ester (68i)

To a solution of (R)-3-amino-3-(4-fluoro-phenyl)-propionic acid methyl ester (67a) hydrochloride (100 mg, 0.428 mmol) in DCE (3 ml) were added triethylamine (0.06 ml, 0.128 mmol), acetone (0.035 ml, 0.471 mmol), AcOH (0.024 ml, 0.428 mmol) and molecular sieves (100 mg). After 1 h of stirring, sodium cyanoborohydride (47 mg, 0.749 mmol) was added and the reaction mixture was stirred at RT for 2 h. The mixture was then quenched with a saturated aqueous $NaHCO_3$ solution and filtered. The filtered solid was washed with $CH_2Cl_2$, and the combined filtrates were extracted with $CH_2Cl_2$. The combined organic phases where washed with a saturated aqueous $NaHCO_3$ solution, dried and the solvent was evaporated. The residue was purified first by flash chromatography (silica, cyclohexane/EtOAc: 2/1 to 1/2), then by preparative HPLC (Method P2). LC MS (ESI): 240.2 $[M+H]^+$; $^1$H-NMR (400 MHz, DMSO-$d^6$) δ (ppm): 7.39 (dd, 1H), 7.13 (dd, 2H), 4.07 (m, 1H), 3.53 (s, 3H), 2.66 (dd, 1H), 2.48 (m, 1H), 2.36 (m, 1H), 2.15 (br s, 1H), 0.90 (d, 3H), 0.88 (d, 3H).

Step B (R)-3-(4-Fluoro-phenyl)-3-isopropylamino-propionic acid (69i)

The title compound was obtained by saponification of ((R)-3-(4-fluoro-phenyl)-3-isopropylamino-propionic acid methyl ester (68i) (118 mg, 0.493 mmol) as described for 69a, step D, and used in the next step without further purification. LC MS (ESI): 226.2 $[M+H]^+$; $^1$H-NMR (400 MHz, DMSO-$d^6$) δ (ppm): 7.34 (dd, 1H), 7.05 (dd, 2H), 3.94 (m, 1H), 2.62 (m, 1H), 2.40 (m, 1H), 2.03 (m, 2H), 0.93 (d, 3H), 0.84 (d, 3H).

Synthesis of (R)-3-Dimethylamino-3-phenyl-propionic (69j, $R^8$=phenyl, $R^{10}$=$R^{11}$=methyl)

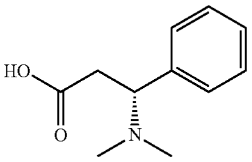

Step A (R)-3-tert-Butoxycarbonylamino-3-phenyl-propionic acid methyl ester (66j)

This compound was synthesized analogously to 66a from (R)-3-tert-butoxycarbonylamino-3-phenyl-propionic acid. LC MS (ESI): 280.2 $[M+H]^+$; $^1$H-NMR (400 MHz, DMSO-$d^6$) δ (ppm): 7.48 (d. 1H), 7.31 (m, 4H), 7.24 (m, 1H), 4.92 (m, 1H), 3.56 (s, 3H), 2.69-2.75 (m, 2H), 1.36 (s, 9H)

Step B (R)-3-Amino-3-phenyl-propionic acid methyl ester (67j)

This compound was synthesized analogously to 67a from (R)-3-tert-butoxycarbonylamino-3-phenyl-propionic acid methyl ester (66j). LC MS (ESI): 180.1 $[M+H]^+$; $^1$H-NMR (400 MHz, methanol-d[4]) δ (ppm): 8.21 (br s, 2H), 7.45 (m, 5H), 4.62 (t, 1H), 3.58 (s, 3H), 3.04 (m, 2H).

Step C(R)-3-Dimethylamino-3-phenyl-propionic acid methyl ester (68j)

Formaldehyde (101 mg, 3.35 mmol) was added dropwise to a solution of (R)-3-amino-3-phenyl-propionic acid methyl ester (67j) (300 mg, 1.674 mmol) and triethylamine (0.233 ml, 1.674 mmol) in $CH_3CN$ (2 ml). AcOH (0.01 ml, 0.167 mmol) was added and the resulting solution was stirred at RT for 30 min. Sodium cyanoborohydride (184 mg, 2.93 mmol) was added over 15 min to the reaction mixture. The mixture was stirred at RT for 30 min before it was extracted with $CH_2Cl_2$. The organic phases were combined, washed with a saturated aqueous $NaHCO_3$ solution, dried and concentrated to give the title compound which was used in the following step without further purification. LC MS (ESI): 208.1 $[M+H]^+$.

Step D (R)-3-Dimethylamino-3-phenyl-propionic (69j)

The title compound was obtained by saponification of (R)-3-dimethylamino-3-phenyl-propionic acid methyl ester (68j) (118 mg, 0.493 mmol) as described for 69a, step D. LC MS (ESI): 194.1 $[M+H]^+$.

The following compounds were prepared analogously to 69i and 69j CH NMR data for some compounds in supplementary table 6):

| | Structure | Chemical Name | MS (ESI) m/z |
|---|---|---|---|
| 69k | 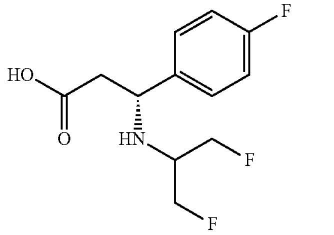 [SMILES: O=C(O)C[C@@H](NC(CF)CF)c1ccc(F)cc1] | (R)-3-(1,3-difluoropropan-2-ylamino)-3-(4-fluorophenyl) propanoic acid | 262.2 $[M + H]^+$ |
| 69l | 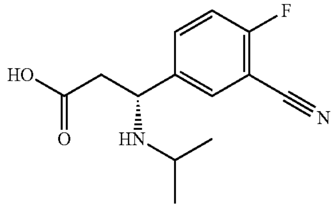 [SMILES: CC(C)N[C@H](CC(=O)O)c1ccc(F)c(C#N)c1] | (R)-3-(3-cyano-4-fluorophenyl)-3-(isopropylamino)propanoic acid | 251.1 $[M + H]^+$ |
| 69m | 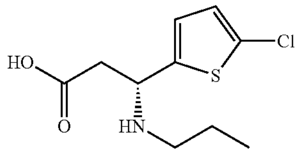 | (R)-3-(5-chlorothiophen-2-yl)-3-(propylamino)propanoic acid | 248.1 $[M + H]^+$ |
| 69n | 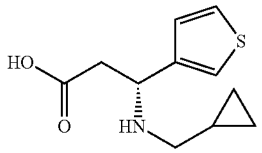 [SMILES: O=C(O)C[C@@H](NCC1CC1)c1ccsc1] | (R)-3-(cyclopropylmethylamino)-3-(thiophen-3-yl)propanoic acid | 226.1 $[M + H]^+$ |
| 69o | 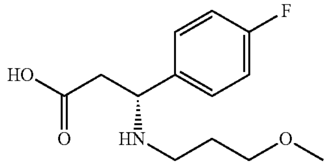 [SMILES: COCCCN[C@H](CC(=O)O)c1ccc(F)cc1] | (R)-3-(4-fluorophenyl)-3-(3-methoxypropylamino)propanoic acid | 256.2 $[M + H]^+$ |
| 69p | 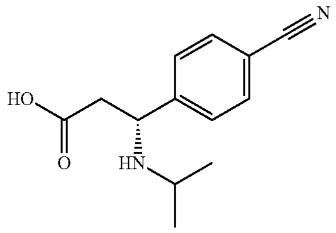 [SMILES: CC(C)N[C@H](CC(=O)O)c1ccc(C#N)cc1] | (R)-3-(4-cyanophenyl)-3-(isopropylamino)propanoic acid | 233.2 $[M + H]^+$. |

-continued

| Structure | Chemical Name | MS (ESI) m/z |
|---|---|---|
| 69q 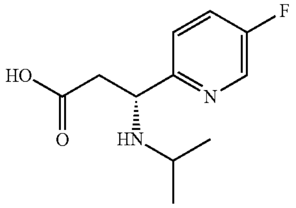 | (R)-3-(5-Fluoro-pyridin-2-yl)-3-isopropylamino-propionic acid | 241.2 [M + H]$^+$ |
| 69r 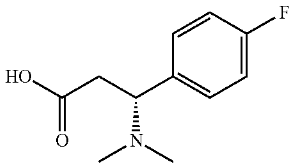 | (R)-3-Dimethylamino-3-(4-fluoro-phenyl)-propionic acid | 212.1 [M + H]$^+$ |

Synthesis of (R)-3-(4-Cyano-phenyl)-3-[(3-methyl-oxetan-3-ylmethyl)-amino]-propionic acid (69s, $R^8$=4-cyanophenyl, $R^{11}$=H, $R^{11}$=3-methyl-oxetan-3-ylmethyl)

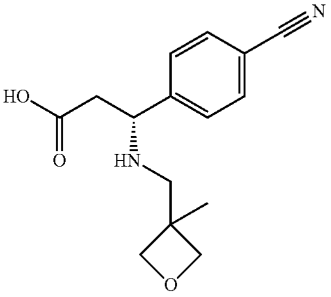 [SMILES: CC1(CN[C@H](CC(=O)O)c2ccc(C#N)cc2)COC1]

Step A: (R)-3-(4-Cyano-phenyl)-3-[(3-methyl-oxetan-3-ylmethyl)-amino]-propionic acid methyl ester (68s)

At RT AcOH (4.71 μL, 0.082 mmol) and 3-methyloxetane-3-carbaldehyde (82 mg, 0.823 mmol) were added to a solution of 67c (168 mg, 0.823 mmol) in $CH_3CN$ (8.3 ml) After stirring for 5 min sodium cyanoborohydride (103 mg, 1.645 mmol) was added and stirring at RT was continued for 3 h. Then the reaction mixture was concentrated and the residue was partioned between $CH_2Cl_2$ and a saturated solution of $NaHCO_3$. The organic phase was separated and the aqueous phase was extracted with $CH_2Cl_2$. The organic phases were dried (phase separator) and the solvent was evaporated. The crude product was purified by preparative HPLC (method P3) to yield (R)-3-(4-cyano-phenyl)-3-[(3-methyl-oxetan-3-ylmethyl)-amino]-propionic acid methyl ester. LC MS (ESI): 289.2 [M+H]$^+$ Step B: (R)-3-(4-Cyano-phenyl)-3-[(3-methyl-oxetan-3-ylmethyl)-amino]-propionic acid (69s)

The title compound was obtained from (R)-3-(4-cyano-phenyl)-3-[(3-methyl-oxetan-3-ylmethyl)-amino]-propionic acid methyl ester (68s) by saponification of the methyl ester as described for 69a, step D. LC MS (ESI): 273.3 [M−H]$^-$ Synthesis of (S)-2-(1-isobutylpyrrolidin-2-yl)acetic acid (72)

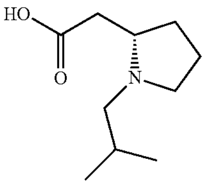

Step A: (S)-methyl 2-(pyrrolidin-2-yl)acetate (70)

TMS-Cl (630 μL, 4.93 mmol) as added to a solution of Boc-L-beta-homoproline (226 mg, 0.986 mmol) in methanol (9857 μL) at RT. Stirring was continued for 15 h. For workup the solvent was evaporated, the residue was dissolved in $CH_2Cl_2$ and the organic phase was washed with a saturated solution of $NaHCO_3$. The organic layer was dried and the solvent was evaporated to afford the title compounds as its free base. LC MS (ESI): 144.1 [M+H]$^+$;

Step B: (S)-methyl 2-(1-isobutylpyrrolidin-2-yl) acetate (71)

At RT, triethylamine (0.068 ml, 0.490 mmol) followed by AcOH (2.80 μl, 0.049 mmol), isobutyraldehyde (0.064 ml, 0.588 mmol) and molecular sieves were added to a solution of (S)-methyl 2-(pyrrolidin-2-yl)acetate (70) (88 mg, 0.490 mmol) in DCE (3 ml). The reaction mixture was stirred at RT for 1 h before sodium cyanoborohydride (61.6 mg, 0.980 mmol) was added. Stirred at RT was continued for 2 h. For workup, the reaction mixture was concentrated and the residue partitioned between $CH_2Cl_2$ and a saturated solution of $NaHCO_3$. The organic phase was separated and the aqueous phase extracted with $CH_2Cl_2$. The combined organic phases were dried and the solvent was evaporated to afford the title compound which was used in the next step without further purification. LC MS (ESI): 200.2 [M+H]$^+$;

Step C: (S)-methyl 2-(1-isobutylpyrrolidin-2-yl) acetate (72)

$LiOH.H_2O$ (16.4 mg, 0.391 mmol) was added to a solution of (S)-methyl 2-(1-isobutylpyrrolidin-2-yl)acetate (71, 78 mg, 0.391 mmol) in THF (2 ml) and water (1 ml). The reaction mixture was stirred at RT for 2 h before the solvent was evaporated to yield the title compound which was used without further purification. LC MS (ESI): 186.1 $[M+H]^+$; $^1H$ NMR (400 MHz, DMSO-$d^6$) δ (ppm): 2.97 (m, 1H), 2.59 (m, 2H), 2.36-2.17 (m, 21H), 2.12-1.84 (m, 4H), 1.63 (m, 3H), 0.86 (d, 3H), 0.84 (d, 3H).

Reaction Scheme 15:

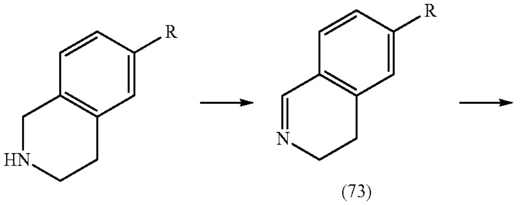

(73)

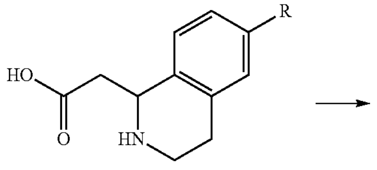

(74)

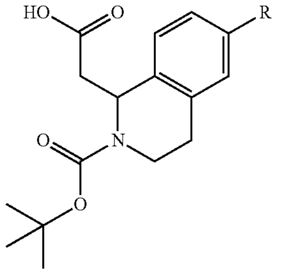

(75)

Synthesis of 1-carboxymethyl-3,4-dihydro-1H-isoquinoline-2-carboxylic acid tert-butyl ester (75a, R=H)

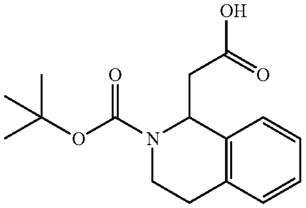 [SMILES: CC(C)(C)OC(=O)N1CCc2ccccc2C1CC(=O)O]

This compound was synthesized analogously to 60a from (1,2,3,4-tetrahydro-isoquinolin-1-yl)-acetic acid. LC MS (ESI): 313.9 $[M+Na]^+$; $^1H$ NMR (400 MHz, DMSO-$d^6$) δ ppm 7.08-7.28 (4H, m), 5.36-5.51 (1H, m), 3.73-4.06 (1H, m), 2.78 (2H, br. s.), 2.58-2.72 (2H, m), 1.42 (9H, s).

Synthesis of 1-carboxymethyl-3,4-dihydro-1H-isoquinoline-2-carboxylic acid tert-butyl ester (75b, R=F)

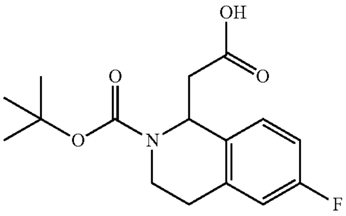 [SMILES: CC(C)(C)OC(=O)N1CCc2cc(F)ccc2C1CC(=O)O]

Step A 6-Fluoro-3,4-dihydro-isoquinoline (73b)

N-Bromosuccinimide (300 mg, 1.688 mmol) was added to a solution of 6-fluoro-1,2,3,4-tetrahydroisoquinoline (0.202 ml, 1.535 mmol) in $CH_2Cl_2$ (4 ml) under ice-bath-cooling over 20 min. After stirring for 40 min, 30% aqueous NaOH solution (2 ml) was added to the reaction solution, the organic layer was washed with water and then extracted with 2N aqueous HCl (10 ml). The aqueous layer was washed with $CH_2Cl_2$, basified with aqueous ammonia, and then extracted with $CH_2Cl_2$. The extract was dried over sodium sulfate and then evaporated to afford the title compound which was used without further purification. LC MS (ESI): 242.2 $[M-H]^-$ $^1H$ NMR (400 MHz, DMSO-$d^6$) δ (ppm): 8.33 (s, 1H), 7.47 (s, 1H), 7.13 (s, 2H), 3.63 (s, 2H), 2.72 (s, 2H)

Step B (6-Fluoro-1,2,3,4-tetrahydro-isoquinolin-1-yl)-acetic acid (74b)

A mixture of 6-fluoro-3,4-dihydroisoquinoline (220 mg, 1.475 mmol) (73b) and malonic acid (153 mg, 1.475 mmol) was stirred at RT for 30 min and then at 120° C. for another 30 min. After cooling to RT, the solid residue was washed with small portions of 2-propanol to give the title compound which was used without further purification LC MS (ESI): 209.9 $[M+H]^+$; $^1H$ NMR (400 MHz, DMSO-$d^6$) δ ppm 7.24-7.33 (1H, m), 6.97-7.11 (2H, m), 4.30-4.42 (1H, m), 3.06-3.20 (2H, m), 2.83 (2H, t), 2.53-2.58 (2H, m).

Step C 1-Carboxymethyl-3,4-dihydro-1H-isoquinoline-2-carboxylic acid tert-butyl ester (75b)

This compound was synthesized analogously to 60a from 6-fluoro-1,2,3,4-tetrahydro-isoquinolin-1-yl)-acetic acid (74b) and used without further purification. LC MS (ESI): 331.9 $[M+Na]^+$; $^1H$-NMR (400 MHz, DMSO-$d^6$) δ (ppm): 12.28 (s, 1H), 7.28 (m, 1H), 7.03 (m, 2H), 5.42 (m, 1H), 3.95 (m, 2H), 2.78 (m, 2H), 2.62 (m, 2H), 1.42 (s, 9H)

Synthesis of (R)-4-(R)-4-Benzyl-2-oxo-oxazolidin-3-yl)-3-(4-fluoro-phenyl)-4-oxo-butyric acid (78)

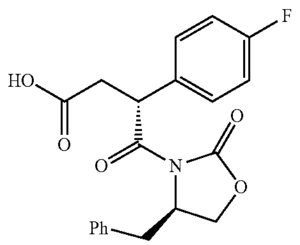 [SMILES: O=C(O)C[C@@H](C(=O)N1C(=O)OC[C@H]1Cc1ccccc1)c1ccc(F)cc1]

Step A (R)-4-Benzyl-3-[2-(4-fluoro-phenyl)-acetyl]-oxazolidin-2-one (76)

At −78° C. n-BuLi (2.5 M in hexane) (2.92 ml, 7.29 mmol) was added slowly to a solution of (R)-(+4-benzyl-1, Reaction Scheme 16:

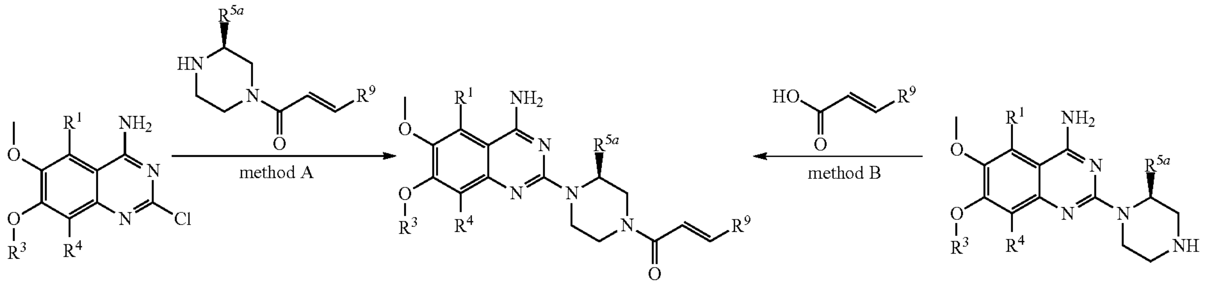

3-oxazolidin-2-one (1.293 g, 7.29 mmol) in THF (10 ml), and stirring at −78° C. was continued for 30 min. Then 4-fluorophenylacetyl chloride (1 ml, 7.29 mmol) in THF (2 ml) was added dropwise, and the mixture stirred at −78° C. for another 1.5 h. The reaction mixture was treated with a concentrated aqueous solution of $NH_4Cl$ and allowed to warm to RT before it was extracted with EtOAc. The organic phase was dried over $MgSO_4$ and the solvent was evaporated. The product was purified by chromatography (silica, flow=30 ml/min, cyclohexane 100% to cyclohexane/EtOAc: 7/3). $^1$H NMR (400 MHz, DMSO-$d^6$) δ ppm 7.23-7.39 (7H, m), 7.16 (2H, t), 5.32 (1H, dd), 4.64-4.72 (1H, m), 4.24 (1H, t), 4.14 (1H, dd), 3.11 (1H, dd), 2.95-3.00 (2H, m), 2.67 (1H, dd).

Step B (R)-4-(R)-4-Benzyl-2-oxo-oxazolidin-3-yl)-3-(4-fluoro-phenyl)-4-oxo-butyric acid tert-butyl ester (77)

At −78° C. NaHMDS (2M in THF) (2.394 ml, 4.79 mmol) was slowly added to a solution of (R)-4-benzyl-3-(2-(4-fluorophenyl)acetyl)oxazolidin-2-one (76) (1.5 g, 4.79 mmol) in THF (10 ml) and the mixture was stirred at −78° C. for 1 h. Then tert-butyl 2-bromoacetate (0.707 ml, 4.79 mmol) was added dropwise, and stirring at −78° C. was continued for 1 h. The reaction mixture was treated with a concentrated aqueous solution of $NH_4Cl$, allowed to warm to RT and extracted with EtOAc. The organic phases were dried over $MgSO_4$ and the solvent was evaporated. The crude product was purified by chromatography (silica, cyclohexane/EtOAc/1/0 to 7/3). LC MS (ESI): 450.0 $[M+Na]^+$; $^1$H NMR (DMSO-$d^6$) d: 7.11-7.37 (m, 9H), 5.34 (dd, 1H), 4.60-4.70 (m, 1H), 4.17-4.23 (m, 1H), 4.09-4.30 (m, 2H), 3.00-3.12 (m, 2H), 2.87-2.98 (m, 1H), 2.70 (s, 1H), 1.39 (s, 9H).

Step C: (R)-4-((R)-4-Benzyl-2-oxo-oxazolidin-3-yl)-3-(4-fluoro-phenyl)-4-oxo-butyric acid (78)

A solution of (R)-4-((R)-4-benzyl-2-oxo-oxazolidin-3-yl)-3-(4-fluoro-phenyl)-4-oxo-butyric acid tert-butyl ester (77) (744 mg, 1.740 mmol) in TFA/$CH_2Cl_2$ 1/1 (10 ml) was stirred at RT for 1 h. The solvents were evaporated and the residue dried under vacuum to afford the title compound which was used in the next step without further purification. $^1$H NMR (400 MHz, DMSO-$d^6$) δ ppm 7.23-7.39 (7H, m), 7.16 (2H, t), 5.32 (1H, dd), 4.68 (1H, br. s), 4.24 (1H, t), 4.14 (1H, dd), 3.11 (1H, dd), 2.95-3.02 (2H, m), 2.67 (1H, dd).

Synthesis of the examples

Example 1

Method A

Synthesis of (E)-1-[4-(4-Amino-8-fluoro-6,7-dimethoxy-quinazolin-2-yl)-piperazin-1-yl]-3-cyclopropyl-propenone hydrochloride ($R^1$=H, $R^3$=methyl, $R^4$=F, $R^{5a}$=H, $R^9$=cyclopropyl)

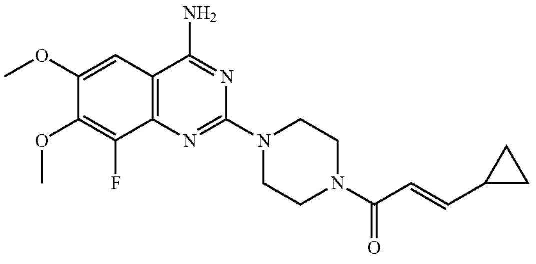 [SMILES: COc1cc2c(N)nc(N3CCN(C(=O)/C=C/C4CC4)CC3)nc2c(F)c1OC]

(E)-3-Cyclopropyl-1-piperazin-1-yl-propenone hydrochloride (57a) (46 mg, 0.213 mmol) and triethylamine (0.03 ml, 0.213 mmol) were added to a solution of 2-chloro-8-fluoro-6,7-dimethoxy-quinazolin-4-ylamine (9) (50 mg, 0.194 mmol) in isopentyl alcohol (0.5 ml). The reaction mixture was stirred at 135° C. for 2 h. The solvent was then evaporated and the residue was purified by preparative HPLC (Method P4). The purified solid was dissolved in a 1.25 N solution of HCl in methanol. After 15 min, the solvent was evaporated, the residue was dissolved in water, frozen and lyophilized to afford the title compound as mono-hydrochloride salt. LC MS (ESI): 402.4 $[M+H]^+$, $t_R$=0.58 min (Method A1); $^1$H-NMR (400 MHz, DMSO-$d^6$) δ (ppm): 9.04 (br s, 2H), 7.74 (s, 1H), 6.65 (d, 1H), 6.29 (dd, 1H), 4.02 (s, 3H), 3.91 (s, 3H), 3.60-3.90 (m, 8H), 1.65 (m, 1H), 0.90 (m, 2H), 0.61 (m, 2H).

Example 2

Method B

Synthesis of 4-{(E)-3-[4-(4-Amino-8-fluoro-6,7-dimethoxy-quinazolin-2-yl)-piperazin-1-yl]-3-oxo-propenyl}-benzonitrile ($R^1$=H, $R^3$=methyl, $R^4$=F, $R^{5a}$=H, $R^9$=4-cyanophenyl)

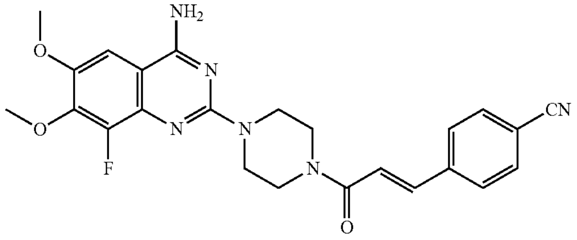 [SMILES: COc1cc2c(N)nc(N3CCN(C(=O)/C=C/c4ccc(C#N)cc4)CC3)nc2c(F)c1OC]

8-Fluoro-6,7-dimethoxy-2-piperazin-1-yl-quinazolin-4-ylamine (21a) (80 mg, 0.260 mmol), (E)-3-(4-cyanophenyl) acrylic acid (45.1 mg, 0.260 mmol), HOBT (51.8 mg, 0.338 mmol), EDC (74.9 mg, 0.390 mmol) and $NEt_3$ (0.090 ml, 0.649 mmol) were dissolved in $CH_2Cl_2$ (5 ml) and stirred for 16 h at RT. The reaction mixture was diluted with $CH_2Cl_2$, washed with a saturated solution of $NaHCO_3$ and brine. The organic phase was dried over $Na_2SO_4$ and the solvent was evaporated under reduced pressure. The crude product was purified by flash chromatography (silicagel, 50-100% EtOAc in hexane) to give the title compound as TFA salt. LC MS (ESI): 463.2 $[M+H]^+$, $t_R$=0.79 min (Method A2); $^1$H-NMR (600 MHz, DMSO-$d^6$) δ (ppm): 7.94 (d, 2H), 7.89 (d, 2H), 7.55 (d, 1H), 7.48 (d, 1H), 7.41 (s, 1H), 3.89 (s, 3H), 3.84 (s, 3H), 3.6-3.8 (m, 8H).

Example 3

Method B

Synthesis of ((E)-1-[(R)-4-(4-Amino-8-fluoro-6,7-dimethoxy-quinazolin-2-yl)-3-methoxymethyl-piperazin-1-yl]-3-cyclopropyl-propenone ($R^1$=H, $R^3$=methyl, $R^4$=F, $R^{5a}$=methoxymethyl, $R^9$=cyclopropyl)

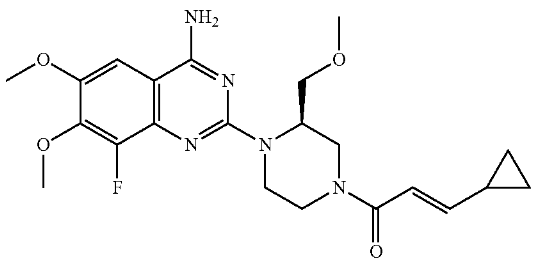 [SMILES: COC[C@H]1CN(C(=O)/C=C/C2CC2)CCN1c1nc(N)c2cc(OC)c(OC)c(F)c2n1]

A solution of (E)-3-cyclopropylacrylic acid (19.15 mg, 0.171 mmol) and HATU (81 mg, 0.213 mmol) in $CH_3CN$ (2 ml) was stirred at RT for 10 min before 8-fluoro-6,7-dimethoxy-2-((R)-2-methoxymethyl-piperazin-1-yl)-quinazolin-4-ylamine (21j) (50 mg, 0.142 mmol) and DIPEA (0.050 ml, 0.285 mmol) were added. Stirring at RT was continued for 12 h. For workup a saturated solution of $NaHCO_3$ was added and the mixture was extracted with $CH_2Cl_2$. The combined organic layers were dried and concentrated to afford the crude product which was purified by preparative HPLC (method P8). The fractions containing the desired product were diluted with $CH_2Cl_2$ and washed with a saturated solution of $NaHCO_3$. Drying of the organic phase and evaporation of the solvent gave the title compound as its free base. LC MS (ESI): 446.3 $[M+H]^+$, $t_R$=0.75 min (Method A1); $^1$H-NMR (400 MHz, methanol-$d^4$) δ (ppm): 7.26 (s, 1H), 6.59 (m, 1H), 6.38 (m, 1H), 5.09 (m, 1H), 4.63-4.56 (m, 6H), 4.01 (s, 3H), 3.94 (s, 3H), 3.47 (m, 2H), 0.98 (m, 2H), 0.65 (m, 2H).

Example 4

Method B

Synthesis of (E)-1-[4-(4-Amino-8-fluoro-6,7-dimethoxy-quinazolin-2-yl)-3-(2-methoxy-ethyl)-piperazin-1-yl]-3-cyclopropyl-propenone ($R^1$=H, $R^3$=methyl, $R^4$=F, $R^{5a}$=2-methoxyethyl, $R^9$=cyclopropyl)

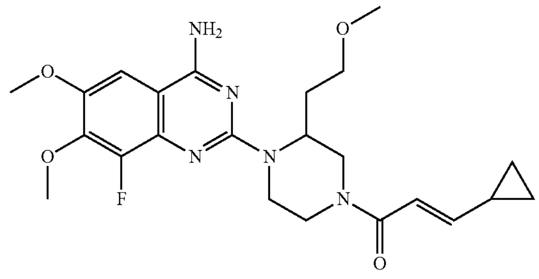 [SMILES: COCCC1CN(C(=O)/C=C/C2CC2)CCN1c1nc(N)c2cc(OC)c(OC)c(F)c2n1]

To a solution of (E)-3-cyclopropylacrylic acid and HBTU in $CH_3CN$ were added 8-fluoro-6,7-dimethoxy-2-[2-(2-methoxy-ethyl)-piperazin-1-yl]-quinazolin-4-ylamine (21k) and $Et_3N$. The reaction mixture was stirred at RT during 16 h. For workup a saturated solution of $NaHCO_3$ was added and the mixture was extracted with $CH_2Cl_2$. The combined organic layers were dried and concentrated to afford the crude product which was purified by preparative HPLC (method P2). The pure product was treated with 1.25M HCl in methanol, the solvent was evaporated, the residue suspended in water, frozen and lyophilized to give the title compound as its hydrochloride salt. LC MS (ESI): 460.4 $[M+H]^+$, $t_R$=0.75 min (Method A1); $^1$H-NMR (400 MHz, methanol-$d^4$) δ (ppm): 7.59 (s, 1H), 6.61 (d, 1H), 6.41 (dd, 1H), 4.67 (m, 2H), 4.50 (m, 1H), 4.24 (m, 1H), 4.14 (s, 3H), 4.00 (s, 3H), 3.68-3.44 (m, 5H), 3.41 (s, 3H), 2.02 (m, 2H), 1.72 (m, 1H), 1.00 (m, 2H), 0.67 (m, 2H).

Example 5

Method B

Synthesis of 4-Amino-2-[4-((E)-3-cyclopropyl-acryloyl)-piperazin-1-yl]-6,7-dimethoxy-quinazoline-8-carbonitrile ($R^1$=H, $R^3$=methyl, $R^4$=CN, $R^{5a}$=H, $R^9$=cyclopropyl)

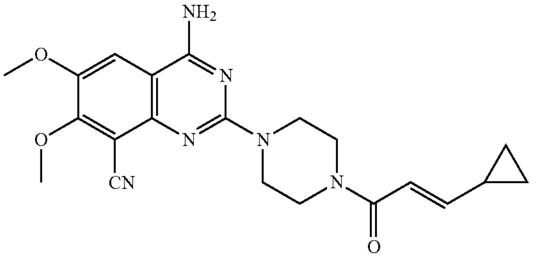 [SMILES: COc1cc2c(N)nc(N3CCN(C(=O)/C=C/C4CC4)CC3)nc2c(C#N)c1OC]

T3P (50% wt in EtOAc) (0.075 ml, 0.127 mmol) was added to a solution of 4-amino-6,7-dimethoxy-2-piperazin-1-yl-quinazoline-8-carbonitrile (32) (200 mg, 0.127 mmol), (E)-3-cyclopropylacrylic acid (17.12 mg, 0.153 mmol) and DIPEA (0.067 ml, 0.382 mmol) in $CH_2Cl_2$ (5 ml) at RT and stirring was continued for 2 h. Then, the solvent was removed under reduced pressure and the residue subjected to purification by preparative HPLC (method P10) to afford the title compound as its free base. LC MS (ESI): 409.5 $[M+H]^+$, $t_R$=0.86 min (Method A1); $^1$H-NMR (400 MHz, methanol-$d^4$) δ (ppm): 7.74 (s, 1H), 6.62 (d, 1H), 6.35 (dd, 1H), 4.14 (s, 3H), 3.96 (s, 3H), 3.94 (m, 4H), 3.74 (m, 4H), 1.70 (m, 1H), 0.98 (m, 2H), 0.65 (m, 2H).

The following compounds were prepared with similar methods

| Ex. | Structure/Chemical Name<br>Synthesis Method | MS (ESI)<br>m/z<br>$[M + H]^+$<br>$t_R$ [min]<br>(method) | $^1$H NMR |
|---|---|---|---|
| 6 | 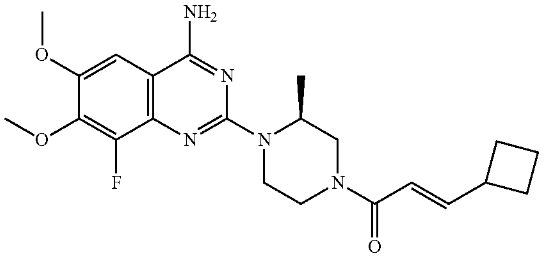 [SMILES: COc1cc2c(N)nc(N3CCN(C(=O)/C=C/C4CCC4)C[C@@H]3C)nc2c(F)c1OC]<br>(E)-1-[(S)-4-(4-Amino-8-fluoro-6,7-dimethoxy-quinazolin-2-yl)-3-methyl-piperazin-1-yl]-3-cyclobutyl-propenone<br>Method B (example 2) | 430.5<br>0.85 (A2) | (600 MHz, DMSO-$d^6$) δ (ppm): 7.95 (br, 1H), 7.3-7.4 (br, 2H), 7.37 (s, 1 H), 6.80 (m, 1H), 6.39 (m, 1H), 4.96 (m, 1H), 4.5 (d, 1H), 3.9-4.45 (m, 2H), 3.88 (s, 3H), 3.83 (s, 3H), 2.85-3.2 (m, 3H), 2.15 (m, 2H), 1.85-1.95 (m, 3H), 1.75-1.85 (m, 2H), 1.03 (m, 3H). (rotameres) |
| 7 | 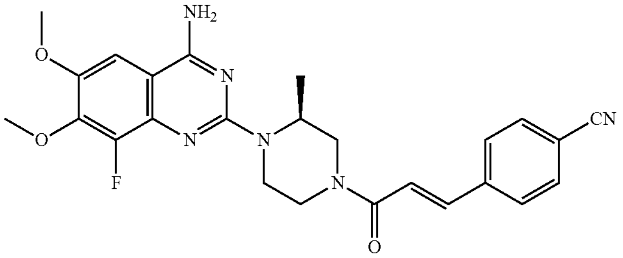 [SMILES: COc1cc2c(N)nc(N3CCN(C(=O)/C=C/c4ccc(C#N)cc4)C[C@@H]3C)nc2c(F)c1OC]<br>4-{(E)-3-[(S)-4-(4-Amino-8-fluoro-6,7-dimethoxy-quinazolin-2-yl)-3-methyl-piperazin-1-yl]-3-oxo-propenyl}-benzonitrile<br>Method B (example 2) | 477.4<br>0.86 (A2) | (600 MHz, DMSO-$d^6$) δ (ppm): 7.95 (d, 2H), 7.89 (d, 2H), 7.57 (m, 1H), 7.46 (m, 1H), 7.38 (br, 3H), 5.00 (m, 1H), 4.55 (m, 1H), 4.2-4.5 (m, 2H), 3.89 (s, 3H), 3.84 (s, 3H), 2.75-3.45 (m, 3H), 1.06 (m, 3H). (rotamers) |

-continued

| Ex. | Structure/Chemical Name Synthesis Method | MS (ESI) m/z $[M + H]^+$ $t_R$ [min] (method) | $^1H$ NMR |
|---|---|---|---|
| 8 | 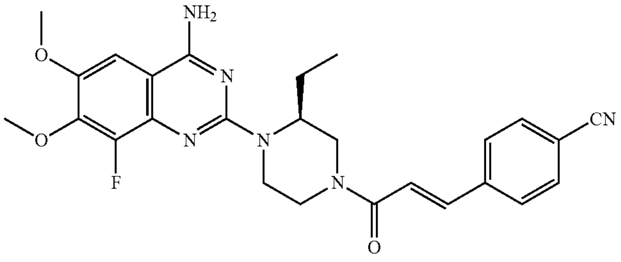 [SMILES: CC[C@H]1CN(C(=O)/C=C/c2ccc(C#N)cc2)CCN1c1nc(N)c2cc(OC)c(OC)c(F)c2n1] 4-{(E)-3-[(S)-4-(4-Amino-8-fluoro-6,7-dimethoxy-quinazolin-2-yl)-3-ethyl-piperazin-1-yl]-3-oxo-propenyl}-benzonitrile Method B (example 2) | 491.5 0.88 (A2) | (600 MHz, DMSO-$d^6$) δ (ppm): 7.96 (d, 2H), 7.89 (d, 2H), 7.59 (m, 1H), 7.46 (m, 1H), 7.37 (br, 3H), 4.87 (m, 1H), 4.65 (m, 1H), 4.5 (m, 1H), 4.3 (m, 1H), 3.89 (s, 3H), 3.83 (s, 3H), 2.75-3.35 (m, 3H), 1.4-1.55 (m, 2H), 0.8-0.9 (m, 3H). (rotameres) |
| 9 | 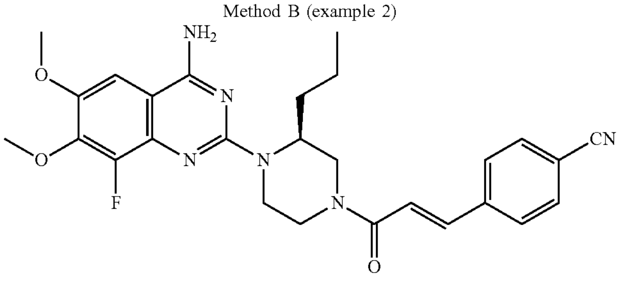 4-{(E)-3-[(S)-4-(4-Amino-8-fluoro-6,7-dimethoxy-quinazolin-2-yl)-3-propyl-piperazin-1-yl]-3-oxo-propenyl}-benzonitrile Method B (example 2) | 505.4 0.94 (A2) | (600 MHz, DMSO-$d^6$) δ (ppm): 7.95 (d, 2H), 7.89 (d, 2H), 7.56 (m, 1H), 7.4 (m, 1H), 7.37 (br, 3H), 4.99 (m, 1H), 4.65 (m, 1H), 4.5 (m, 1H), 4.35 (m, 1H), 3.89 (s, 3H), 3.83 (s, 3H), 2.75-3.4 (m, 3H), 1.45 (m, 2H), 1.23 (m, 2H), 0.8-0.9 (m, 3H). (rotamers) |
| 10 | 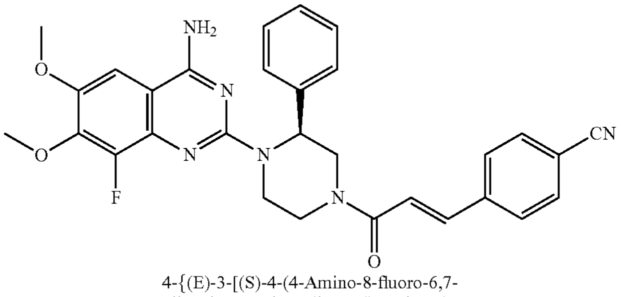 4-{(E)-3-[(S)-4-(4-Amino-8-fluoro-6,7-dimethoxy-quinazolin-2-yl)-3-phenyl-piperazin-1-yl]-3-oxo-propenyl}-benzonitrile Method B (example 2) | 539.4 0.99 (A2) | (600 MHz, DMSO-$d^6$) δ (ppm): 7.85-7.95 (m, 4H), 7.10-7.55 (m, 10H), 6.21/6.10 (2 s, 1H, rotamers), 5.10/4.95 (2 m, 1H, rotamers), 4.75 (m, 1H), 4.27 (m, 1H), 3.90 (s, 3H), 3.85 (s, 3H), 3.05-3.40 (m, 3H) |
| 11 | 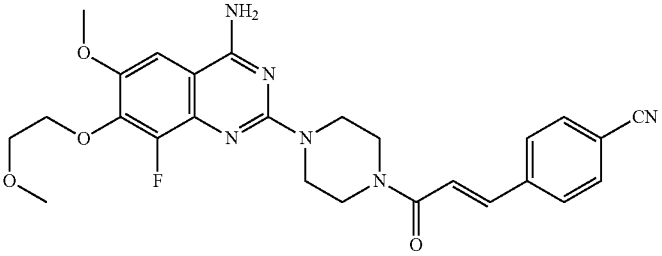 [SMILES: COCCOc1c(OC)cc2c(N)nc(N3CCN(C(=O)/C=C/c4ccc(C#N)cc4)CC3)nc2c1F] 4-((E)-3-{4-[4-Amino-8-fluoro-6-methoxy-7-(2-methoxy-ethoxy)-quinazolin-2-yl]-piperazin-1-yl}-3-oxo-propenyl)-benzonitrile Method B (example 2) | 507.2 0.80 (A2) | (400 MHz, DMSO-$d^6$) δ (ppm): 7.98 (d, 2H), 7.9 (d, 2H), 7.6 (d, 1H), 7.5 (d, 1H), 7.45 (br, 1H), 7.4 (s, 1H), 4.2 (t, 2H), 3.85 (s, 3H), 3.8 (m, 4H), 3.65 (m, 2H), 3.6 (t, 2H), 3.4 (m, 4H), 3.35 (s, 3H) |

-continued

| Ex. | Structure/Chemical Name Synthesis Method | MS (ESI) m/z $[M + H]^+$ $t_R$ [min] (method) | $^1H$ NMR |
|---|---|---|---|
| 12 | 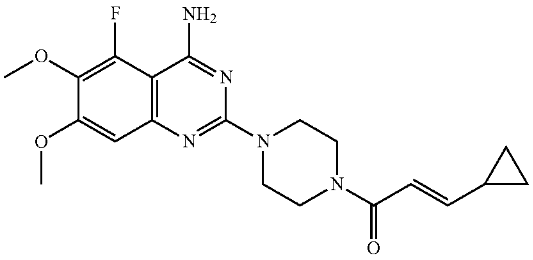 [SMILES: COc1cc2nc(N3CCN(C(=O)/C=C/C4CC4)CC3)nc(N)c2c(F)c1OC] (E)-1-[4-(4-Amino-5-fluoro-6,7-dimethoxy-quinazolin-2-yl)-piperazin-1-yl]-3-cyclopropyl-propenone Method A | 402.3 0.55 (A1) | (400 MHz, methanol-$d^4$) δ (ppm): 6.76 (s, 1H), 6.60 (d, 1H), 6.35 (dd, 1H), 3.97 (s, 3H), 3.90 (m, 4H), 3.88 (s, 3H), 3.73 (m, 4H), 1.70 (m, 1H), 0.97 (m, 2H), 0.65 (m, 2H) |
| 13 | 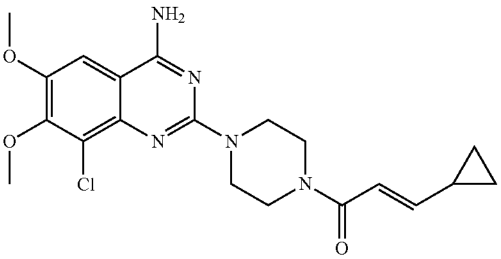 [SMILES: COc1cc2c(N)nc(N3CCN(C(=O)/C=C/C4CC4)CC3)nc2c(Cl)c1OC] (E)-1-(4-(4-Amino-8-chloro-6,7-dimethoxyquinazolin-2-yl)piperazin-1-yl)-3-cyclopropylprop-2-en-1-one Method A | 418.3 0.66 (A1) | (400 MHz, DMSO-$d^6$) δ (ppm): 7.69 (s, 1H), 6.63 (d, 1H), 6.25 (dd, 1H), 3.90 (s, 3H), 3.88 (s, 3H), 3.75-3.85 (m, 4 h), 3.6-3.75 (m, 4H), 1.66 (m, 1H), 0.90 (m, 2H), 0.61 (m, 2H) |
| 14 | 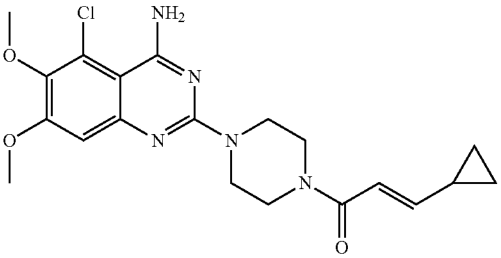 [SMILES: COc1cc2nc(N3CCN(C(=O)/C=C/C4CC4)CC3)nc(N)c2c(Cl)c1OC] (E)-1-(4-(4-Amino-5-chloro-6,7-dimethoxyquinazolin-2-yl)piperazin-1-yl)-3-cyclopropylprop-2-en-1-one | 418.4 0.60 (A1) | (400 MHz, DMSO-$d^6$) δ (ppm): 9.20 (s br, 1H), 8.46 (s br, 1H), 7.60 (s br, 1H), 6.69 (d, 1H), 6.27 (dd, 1H), 3.97 (s, 3H), 3.85-3.95 (m, 4H), 3.79 (s, 3H), 3.65-3.8 (m, 4H), 1.66 (m, 1H), 0.90 (m, 2H), 0.62 (m, 2H) |
| 15 | 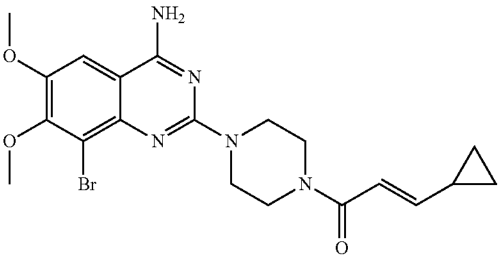 [SMILES: COc1cc2c(N)nc(N3CCN(C(=O)/C=C/C4CC4)CC3)nc2c(Br)c1OC] (E)-1-(4-(4-Amino-8-bromo-6,7-dimethoxyquinazolin-2-yl)piperazin-1-yl)-3-cyclopropylprop-2-en-1-one Method B (example 3) | 462.2 0.88 (A1) | (400 MHz, methanol-$d^4$) δ (ppm): 7.47 (s, 1H), 6.6 (d, 1H), 6.35 (dd, 1H), 3.95 (s, 3H), 3.93 (s, 3H), 3.9-4.0 (m, 4H), 3.7-3.8 (m, 4H), 1.70 (m, 1H), 0.95 (m, 2H), 0.65 (m, 2H) |

-continued

| Ex. | Structure/Chemical Name Synthesis Method | MS (ESI) m/z $[M + H]^+$ $t_R$ [min] (method) | $^1H$ NMR |
|---|---|---|---|
| 16 | 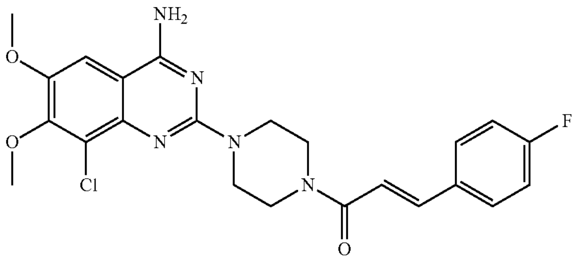 [SMILES: COc1cc2c(N)nc(N3CCN(C(=O)/C=C/c4ccc(F)cc4)CC3)nc2c(Cl)c1OC] (E)-1-(4-(4-Amino-8-chloro-6,7-dimethoxyquinazolin-2-yl)piperazin-1-yl)-3-(4-fluorophenyl)prop-2-en-1-one Method B (example 2) | 472.4 0.95 (A2) | (600 MHz, DMSO-$d^6$) δ (ppm): 7.83 (m, 2H), 7.57 (s, 1H), 7.53 (d, 1H), 7.47 (br, 2H), 7.23-7.30 (m, 3H), 3.86 (s, 3H), 3.83 (s, 3H), 3.75-3.85 (m, 6H), 3.65 (m, 2H) |

Reaction Scheme 17:

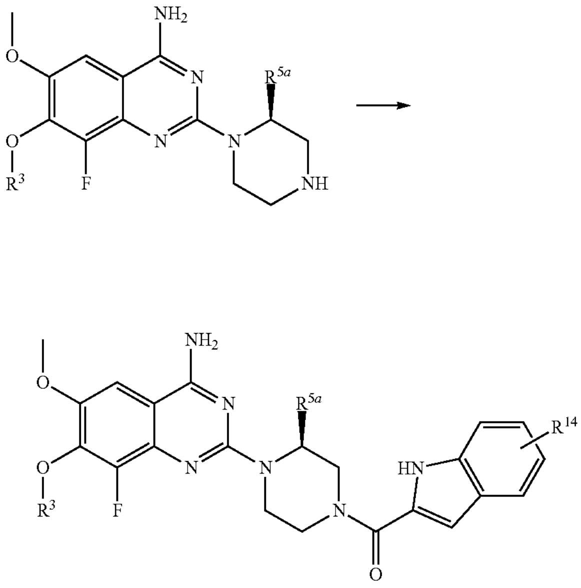

Example 17

Synthesis of [4-(4-Amino-8-fluoro-6,7-dimethoxy-quinazolin-2-yl)-piperazin-1-yl]-(1H-indol-2-yl)-methanone ($R^3$=methyl, $R^{5a}$=2-methoxyethyl, $R^{14}$=H)

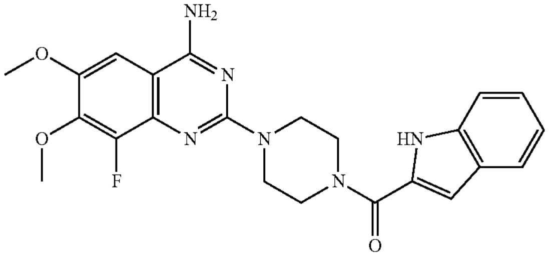 [SMILES: COc1cc2c(N)nc(N3CCN(C(=O)c4cc5ccccc5[nH]4)CC3)nc2c(F)c1OC]

This compound (as its free base) was synthesized analogously to example 2 (Method B) from 8-fluoro-6,7-dimethoxy-2-piperazin-1-yl-quinazolin-4-ylamine (21a) and (1H-indole-2-carboxylic acid (42.0 mg, 0.260 mmol). LC MS (ESI): 451.3 $[M+H]^+$, $t_R$=0.82 min (Method A2); $^1H$-NMR (600 MHz, DMSO-$d^6$) δ (ppm): 11.59 (s, 1H), 7.63 (d, 1H), 7.45 (d, 1H), 7.43 (br, 2H), 7.40 (s, 1H), 7.19 (dd, 1H), 7.06 (dd, 1H), 6.87 (s, 1H), 3.90 (s, 3H), 3.85 (s, 3H).

The following compounds were prepared with similar method

| Ex. | Structure/ Chemical Name | MS (ESI) m/z $[M + H]^+$ $t_R$ [min] (method) | $^1H$ NMR |
|---|---|---|---|
| 18 | 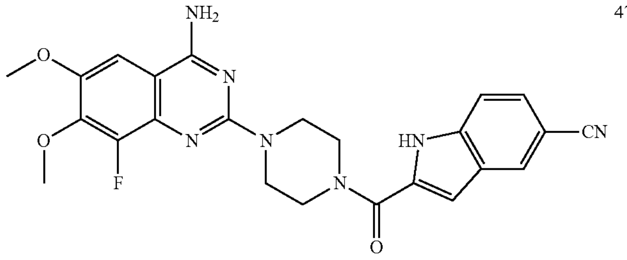 | 476.3 0.77 (A2) | (600 MHz, DMSO-$d^6$) δ (ppm): 12.15 (br, 1H), 8.14 (s, 1H), 7.54 (d, 1H), 7.50 (d, 1H), 7.36 (s, 1H), 6.97 (s, 1H), 3.86 (s, 3H), 3.80 (s, 3H), 3.75-3.9 (m, 10H) |

-continued

| Ex. | Structure/ Chemical Name | MS (ESI) m/z $[M + H]^+$ $t_R$ [min] (method) | $^1H$ NMR |
|---|---|---|---|
| | 2-[4-(4-Amino-8-fluoro-6,7-dimethoxy-quinazolin-2-yl)-piperazine-1-carbonyl]-1H-indole-5-carbonitrile | | |
| 19 | 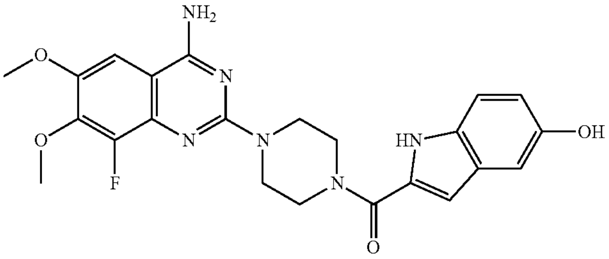 [SMILES: COc1cc2c(N)nc(N3CCN(C(=O)c4cc5cc(C#N)ccc5[nH]4)CC3)nc2c(F)c1OC] [4-(4-Amino-8-fluoro-6,7-dimethoxy-quinazolin-2-yl)-piperazin-1-yl]-(5-hydroxy-1H-indol-2-yl)-methanone | 467.3 0.64 (A2) | (600 MHz, DMSO-$d^6$) δ (ppm): 11.27 (br, 1H), 8.79 (s, 1H), 7.43 (br, 2H), 7.40 (s, 1H), 7.23 (d, 1H), 6.90 (s, 1H), 6.74 (d, 1H), 6.68 (s, 1H), 3.90 (s, 3H), 3.84 (s, 3H), 3.75-3.9 (m, 8H) |
| 20 | 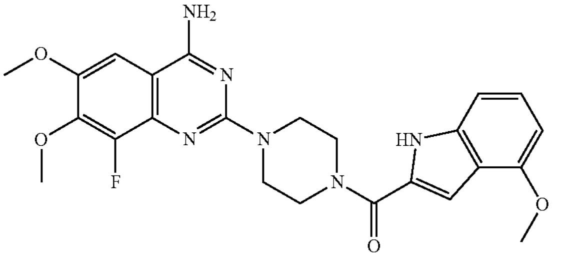 [SMILES: COc1cc2c(N)nc(N3CCN(C(=O)c4cc5c(OC)cccc5[nH]4)CC3)nc2c(F)c1OC] [4-(4-Amino-8-fluoro-6,7-dimethoxy-quinazolin-2-yl)-piperazin-1-yl]-(4-methoxy-1H-indol-2-yl)-methanone | 481.3 0.80 (A2) | (600 MHz, DMSO-$d^6$) δ (ppm): 11.59 (br, 1H), 7.43 (br, 2H), 7.40 (s, 1H), 7.10 (dd, 1H), 7.04 (d, 1H), 6.82 (s, 1H), 6.54 (d, 1H), 3.9 (s, 3H), 3.89 (s, 3H), 3.84 (s, 3H), 3.8-3.9 (m, 8H) |
| 21 | 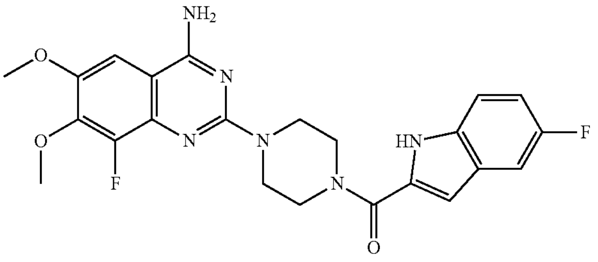 [SMILES: COc1cc2c(N)nc(N3CCN(C(=O)c4cc5cc(F)ccc5[nH]4)CC3)nc2c(F)c1OC] [4-(4-Amino-8-fluoro-6,7-dimethoxy-quinazolin-2-yl)-piperazin-1-yl]-(5-fluoro-1H-indol-2-yl)-methanone | 469.3 0.83 (A2) | (600 MHz, DMSO-$d^6$) δ (ppm): 11.17 (s, 1H), 7.47 (br, 2H), 7.43 (d, 1H), 7.40 (d, 1H), 7.36 (s, 1H), 7.06 (m, 1H), 6.85 (s, 1H), 3.9 (s, 3H), 3.84 (s, 3H), 3.8-3.9 (m, 8H) |
| 22 | 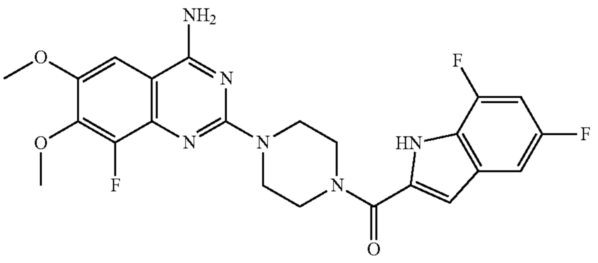 [SMILES: COc1cc2c(N)nc(N3CCN(C(=O)c4cc5cc(F)cc(F)c5[nH]4)CC3)nc2c(F)c1OC] [4-(4-Amino-8-fluoro-6,7-dimethoxy-quinazolin-2-yl)-piperazin-1-yl]-(5,7-difluoro-1H-indol-2-yl)-methanone | 487.3 0.86 (A2) | (600 MHz, DMSO-$d^6$) δ (ppm): 12.21 (s, 1H), 7.44 (br, 2H), 7.40 (s, 1H), 7.26 (dd, 1H), 7.08 (dt, 1H), 6.88 (s, 1H), 3.90 (s, 3H), 3.85 (s, 3H), 3.77 (m, 8H) |

-continued

| Ex. | Structure/<br>Chemical Name | MS (ESI)<br>m/z [M + H]$^+$<br>$t_R$ [min]<br>(method) | $^1$H NMR |
|---|---|---|---|
| 23 | 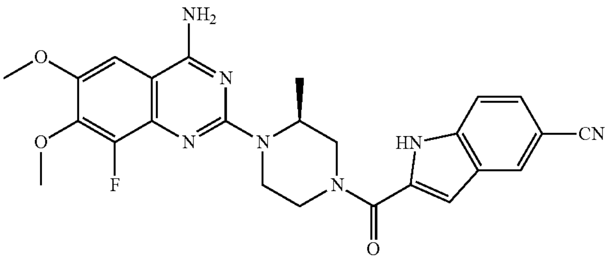 [SMILES: COc1cc2c(N)nc(N3CCN(C(=O)c4cc5cc(C#N)ccc5[nH]4)C[C@@H]3C)nc2c(F)c1OC]<br>2-[(S)-4-(4-Amino-8-fluoro-6,7-dimethoxy-quinazolin-2-yl)-3-methyl-piperazine-1-carbonyl]-1H-indole-5-carbonitrile | 490.3<br>0.81 (A2) | (600 MHz, DMSO-d$^6$) δ (ppm): 12.22 (s, 1H), 8.19 (s, 1H), 7.58 (d, 1H), 7.53 (d, 1H), 7.41 (br, 2H), 7.39 (s, 1H), 7.01 (br, 1H), 5.04 (m, 1H), 4.57 (m, 1H), 4.43 (m, 1 H), 4.3 (m, 1 H), 3.89 (s, 3H), 3.84 (s, 3H), 3.24 (m, 3H), 1.13 (d, 3H) |
| 24 | 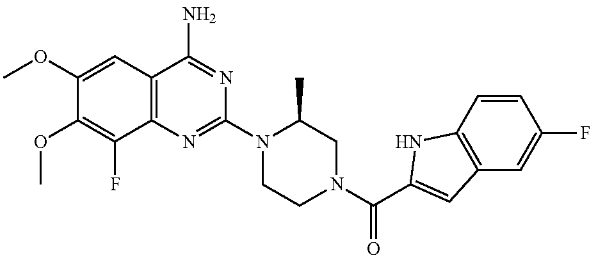 [SMILES: COc1cc2c(N)nc(N3CCN(C(=O)c4cc5cc(F)ccc5[nH]4)C[C@@H]3C)nc2c(F)c1OC]<br>[(S)-4-(4-Amino-8-fluoro-6,7-dimethoxy-quinazolin-2-yl)-3-methyl-piperazin-1-yl]-(5-fluoro-1H-indol-2-yl)-methanone | 483.3<br>0.88 (A2) | 600 MHz, DMSO-d$^6$) δ (ppm): 11.74 (s, 1H), 7.44 (m, 1H), 7.39 (br, 2H), 7.39 (s, 1H), 7.37 (d, 1H), 7.05 (dt, 1H), 6.85 (br, 1H), 5.03 (m, 1H), 4.55 (m, 1H), 4.45 (m, 1H), 4.35 (m, 1H), 3.89 (s, 3H), 3.84 (s, 3H), 3.2 (m, 3H), 1.13 (d, 3H) |
| 25 | 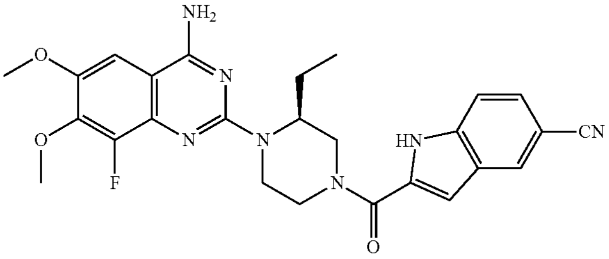 [SMILES: CC[C@H]1CN(C(=O)c2cc3cc(C#N)ccc3[nH]2)CCN1c1nc(N)c2cc(OC)c(OC)c(F)c2n1]<br>2-[(S)-4-(4-Amino-8-fluoro-6,7-dimethoxy-quinazolin-2-yl)-3-ethyl-piperazine-1-carbonyl]-1H-indole-5-carbonitrile | 504.3<br>0.86 (A2) | (600 MHz, DMSO-d$^6$) δ (ppm): 11.70 (br, 1H), 8.07 (s, 1H), 7.56 (d, 1H), 7.42 (m, 1H), 7.32 (s, 1H), 6.91 (s, 1H), 6.86 (br, 2H), 4.86 (m, 1H), 4.66 (m, 1H), 4.29 (m, 2H), 3.91 (s, 3H), 3.85 (s, 3H), 3.35 (m, 1H), 3.25 (m, 2H), 1.62 (m, 2H), 0.84 (t, 3H) |
| 26 | 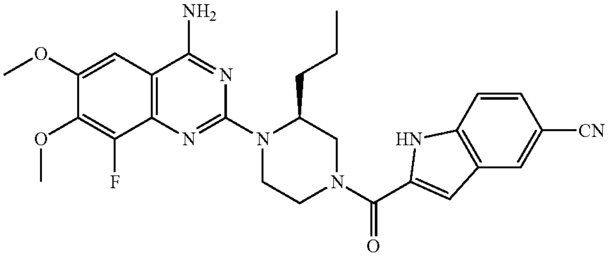 [SMILES: CCC[C@H]1CN(C(=O)c2cc3cc(C#N)ccc3[nH]2)CCN1c1nc(N)c2cc(OC)c(OC)c(F)c2n1]<br>2-[(S)-4-(4-Amino-8-fluoro-6,7-dimethoxy-quinazolin-2-yl)-3-propyl-piperazine-1-carbonyl]-1H-indole-5-carbonitrile | 518.3<br>0.92 (A2) | (600 MHz, DMSO-d$^6$) δ (ppm): 12.24 (s, 1H), 8.19 (s, 1H), 7.57 (d, 1H), 7.56 (d, 1H), 7.38 (s, 1H), 7.3-7.5 (br, 2H), 7.00 (br, 1H), 5.03 (m, 1H), 4.65 (m, 1H), 4.4 (m, 2H), 3.89 (s, 3H), 3.84 (s, 3H), 3.15 (m, 3H), 1.57 (m, 2H), 1.14 (m, 2H), 0.86 (m, 3H) |

-continued

| Ex. | Structure/ Chemical Name | MS (ESI) m/z [M + H]+ $t_R$ [min] (method) | $^1$H NMR |
|---|---|---|---|
| 27 | 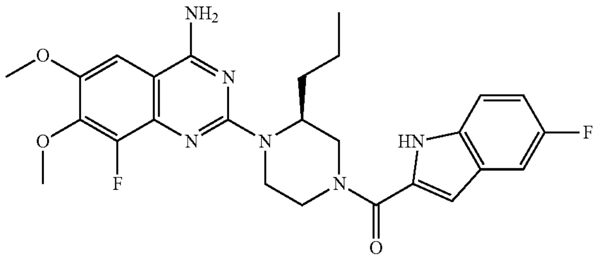 [SMILES: CCC[C@H]1CN(C(=O)c2cc3cc(F)ccc3[nH]2)CCN1c1nc(N)c2cc(OC)c(OC)c(F)c2n1] [(S)-4-(4-Amino-8-fluoro-6,7-dimethoxy-quinazolin-2-yl)-3-propyl-piperazin-1-yl]-(5-fluoro-1H-indol-2-yl)-methanone | 511.3 1.00 (A2) | (600 MHz, DMSO-d$^6$) δ (ppm): 11.74 (s, 1H), 7.42 (m, 1H), 7.4 (br, 2H), 7.38 (s, 1H), 7.37 (m, 1H), 7.05 (m, 1H), 6.83 (br, 1H), 4.99 (m, 1H), 4.66 (m, 1H), 4.42 (m, 2H), 3.89 (s, 3H), 3.83 (s, 3H), 3.14 (m, 3H), 1.56 (m, 2H), 1.23 (m, 2H), 0.85 (m, 3H) |
| 28 | 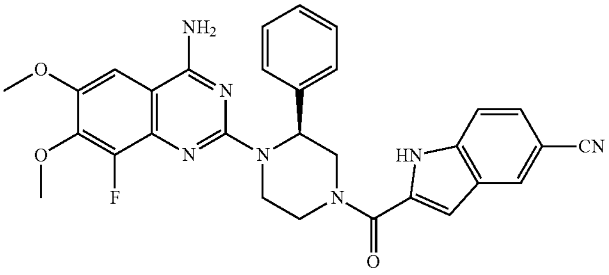 [SMILES: COc1cc2c(N)nc(N3CCN(C(=O)c4cc5cc(C#N)ccc5[nH]4)C[C@@H]3c3ccccc3)nc2c(F)c1OC] 2-[(S)-4-(4-Amino-8-fluoro-6,7-dimethoxy-quinazolin-2-yl)-3-phenyl-piperazine-1-carbonyl]-1H-indole-5-carbonitrile | 552.3 0.98 (A2) | (600 MHz, DMSO-d$^6$) δ (ppm): 12.15 (s, 1H), 8.17 (s, 1H), 7.6 (d, 1H), 7.55 (d, 1H), 7.41 (s, 1H), 7.0-7.5 (m, 7H), 6.92 (br, 1H), 6.20 (m, 1H), 3.5-5.2 (m, 6H), 3.90 (s, 3H), 3.85 (s, 3H) |
| 29 | 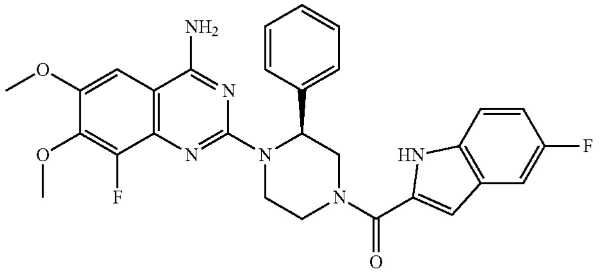 [(S)-4-(4-Amino-8-fluoro-6,7-dimethoxy-quinazolin-2-yl)-3-phenyl-piperazin-1-yl]-(5-fluoro-1H-indol-2-yl)-methanone | 545.3 1.05 (A2) | (600 MHz, DMSO-d$^6$) δ (ppm): 11.67 (br, 1H), 7.45 (br, 2H), 7.42 (m, 1H), 7.41 (s, 1H), 7.34 (m, 1H), 7.26 (m, 4H), 7.19 (m, 1H), 7.05 (m, 1H), 6.76 (br, 1H), 6.17 (m, 1H), 4.96 (m, 1H), 4.71 (m, 1H), 4.29 (m, 1H), 3.90 (s, 3H), 3.84 (s, 3H), 3.3-3.7 (m, 3H) |
| 30 | 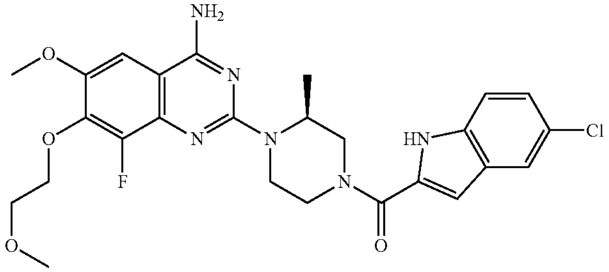 [SMILES: COCCOc1c(OC)cc2c(N)nc(N3CCN(C(=O)c4cc5cc(Cl)ccc5[nH]4)C[C@@H]3C)nc2c1F] {(S)-4-[4-Amino-8-fluoro-6-methoxy-7-(2-methoxy-ethoxy)-quinazolin-2-yl]-3-methyl-piperazin-1-yl}-(5-chloro-1H-indol-2-yl)-methanone | 543.2 0.97 (A2) | (600 MHz, DMSO-d$^6$) δ (ppm): 11.8 (s, 1H), 7.68 (d, 1H), 7.45 (d, 1H), 7.43 (br, 2H), 7.40 (s, 1H), 7.21 (dd, 1H), 6.86 (br, 1H), 5.05 (m, 1H), 4.58 (m, 1H), 4.45 (m, 1H), 4.32 (m, 1H), 4.2 (t, 2H), 3.85 (s, 3H), 3.62 (t, 2H), 3.3 (s, 3H), 3.1-3.4 (m, 3H), 1.15 (m, 3H) |

Reaction Scheme 18:

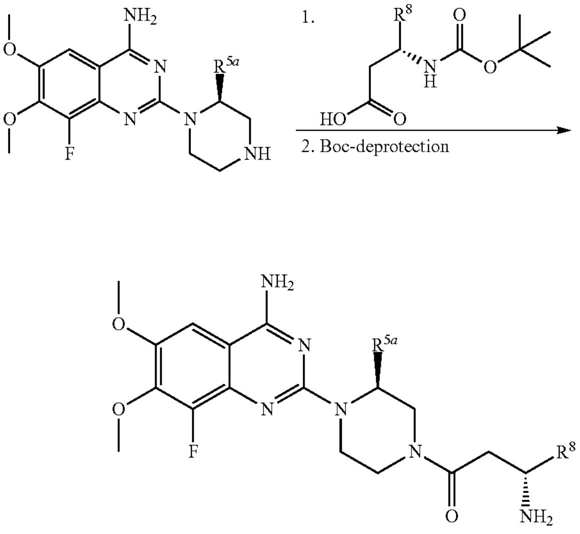

Example 31

Synthesis of (S)-3-Amino-1-[4-(4-amino-8-fluoro-6,7-dimethoxy-quinazolin-2-yl)-piperazin-1-yl]-hex-5-yn-1-one ($R^{5a}$=H, $R^8$=propargyl)

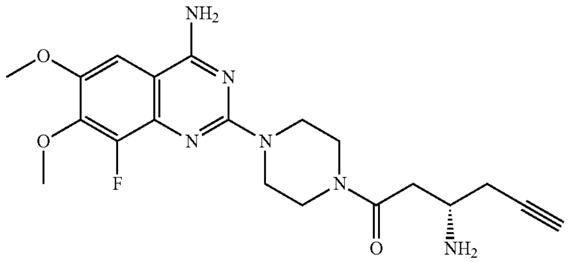 [SMILES: C#CC[C@H](N)CC(=O)N1CCN(c2nc(N)c3cc(OC)c(OC)c(F)c3n2)CC1]

Step A ((S)-1-{2-[4-(4-Amino-8-fluoro-6,7-dimethoxy-quinazolin-2-yl)-piperazin-1-yl]-2-oxo-ethyl}-but-3-ynyl)-carbamic acid tert-butyl ester 8-Fluoro-6,7-dimethoxy-2-piperazin-1-yl-quinazolin-4-ylamine (21a) (80 mg, 0.260 mmol), (S)-3-(tert-butoxycarbonylamino)hex-5-ynoic acid (59.2 mg, 0.260 mmol), HOBT (51.8 mg, 0.338 mmol), $Et_3N$ (0.090 ml, 0.651 mmol) and EDC (74.9 mg, 0.390 mmol) were dissolved in $CH_2Cl_2$ (2 ml). The reaction mixture was stirred for 16 h at RT. Then the mixture was diluted with $CH_2Cl_2$, washed with $NaHCO_3$ and brine, dried over $Na_2SO_4$ and the solvent was evaporated. The crude product was purified by flash chromatography (silica, 50-100% EtOAc in cyclohexane). LC MS (ESI): 517.5 $[M+H]^+$, $t_R$=0.80 min (Method A2); $^1$H-NMR (600 MHz, DMSO-$d^6$) δ (ppm): 7.41 (br, 2H), 7.38 (s, 1H), 6.78 (br d, 1H), 3.94 (m, 1H), 3.89 (s, 3H), 3.84 (s, 3H), 3.4-3.8 (m, 8H), 2.83 (s, 1H), 2.58 (m, 2H), 2.37 (m, 2H), 1.36 (s, 9H).

Step B: (S)-3-Amino-1-[4-(4-amino-8-fluoro-6,7-dimethoxy-quinazolin-2-yl)-piperazin-1-yl]-hex-5-yn-1-one 4N HCl in dioxane (0.823 ml, 3.29 mmol) was added to a solution of ((S)-1-{2-[4-(4-amino-8-fluoro-6,7-dimethoxy-quinazolin-2-yl)-piperazin-1-yl]-2-oxo-ethyl}-but-3-ynyl)-carbamic acid tert-butyl ester (85 mg, 0.165 mmol) in dioxane (0.3 ml) and the reaction mixture was stirred for 2 h at RT. Then the product was collected by filtration, washed with ether and dried under high vacuum. The crude product was purified by SFC chromatography to afford the title compound as its hydrochloride salt. LC MS (ESI): 417.3 $[M+H]^+$, $t_R$=0.47 min (Method A2); $^1$H-NMR (600 MHz, DMSO-$d^6$) δ (ppm): 8.94 (br, 2H), 8.28 (br, 2H), 7.81 (s, 1H), 3.99 (s, 3H), 3.91 (s, 3H), 3.1-3.8 (m, 10H), 2.87 (m, 2H), 2.67 (m, 2H).

Example 32

Synthesis of (R)-3-Amino-1-[4-(4-amino-8-fluoro-6,7-dimethoxy-quinazolin-2-yl)-piperazin-1-yl]-3-cyclopentyl-propan-1-one (R1=H, R2=cyclopentyl)

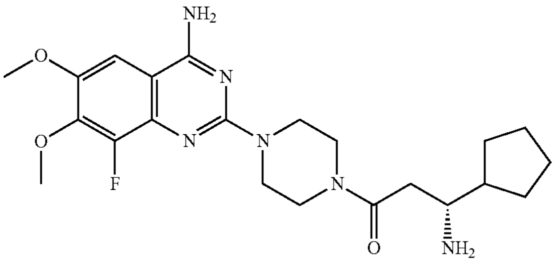 [SMILES: COc1cc2c(N)nc(N3CCN(C(=O)C[C@@H](N)C4CCCC4)CC3)nc2c(F)c1OC]

8-Fluoro-6,7-dimethoxy-2-piperazin-1-yl-quinazolin-4-ylamine (21a) (100 mg, 0.291 mmol) and triethylamine (0.162 ml, 1.164 mmol) were added to a solution of (R)-3-tert-butoxycarbonyl-amino-3-cyclopentyl-propionic acid (59a) (74.9 mg, 0.291 mmol), HOBT (49.0 mg, 0.320 mmol) and HBTU (121 mg, 0.320 mmol) in $CH_3CN$ (6 ml), Stirring at RT was continued for 12 h. For workup EtOAc was added and the organic phase was washed with a saturated solution of $NaHCO_3$. The organic phase was dried over a phase separator and concentrated. Boc-deprotection was performed as described in example 31, step B. The crude product was purified by preparative HPLC (method P5). After evaporation of the solvent the residue was dissolved in $CH_3CN$/water, 4N HCl in dioxane was added, the mixture was frozen followed by lyophilization to yield the title compound as its hydrochloride salt. LC MS (ESI): 469.1 $[M+Na]^+$, $t_R$=0.78 min (Method A3); $^1$H NMR (400 MHz, DMSO-$d^6$) δ ppm 7.95 (3H, br. s), 7.75 (1H, br. s), 4.00 (3H, s), 3.91 (3H, s), 3.83 (4H, br. s), 3.64 (4H, br. s), 2.66-2.86 (2H, m), 2.11 (1H, dq), 1.42-1.90 (6H, m), 1.18-1.39 (2H, m).

The following compounds were prepared with similar methods

| Ex. | Structure/Chemical Name<br>Coupling Method, solvent<br>Boc-deprotection | MS (ESI)<br>m/z [M + H]$^+$<br>$t_R$ [min]<br>(method) | $^1$H NMR |
|---|---|---|---|
| 33 | 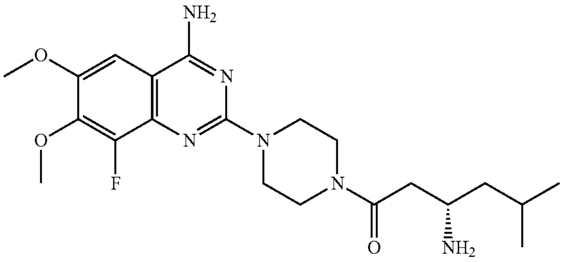 [SMILES: COc1cc2c(N)nc(N3CCN(C(=O)C[C@@H](N)CC(C)C)CC3)nc2c(F)c1OC]<br>(S)-3-Amino-1-[4-(4-amino-8-fluoro-6,7-dimethoxy-quinazolin-2-yl)-piperazin-1-yl]-5-methyl-hexan-1-one<br>example 3, DMF<br>TFA in $CH_2Cl_2$ | 435.1<br>0.67 (A3) | (400 MHz, DMSO-d$^6$) δ (ppm): 7.43 (brs, 1H), 7.39 (s, 1H), 3.90 (s, 3H), 3.85 (s, 3H), 3.76-3.72 (m, 4H), 3.56-3.52 (m, 4H), 3.015 (m, 1H), 2.42 (m, 2H), 1.76 (m, 1H), 1.22 (m, 2H), 0.88 (dd, 6H) |
| 34 | 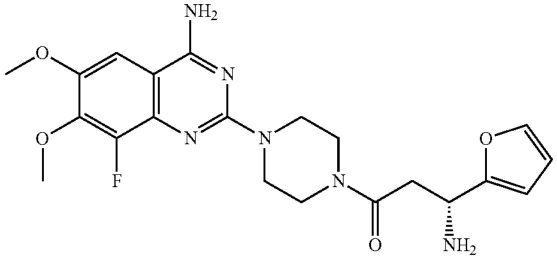 [SMILES: COc1cc2c(N)nc(N3CCN(C(=O)C[C@@H](N)c4ccco4)CC3)nc2c(F)c1OC]<br>(R)-3-Amino-1-[4-(4-amino-8-fluoro-6,7-dimethoxy-quinazolin-2-yl)-piperazin-1-yl]-3-furan-2-yl-propan-1-one hydrochloride<br>example 2, $CH_2Cl_2$<br>4N HCl/dioxane (ex. 31, step B) | 445.4<br>0.50 (A2) | (600 MHz, DMSO-d$^6$) δ (ppm): 9.0 (br, 2H), 8.58 (br, 3H), 7.78 (m, 1H), 7.74 (s, 1H), 6.62 (m, 1H), 6.51 (m, 1H), 4.74 (m, 1H), 3.99 (s, 3H), 3.91 (s, 3H), 3.5-3.85 (m, 8H), 3.17 (d, 2H). |
| 35 | 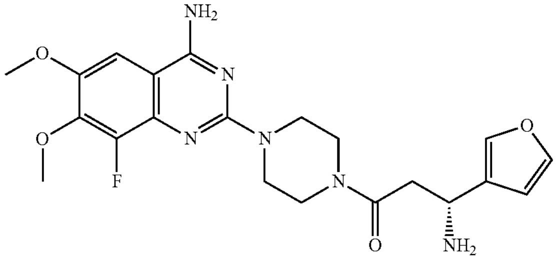 [SMILES: COc1cc2c(N)nc(N3CCN(C(=O)C[C@@H](N)c4ccoc4)CC3)nc2c(F)c1OC]<br>(R)-3-Amino-1-[4-(4-amino-8-fluoro-6,7-dimethoxy-quinazolin-2-yl)piperazin-1-yl]-3-furan-3-yl-propan-1-one hydrochloride<br>example 4, $CH_3CN$<br>4N HCl/dioxane (ex. 31, step B) | 445.0<br>0.28 (A3) | (400 MHz, methanol-d$^4$) δ (ppm): 7.79 (s, 1H), 7.63 (d, 1H), 7.59 (d, 1H), 6.71 (s, 1H), 4.80 (dd, 1H), 4.13 (s, 3H), 4.00 (s, 3H), 3.96 (m, 4H), 3.81 (m, 4H), 3.20 (d, 2H) |
| 36 | 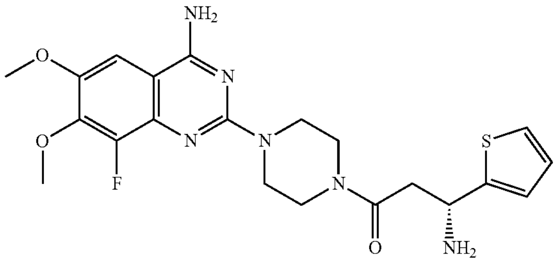 [SMILES: COc1cc2c(N)nc(N3CCN(C(=O)C[C@@H](N)c4cccs4)CC3)nc2c(F)c1OC]<br>(R)-3-Amino-1-[4-(4-amino-8-fluoro-6,7-dimethoxy-quinazolin-2-yl)-piperazin-1-yl]-3-thiophen-2-yl-propan-1-one hydrochloride<br>example 32, $CH_3CN$/DMF 4:1<br>4N HCl/dioxane (ex. 31, step B) | 461.0<br>0.45 (A3) | (400 MHz, DMSO-d$^6$) δ (ppm) 7.35 (d, J = 4.9 Hz, 1H), 7.39 (s, 2H), 6.91-7.03 (m, 2H), 4.55 (br, 1H), 3.90 (s, 3H), 3.85 (s, 3H), 3.70-3.80 (m, 2H), 3.48 (br. s., 6H), 2.62-2.84 (m, 2H) |

-continued

| Ex. | Structure/Chemical Name<br>Coupling Method, solvent<br>Boc-deprotection | MS (ESI)<br>m/z $[M + H]^+$<br>$t_R$ [min]<br>(method) | $^1$H NMR |
|---|---|---|---|
| 37 | 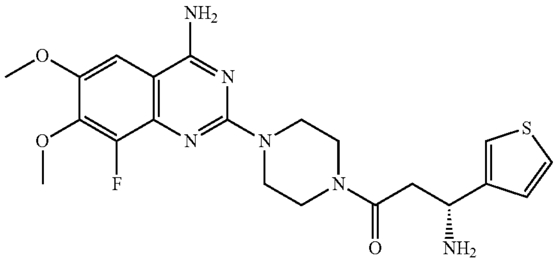 [SMILES: COc1cc2c(N)nc(N3CCN(C(=O)C[C@@H](N)c4ccsc4)CC3)nc2c(F)c1OC]<br>(R)-3-Amino-1-[4-(4-amino-8-fluoro-6,7-dimethoxy-quinazolin-2-yl)-piperazin-1-yl]-3-thiophen-3-yl-propan-1-one<br>example 4, $CH_3CN$<br>4N HCl/dioxane (ex. 31, step B) | 461.0<br>0.40 (A3) | (400 MHz, methanol-d$^4$) δ (ppm): 7.40 (dd, 1H), 7.33 (m, 1H), 7.25 (s, 1H), 7.20 (dd, 1H), 4.54 (dd, 1H), 4.00 (s, 3H), 3.93 (s, 3H), 3.85-3.53 (m, 8H), 2.89 (m, 2H) |
| 38 | 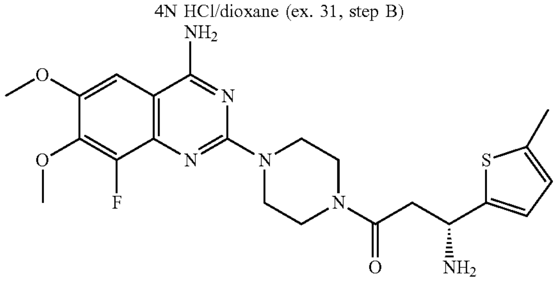<br>(R)-3-Amino-1-[4-(4-amino-8-fluoro-6,7-dimethoxy-quinazolin-2-yl)piperazin-1-yl]-3-(5-methyl-thiophen-2-yl)-propan-1-one (R1 = H, R2 = 5-methyl-thiophen-2-yl)hydrochloride<br>example 32, $CH_3CN$<br>4N HCl/dioxane (ex. 31, step B) | 475.0<br>0.73 (A3) | (400 MHz, DMSO-d$^6$) δ: 7.72 (br. s., 1H), 7.12 (d, J = 3.4 Hz, 1H), 6.76 (dd, J = 3.4, 1.2 Hz, 1H), 4.84 (br. s., 1H), 4.00 (s, 3H), 3.91 (s, 3H), 3.82 (br. s., 4H), 3.63 (br. s., 4H), 3.16 (br. s., 2H), 2.44 (s, 3H) |
| 39 | 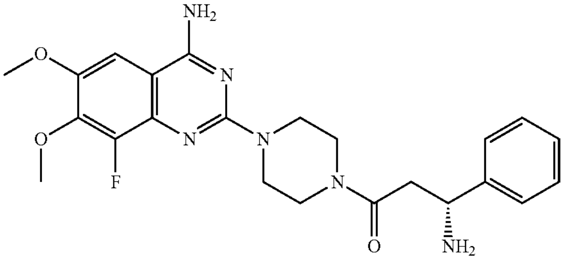 [SMILES: COc1cc2c(N)nc(N3CCN(C(=O)C[C@@H](N)c4ccccc4)CC3)nc2c(F)c1OC]<br>(R)-3-Amino-1-[4-(4-amino-8-fluoro-6,7-dimethoxy-quinazolin-2-yl)-piperazin-1-yl]-3-phenyl-propan-1-one<br>example 32, $CH_3CN$/DMF 4:1<br>4N HCl/dioxane (ex. 31, step B) | 455.3<br>0.41 (A1) | (400 MHz, DMSO-d$^6$) δ (ppm): 8.41 (br s, 3H), 7.63-7.62 (m, 2H), 7.60 (br s, 3H), 7.56 (d, 1H), 7.48-7.37 (m, 3H), 4.66 (br s, 1H), 3.98 (s, 3H), 3.89 (s, 3H), 3.85-3.77 (m, 2H), 3.76-3.67 (m, 2H), 3.64-3.50 (m, 7H), 3.20-2.99 (m, 3H) |
| 40 | 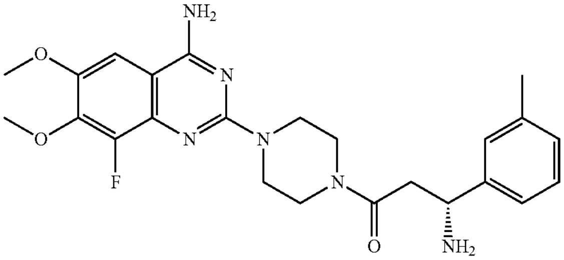 [SMILES: COc1cc2c(N)nc(N3CCN(C(=O)C[C@@H](N)c4cccc(C)c4)CC3)nc2c(F)c1OC]<br>(R)-3-Amino-1-[4-(4-amino-8-fluoro-6,7-dimethoxy-quinazolin-2-yl)-piperazin-1-yl]-3-m-tolyl-propan-1-one<br>example 4, $CH_3CN$<br>4N HCl/dioxane (ex. 31, step B) | 491.0<br>$[M + Na]^+$<br>0.78 (A3) | (400 MHz, methanol-d$^4$) δ (ppm): 7.25 (s, 1H), 7.23 (m, 2H), 7.10 (m, 1H), 4.36 (dd, 1H), 4.00 (s, 3H), 3.93 (s, 3H), 3.93-3.47 (m, 8H), 2.83 (dd, 2H), 2.36 (s, 3H) |

-continued

| Ex. | Structure/Chemical Name Coupling Method, solvent Boc-deprotection | MS (ESI) m/z $[M + H]^+$ $t_R$ [min] (method) | $^1H$ NMR |
|---|---|---|---|
| 41 | 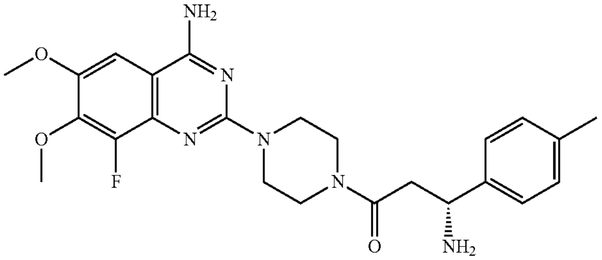 (R)-3-Amino-1-[4-(4-amino-8-fluoro-6,7-dimethoxy-quinazolin-2-yl)-piperazin-1-yl]-3-p-tolyl-propan-1-one example 4, $CH_3CN$ 4N HCl/dioxane (ex. 31, step B) | 469.0 0.85 (A3) | (400 MHz, methanol-$d^4$) δ (ppm): 7.31 (dd, 2H), 7.25 (s, 1H), 7.19 (dd, 2H), 4.38 (dd, 1H), 4.00 (s, 3H), 3.93 (s, 3H), 3.85-3.48 (m, 8H), 2.84 (m, 2H), 2.32 (s, 3H) |
| 42 | 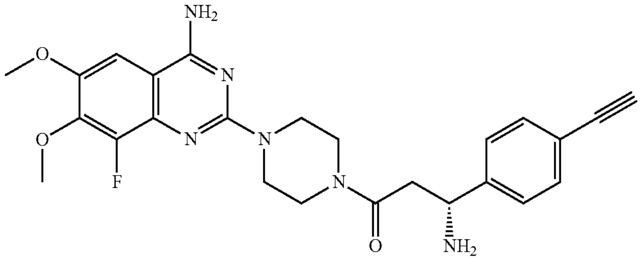 [SMILES: C#Cc1ccc([C@H](N)CC(=O)N2CCN(c3nc(N)c4cc(OC)c(OC)c(F)c4n3)CC2)cc1] (R)-3-Amino-1-[4-(4-amino-8-fluoro-6,7-dimethoxy-quinazolin-2-yl)-piperazin-1-yl]-3-(4-ethynyl-phenyl)-propan-1-one hydrochloride example 2, $CH_2Cl_2$ 4N HCl/dioxane (ex. 31, step B) | 479.3 0.60 (A2) | (600 MHz, DMSO-$d^6$) δ (ppm): 9.28 (br, 1H), 8.96 (br, 1H), 8.7 (br, 2H), 7.84 (s, 1H), 7.62 (d, 2H), 7.53 (d, 2H), 4.64 (m, 1H), 4.24 (s, 1H), 3.99 (s, 3H), 3.91 (s, 3H), 3.5-3.9 (m, 8H), 3.25 (m, 1 H), 3.08 (m, 1H) |
| 43 | 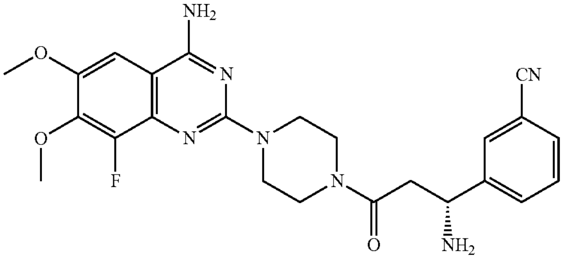 [SMILES: COc1cc2c(N)nc(N3CCN(C(=O)C[C@@H](N)c4cccc(C#N)c4)CC3)nc2c(F)c1OC] 3-{(R)-1-Amino-3-[4-(4-amino-8-fluoro-6,7-dimethoxy-quinazolin-2-yl)-piperazin-1-yl]-3-oxo-propyl}-benzonitrile example 4, $CH_3CN$ 4N HCl/dioxane (ex. 31, step B) | 502.0 $[M + Na]^+$ 0.58 (A3) | (400 MHz, methanol-$d^4$) δ (ppm): 7.84 (s, 1H), 7.75 (d, 1H), 7.56 (dd, 1H), 7.25 (s, 1H), 4.47 (dd, 1H), 4.00 (s, 3H), 3.93 (s, 3H), 3.84-3.51 (m, 8H), 2.87 (d, 2H) |
| 44 | 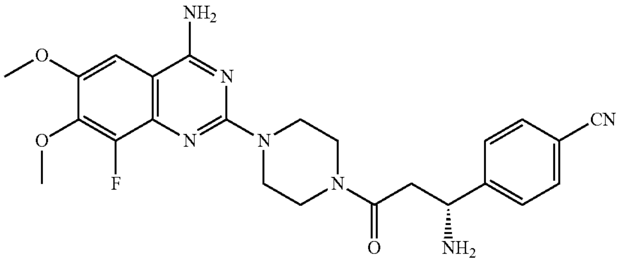 [SMILES: COc1cc2c(N)nc(N3CCN(C(=O)C[C@@H](N)c4ccc(C#N)cc4)CC3)nc2c(F)c1OC] 4-{(R)-1-Amino-3-[4-(4-amino-8-fluoro-6,7-dimethoxy-quinazolin-2-yl)piperazin-1-yl]-3-oxo-propyl}-benzonitrile hydrochloride example 2, $CH_2Cl_2$ 4N HCl/dioxane (ex. 31, step B) | 480.5 0.54 (A2) | (600 MHz, DMSO-$d^6$) δ (ppm): 8.76 (br,4H), 7.91 (d, 2H), 7.82 (d, 2H), 7.78 (s, 1H), 4.74 (m, 1H), 3.99 (s, 3H), 3.90 (s, 3H), 3.7-3.9 (m, 4H), 3.5-3.7 (m,4H), 3.26 (m, 1H), 3.10 (m, 1H) |

-continued

| Ex. | Structure/Chemical Name<br>Coupling Method, solvent<br>Boc-deprotection | MS (ESI)<br>m/z $[M + H]^+$<br>$t_R$ [min]<br>(method) | $^1H$ NMR |
|---|---|---|---|
| 45 | 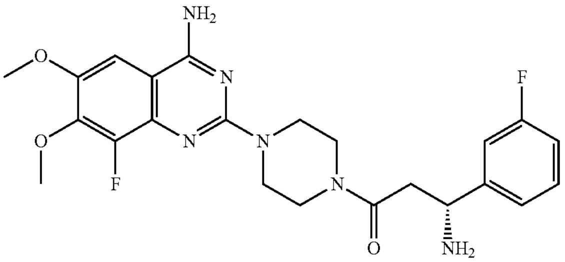<br>(R)-3-Amino-1-[4-(4-amino-8-fluoro-6,7-dimethoxy-quinazolin-2-yl)-piperazin-1-yl]-3-(3-fluoro-phenyl)-propan-1-one<br>example 4, $CH_3CN$<br>4N HCl/dioxane (ex. 31, step B) | 473.0<br>0.59 (A3) | (400 MHz, methanol-$d^4$) δ (ppm): 7.38 (m, 1 H), 7.25 (s, 1H), 7.21 (m, 2H), 7.01 (m, 1H), 4.42 (dd, 1H), 4.00 (s, 3H), 3.93 (s, 3H), 3.84-3.51 (m, 8H), 2.85 (m, 2H) |
| 46 | 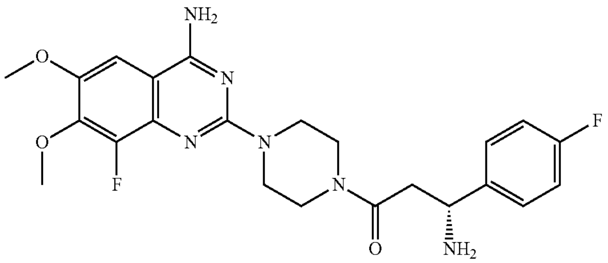 [SMILES: COc1cc2c(N)nc(N3CCN(C(=O)C[C@@H](N)c4ccc(F)cc4)CC3)nc2c(F)c1OC]<br>(R)-3-Amino-1-[4-(4-amino-8-fluoro-6,7-dimethoxy-quinazolin-2-yl)-piperazin-1-yl]-3-(4-fluoro-phenyl)-propan-1-one<br>example 32, $CH_3CN$<br>4N HCl/dioxane (ex. 31, step B) | 473.0<br>0.45 (A3) | (400 MHz, DMSO-$d^6$) δ (ppm): 7.71-7.68 (m, 1H), 7.64 (dd, 2H), 7.30 (t, 2H), 4.67 (br s, 1H), 3.99 (s, 3H), 3.90 (s, 4H), 3.79 (br s, 4H), 3.60 (br s, 7H), 3.25-3.00 (m, 3H) |
| 47 | 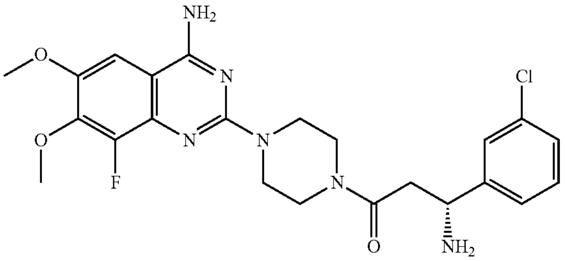<br>(R)-3-Amino-1-[4-(4-amino-8-fluoro-6,7-dimethoxy-quinazolin-2-yl)-piperazin-1-yl]-3-(3-chloro-phenyl)-propan-1-one<br>example 4, $CH_3CN$<br>4N HCl/dioxane (ex. 31, step B) | 511.0<br>$[M + Na]^+$<br>0.89 (A3) | (400 MHz, methanol-$d^4$) δ (ppm): 7.49 (s, 1H), 7.36 (m, 2H), 7.30 (m, 1H), 7.25 (s, 1H), 4.41 (m, 1H), 4.00 (s, 3H), 3.93 (s, 3H), 3.85-3.53 (m, 8H), 2.85 (m, 2H) |
| 48 | 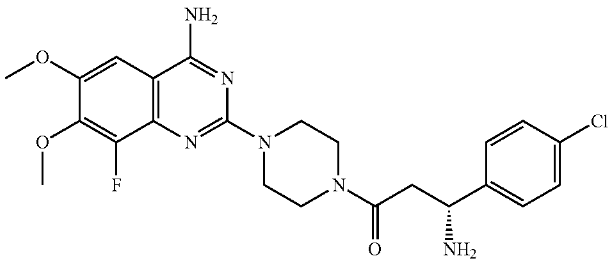 [SMILES: COc1cc2c(N)nc(N3CCN(C(=O)C[C@@H](N)c4ccc(Cl)cc4)CC3)nc2c(F)c1OC]<br>(R)-3-Amino-1-[4-(4-amino-8-fluoro-6,7-dimethoxy-quinazolin-2-yl)-piperazin-1-yl]-3-(4-chloro-phenyl)-propan-1-one hydrochloride<br>example 32, $CH_3CN$/DMF 1:1<br>4N HCl/dioxane (ex. 31, step B) | 489.0<br>1.06 (A3) | (400 MHz, DMSO-$d^6$) δ: 7.55 (s, 5H), 4.68 (br. s., 1H), 3.96 (br. s., 3H), 3.88 (s, 3H), 3.68-3.84 (m, 4H), 3.58 (s, 5H), 3.08 (br. s., 2H) |

-continued

| Ex. | Structure/Chemical Name<br>Coupling Method, solvent<br>Boc-deprotection | MS (ESI)<br>m/z [M + H]$^+$<br>$t_R$ [min]<br>(method) | $^1$H NMR |
|---|---|---|---|
| 49 | 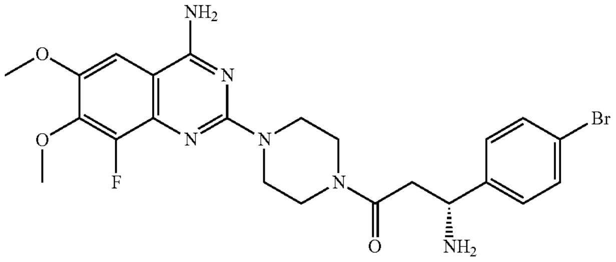 [SMILES: COc1cc2c(N)nc(N3CCN(C(=O)C[C@@H](N)c4ccc(Br)cc4)CC3)nc2c(F)c1OC]<br>(R)-3-Amino-1-[4-(4-amino-8-fluoro-6,7-dimethoxy-quinazolin-2-yl)-piperazin-1-yl]-3-(4-bromo-phenyl)-propan-1-one hydrochloride<br>example 32, $CH_3CN$<br>4N HCl/dioxane (ex. 31, step B) | 534.0<br>1.13 (A3) | (400 MHz, DMSO-d$^6$) δ (ppm): 8.44 (brs, 3H), 7.68-7.52 (m, 5H), 4.67 (m, 1H), 3.97 (s, 3H), 3.89 (s, 3H), 3.77-3.67 (m, 8H), 3.13 (m, 2H) |
| 50 | 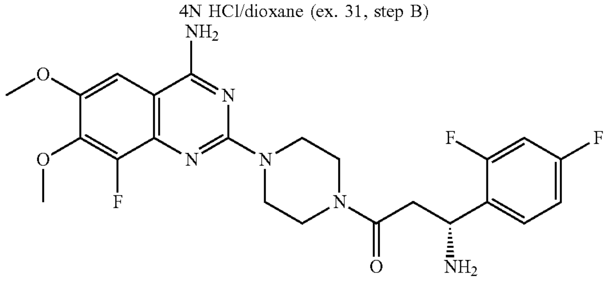<br>(R)-3-Amino-1-[4-(4-amino-8-fluoro-6,7-dimethoxy-quinazolin-2-yl)-piperazin-1-yl]-3-(2,4-difluoro-phenyl)-propan-1-one hydrochloride<br>example 2, $CH_2Cl_2$<br>4N HCl/dioxane (ex. 31, step B) | 491.3<br>0.57 (A2) | (600 MHz, DMSO-d$^6$) δ (ppm): 8.81 (br, 3H), 7.93 (m, 1H), 7.88 (s, 1H), 7.32 (m, 1H), 7.20 (m, 1H), 4.83 (m, 1H), 4.00 (s, 3H), 3.91 (s, 3H), 3.7-3.9 (m, 4H), 3.6-3.7 (m, 4H), 3.36 (m, 1H), 3.15 (m, 1H) |
| 51 | 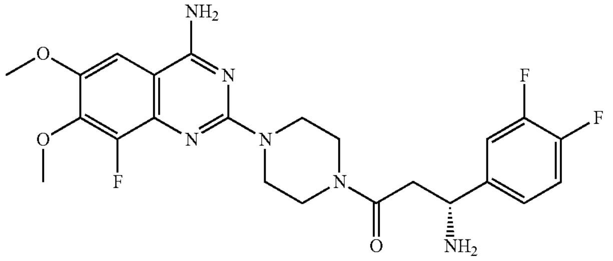 [SMILES: COc1cc2c(N)nc(N3CCN(C(=O)C[C@@H](N)c4ccc(F)c(F)c4)CC3)nc2c(F)c1OC]<br>(R)-3-Amino-1-[4-(4-amino-8-fluoro-6,7-dimethoxy-quinazolin-2-yl)piperazin-1-yl]-3-(3,4-difluoro-phenyl)-propan-1-one hydrochloride<br>example 4, $CH_3CN$<br>4N HCl/dioxane (ex. 31, step B) | 513.0<br>[M + Na]$^+$<br>0.84 (A3) | (400 MHz, methanol-d$^4$) δ (ppm): 7.59 (s, 1H), 7.58 (m, 1 H), 7.43 (m, 2H), 4.82 (m, 1H), 4.12 (s, 3H), 4.00 (s, 3H), 3.95-3.75 (m, 8H), 3.25 (m, 2H) |
| 52 | 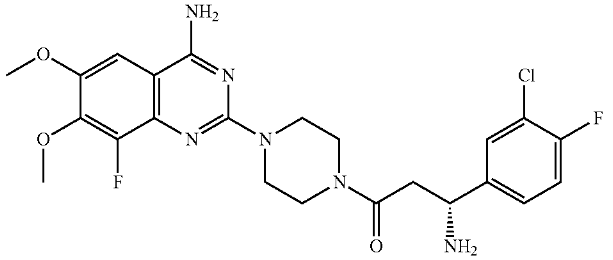 [SMILES: COc1cc2c(N)nc(N3CCN(C(=O)C[C@@H](N)c4ccc(F)c(Cl)c4)CC3)nc2c(F)c1OC]<br>(R)-3-Amino-1-[4-(4-amino-8-fluoro-6,7-dimethoxy-quinazolin-2-yl)-piperazin-1-yl]-3-(3-chloro-4-fluoro-phenyl)-propan-1-one hydrochloride<br>example 4, $CH_3CN$<br>4N HCl/dioxane (ex. 31, step B) | 529.0<br>[M + Na]$^+$<br>0.94 (A3) | (400 MHz, methanol-d$^4$) δ (ppm): 7.78 (m, 1H), 7.59 (s, 1H), 7.55 (m, 1H), 7.39 (m, 1H), 4.82 (m, 1H), 4.12 (s, 3H), 4.00 (s, 3H), 3.95-3.75 (m, 8H), 3.26 (m, 2H) |

-continued

| Ex. | Structure/Chemical Name<br>Coupling Method, solvent<br>Boc-deprotection | MS (ESI)<br>m/z $[M + H]^+$<br>$t_R$ [min]<br>(method) | $^1H$ NMR |
|---|---|---|---|
| 53 | 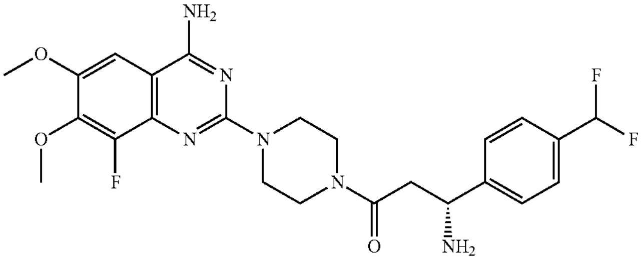 [SMILES: COc1cc2c(N)nc(N3CCN(C(=O)C[C@@H](N)c4ccc(C(F)F)cc4)CC3)nc2c(F)c1OC]<br>(R)-3-Amino-1-[4-(4-amino-8-fluoro-6,7-dimethoxy-quinazolin-2-yl)piperazin-1-yl]-3-(4-difluoromethyl-phenyl)-propan-1-one hydrochloride<br>example 32, $CH_3CN$<br>4N HCl/dioxane (ex. 31, step B) | 505.0<br>0.85 (A3) | (400 MHz, DMSO-$d^6$) δ ppm 8.41-8.66 (3 H, m), 7.57-7.78 (4 H, m), 7.07 (1 H, t), 4.68-4.77 (1 H, m), 3.98 (3 H, s), 3.89 (3 H, s), 3.70-3.85 (1 H, m), 3.54-3.68 (4 H, m), 3.03-3.15 (2 H, m) |
| 54 | 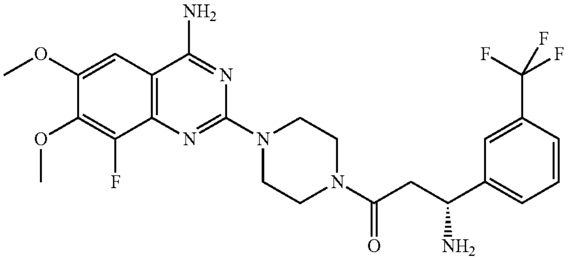 [SMILES: COc1cc2c(N)nc(N3CCN(C(=O)C[C@@H](N)c4cccc(C(F)(F)F)c4)CC3)nc2c(F)c1OC]<br>(R)-3-Amino-1-[4-(4-amino-8-fluoro-6,7-dimethoxy-quinazolin-2-yl)-piperazin-1-yl]-3-(3-trifluoromethyl-phenyl)-propan-1-one<br>example 4, $CH_3CN$<br>4N HCl/dioxane (ex. 31, step B) | 523.0<br>0.97 (A3) | (400 MHz, methanol-$d^4$) δ (ppm): 7.79-7.57 (m, 4H), 7.25 (s, 1H), 4.51 (m, 1H), 4.00 (s, 3H), 3.93 (s, 3H), 3.88-3.51 (m, 8H), 2.88 (m, 2H) |
| 55 | 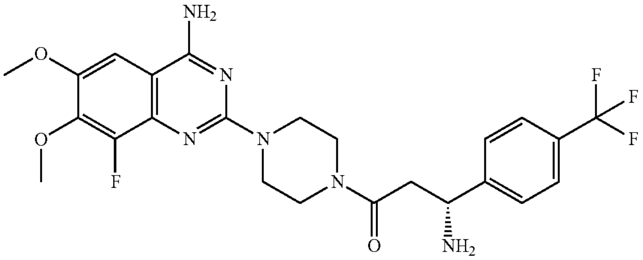 [SMILES: COc1cc2c(N)nc(N3CCN(C(=O)C[C@@H](N)c4ccc(C(F)(F)F)cc4)CC3)nc2c(F)c1OC]<br>(R)-3-Amino-1-[4-(4-amino-8-fluoro-6,7-dimethoxy-quinazolin-2-yl)piperazin-1-yl]-3-(4-trifluoromethyl-phenyl)-propan-1-one hydrochloride<br>example 32, $CH_3CN$/DMF 8:1<br>4N HCl/dioxane (ex. 31, step B) | 523.0<br>1.21 (A3) | (400 MHz, DMSO-$d^6$) δ ppm 8.47 (3 H, br. s.), 7.75-7.88 (4 H, m), 7.55 (1 H, br), 4.79 (1 H, br), 3.97 (3 H, s), 3.88 (3 H, s), 3.69-3.85 (4 H, m), 3.49-3.66 (4 H, m), 3.06-3.20 (2 H, m) |

-continued

| Ex. | Structure/Chemical Name<br>Coupling Method, solvent<br>Boc-deprotection | MS (ESI)<br>m/z [M + H]$^+$<br>$t_R$ [min]<br>(method) | $^1$H NMR |
|---|---|---|---|
| 56 | 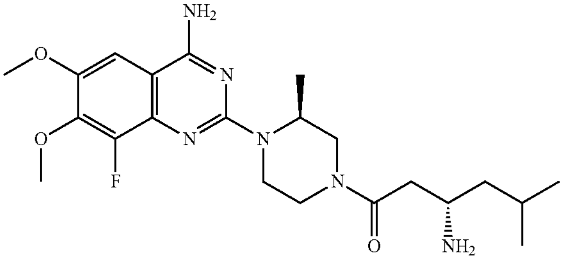 [SMILES: COc1cc2c(N)nc(N3CCN(C(=O)C[C@@H](N)CC(C)C)C[C@@H]3C)nc2c(F)c1OC]<br>(S)-3-Amino-1-[(S)-4-(4-amino-8-fluoro-6,7-dimethoxy-quinazolin-2-yl)-3-methyl-piperazin-1-yl]-5-methyl-hexan-1-one hydrochloride<br>example 2, $CH_2Cl_2$<br>4N HCl/dioxane (ex. 31, step B) | 449.5<br>0.61 (A2) | (600 MHz, DMSO-d$^6$) δ (ppm): 9.34 (br, 1H), 8.93 (br, 1H), 8.11 (br, 2H), 7.85 (s, 1H), 4.92 (m, 1H), 3.8-4.4 (m, 3H), 3.99 (s, 3H), 3.90 (s, 3H), 3.38 (m, 1H), 2.6-3.6 (m, 5H), 1.77 (m, 1H), 1.55 (m, 1H), 1.45 (m, 1H), 1.23/1.16 (d, 3H), 0.88 (d, 3H), 0.87 (d, 3H) |
| 57 | 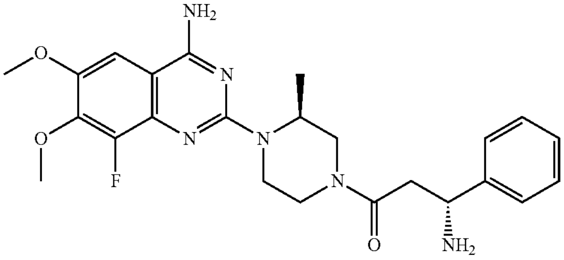 [SMILES: COc1cc2c(N)nc(N3CCN(C(=O)C[C@@H](N)c4ccccc4)C[C@@H]3C)nc2c(F)c1OC]<br>(R)-3-Amino-1-[(S)-4-(4-amino-8-fluoro-6,7-dimethoxy-quinazolin-2-yl)-3-methyl-piperazin-1-yl]-3-phenyl-propan-1-one hydrochloride<br>example 2, $CH_2Cl_2$<br>4N HCl/dioxane (ex. 31, step B) | 469.4<br>0.58 (A2) | (600 MHz, DMSO-d$^6$) δ (ppm): 8.35 (br, 2H), 7.35-7.6 (m, 6H), 4.92 (m, 1H), 4.66 (m, 1H), 3.95 (s, 3H), 3.88 (s, 3H), 2.6-4.5 (m, 8H)(rotamers) |
| 58 | 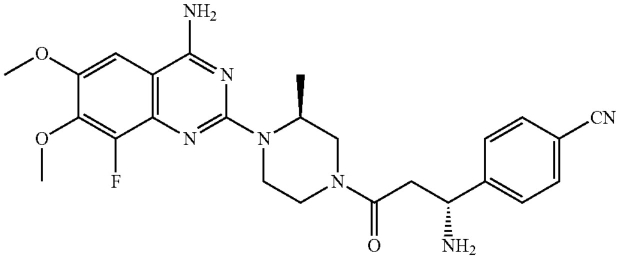 [SMILES: COc1cc2c(N)nc(N3CCN(C(=O)C[C@@H](N)c4ccc(C#N)cc4)C[C@@H]3C)nc2c(F)c1OC]<br>4-{(R)-1-Amino-3-[(S)-4-(4-amino-8-fluoro-6,7-dimethoxy-quinazolin-2-yl)-3-methyl-piperazin-1-yl]-3-oxo-propyl}-benzonitrile hydrochloride<br>example 2, $CH_2Cl_2$<br>4N HCl/dioxane (ex. 31, step B) | | |
| 59 | 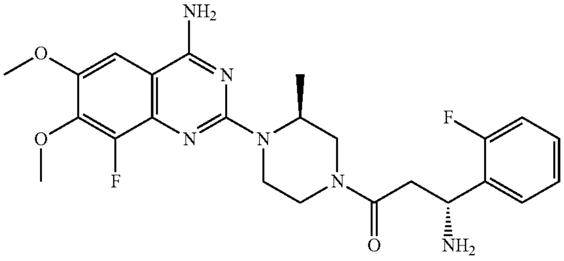 [SMILES: COc1cc2c(N)nc(N3CCN(C(=O)C[C@@H](N)c4ccccc4F)C[C@@H]3C)nc2c(F)c1OC]<br>(R)-3-Amino-1-[(S)-4-(4-amino-8-fluoro-6,7-dimethoxy-quinazolin-2-yl)-3-methyl-piperazin-1-yl]-3-(2-fluoro-phenyl)-propan-1-one hydrochloride<br>example 2, DMF<br>4N HCl/dioxane (ex. 31, step B) | 487.4<br>0.58 (A2) | (600 MHz, DMSO-d$^6$) δ (ppm): 9.0 (br, 2H), 8.7 (br, 2H), 7.78 (m, 2H), 7.45 (m, 1H), 7.3 (m, 1H), 7.28 (m, 1H), 4.9 (m, 2H), 2.8-4.4 (m, 8H), 4.00 (s, 3H), 3.91 (s, 3H), 1.16 (m, 3H) |

-continued

| Ex. | Structure/Chemical Name<br>Coupling Method, solvent<br>Boc-deprotection | MS (ESI)<br>m/z $[M + H]^+$<br>$t_R$ [min]<br>(method) | $^1H$ NMR |
|---|---|---|---|
| 60 | 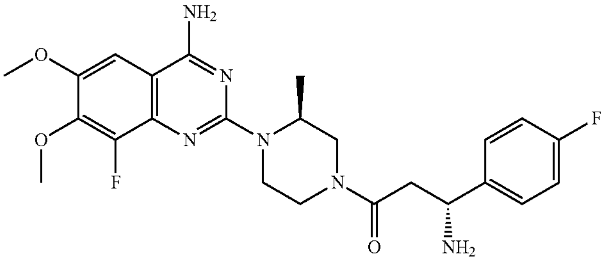 [SMILES: COc1cc2c(N)nc(N3CCN(C(=O)C[C@@H](N)c4ccc(F)cc4)C[C@@H]3C)nc2c(F)c1OC]<br>(R)-3-Amino-1-[(S)-4-(4-amino-8-fluoro-6,7-dimethoxy-quinazolin-2-yl)-3-methyl-piperazin-1-yl]-3-(4-fluoro-phenyl)-propan-1-one hydrochloride<br>example 2, $CH_2Cl_2$<br>4N HCl/dioxane (ex. 31, step B) | 487.5<br>0.60 (A2) | (600 MHz, DMSO-$d^6$) δ (ppm): 9.45 (br, 1H), 8.95 (br, 1H), 8.75 (br, 2H), 7.91 (s, 1H), 7.68 (m, 2H), 7.24 (m, 2H), 4.89 (m, 1H), 4.65 (m, 1H), 4.1-4.4 (m, 2H), 3.99 (s, 3H), 3.91 (s, 3H), 2.6-3.9 (m, 6H), 1.14 (m, 3H) |
| 61 | 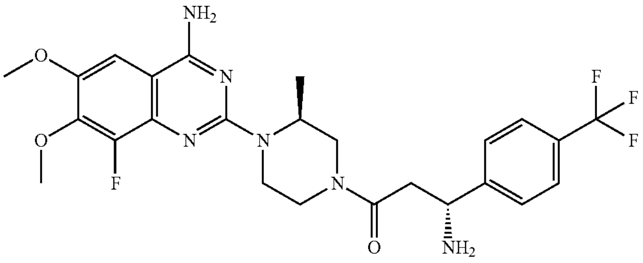 [SMILES: COc1cc2c(N)nc(N3CCN(C(=O)C[C@@H](N)c4ccc(C(F)(F)F)cc4)C[C@@H]3C)nc2c(F)c1OC]<br>(R)-3-Amino-1-[(S)-4-(4-amino-8-fluoro-6,7-dimethoxy-quinazolin-2-yl)-3-methyl-piperazin-1-yl]-3-(4-trifluoromethyl-phenyl)-propan-1-one hydrochloride<br>example 2, $CH_2Cl_2$<br>4N HCl/dioxane (ex. 31, step B) | 537.5<br>0.69 (A2) | (600 MHz, DMSO-$d^6$) δ (ppm): 9.1 (br, 2H), 8.80 (br, 3H), 7.80-7.87 (m, 5H), 4.89 (m, 1H), 4.77 (m, 1H), 4.1-4.5 (m, 2H), 3.99 (s, 3H), 3.91 (s, 3H), 2.6-3.9 (m, 6H), 1.14 (m, 3H) (rotamers) |
| 62 | 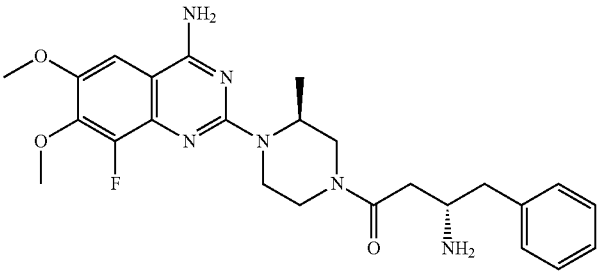 [SMILES: COc1cc2c(N)nc(N3CCN(C(=O)C[C@@H](N)Cc4ccccc4)C[C@@H]3C)nc2c(F)c1OC]<br>(S)-3-Amino-1-[(S)-4-(4-amino-8-fluoro-6,7-dimethoxy-quinazolin-2-yl)-3-methyl-piperazin-1-yl]-4-phenyl-butan-1-one hydrochloride<br>example 2, $CH_2Cl_2$<br>4N HCl/dioxane (ex. 31, step B) | 483.5<br>0.63 (A2) | (600 MHz, DMSO-$d^6$) δ (ppm): 11.27 (s, 1H), 8.79 (s, 1H), 7.43 (br, 2H), 7.40 (s, 1H), 7.23 (d, 1H), 6.90 (s, 1H), 6.74 (d, 1H), 6.68 (m, 1H), 3.90 (s, 3H), 3.84 (s, 3H), 3.8-3.9 (m, 8H) |

-continued

| Ex. | Structure/Chemical Name Coupling Method, solvent Boc-deprotection | MS (ESI) m/z $[M + H]^+$ $t_R$ [min] (method) | $^1H$ NMR |
|---|---|---|---|
| 63 | 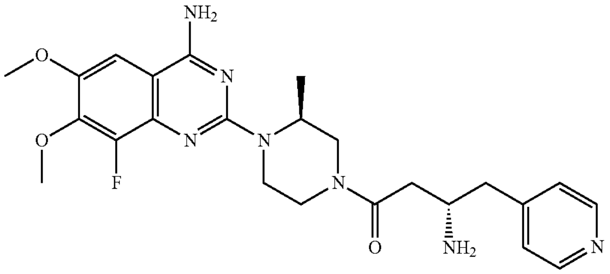 [SMILES: COc1cc2c(N)nc(N3CCN(C(=O)C[C@@H](N)Cc4ccncc4)C[C@@H]3C)nc2c(F)c1OC] (S)-3-Amino-1-[(S)-4-(4-amino-8-fluoro-6,7-dimethoxy-quinazolin-2-yl)-3-methyl-piperazin-1-yl]-4-pyridin-4-yl-butan-1-one hydrochloride example 2, $CH_2Cl_2$ 4N HCl/dioxane (ex. 31, step B) | 484.5 0.45 (A2) | (600 MHz, DMSO-$d^6$) δ (ppm): 9.35 (br, 1H), 8.9 (br, 1H), 8.88 (m, 2H), 8.51 (br, 2H), 8.1 (m, 2H), 7.9 (1, 1H), 4.92 (m, 1H), 4.0-4.4 (m, 3H), 4.00 (s, 3H), 3.92 (s, 3H), 2.75-4.0 (m, 8H), 1.18 (m, 3H) |
| 64 | 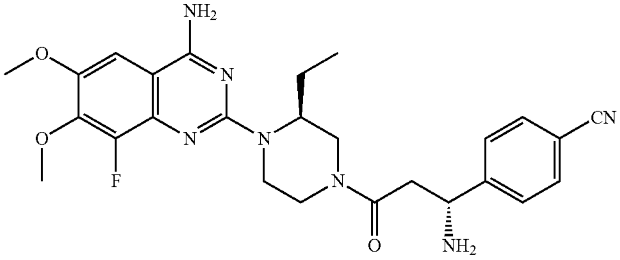 4-{(R)-1-Amino-3-[(S)-4-(4-amino-8-fluoro-6,7-dimethoxy-quinazolin-2-yl)-3-ethyl-piperazin-1-yl]-3-oxo-propyl}-benzonitrile hydrochloride example 2, $CH_2Cl_2$ 4N HCl/dioxane (ex. 31, step B) | 508.5 0.61 (A2) | (600 MHz, DMSO-$d^6$) δ (ppm): 8.83 (br, 2H), 7.91 (m, 2H), 7.81 (m, 2H), 4.74 (m, 2H), 4.3 (m, 2H), 3.99 (s, 3H), 3.90 (s, 3H), 2.8-4.0 (m, 7H), 1.49 (m, 2H), 0.81 (m, 3H) (rotamers) |
| 65 | 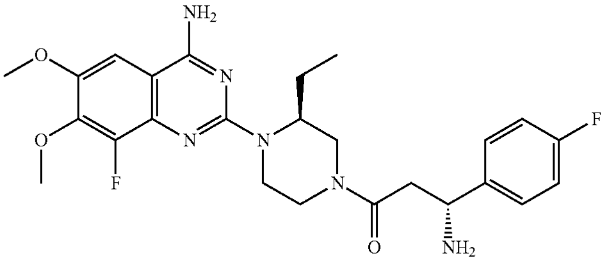 [SMILES: CC[C@H]1CN(C(=O)C[C@@H](N)c2ccc(F)cc2)CCN1c1nc(N)c2cc(OC)c(OC)c(F)c2n1] (R)-3-Amino-1-[(S)-4-(4-amino-8-fluoro-6,7-dimethoxy-quinazolin-2-yl)-3-ethyl-piperazin-1-yl]-3-(4-fluoro-phenyl)-propan-1-one hydrochloride example 2, $CH_2Cl_2$ 4N HCl/dioxane (ex. 31, step B) | 501.5 0.64 (A2) | (600 MHz, DMSO-$d^6$) δ (ppm): 9.2 (br, 1H), 8.85 (br, 1H), 8.65 (br, 2H), 7.81 (s, 1H), 7.65 (m, 2H), 7.25 (m, 2H), 4.77 (m, 1H), 4.65 (m, 1H), 4.33 (m, 2H), 3.99 (s, 3H), 3.90 (s, 3H), 2.75-4.0 (m, 6H), 1.52 (m, 2H), 0.81 (m, 3H) |

-continued

| Ex. | Structure/Chemical Name Coupling Method, solvent Boc-deprotection | MS (ESI) m/z $[M + H]^+$ $t_R$ [min] (method) | $^1H$ NMR |
|---|---|---|---|
| 66 | 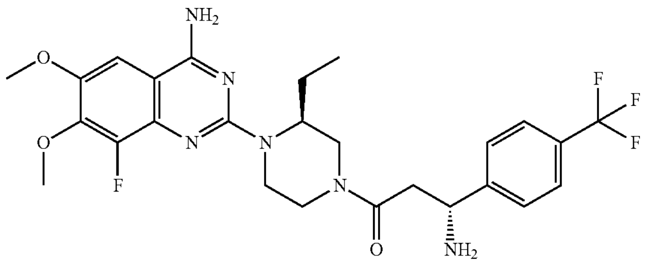 [SMILES: CC[C@H]1CN(C(=O)C[C@@H](N)c2ccc(C(F)(F)F)cc2)CCN1c1nc(N)c2cc(OC)c(OC)c(F)c2n1] (R)-3-Amino-1-[(S)-4-(4-amino-8-fluoro-6,7-dimethoxy-quinazolin-2-yl)-3-ethyl-piperazin-1-yl]-3-(4-trifluoromethyl-phenyl)-propan-1-one hydrochloride example 2, $CH_2Cl_2$ 4N HCl/dioxane (ex. 31, step B) | 551.5 0.74 (A2) | (600 MHz, DMSO-$d^6$) δ (ppm): 8.83 (br, 5H), 7.8-7.84 (m, 5H), 4.76 (m, 2H), 4.3 (m, 2H), 3.99 (s, 3H), 3.91 (s, 3H), 3.0-4.0 (m, 6H), 1.49 (m, 2H), 0.81 (m, 3H) (rotamers) |
| 67 | 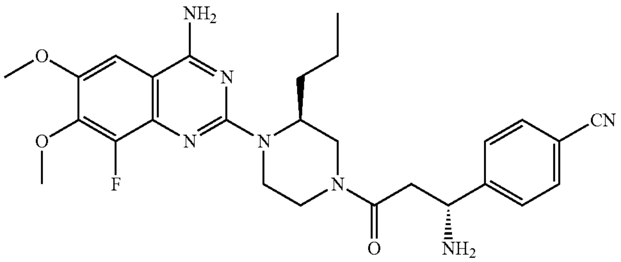 [SMILES: CCC[C@H]1CN(C(=O)C[C@@H](N)c2ccc(C#N)cc2)CCN1c1nc(N)c2cc(OC)c(OC)c(F)c2n1] 4-{(R)-1-Amino-3-[(S)-4-(4-amino-8-fluoro-6,7-dimethoxy-quinazolin-2-yl)-3-propyl-piperazin-1-yl]-3-oxo-propyl}-benzonitrile hydrochloride example 2, $CH_2Cl_2$ 4N HCl/dioxane (ex. 31, step B) | 522.5 0.67 (A2) | (600 MHz, DMSO-$d^6$) δ (ppm): 9.31 (br, 1H), 8.86 (br, 3H), 7.91 (m, 2H), 7.82 (m, 3H), 4.84 (m, 1H), 4.74 (m, 1H), 4.3 (m, 2H), 3.99 (s, 3H), 3.91 (s, 3H), 2.8-3.9 (m, 6H), 1.4-1.55 (m, 2H), 1.19 (m, 2H), 0.86 (m, 3H) |
| 68 | 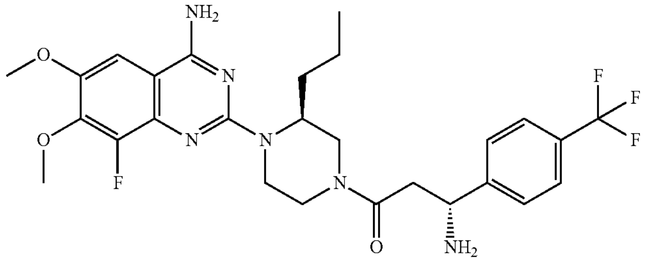 (R)-3-Amino-1-[(S)-4-(4-amino-8-fluoro-6,7-dimethoxy-quinazolin-2-yl)-3-propyl-piperazin-1-yl]-3-(4-trifluoromethyl-phenyl)-propan-1-one hydrochloride example 2, $CH_2Cl_2$ 4N HCl/dioxane (ex. 31, step B) | 565.5 0.79 (A2) | (600 MHz, DMSO-$d^6$) δ (ppm): 9.4 (br, 1H), 8.86 (br, 3H), 7.85 (m, 3H), 7.80 (m, 2H), 4.88 (m, 1H), 4.75 (m, 1H), 4.3 (m, 2H), 3.99 (s, 3H), 3.91 (s, 3H), 2.7-4.0 (m, 6H), 1.4-1.55 (m, 2H), 1.23 (m, 2H), 0.85 (m, 3H) |

-continued

| Ex. | Structure/Chemical Name<br>Coupling Method, solvent<br>Boc-deprotection | MS (ESI)<br>m/z $[M + H]^+$<br>$t_R$ [min]<br>(method) | $^1H$ NMR |
|---|---|---|---|
| 69 | 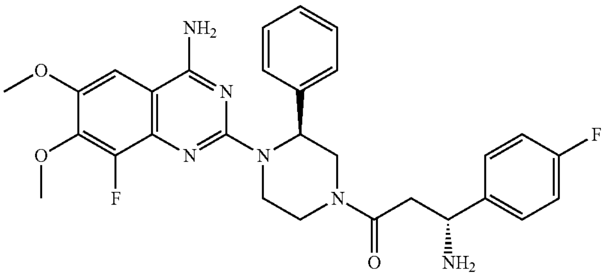 [SMILES: COc1cc2c(N)nc(N3CCN(C(=O)C[C@@H](N)c4ccc(F)cc4)C[C@@H]3c3ccccc3)nc2c(F)c1OC]<br>(R)-3-Amino-1-[(S)-4-(4-amino-8-fluoro-6,7-dimethoxy-quinazolin-2-yl)-3-phenyl-piperazin-1-yl]-3-(4-fluoro-phenyl)-propan-1-one hydrochloride<br>example 2, $CH_2Cl_2$<br>4N HCl/dioxane (ex. 31, step B) | 549.5<br>0.74 (A2) | (600 MHz, DMSO-$d^6$) δ (ppm): 8.63 (br, 3H), 7.8 (br, 1H), 7.53 (m, 2H), 7.3-7.4 (m, 4H), 7.19 (m, 2H), 6.04 (m, 1H), 4.4-4.8 (m, 3H), 3.98 (s, 3H), 3.89 (s, 3H), 2.8-4.0 (m, 6H) |

Reaction Scheme 19:

-continued

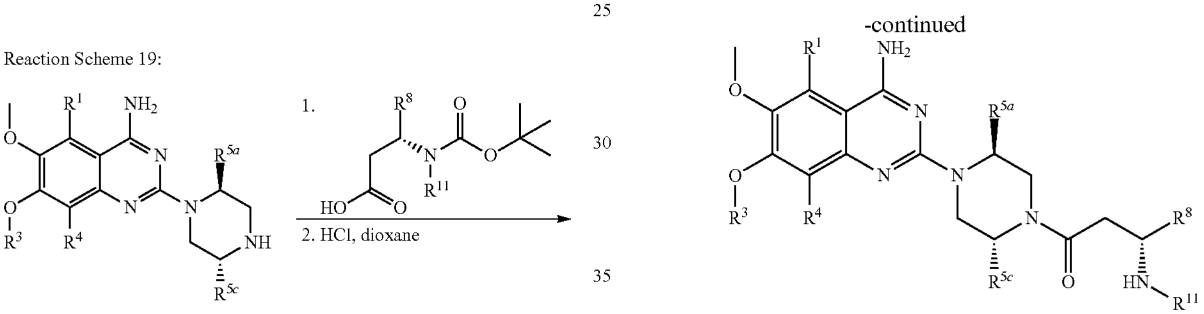

| Ex. | Structure/Chemical Name<br>Coupling Method, solvent<br>Boc-deprotection | MS (ESI)<br>m/z<br>$[M + H]^+$<br>$t_R$ [min]<br>(method) | $^1H$ NMR |
|---|---|---|---|
| 70 | 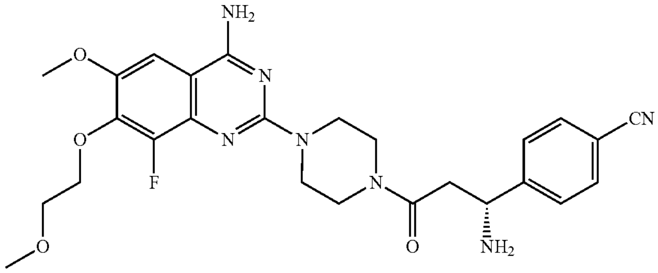<br>4-((R)-1-Amino-3-{4-[4-amino-8-fluoro-6-methoxy-7-(2-methoxy-ethoxy)-quinazolin-2-yl]-piperazin-1-yl}-3-oxo-propyl)-benzonitrile hydrochloride<br>example 2, $CH_2Cl_2$<br>4N HCl/dioxane (ex. 31, step B) | 524.3<br>0.57 (A2) | (600 MHz, DMSO-$d^6$) δ (ppm): 8.78 (br, 4H), 7.92 (m, 2H), 7.83 (m, 2H), 7.80 (s, 1H), 4.74 (m, 1H), 4.32 (m, 2H), 3.91 (s, 3H), 3.7-3.9 (m, 4H), 3.64 (m, 2H), 3.6 (m, 4H), 3.31 (m, 2H), 3.28 (s, 3H) |

-continued

| Ex. | Structure/Chemical Name Coupling Method, solvent Boc-deprotection | MS (ESI) m/z [M + H]+ $t_R$ [min] (method) | $^1$H NMR |
|---|---|---|---|
| 71 | 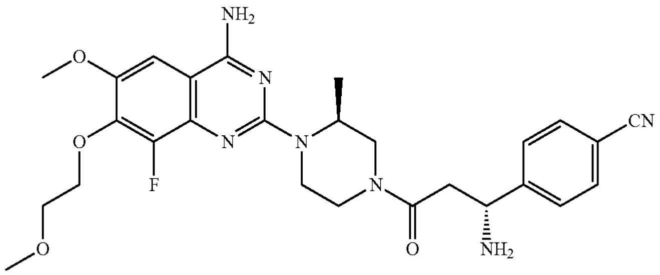 4-((R)-1-Amino-3-{(S)-4-[4-amino-8-fluoro-6-methoxy-7-(2-methoxy-ethoxy)-quinazolin-2-yl]-3-methyl-piperazin-1-yl}-3-oxo-propyl)-benzonitrile hydrochloride example 2, $CH_2Cl_2$ 4N HCl/dioxane (ex. 31, step B) | 538.3 0.59 (A2) | (600 MHz, DMSO-d$^6$) δ (ppm): 8.65 (br, 4H), 7.95 (m, 2H), 7.8 (m, 2H), 7.7 (br, 1H), 4.9 (m, 1H), 4.8 (m, 1H), 4.2-4.4 (m, 4H), 3.9 (s, 3H), 3.63 (m, 2H), 3.55 (s, 3H), 3.3-3.5 (m, 6H), 1.1 (m, 3H) |
| 72 | 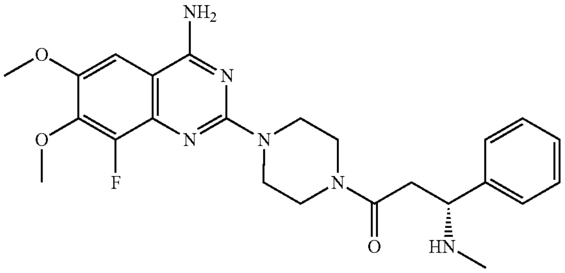 (R)-1-[4-(4-Amino-8-fluoro-6,7-dimethoxy-quinazolin-2-yl)-piperazin-1-yl]-3-methylamino-3-phenyl-propan-1-one hydrochloride example 32, $CH_3CN$ 4N HCl/dioxane (ex. 31, step B) | 469.0 0.58 (A3) | (400 MHz, DMSO-d$^6$) δ ppm 9.33 (2 H, br), 7.70 (1 H, br), 7.62 (2 H, d, J = 6.85 Hz), 7.39-7.51 (3 H, m), 4.57-4.69 (1 H, m), 4.00 (3 H, s), 3.90 (3 H, s), 3.66-3.86 (8 H, m), 3.05-3.23 (2 H, m), 2.40 (3 H, m) |
| 73 | 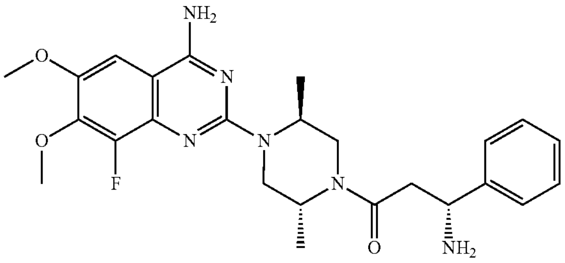 (R)-3-Amino-1-[(2R,5S)-4-(4-amino-8-fluoro-6,7-dimethoxy-quinazolin-2-yl)-2,5-dimethyl-piperazin-1-yl]-3-phenyl-propan-1-one hydrochloride example 3, $CH_3CN$ 4N HCl/dioxane (ex. 31, step B) | 483.3 0.56 (A1) | (400 MHz, methanol-d$^4$) δ (ppm): 7.59-7.45 (m, 6H), 4.63-4.14 (m, 3H), 4.12 (s, 3H), 4.00 (s, 3H), 3.94-3.71 (m, 2H), 3.66-3.45 (m, 2H), 3.30-3.08 (m, 2H), 1.26 (d, 3H), 1.26 (dd, 3H) |

-continued

| Ex. | Structure/Chemical Name<br>Coupling Method, solvent<br>Boc-deprotection | MS (ESI)<br>m/z<br>[M + H]+<br>$t_R$ [min]<br>(method) | $^1$H NMR |
|---|---|---|---|
| 74 | 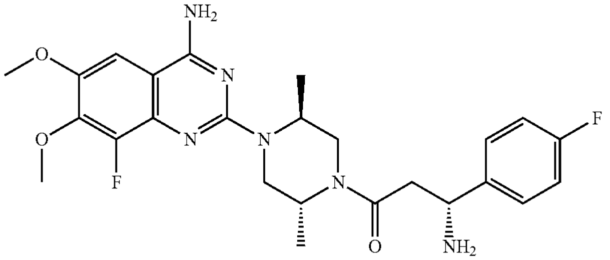<br>(R)-3-amino-1-[(2R,5S)-4-(4-amino-8-fluoro-6,7-dimethoxy-quinazolin-2-yl)-2,5-dimethyl-piperazin-1-yl]-3-(4-fluorophenyl)-propan-1-one hydrochloride<br>example 3, $CH_3CN$<br>4N HCl/dioxane (ex. 31, step B) | 501.3<br>0.59 (A1) | (400 MHz, methanol-d$^4$) δ (ppm): 7.66-7.59 (m, 3H), 7.24 (dt, 2H), 4.12 (s, 3H), 4.00 (s, 3H), 4.49-4.15 (m, 3H), 3.91-3.72 (m, 2H), 3.66-3.49 (m, 2H), 3.31-3.07 (m, 2H), 1.32 (d, 3H), 1.25 (dd, 3H) |
| 75 | 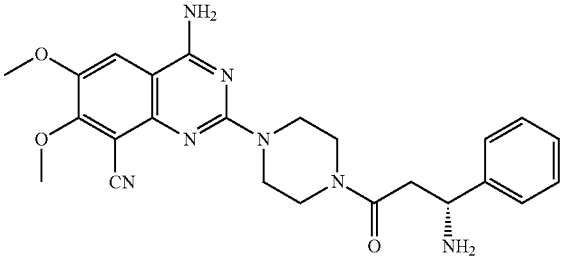<br>4-Amino-2-[4-((R)-3-amino-3-phenyl-propionyl)-piperazin-1-yl]-6,7-dimethoxy-quinazoline-8-carbonitrile<br>example 5, $CH_2Cl_2$<br>4N HCl/dioxane (ex. 31, step B) | 462.5<br>0.64 (A1) | (400 MHz, methanol-d$^4$) δ (ppm): 7.75 (s, 1H), 7.49 (m, 5H), 4.14 (s, 3H), 3.96 (s, 3H), 3.88 (m, 4H), 3.70-3.46 (m, 5H), 3.18-3.15 (m, 2H) |
| 76 | 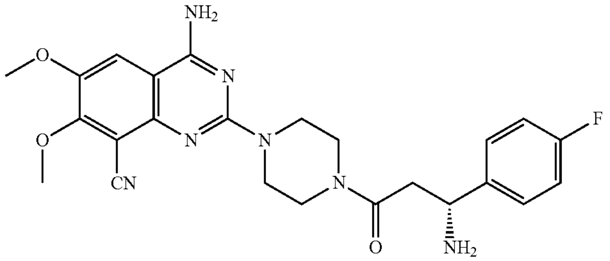<br>4-Amino-2-{4-[(R)-3-amino-3-(4-fluoro-phenyl)-propionyl]-piperazin-1-yl}-6,7-dimethoxy-quinazoline-8-carbonitrile hydrochloride<br>example 3, $CH_3CN$<br>4N HCl/dioxane (ex. 31, step B) | 480.3<br>0.67 (A1) | (400 MHz, methanol-d$^4$) δ (ppm): 7.98 (s, 1H), 7.60 (dd, 2H), 7.25 (dd, 2H), 4.26 (s, 3H), 4.03 (s, 3H), 3.98-3.62 (m, 9H), 3.22 (m, 2H) |

-continued

| Ex. | Structure/Chemical Name<br>Coupling Method, solvent<br>Boc-deprotection | MS (ESI)<br>m/z<br>$[M + H]^+$<br>$t_R$ [min]<br>(method) | $^1H$ NMR |
|---|---|---|---|
| 77 | 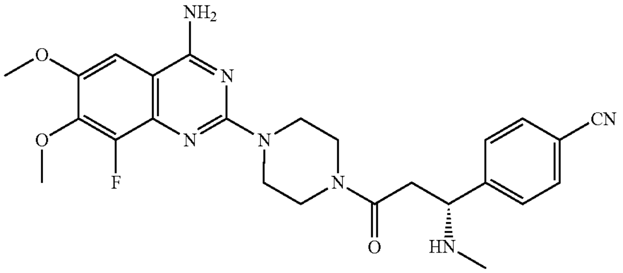<br>(R)-4-(3-(4-(4-amino-8-fluoro-6,7-dimethoxyquinazolin-2-yl)piperazin-1-yl)-1-(methylamino)-3-oxopropyl)benzonitrile hydrochloride<br>example 4, $CH_3CN$<br>4N HCl/dioxane (ex. 31, step B) | 494.0<br>3.11 (A4) | (400 MHz, methanol-$d^4$) δ (ppm): 7.88 (d, 2H), 7.79 (d, 2H), 7.55 (d, 1H), 4.18-4.03 (m, 3H), 4.03-3.86 (m, 7H), 3.85-3.67 (m, 5H), 3.50-3.34 (m, 1H), 3.28-3.14 (m, 1H), 2.62 (s, 3H). |
| 78 | 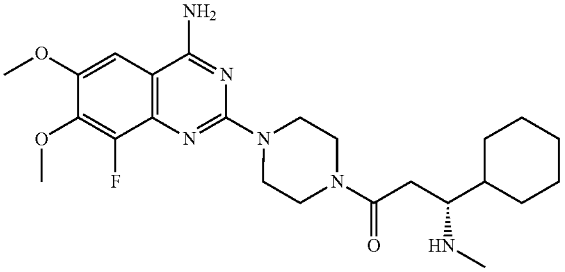<br>(R)-1-(4-(4-amino-8-fluoro-6,7-dimethoxyquinazolin-2-yl)piperazin-1-yl)-3-cyclohexyl-3-(methylamino)propan-1-one<br>example 32, $CH_3CN$<br>4N HCl/dioxane (ex. 31, step B) | 475.4<br>0.65 (A2) | (400 MHz, DMSO-$d^6$) δ (ppm): 7.44 (brs., 2H), 7.40 (s, 1H), 3.90 (s, 3H), 3.85 (s, 3H), 3.80-3.66 (m, 4H), 3.55 (s br., 4H), 2.75 (s br., 1H), 2.46-2.34 (m, 2H), 2.31 (s, 3H), 1.76-1.60 (m, 5H), 1.54-1.40 (m, 1H), 1.29-0.94 (m, 5H) |
| 79 | 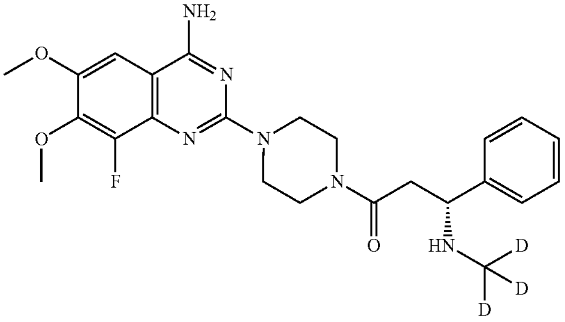<br>(R)-1-[4-(4-Amino-8-fluoro-6,7-dimethoxy-quinazolin-2-yl)-piperazin-1-yl]-3-$d^3$-methylamino-3-phenyl-propan-1-one hydrochloride<br>example 4, $CH_3CN$<br>4N HCl/dioxane (ex. 31, step B) | 471.8<br>0.55 (A6) | (400 MHz, DMSO-$d^6$) δ ppm 9.22 (m, 2H), 7.80 (s br., 1H), 7.65 (d, 2H), 7.44 (m, 3H), 4.60 (m, 1H), 4.00 (s, 3H), 3.90 (s, 3H), 3.6-3.9 (m, 8H), 3.40 (m, 1H), 3.2 (m, 1H) |

-continued

| Ex. | Structure/Chemical Name<br>Coupling Method, solvent<br>Boc-deprotection | MS (ESI)<br>m/z<br>[M + H]+<br>$t_R$ [min]<br>(method) | $^1$H NMR |
|---|---|---|---|
| 80 | 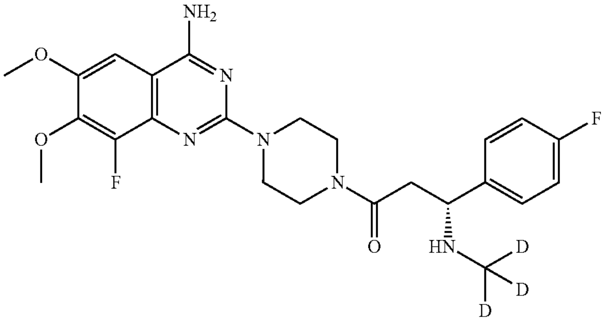<br>(R)-1-(4-(4-amino-8-fluoro-6,7-dimethoxyquinazolin-2-yl)piperazin-1-yl)-3-(4-fluorophenyl)-3-($d^3$-methylamino)propan-1-one hydrochloride<br>example 4, $CH_3CN$<br>4N HCl/dioxane (ex. 31, step B) | 490.4<br>0.56 (A6) | (400 MHz, DMSO-$d^6$) δ ppm 9.7 (m, 2H), 7.87 (s, 1H), 7.75 (dd, 2H), 7.29 (dd, 2H), 4.64 (m, 1H), 4.01 (s, 3H), 3.92 (s, 3H), 3.50-3.88 (m, 8H), 3.47 (m, 1H), 3.25 (m, 1H) |
| 81 | 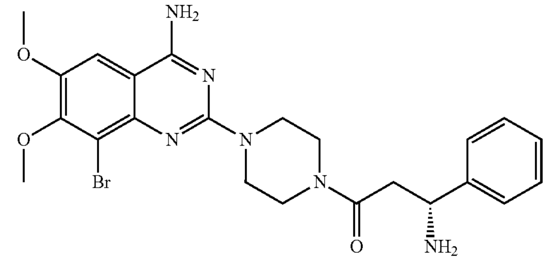<br>(R)-3-Amino-1-(4-(4-amino-8-bromo-6,7-dimethoxyquinazolin-2-yl)piperazin-1-yl)-3-phenylpropan-1-one<br>example 5, $CH_2Cl_2$<br>4N HCl/dioxane (ex. 31, step B) | 515.1<br>0.56 (A1) | (400 MHz, methanol-$d^4$) δ (ppm): 7.3-7.5 (m, 6H), 4.59 (m, 1H), 3.95 (s, 3H), 3.92 (s, 3H), 3.65-3.92 (m, 6H), 3.55 (m, 2H), 3.01 (m, 2H) |
| 82 | 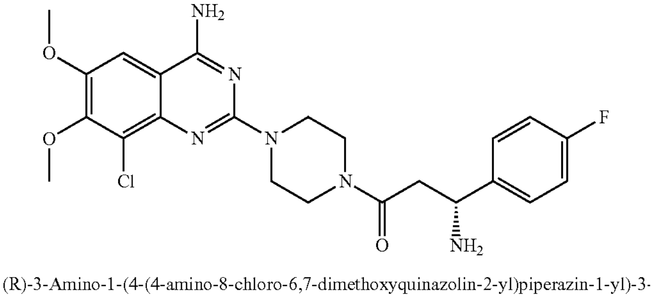<br>(R)-3-Amino-1-(4-(4-amino-8-chloro-6,7-dimethoxyquinazolin-2-yl)piperazin-1-yl)-3-(4-fluorophenyl)propan-1-one hydrochloride<br>example 32, DMF<br>4N HCl/dioxane (ex. 31, step B) | 489.4<br>0.65 (A2) | (600 MHz, DMSO-$d^6$) δ (ppm): 9.8 (br, 1H), 9.25 (br, 1H), 8.9 (br, 1H), 8.71 (m, 3H), 8.16 (m, 1H), 7.67 (dd, 2H), 7.25 (dd, 2H), 4.6 (m, 1H), 3.95 (s, 3H), 3.93 (s, 3H), 3.7-3.9 (m, 4H), 3.6-3.7 (m, 4H), 3.29 (m, 1H), 3.07 (m, 1H) |

Example 83

Synthesis of (R)-3-Amino-1-[4-(4-amino-5-fluoro-6,7-dimethoxy-quinazolin-2-yl)-piperazin-1-yl]-3-(4-fluoro-phenyl)-propan-1-one ($R^1$=F, $R^3$=methyl, $R^4$=H, $R^{5a}$=$R^{5c}$=H, $R^8$=4-fluorophenyl, $R^{11}$=H)

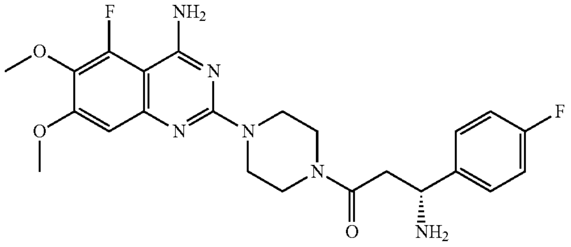 [SMILES: COc1cc2nc(N3CCN(C(=O)C[C@@H](N)c4ccc(F)cc4)CC3)nc(N)c2c(F)c1OC]

Step A: [(R)-3-[4-(4-Amino-5-fluoro-6,7-dimethoxy-quinazolin-2-yl)-piperazin-1-yl]-1-(4-fluoro-phenyl)-3-oxo-propyl]-carbamic acid tert-butyl ester A solution of 2-chloro-5-fluoro-6,7-dimethoxy-quinazolin-4-ylamine (55) (70 mg, 0.272 mmol), [(R)-1-(4-fluoro-phenyl)-3-oxo-3-piperazin-1-yl-propyl]-carbamic acid (57b) (143 mg, 0.41 mmol) and triethylamine (0.057 ml, 0.41 mmol) in isopentyl alcohol (2 ml) was stirred at 130° C. for 12 h. The solvent was evaporated and the residue purified by preparative HPLC (method P9) LC MS (ESI): 573.3 $[M+H]^+$

Step B: (R)-3-Amino-1-[4-(4-amino-5-fluoro-6,7-dimethoxy-quinazolin-2-yl)-piperazin-1-yl]-3-(4-fluoro-phenyl)-propan-1-one The title compound (as its hydrochloride salt) was obtained from [(R)-3-[4-(4-amino-5-fluoro-6,7-dimethoxy-quinazol in-2-yl)-piperazin-1-yl]-1-(4-fluoro-phenyl)-3-oxo-propyl]-carbamic acid tert-butyl ester as described in example 31, step B. LC MS (ESI): 473.4 $[M+H]^+$, $t_R$=0.45 min (Method A1); $^1$H-NMR (400 MHz, methanol-$d^4$) δ (ppm): 8.00 (s, 1H), 7.60 (dd, 2H), 7.24 (t, 2H), 4.7 (s, 3H), 4.03 (s, 3H), 3.90-4.00 (m, 4H), 3.80-3.85 (m, 2H), 3.75-3.80 (m, 2H), 3.70 (m, 1H), 3.20-3.25 (m, 2H).

Reaction Scheme 20:

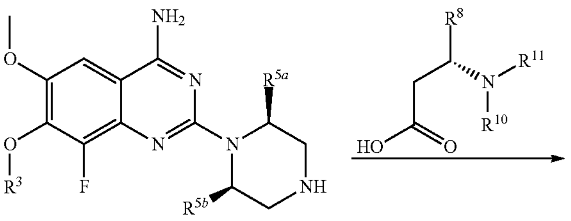

-continued

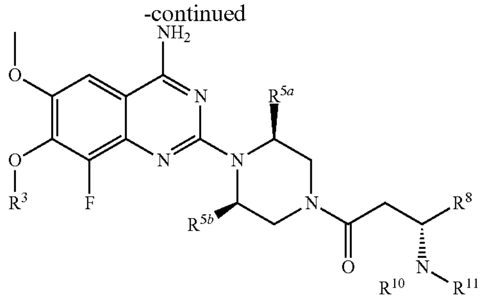

Example 84

Synthesis of (R)-1-[4-(4-Amino-8-fluoro-6,7-dimethoxy-quinazolin-2-yl)-piperazin-1-yl]-3-ethylamino-3-(4-fluoro-phenyl)-propan-1-one ($R^3$=methyl, $R^{5a}$=$R^{5b}$=H, $R^5$=4-fluorophenyl, $R^{15}$=H, $R^{11}$=ethyl)

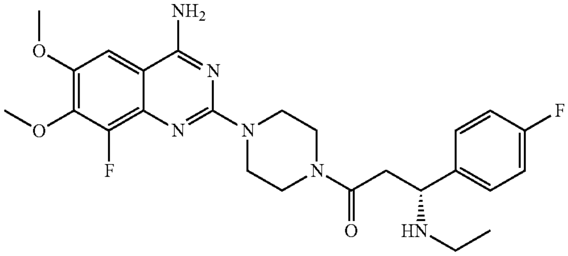 [SMILES: CCN[C@H](CC(=O)N1CCN(c2nc(N)c3cc(OC)c(OC)c(F)c3n2)CC1)c1ccc(F)cc1]

8-Fluoro-6,7-dimethoxy-2-piperazin-1-yl-quinazolin-4-ylamine (21a) (91 mg, 0.238 mmol) and triethylamine (0.10 ml, 0.715 mmol) were added to a solution of (R)-3-ethylamino-3-(4-fluoro-phenyl)-propionic acid (69b) (52 mg, 0.238 mmol) and HBTU (108 mg, 0.286 mmol) in DMF (2 ml). Stirring at RT was continued for 1 h. The reaction solution was filtered and purified by two consecutive preparative HPLC's (method P6 followed by P7). Pure fractions were combined, a saturated solution of $NaHCO_3$ was added and the mixture was extracted with $CH_2Cl_2$. Drying of the extracts followed by evaporation of the solvent yielded the title compound as its free base. LC MS (ESI): 501.2 $[M+H]^+$, $t_R$=0.52 min (Method A5); $^1$H NMR (400 MHz, methanol-$d^4$) δ (ppm): 7.42 (dd, 2H), 7.25 (d, 1H), 7.10 (t, 2H), 4.16 (t, 1H), 4.00 (s, 3H), 3.93 (s, 3H), 3.80-3.90 (m, 2H), 3.60-3.70 (m, 2H), 3.45-3.60 (m, 4H), 2.85 (d, 2H), 2.40-2.55 (m, 2H), 1.11 (t, 3H).

The following compounds were prepared with similar methods

| Ex. | Structure/Chemical Name Coupling Method, solvent | MS (ESI) m/z $[M + H]^+$ $t_R$ [min] (method) | $^1H$ NMR |
|---|---|---|---|
| 85 | 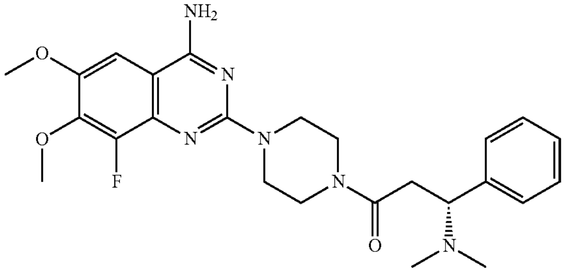 (R)-1-[4-(4-Amino-8-fluoro-6,7-dimethoxy-quinazolin-2-yl)-piperazin-1-yl]-3-dimethylamino-3-phenyl-propan-1-one example 3, $CH_3CN$ | 483.3 0.52 (A1) | (400 MHz, methanol-$d^4$) δ (ppm): 7.37 (m, 4H), 7.30 (m, 1H), 7.24 (d, 1H), 4.00 (s, 3H), 3.93 (s, 3H), 3.91-3.93 (m, 3H), 3.66-3.38 (m, 6H), 3.09-2.97 (m, 2H) |
| 86 | 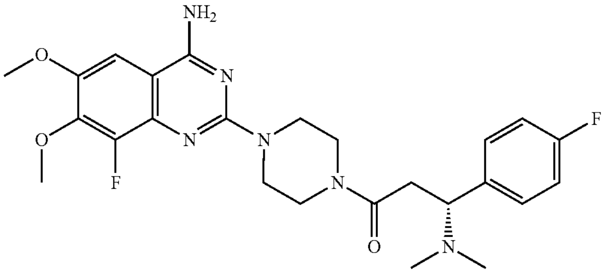 (R)-1-[4-(4-Amino-8-fluoro-6,7-dimethoxy-quinazolin-2-yl)-piperazin-1-yl]-3-dimethylamino-3-phenyl-propan-1-one example 3, $CH_3CN$ | 501.3 0.54 (A1) | (400 MHz, methanol-$d^4$) δ (ppm): 7.38 (dd, 2H), 7.24 (s, 1H), 7.10 (dd, 2H), 4.00 (s, 3H), 3.93 (s, 3H), 3.90-3.82 (m, 3H), 3.65-3.43 (m, 6H), 3.01 (d, 1H), 2.24 (s, 6H) |
| 87 | 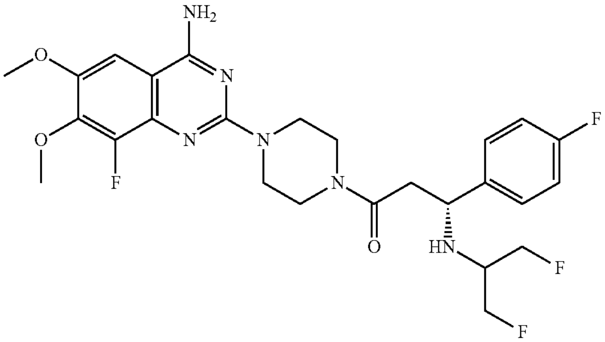 (R)-1-(4-(4-amino-8-fluoro-6,7-dimethoxyquinazolin-2-yl)piperazin-1-yl)-3-(1,3-difluoropropan-2-ylamino)-3-(4-fluorophenyl)propan-1-one hydrochloride example 4, $CH_3CN$ | 551.3 0.80 (A1) | (400 MHz, DMSO-$d^6$) δ (ppm): 7.78 (br, 2H), 7.63 (br, 1H), 7.33 (dd, 2H), 4.60-5.00 (m, 4H), 3.99 (s, 3H), 3.90 (s, 3H), 3.50-3.90 (m, 12H) |

-continued

| Ex. | Structure/Chemical Name Coupling Method, solvent | MS (ESI) m/z $[M + H]^+$ $t_R$ [min] (method) | $^1H$ NMR |
|---|---|---|---|
| 88 | 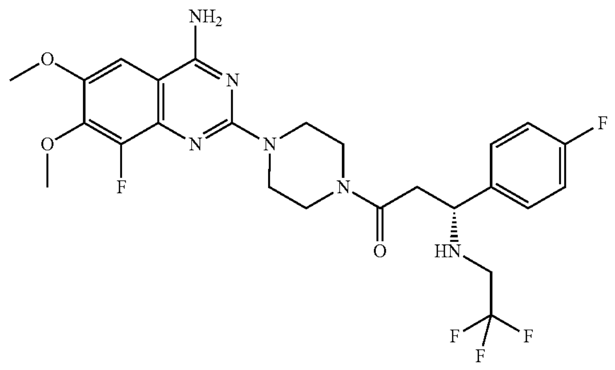 (R)-1-[4-(4-Amino-8-fluoro-6,7-dimethoxy-quinazolin-2-yl)-piperazin-1-yl]-3-(4-fluoro-phenyl)-3-(2,2,2-trifluoro-ethylamino)-propan-1-one hydrochloride example 4, $CH_3CN$ | 555.3 0.94 (A1) | (400 MHz, DMSO-$d^6$) δ (ppm): 7.79 (s, 1H), 7.59 (m, 2H), 7.24 (dd, 2H), 4.02 (s, 3H), 3.92 (s, 3H), 2.95-3.87 (m, 13H) |
| 89 | 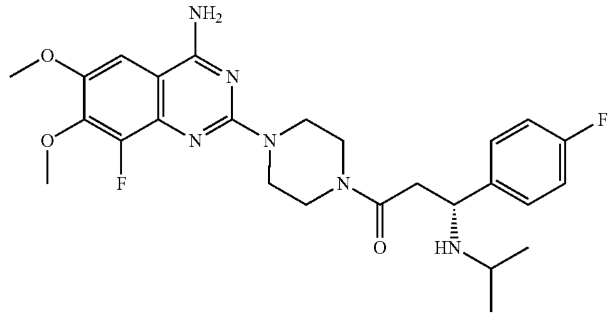 (R)-1-[4-(4-Amino-8-fluoro-6,7-dimethoxy-quinazolin-2-yl)-piperazin-1-yl]-3-(4-fluoro-phenyl)-3-isopropylamino-propan-1-one example 3, $CH_3CN$ | 515.3 0.59 (A1) | (400 MHz, methanol-$d^4$) δ (ppm): 7.42 (dd, 2H), 7.25 (s, 1H), 7.10 (dd, 2H), 4.30 (dd, 1H), 4.01 (s, 3H), 3.93 (s, 3H), 3.89-3.41 (m, 8H), 2.84 (dd, 2H), 2.61 (m, 1H), 1.09 (d, 3H), 1.04 (d, 3H) |
| 90 | 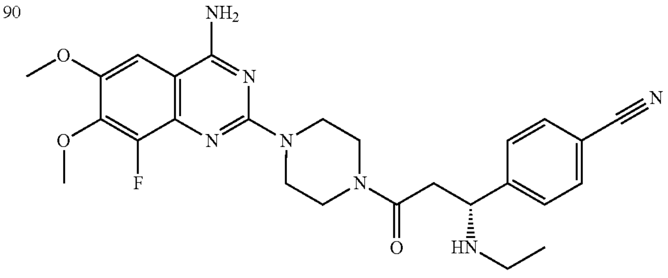 (R)-4-(3-(4-(4-amino-8-fluoro-6,7-dimethoxyquinazolin-2-yl)piperazin-1-yl)-1-(ethylamino)-3-oxopropyl)benzonitrile hydrochloride example 4, DMF | 508.3 0.49 (A1) | (400 MHz, DMSO-$d^6$) δ (ppm): 8.01-7.84 (m, 4H), 7.69 (brs., 1H), 4.76 (brs., 1H), 3.98 (s, 3H), 3.89 (s, 3H), 3.86-3.67 (m, 6H), 3.67-3.47 (m, 2H), 3.41 (dd, 1H), 3.24 (dd, 1H), 2.94-2.77 (m, 1H), 2.77-2.60 (m, 1H), 1.20 (t, 3H) |

-continued

| Ex. | Structure/Chemical Name<br>Coupling Method, solvent | MS (ESI)<br>m/z<br>$[M + H]^+$<br>$t_R$ [min]<br>(method) | $^1H$ NMR |
|---|---|---|---|
| 91 | 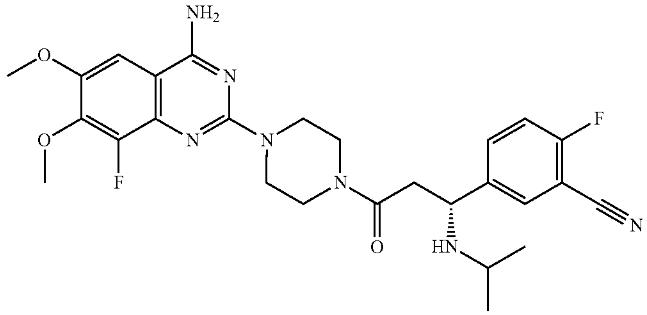<br>(R)-5-(3-(4-(4-amino-8-fluoro-6,7-dimethoxyquinazolin-2-yl)piperazin-1-yl)-1-(isopropylamino)-3-oxopropyl)-2-fluorobenzonitrile<br>example 4, DMF | 540.3<br>0.64 (A2) | (400 MHz, DMSO-$d^6$) δ (ppm): 7.95 (d, 1H), 7.83 (t, 1H), 7.56-7.39 (m, 3H), 7.37 (s, 1H), 4.18 (brs., 1H), 3.88 (s, 3H), 3.83 (s, 3H), 3.79-3.41 (m, 8H), 2.81-2.56 (m, 2H), 2.39 (br., 1H), 1.03-0.76 (m, 6H) |
| 92 | 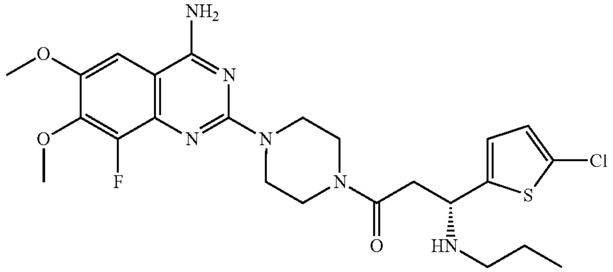<br>(R)-1-(4-(4-amino-8-fluoro-6,7-dimethoxyquinazolin-2-yl)piperazin-1-yl)-3-(5-chlorothiophen-2-yl)-3-(propylamino)propan-1-one<br>example 4, DMF | 537.2<br>0.67 (A1) | (400 MHz, DMSO-$d^6$) δ (ppm): 7.46-7.35 (m, 3H), 6.90 (d, 1H), 6.83 (d, 1H), 4.20 (t, 1H), 3.88 (s, 3H), 3.83 (s, 3H), 3.79-3.68 (m, 2H), 3.68-3.56 (m, 2H), 3.56-3.35 (m, 4H), 2.72 (d, 2H), 2.47-2.32 (m, 3H), 1.47-1.29 (m, 2H), 0.85 (t, 3H) |
| 93 | 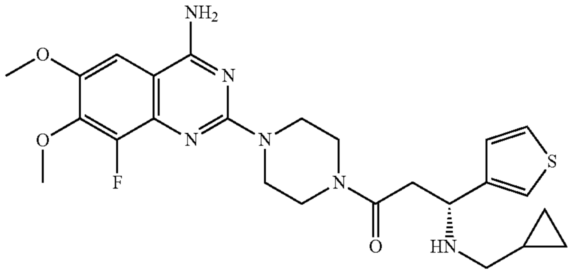<br>(R)-1-(4-(4-amino-8-fluoro-6,7-dimethoxyquinazolin-2-yl)piperazin-1-yl)-3-(cyclopropylmethylamino)-3-(thiophen-3-yl)propan-1-one<br>example 4, $CH_3CN$ | 515.3<br>0.57 (A1) | (400 MHz, methanol-$d^4$) δ (ppm): 7.40 (dd, 1H), 7.28 (d, 1H), 7.22 (s, 1H), 7.16 (d, 1H), 4.32 (t, 1H), 3.98 (s, 3H), 3.90 (s, 3H), 3.89-3.74 (m, 2H), 3.74-3.57 (m, 2H), 3.57-3.38 (m, 4H), 2.97-2.69 (m, 2H), 2.31 (d, 2H), 0.99-0.88 (m, 1H), 0.48 (m, 2H), 0.15-0.00 (m, 2H) |
| 94 | 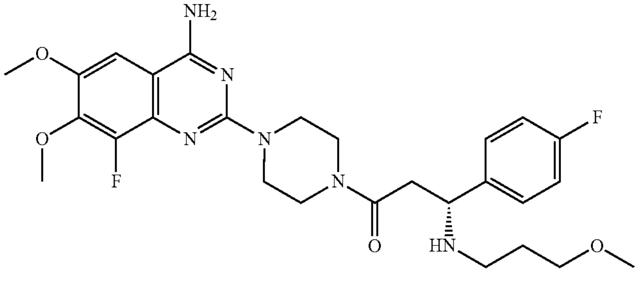<br>(R)-1-(4-(4-amino-8-fluoro-6,7-dimethoxyquinazolin-2-yl)piperazin-1-yl)-3-(4-fluorophenyl)-3-(3-methoxypropylamino)propan-1-one<br>example 4, DMF | 545.3<br>0.62 (A1) | (400 MHz, DMSO-$d^6$) δ (ppm): 7.49-7.30 (m, 5H), 7.13 (t, 2H), 3.96 (brs., 1H), 3.88 (s, 3H), 3.83 (s, 3H), 3.77-3.26 (m, 10H), 3.16 (s, 3H), 2.75-2.53 (m, 2H), 2.41-2.11 (m, 3H), 1.66-1.44 (m, 2H) |

-continued

| Ex. | Structure/Chemical Name<br>Coupling Method, solvent | MS (ESI)<br>m/z<br>$[M + H]^+$<br>$t_R$ [min]<br>(method) | $^1H$ NMR |
|---|---|---|---|
| 95 | 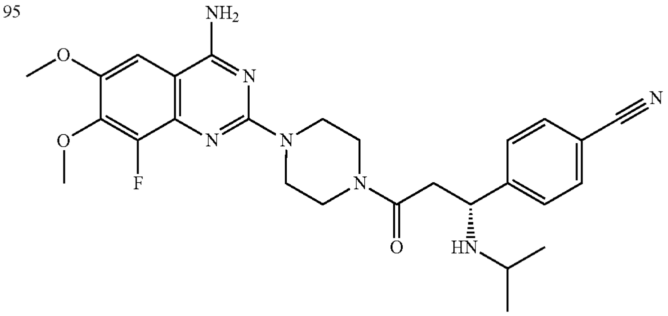<br>(R)-4-(3-(4-(4-amino-8-fluoro-6,7-dimethoxyquinazolin-2-yl)piperazin-1-yl)-1-(isopropylamino)-3-oxopropyl)benzonitrile<br>example 4, $CH_3CN$ | 522.3<br>0.55 (A1) | (400 MHz, methanol-$d^4$) δ (ppm): 7.71 (m, 2H), 7.59 (m, 2H), 7.22 (s, 1H), 4.35 (t, 1H), 3.98 (s, 3H), 3.91 (s, 3H), 3.86-3.74 (m, 2H), 3.70-3.40 (m, 6H), 2.83 (m, 2H), 2.60-2.43 (m, 1H), 1.03 (dd, 6H) |
| 96 | 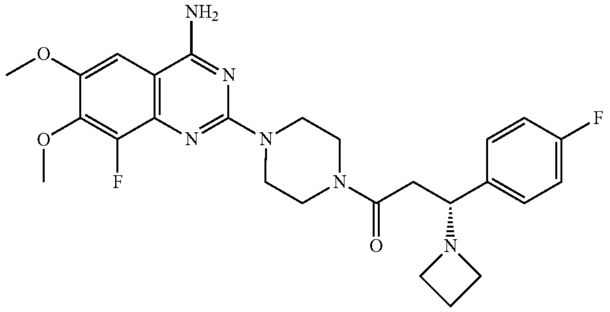<br>(R)-1-(4-(4-amino-8-fluoro-6,7-dimethoxyquinazolin-2-yl)piperazin-1-yl)-3-(azetidin-1-yl)-3-(4-fluorophenyl)propan-1-one<br>example 4, DMF | 513.3<br>0.64 (A2) | (400 MHz, methanol-$d^4$) δ (ppm): 7.41 (dd, 2H), 7.22 (d, 1H), 7.09 (t, 2H), 5.88 (m, 1H), 5.22-5.07 (m, 2H), 4.21 (t, 1H), 3.98 (s, 3H), 3.90 (s, 3H), 3.87-3.76 (m, 2H), 3.70-3.41 (m, 6H), 3.18-2.97 (m, 2H), 2.85 (d, 2H) |
| 97 | 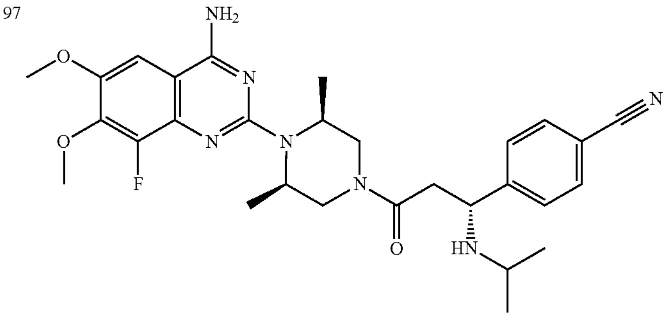<br>4-((R)-3-((3R,5S)-4-(4-amino-8-fluoro-6,7-dimethoxyquinazolin-2-yl)-3,5-dimethylpiperazin-1-yl)-1-(isopropylamino)-3-oxopropyl)benzonitrile<br>example 2, $CH_2Cl_2$ | 550.4<br>0.67 (A2) | (600 MHz, DMSO-$d^6$) δ (ppm): 7.76 (m, 2H), 7.62 (m, 2H), 7.36 (s, 1H), 7.30-7.4 (br, 3H), 4.82 (m, 2H), 4.29 (m, 2H), 3.88 (s, 3H), 3.82 (s, 3H), 3.75-3.80 (m, 2H), 3.25-3.05 (m, 2H), 2.69 (m, 1H), 2.40 (m, 1H), 1.3-1.05 (m, 6H), 0.95 (d, 3H), 0.90 (d, 3H) (rotamers) |

-continued

| Ex. | Structure/Chemical Name Coupling Method, solvent | MS (ESI) m/z $[M + H]^+$ $t_R$ [min] (method) | $^1$H NMR |
|---|---|---|---|
| 98 | 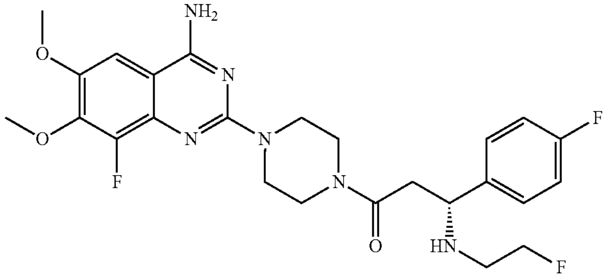 ((R)-1-[4-(4-Amino-8-fluoro-6,7-dimethoxy-quinazolin-2-yl)-piperazin-1-yl]-3-(2-fluoro-ethylamino)-3-(4-fluoro-phenyl)-propan-1-one hydrochloride example 4, $CH_3CN$ | 519.3 0.56 (A1) | (400 MHz, DMSO-$d^6$) δ (ppm): 10.09 (b, 1H), 9.95 (b, 1H), 8.80-9.45 (b, 2H), 7.81 (s, 1H), 7.75/m, 2H), 7.30 (t, 2H), 7.48 (m, 2H), 4.68 (m, 1H), 4.01 (s, 3H), 3.91 (s, 3H), 3.50-3.90 (m, 8H), 3.45 (m, 1H), 3.10-3.30 (m, 2H), 2.85-3.00 (m, 1H) |
| 99 | 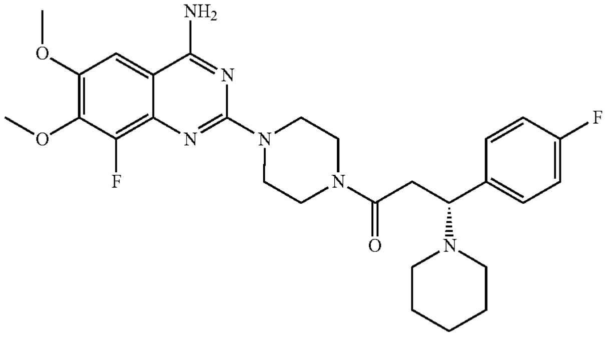 (R)-1-[4-(4-Amino-8-fluoro-6,7-dimethoxy-quinazolin-2-yl)-piperazin-1-yl]-3-(4-fluoro-phenyl)-3-piperidin-1-yl-propan-1-one hydrochloride example 4, DMF | 541.3 0.58 (A1) | (400 MHz, DMSO-$d^6$) δ (ppm): 7.77 (s, 1H), 7.72 (m, 2H), 7.31 (t, 2H), 4.83 (m, 1H), 4-02 (s, 3), 3.92 (s, 3H), 3.30-3.80 (m, 12H), 2.50-2.65 (m, 2H), 1.90-2.00 (m, 1H), 1.80-1.90 (m, 1H), 1.70-1.80 (m, 2H), 1.60-1.70 (m, 1H), 1.20-1.35 (m, 1H) |
| 100 | 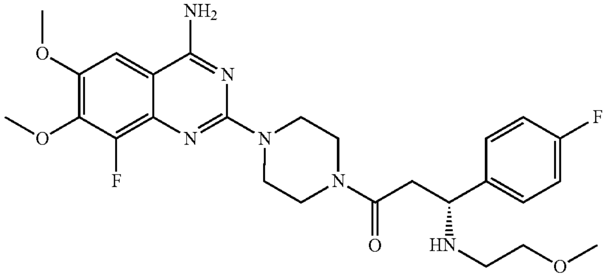 (R)-1-[4-(4-Amino-8-fluoro-6,7-dimethoxy-quinazolin-2-yl)-piperazin-1-yl]-3-(4-fluoro-phenyl)-3-(2-methoxy-ethylamino)-propan-1-one hydrochloride example 4, DMF | 531.3 0.56 (A1) | (400 MHz, DMSO-$d^6$) δ (ppm): 7.73 (m, 3H), 7.31 (t, 2H), 7.09 (t, 2H), 4.74 (m, 1H), 4.00 (s, 3H), 3.91 (s, 3H), 3.70-3.90 (m, 10H), 3.30-3.40 (m, 1H), 3.29 (s, 3H), 3.20-3.30 (m, 1H), 3.01 (b, 1H), 2.78/b, 1H) |

-continued

| Ex. | Structure/Chemical Name Coupling Method, solvent | MS (ESI) m/z $[M + H]^+$ $t_R$ [min] (method) | $^1H$ NMR |
|---|---|---|---|
| 101 | 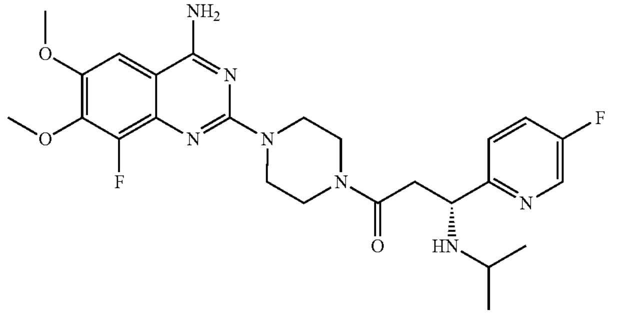 (R)-1-[4-(4-Amino-8-fluoro-6,7-dimethoxy-quinazolin-2-yl)-piperazin-1-yl]-3-(5-fluoro-pyridin-2-yl)-3-isopropylamino-propan-1-one example 4, DMF | 516.3 0.57 (A5) | (400 MHz, DMSO-$d^6$) δ (ppm): 8.51 (d, 1H), 7.70 (m, 1H), 7.57 (m, 1H), 7.43 (b, 2H), 7.39 (s, 1H), 4.23 (m, 1H), 3.90 (s, 3H), 3.85 (s, 3H), 3.62 - 3.73 (m, 4H), 3.40-3.50 (m, 4H), 2.73 (d, 2H), 2.48/b, 1H), 2.11 (m, 1H), 0.97 (d, 3H), 0.89 (d, 3H) |
| 102 | 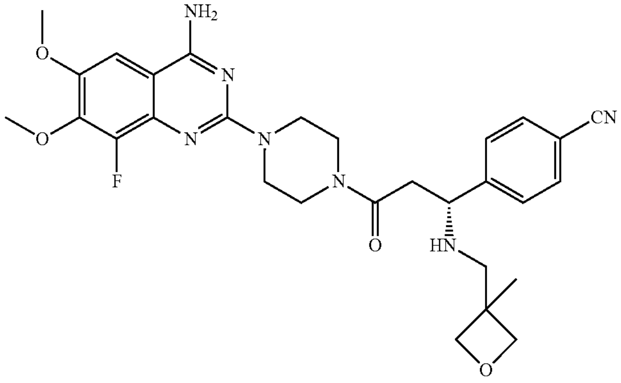 (4-{(R)-3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile example 4, DMF | 564.3 0.60 (A5) | (400 MHz, DMSO-$d^6$) δ (ppm): 7.82 (d, 2H), 7.63 (d, 2H), 7.43 (b, 2H), 7.38 (s, 1H), 4.26 (m, 2H), 4.16 (m, 2H), 4.08 (b, 1H), 3.90 (s, 3H), 3.84 (s, 3H), 3.30-3.75 (m, 10H), 2.78 (m, 1H), 2.69 (m, 1H), 2.35 (b, 1H), 1.21 (s, 3H) |
| 103 | 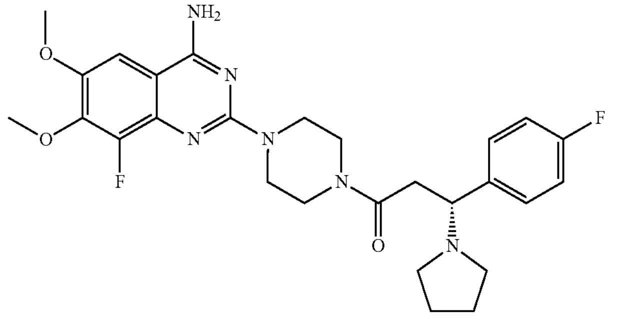 (4-{(R)-3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile hydrochloride example 4, DMF | 527.3 0.55 (A1) | (400 MHz, DMSO-$d^6$) δ (ppm): 7.77 (m, 2H), 7.67 (b, 1H), 7.29 (t, 2H), 4.85 (m, 2H), 3.99 (s, 3H), 3.90 (s, 3H), 3.35-3.90 (m, 12H), 3.10 (m, 1H), 2.92 (m, 2H), 1.75-2.05 (m, 4H) |

Reaction Scheme 21:

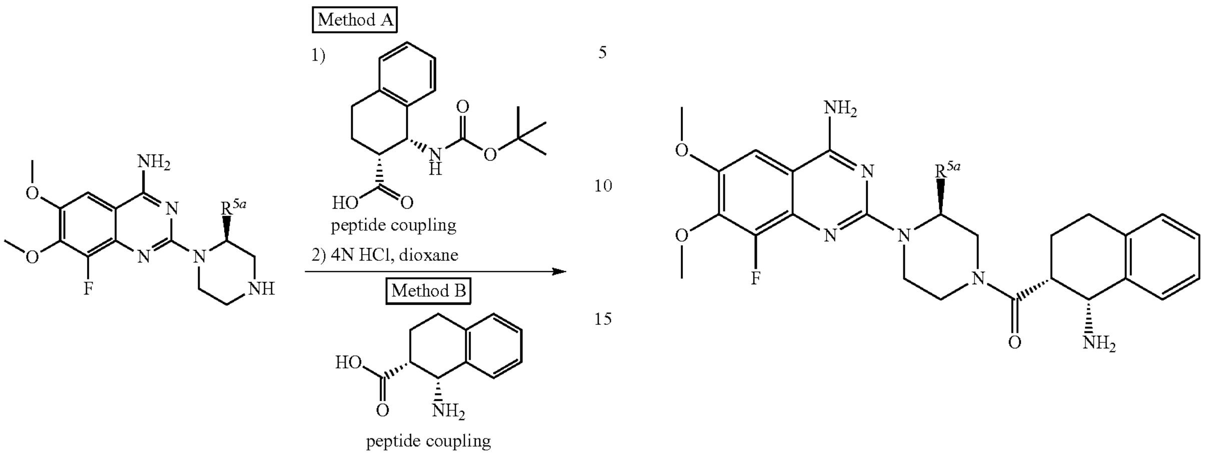

-continued

| Ex. | Structure/Chemical Name<br>Peptide Coupling Method, solvent<br>Boc-deprotection | MS (ESI)<br>m/z<br>[M + H]$^+$<br>$t_R$ [min]<br>(method) | $^1$H NMR |
|---|---|---|---|
| 104 | 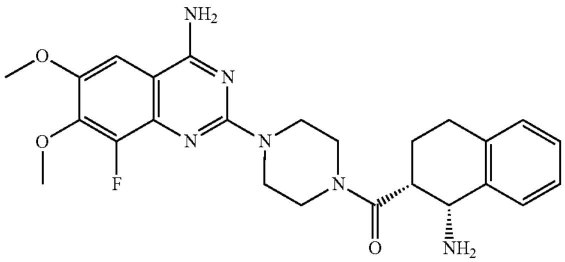<br>[4-(4-Amino-8-fluoro-6,7-dimethoxy-quinazolin-2-yl)-piperazin-1-yl]-((1R,2R)-1-amino-1,2,3,4-tetrahydro-naphthalen-2-yl)-methanone hydrochloride<br>Method A<br>example 32, $CH_3CN$<br>4N HCl/dioxane (ex. 31, step B) | 481.0<br>0.91 (A3) | (400 MHz, DMSO-d$^6$) δ ppm 8.39 (2 H, br), 7.16-7.53 (4 H, m), 4.54-4.65 (1 H, m), 3.97 (3 H, s), 3.88 (3 H, s), 3.67-3.82 (4 H, m), 3.46-3.63 (4 H, m), 2.83-3.10 (2 H, m), 1.87-2.23 (2 H, m), 1.13-1.40 (3 H, m) |
| 105 | 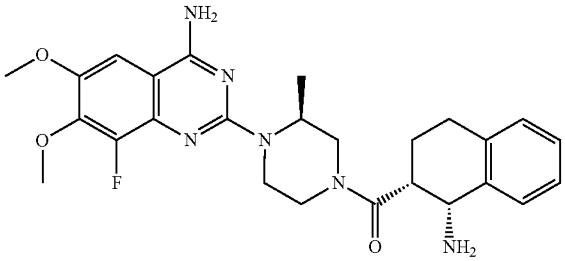<br>[(S)-4-(4-Amino-8-fluoro-6,7-dimethoxy-quinazolin-2-yl)-3-methyl-piperazin-1-yl]-((1R,2R)-1-amino-1,2,3,4-tetrahydro-naphthalen-2-yl)-methanone<br>Method A<br>example 2, $CH_3CN$<br>4N HCl/dioxane (ex. 31, step B) | 495.3<br>0.63 (A2) | (600 MHz, DMSO-d$^6$) δ (ppm): 8.5-9.6 (br, 4H), 7.86 (br, 1H), 7.50 (m, 1H), 7.31 (m, 1H), 7.15-7.3 (m, 2H), 4.85-5.0 (m, 1H), 4.5-4.7 (m, 1H), 3.99 (s, 3H), 3.91 (s, 3H), 2.75-4.5 (m, 6H), 2.75-3.1 (m, 3H), 1.8-2.2 (m, 2H), 1.1-1.3 (m, 3H) (rotamers) |

-continued

| Ex. | Structure/Chemical Name<br>Peptide Coupling Method, solvent<br>Boc-deprotection | MS (ESI)<br>m/z<br>$[M + H]^+$<br>$t_R$ [min]<br>(method) | $^1H$ NMR |
|---|---|---|---|
| 106 | 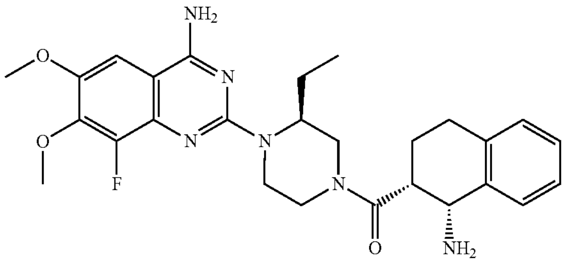<br>[(S)-4-(4-Amino-8-fluoro-6,7-dimethoxy-quinazolin-2-yl)-3-ethyl-piperazin-1-yl]-((1R,2R)-1-amino-1,2,3,4-tetrahydro-naphthalen-2-yl)-methanone<br>Method B<br>example 2, $CH_3CN$ | 509.5<br>0.68 (A2) | (600 MHz, DMSO-$d^6$) δ (ppm): 7.4-7.45 (m, 2H), 7.14-7.25 (m, 3H), 4.84 (m, 1H), 2.7-4.7 (m, 6H), 4.35 (m, 1H), 4.04 (m, 1H), 3.88 (s, 3H), 3.83 (s, 3H), 2.83 (m, 2H), 1.75-2.25 (m, 2H), 1.4-1.7 (m, 2H), 0.84 (m, 3H) |
| 107 | 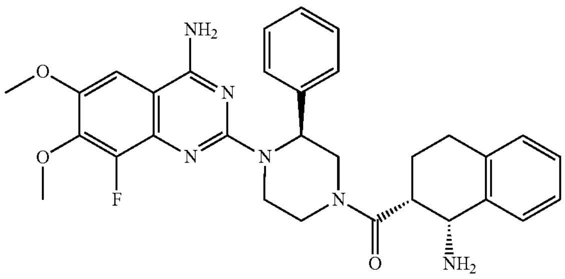<br>[(S)-4-(4-Amino-8-fluoro-6,7-dimethoxy-quinazolin-2-yl)-3-phenyl-piperazin-1-yl]-((1R,2R)-1-amino-1,2,3,4-tetrahydro-naphthalen-2-yl)-methanone hydrochloride<br>Method A<br>example 2, $CH_3CN$<br>4N HCl/dioxane (ex. 31, step B) | 557.4<br>0.81 (A2) | (600 MHz, DMSO-$d^6$) δ (ppm): 8.3-8.65 (br, 4H), 7.2-7.8 (br, 11H), 6.0-6.15 (m, 1H), 3.3-5.0 (m, 6H), 4.53 (m, 1H), 3.98 (s, 3H), 3.91 (s, 3H), 3.46 (m, 1H), 2.6-3.0 (m, 2H), 1.6-2.2 (m, 2H) (rotamers) |

Reaction Scheme 22:

-continued

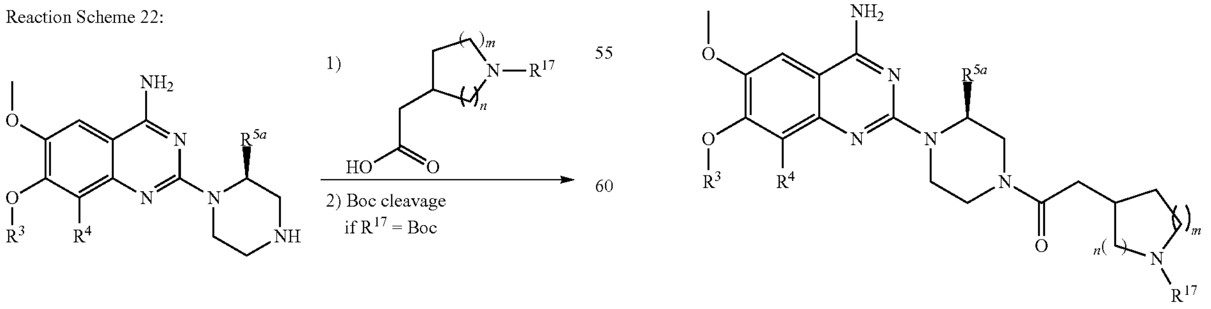

Example 108

Synthesis of (S)-1-(4-(4-amino-8-fluoro-6,7-dimethoxyquinazolin-2-yl)piperazin-1-yl)-2-(1-isobutylpyrrolidin-2-yl)ethanone ($R^3$=methyl, $R^4$=F, $R^{5a}$=H, $R^{17}$=isobutyl, n=0, m=2)

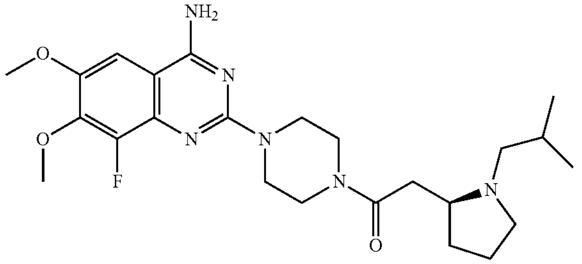 [SMILES: COc1cc2c(N)nc(N3CCN(C(=O)C[C@@H]4CCCN4CC(C)C)CC3)nc2c(F)c1OC]

8-Fluoro-6,7-dimethoxy-2-piperazin-1-yl-quinazolin-4-ylamine (21a) (142 mg, 0.375 mmol) and triethylamine (0.157 ml, 1.124 mmol) were added to a solution of (S)-2-(1-isobutylpyrrolidin-2-yl)acetic acid (72) (72 mg, 0.375 mmol) and HBTU (170 mg, 0.450 mmol) in DMF (4 ml). Stirring at RT was continued for 15 min before the reaction mixture was filtered. The filtrate was concentrated and the residue was purified by preparative HPLC (Method P6). Pure fractions were combined, frozen and lyophilized to afford the title compound as free base. LC MS (ESI): 475.3 $[M+H]^+$, $t_R$=0.50 min (Method A1); $^1H$ NMR (400 MHz, DMSO-$d^6$) δ (ppm): 7.52-7.35 (m, 3H), 7.32 (d, 1H), 3.89 (s, 3H), 3.83 (s, 3H), 3.80-3.62 (m, 4H), 3.58-3.43 (m, 4H), 3.05-2.91 (m, 1H), 2.74-2.58 (m, 2H), 2.37 (t, 1H), 2.30-2.14 (m, 1H), 2.10-1.95 (m, 2H), 1.75-1.50 (m, 3H), 1.47-1.23 (m, 2H), 0.86 (m, 6H).

Example 109

Synthesis of 1-[4-(4-Amino-8-fluoro-6,7-dimethoxy-quinazolin-2-yl)-piperazin-1-yl]-2-(S)-azetidin-2-yl-ethanone ($R^3$=methyl, $R^4$=F, $R^{5a}$=H, $R^{17}$=H, n=0, m=1)

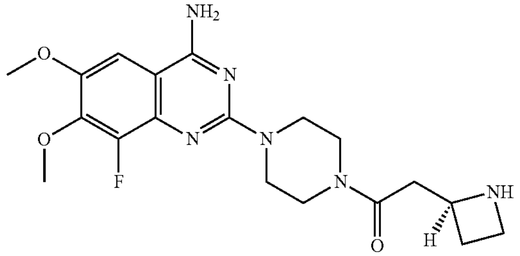 [SMILES: COc1cc2c(N)nc(N3CCN(C(=O)C[C@@H]4CCN4)CC3)nc2c(F)c1OC]

This compound was synthesized analogously to example 31 from 8-fluoro-6,7-dimethoxy-2-piperazin-1-yl-quinazolin-4-ylamine (21a) and (S)-2-carboxymethyl-azetidine-1-carboxylic acid tert-butyl ester (61f) using the same coupling reagents as in example 4 and $CH_3CN$ as solvent. Boc-deprotection was performed as described in example 31, step B to yield the title compound as hydrochloride salt. LC MS (ESI): 405.0 $[M+H]^+$, $t_R$=0.23 min (Method A3); $^1H$-NMR (400 MHz, methanol-$d^4$) δ (ppm): 7.56 (s, 1H), 4.12 (s, 3H), 4.00 (s, 3H), 3.95-3.74 (m, 10H), 3.15 (m, 2H), 2.72-2.45 (m, 2H).

The following compounds were prepared with similar methods

| Ex. | Structure/Chemical Name<br>Coupling Method, solvent<br>Boc-deprotection | MS (ESI)<br>m/z<br>$[M + H]^+$<br>$t_R$ [min]<br>(method) | $^1H$ NMR |
|---|---|---|---|
| 110 | 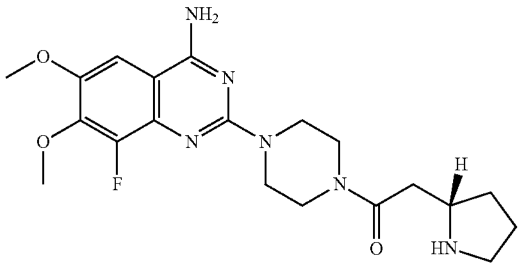<br>1-[4-(4-Amino-8-fluoro-6,7-dimethoxy-quinazolin-2-yl)-piperazin-1-yl]-2-(S)-pyrrolidin-2-yl-ethanone<br>example 5, $CH_2Cl_2$<br>4N HCl/dioxane (ex. 31, step B) | 419.5<br>0.33 (A1) | (400 MHz, methanol-$d^4$) δ (ppm): 7.58 (d, 1H), 4.12 (s, 3H), 4.05-4.03 (m, 2H), 4.00 (s, 3H), 3.97-3.91 (m, 3H), 3.81 (m, 2H), 3.75 (m, 2H), 3.38 (m, 1H), 3.29 (m, 1H), 3.14 (dd, 1H), 2.92 (dd, 1H), 2.33-2.26 (m, 1H), 2.16-1.99 (m, 2H), 1.86-1.79 (m, 1H) |

-continued

| Ex. | Structure/Chemical Name<br>Coupling Method, solvent<br>Boc-deprotection | MS (ESI)<br>m/z<br>$[M + H]^+$<br>$t_R$ [min]<br>(method) | $^1$H NMR |
|---|---|---|---|
| 111 | 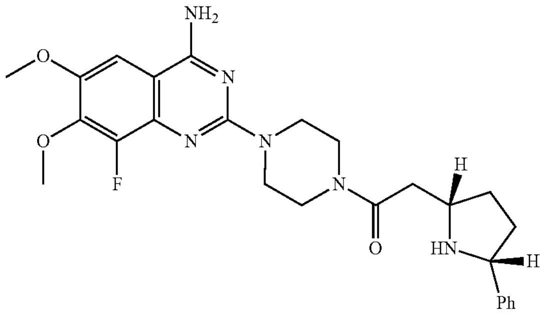<br>1-[4-(4-Amino-8-fluoro-6,7-dimethoxy-quinazolin-2-yl)-piperazin-1-yl]-2-((2S,5R)-5-phenyl-pyrrolidin-2-yl)-ethanone hydrochloride<br>example 4, $CH_3CN$<br>4N HCl/dioxane (ex. 31, step B) | 495<br>0.48 (A3) | (400 MHz, methanol-d$^4$) δ (ppm): 7.56-7.47 (m, 6H), 4.75 (m, 1H), 4.17 (m, 1H), 4.12 (s, 3H), 4.00 (s, 3H), 4.00-3.82 (m, 8H), 3.10 (m, 2H), 2.54 (m, 2H), 2.38 (m, 1H), 2.11 (m, 1H) |
| 112 | 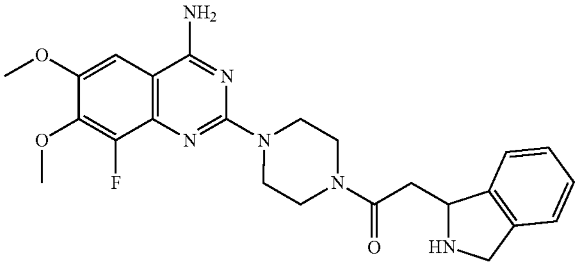<br>1-[4-(4-Amino-8-fluoro-6,7-dimethoxy-quinazolin-2-yl)-piperazin-1-yl]-2-(2,3-dihydro-1H-isoindol-1-yl)-ethanone hydrochloride<br>example 32, $CH_3CN$<br>4N HCl/dioxane (ex. 31, step B) | 467.0<br>0.69 (A3) | (400 MHz, methanol-d$^4$) δ ppm 7.30-7.41 (4 H, m), 5.03 (1 H, br), 4.36 (2 H, br), 4.01 (3 H, s), 3.94 (3 H, s), 3.85-3.91 (4 H, m), 3.69-3.77 (2 H, m), 3.58-3.66 (2 H, m), 3.14-3.26 (1 H, m), 2.79-2.95 (1 H, m) |
| 113 | 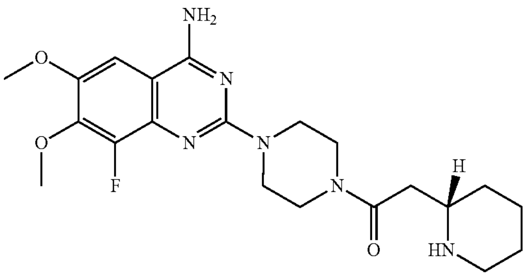<br>1-[4-(4-Amino-8-fluoro-6,7-dimethoxy-quinazolin-2-yl)-piperazin-1-yl]-2-(S)-piperidin-2-yl-ethanone<br>example 5, $CH_2Cl_2$<br>4N HCl/dioxane (ex. 31, step B) | 433.5<br>0.35 (A1) | (400 MHz, methanol-d$^4$) δ (ppm): 7.26 (d, 1H), 4.01 (s, 3H), 3.94 (s, 3H), 3.92-3.89 (m, 2H), 3.87-3.84 (m, 2H), 3.70-3.62 (m, 4H), 3.16-3.07 (m, 2H), 2.81-2.75 (m, 1H), 2.68-2.52 (m, 2H), 188-1.69 (m, 3H), 1.57-1.45 (m, 2H), 1.39-1.29 (m, 1H) |

-continued

| Ex. | Structure/Chemical Name Coupling Method, solvent Boc-deprotection | MS (ESI) m/z $[M + H]^+$ $t_R$ [min] (method) | $^1H$ NMR |
| --- | --- | --- | --- |
| 114 | 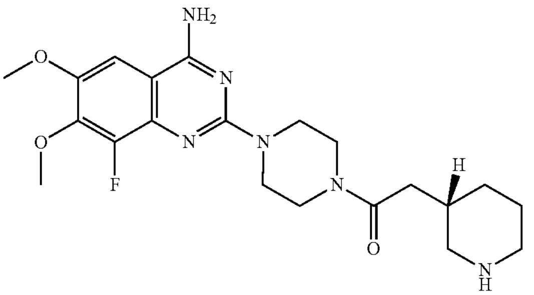 1-[4-(4-Amino-8-fluoro-6,7-dimethoxy-quinazolin-2-yl)-piperazin-1-yl]-2-(S)-piperidin-3-yl-ethanone hydrochloride example 32, $CH_3CN$ 4N HCl/dioxane (ex. 31, step B) | 433.0 0.34 (A3) | (400 MHz, DMSO-$d^6$) δ ppm 6.77 (1H, s), 3.31 (3H, s), 3.17-3.23 (5 H, m), 3.09-3.16 (2 H, m), 2.91-3.02 (4 H, m), 2.64-2.74 (1 H, m), 2.06-2.20 (1 H, m), 1.94 (1 H, t, J = 11.98 Hz), 1.62-1.83 (2 H, m), 1.46-1.59 (1 H, m), 1.11-1.24 (2 H, m), 0.91-1.09 (1 H, m), 0.47-0.68 (2 H, m) |
| 115 | 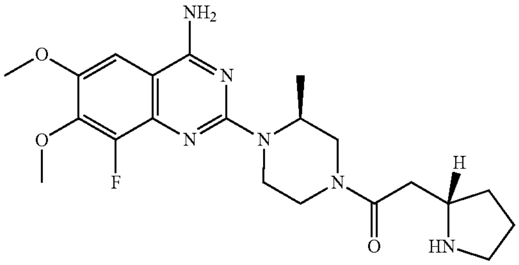 1-[(S)-4-(4-Amino-8-fluoro-6,7-dimethoxy-quinazolin-2-yl)-3-methyl-piperazin-1-yl]-2-(S)-pyrrolidin-2-yl-ethanone hydrochloride example 2, $CH_2Cl_2$ 4N HCl/dioxane (ex. 31, step B) | 433.5 0.48 (A2) | (600 MHz, DMSO-$d^6$) δ (ppm): 8.5-9.7 (br, 4H), 7.85 (s, 1H), 4.92 (m, 1H), 4.2-4.4 (m, 2H), 4.00 (s, 3H), 3.91 (s, 3H), 3.76 (m, 1H), 3.0-4.0 (m, 4H), 3.25 (m, 2H), 2.90 (m, 2H), 2.13 (m, 1H), 1.94 (m, 1H), 1.82 (m, 1H), 1.62 (m, 1H), 1.23 (d, 3H) (rotamers). |
| 116 | 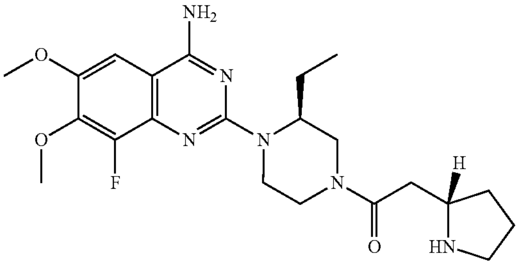 1-[(S)-4-(4-Amino-8-fluoro-6,7-dimethoxy-quinazolin-2-yl)-3-ethyl-piperazin-1-yl]-2-(S)-pyrrolidin-2-yl-ethanone hydrochloride example 2, $CH_2Cl_2$ 4N HCl/dioxane (ex. 31, step B) | 447.5 0.52 (A2) | (600 MHz, DMSO-$d^6$) δ (ppm): 8.99 (br, 2H), 7.61 (s, 1H), 4.79 (m, 1H), 4.5 (m, 1H), 3.97 (s, 3H), 3.90 (s, 3H), 3.8 (m, 1H), 2.5-4.0 (m, 12H), 2.15 (m, 1H), 1.8 (m, 1H), 1.65 (m, 2H), 0.89 (t, 3H) |

-continued

| Ex. | Structure/Chemical Name<br>Coupling Method, solvent<br>Boc-deprotection | MS (ESI)<br>m/z<br>$[M + H]^+$<br>$t_R$ [min]<br>(method) | $^1$H NMR |
|---|---|---|---|
| 117 | 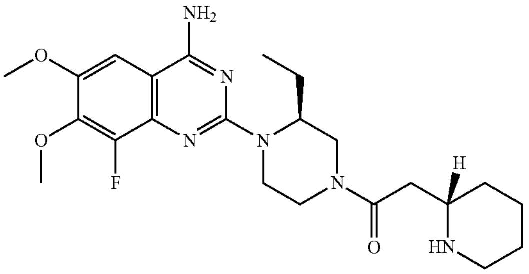<br>1-[(S)-4-(4-Amino-8-fluoro-6,7-dimethoxy-quinazolin-2-yl)-3-ethyl-piperazin-1-yl]-2-(S)-piperidin-2-yl-ethanone hydrochloride<br>example 2, $CH_2Cl_2$<br>4N HCl/dioxane (ex. 31, step B) | 461.5<br>0.56 (A2) | (600 MHz, DMSO-$d^6$) δ (ppm): 8.5-9.5 (br, 4H), 7.81 (s, 1H), 4.76 (m, 1H), 4.4 (m, 2H), 3.99 (s, 3H), 3.90 (s, 3H), 2.6-3.8 (m, 7H), 1.4-1.9 (m, 10H), 0.84 (m, 3H) |
| 118 | 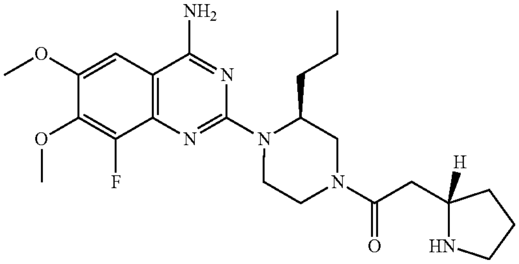<br>1-[(S)-4-(4-Amino-8-fluoro-6,7-dimethoxy-quinazolin-2-yl)-3-propyl-piperazin-1-yl]-2-(S)-pyrrolidin-2-yl-ethanone hydrochloride<br>example 2, $CH_2Cl_2$<br>4N HCl/dioxane (ex. 31, step B) | 461.5<br>0.58 (A2) | (600 MHz, DMSO-$d^6$) δ (ppm): 8.8-9.7 (br, 4H), 7.92 (s, 1H), 4.8 (m, 1H), 4.33 (m, 2H), 4.00 (s, 3H), 3.91 (s, 3H), 2.75-4.0 (m, 9H), 2.12 (m, 1H), 1.93 (m, 1H), 1.84 (m, 1H), 1.66 (m, 1H), 1.58 (m, 2H), 1.26 (m, 2H), 0.89 (m, 3H) |
| 119 | 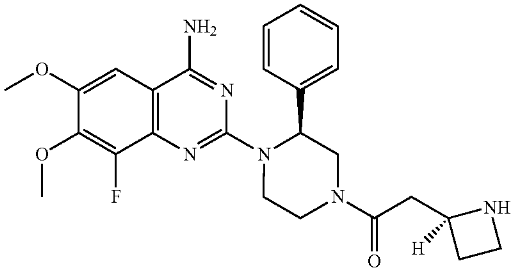<br>1-[(S)-4-(4-Amino-8-fluoro-6,7-dimethoxy-quinazolin-2-yl)-3-phenyl-piperazin-1-yl]-2-(S)-azetidin-2-yl-ethanone hydrochloride<br>example 4, $CH_3CN$<br>4N HCl/dioxane (ex. 31, step B) | 481.0<br>0.83 (A3) | (400 MHz, methanol-$d^4$) δ (ppm): 7.58-7.33 (m, 6H), 6.10 (m, 1H), 4.65-4.34 (m, 2H), 4.11 (d, 3H), 4.05-3.85 (m, 6H), 3.99 (d, 3H), 3.54 (m, 1H), 3.08 (m, 2H), 2.78-2.41 (m, 2H) |

-continued

| Ex. | Structure/Chemical Name Coupling Method, solvent Boc-deprotection | MS (ESI) m/z $[M + H]^+$ $t_R$ [min] (method) | $^1H$ NMR |
|---|---|---|---|
| 120 | 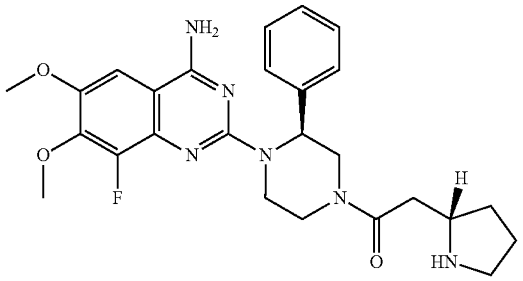 1-[(S)-4-(4-Amino-8-fluoro-6,7-dimethoxy-quinazolin-2-yl)-3-phenyl-piperazin-1-yl]-2-(S)-pyrrolidin-2-yl-ethanone hydrochloride example 2, $CH_2Cl_2$ 4N HCl/dioxane (ex. 31, step B) | 495.5 0.64 (A2) | (600 MHz, DMSO-$d^6$) δ (ppm): 8.8-9.3 (br, 4H), 7.8 (br, 1H), 7.25-7.4 (m, 5H), 6.07 (m, 1H), 4.3-4.8 (m, 2H), 3.98 (s, 3H), 3.89 (s, 3H), 2.6-4.0 (m, 9H), 1.4-2.1 (m, 4H) |
| 121 | 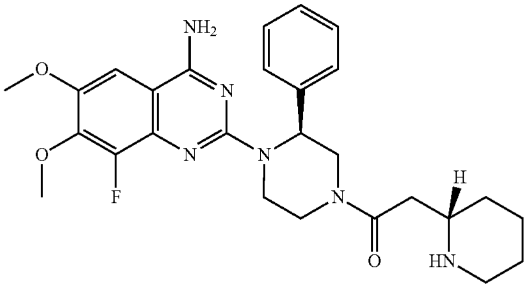 1-[(S)-4-(4-Amino-8-fluoro-6,7-dimethoxy-quinazolin-2-yl)-3-phenyl-piperazin-1-yl]-2-(S)-piperidin-2-yl-ethanone hydrochloride example 2, $CH_2Cl_2$ 4N HCl/dioxane (ex. 31, step B) | 509.5 0.68 (A2) | (600 MHz, DMSO-$d^6$) δ (ppm): 8.7-9.0 (br, 3H), 7.67 (br, 1H), 7.32 (m, 6H), 6.08/6.03 (m, 1H), 4.4-4.9 (m, 2H), 3.97 (s, 3H), 3.89 (s, 3H), 3.1-4.0 (m, 7H), 2.5-2.9 (m, 2H), 1.3-1.8 (m, 6H) (rotamers) |
| 122 | 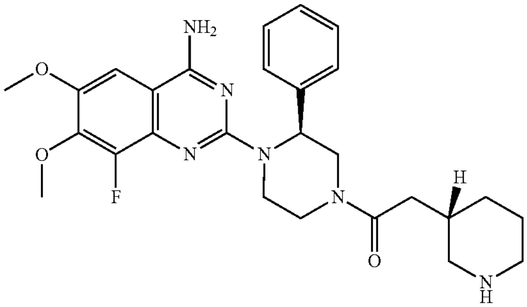 1-[(S)-4-(4-Amino-8-fluoro-6,7-dimethoxy-quinazolin-2-yl)-3-phenyl-piperazin-1-yl]-2-(S)-piperidin-3-yl-ethanone hydrochloride example 32, $CH_2Cl_2$ 4N HCl/dioxane (ex. 31, step B) | 509.2 1.04 (A3) | (400 MHz, DMSO-$d^6$) δ (ppm): 8.55 (brd, 2H), 7.35 (m, 6H), 6.05 (m, 1H), 4.98-.4.43 (m, 1H), 3.95 (d, 3H), 3.86 (d, 3H), 3.75 (m, 5H), 3.17 (m, 6H), 2.03 (m, 3H), 1.68 (m, 3H) |

-continued

| Ex. | Structure/Chemical Name Coupling Method, solvent Boc-deprotection | MS (ESI) m/z $[M + H]^+$ $t_R$ [min] (method) | $^1H$ NMR |
|---|---|---|---|
| 123 | 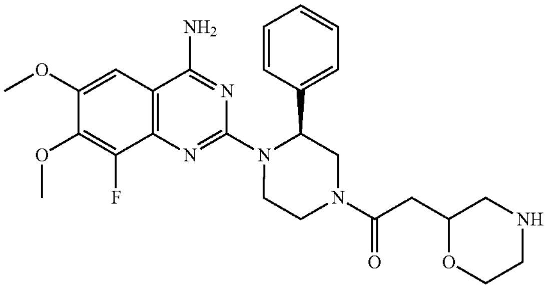 1-[(S)-4-(4-Amino-8-fluoro-6,7-dimethoxy-quinazolin-2-yl)-3-phenyl-piperazin-1-yl]-2-morpholin-2-yl-ethanone hydrochloride example 4, $CH_3CN$ 4N HCl/dioxane (ex. 31, step B) | 511.1 0.95 (A3) | (400 MHz, DMSO-$d^6$) δ (ppm): 8.92 (m, 2H), 7.48 (m, 1H), 7.35-7.22 (m, 6H), 6.05 (m, 1H), 4.93-4.58 (m, 2H), 4.03 (m, 2H), 3.92 (d, 3H), 3.87 (d, 3H), 3.85 (m, 5H), 3.16-2.78 (m, 8H) |
| 124 | 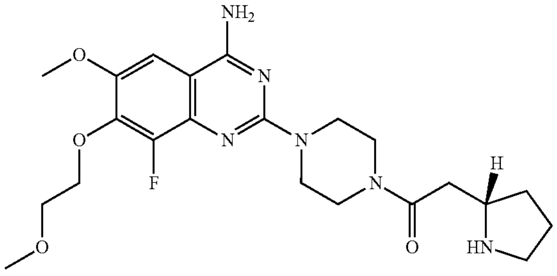 1-{4-[4-Amino-8-fluoro-6-methoxy-7-(2-methoxy-ethoxy)-quinazolin-2-yl]-piperazin-1-yl}-2-(S)-pyrrolidin-2-yl-ethanone hydrochloride example 2, $CH_2Cl_2$ 4N HCl/dioxane (ex. 31, step B) | 463.4 0.48 (A2) | (600 MHz, DMSO-$d^6$) δ (ppm): 9.1 (br, 3H), 7.76 (s, 1H), 4.32 (m, 2H), 3.91 (s, 3H), 3.82 (m, 4H), 3.76 (m, 1H), 3.63 (m, 6H), 3.28 (s, 3H), 3.13 (m, 2H), 2.96 (m, 2H), 2.11 (m, 1H), 1.93 (m, 1H), 1.83 (m, 1H), 1.61 (m, 1H) |
| 125 | 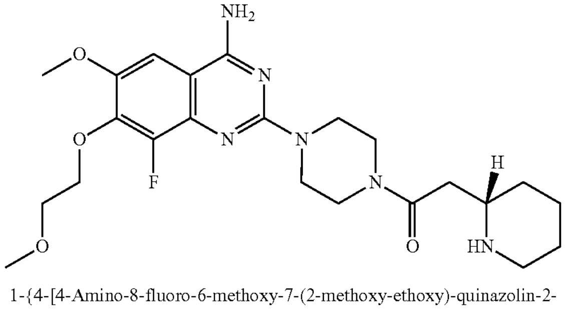 1-{4-[4-Amino-8-fluoro-6-methoxy-7-(2-methoxy-ethoxy)-quinazolin-2-yl]-piperazin-1-yl}-2-(S)-piperidin-2-yl-ethanone hydrochloride example 2, $CH_2Cl_2$ 4N HCl/dioxane (ex. 31, step B) | 477.3 0.51 (A2) | (600 MHz, DMSO-$d^6$) δ (ppm): 9.3 (br, 2H), 8.95 (br, 2H), 7.89 (s, 1H), 4.32 (m, 2H), 3.92 (s, 3H), 3.83 (m, 4H), 3.66 (m, 4H), 3.63 (m, 2H), 3.37 (m, 1H), 3.27 (s, 3H), 3.21 (m, 2H), 2.75-2.95 (m, 2H), 1.4-1.9 (m, 6H) |

-continued

| Ex. | Structure/Chemical Name<br>Coupling Method, solvent<br>Boc-deprotection | MS (ESI)<br>m/z<br>[M + H]$^+$<br>$t_R$ [min]<br>(method) | $^1$H NMR |
|---|---|---|---|
| 126 | 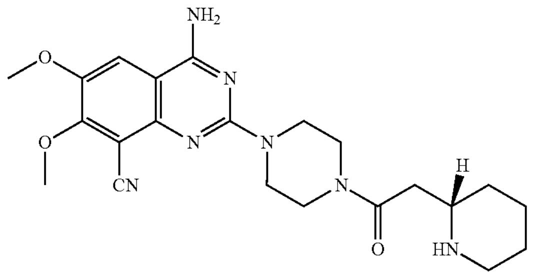<br>(S)-4-Amino-6,7-dimethoxy-2-(4-(2-(piperidin-2-yl)acetyl)piperazin-1-yl)quinazoline-8-carbonitrile<br>Example 5, $CH_2Cl_2$<br>4N HCl/dioxane (ex. 31, step B) | 440.2<br>0.55 (A1) | (400 MHz, methanol-d$^4$) δ (ppm): 7.73 (s, 1H), 4.14 (s, 3H), 3.96 (s, 3H), 3.9 (m, 2H), 3.95-4.0 (m, 2H), 3.90 (m, 2H), 3.75 (m, 1H), 3.65-3.70 (m, 4H), 3.60-3.65 (m, 3H), 2.85 (m, 1H), 2.70-2.75 (m, 1H), 2.55-2.65 (m, 1H), 1.75-1.90 (m, 3H), 1.35-1.65 (m, 3H) |

Example 127

Synthesis of 1-[4-(4-Amino-8-fluoro-6,7-dimethoxy-quinazolin-2-yl)-piperazin-1-yl]-2-(R)-1,2,3,4-tetrahydro-isoquinolin-1-yl-ethanone

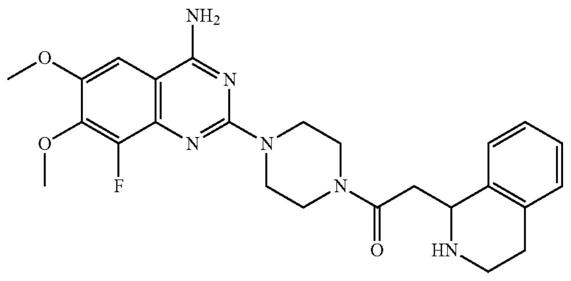 [SMILES: COc1cc2c(N)nc(N3CCN(C(=O)CC4NCCc5ccccc54)CC3)nc2c(F)c1OC]

This compound was synthesized analogously to example 32 from 8-fluoro-6,7-dimethoxy-2-piperazin-1-yl-quinazolin-4-ylamine (21a) and 1-carboxymethyl-3,4-dihydro-1H-isoquinoline-2-carboxylic acid tert-butyl ester (75a) using the same coupling reagents as in example 32 and $CH_3CN$/DMF 7:1 as solvent. The Boc-protected enantiomers were separated by chiral preparative SFC (chiracel OD-H 30×250 mm, $scCO_2$/IPAI: 70/30 isocratic, 80 ml/min). Boc-deprotection was performed as described in example 31, step B affording the title compound as hydrochloride salt. Analytical data for the eutomer: LC MS (ESI): 481.0 [M+H]$^+$, $t_R$=0.8 min (Method A3); $^1$H NMR (400 MHz, DMSO-d$^6$) δ ppm 7.59 (1H, br), 7.35-7.43 (1H, m), 7.21-7.33 (3H, m), 4.90 (1H, br), 3.97 (3H, s), 3.89 (3H, s), 3.77-3.87 (4H, m), 3.55-3.71 (4H, m), 3.17-3.28 (4H, m), 2.94-3.09 (3H, m).

Example 128

Synthesis of 1-[4-(4-Amino-8-fluoro-6,7-dimethoxy-quinazolin-2-yl)-piperazin-1-yl]-2-(6-fluoro-1,2,3,4-tetrahydro-isoquinolin-1-yl)-ethanone

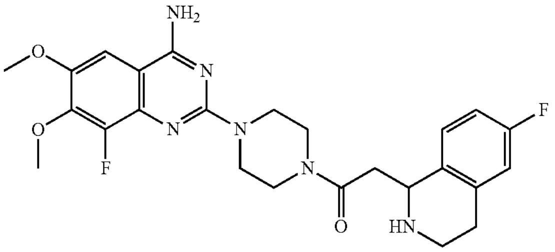 [SMILES: COc1cc2c(N)nc(N3CCN(C(=O)CC4NCCc5cc(F)ccc54)CC3)nc2c(F)c1OC]

This compound was synthesized analogously to example 4 from 8-fluoro-6,7-dimethoxy-2-piperazin-1-yl-quinazolin-4-ylamine (21a) and 1-carboxymethyl-3,4-dihydro-1H-isoquinoline-2-carboxylic acid tert-butyl ester (75b) using the same coupling reagents as in example 4 and $CH_3CN$ as solvent. The Boc-protected enantiomers were separated by chiral chromatography (Chiralpak IC 5 um 250×4.6 mm, hexane/$CH_2Cl_2$/ethanol: 50/40/10+0.1% DEA, 1 ml/min). Boc-deprotection was performed as described in example 31, step B using 3N HCl in methanol. Analytical data for the eutomer: LC MS (ESI): 499.0 [M+H]$^+$, $t_R$=0.93 min (Method A3); $^1$H-NMR (400 MHz, methanol-d$^4$) δ (ppm): 7.26 (s, 1H), 7.23 (m, 1H), 6.90 (m, 2H), 4.52 (m, 1H), 4.01 (s, 3H), 3.94 (s, 3H), 3.88-3.62 (m, 8H), 3.16 (m, 2H), 3.02-2.86 (m, 4H).

Example 129

Synthesis of (R)-4-Amino-1-[4-(4-amino-8-fluoro-6,7-dimethoxy-quinazolin-2-yl)-piperazin-1-yl]-3-phenyl-butan-1-one

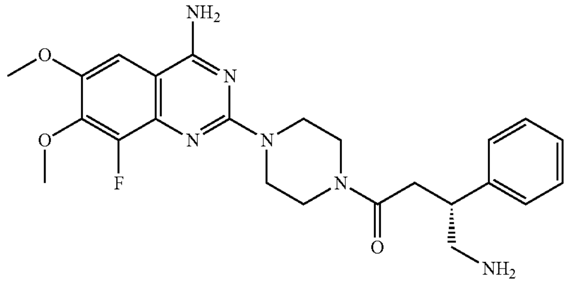 [SMILES: COc1cc2c(N)nc(N3CCN(C(=O)C[C@@H](CN)c4ccccc4)CC3)nc2c(F)c1OC]

This compound was synthesized analogously to example 3 from 8-fluoro-6,7-dimethoxy-2-piperazin-1-yl-quinazolin-4-ylamine (21a) and (R)-4-tert-butoxycarbonyl-amino-3-phenyl-butyric acid (61i) using the same coupling reagents as in example 3 and DMF as solvent. Boc-deprotection was performed using TFA in $CH_2Cl_2$. LC MS (ESI): 469 $[M+H]^+$, $t_R$=0.62 min (Method A3); $^1$H-NMR (400 MHz, DMSO-$d^6$) δ (ppm): 7.41 (br. s, 2H), 7.38 (s, 1H), 7.32-7.17 (m, 5H), 3.90 (s, 3H), 3.85 (s, 3H), 3.74-3.43 (br, 8H), 3.10 (m, 1H), 2.84-2.64 (m, 4H)

Example 130

Synthesis of (R)-4-[4-(4-Amino-8-fluoro-6,7-dimethoxy-quinazolin-2-yl)-piperazin-1-yl]-2-(4-fluoro-phenyl)-4-oxo-butyramide

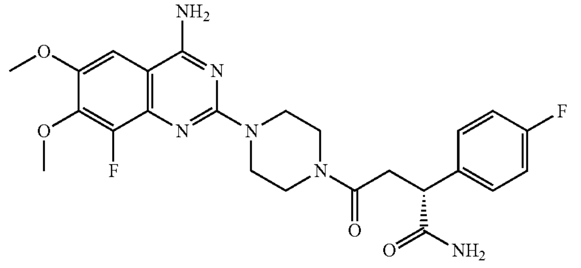 [SMILES: COc1cc2c(N)nc(N3CCN(C(=O)C[C@@H](C(N)=O)c4ccc(F)cc4)CC3)nc2c(F)c1OC]

Step A: (R)-4-[4-(4-Amino-8-fluoro-6,7-dimethoxy-quinazolin-2-yl)-piperazin-1-yl]-1-((R)-4-benzyl-2-oxo-oxazolidin-3-yl)-2-(4-fluoro-phenyl)-butane-1,4-dione (79)

(R)-4-((R)-4-Benzyl-2-oxo-oxazolidin-3-yl)-3-(4-fluoro-phenyl)-4-oxo-butyric acid (78) (216 mg, 0.582 mmol), HOBT (98 mg, 0.640 mmol) and HBTU (243 mg, 0.640 mmol) were dissolved in $CH_3CN$ (6 ml) followed by addition of 8-fluoro-6,7-dimethoxy-2-piperazin-1-yl-quinazolin-4-ylamine (21a) (200 mg, 0.582 mmol) and triethylamine (0.324 ml, 2.327 mmol). The reaction mixture was stirred at RT overnight. For workup EtOAc was added and the organic phase was washed with a saturated solution of $NaHCO_3$. The organic layer was dried and concentrated. The crude product was purified by flash chromatography (silica, $CH_2Cl_2$ 100% to $CH_2Cl_2$/Methanol 9/1 in 30 min, flow=30 ml/min,). LC MS (ESI): 661.1 $[M+H]^+$; $t_R$=1.59 min (Method A3); $^1$H NMR (400 MHz, DMSO-$d^6$) δ ppm 7.25-7.49 (9H, m), 7.18 (2H, t, J=8.93 Hz), 5.40 (1H, dd), 4.62-4.70 (0H, m), 4.22 (1H, t), 4.10 (1H, dd), 3.90 (3H, s), 3.84 (3H, s), 3.80-3.92 (2H, m), 3.41-3.70 (6H, m), 3.00-3.09 (1H, m), 2.88-2.95 (2H, m), 2.81 (1H, dd).

Step B: (R)-4-[4-(4-Amino-8-fluoro-6,7-dimethoxy-quinazolin-2-yl)-piperazin-1-yl]-2-(4-fluoro-phenyl)-4-oxo-butyric acid (80)

$LiOH.H_2O$ (18.87 mg, 0.460 mmol) was added to a solution of (R)-4-[4-(4-Amino-8-fluoro-6,7-dimethoxy-quinazolin-2-yl)-piperazin-1-yl]-1-((R)-4-benzyl-2-oxo-oxazolidin-3-yl)-2-(4-fluoro-phenyl)-butane-1,4-dione (79) (152 mg, 0.230 mmol) in THF (2 ml) and water (1 ml) at 0° C. The reaction mixture was allowed to warm to RT and stirring was continued for 2 h at RT For workup a saturated solution of $NH_4Cl$ was added and the mixture was extracted with EtOAc. The combined organic phases were dried over $Na_2SO_4$ and the solvent was evaporated to yield the title compound which was used without further purification. LC MS (ESI): 502.0 $[M+H]^+$; $t_R$=1.19 min (Method A3); $^1$H NMR (400 MHz, DMSO-$d^6$) δ ppm 7.23-7.41 (3H, m), 7.11-7.21 (2H, m), 4.02-4.11 (1H, m), 3.91 (3H, s), 3.85 (3H, s), 3.73-3.82 (2H, m), 3.40-3.71 (6H, m), 2.72-2.88 (2H, m).

Step C: (R)-4-[4-(4-Amino-8-fluoro-6,7-dimethoxy-quinazolin-2-yl)-piperazin-1-yl]-2-(4-fluoro-phenyl)-4-oxo-butyramide (example 130)

HOBT (26.0 mg, 0.169 mmol) and HBTU (64.3 mg, 0.169 mmol) were added to a solution of (R)-4-[4-(4-Amino-8-fluoro-6,7-dimethoxy-quinazolin-2-yl)-piperazin-1-yl]-2-(4-fluoro-phenyl)-4-oxo-butyric acid (80) (85 mg, 0.169 mmol) in $CH_3CN$ (5 ml), followed by ammonium chloride (10 mg, 0.186 mmol) and triethylamine (0.118 ml, 0.847 mmol). The reaction solution was stirred at RT for 16 h. For workup EtOAc was added and the organic phase was washed with a saturated solution of $NaHCO_3$. The organic phase was dried over sodium sulfate and the solvent was evaporated. The crude product was purified by preparative HPLC (Method P5). LC MS (ESI): 501.1 $[M+H]^+$; =1.10 min (Method A3); $^1$H NMR (400 MHz, DMSO-$d^6$) δ: 7.75 (br. s, 1H), 7.50 (br. s., 1H), 7.41 (dd, J=8.6, 5.6 Hz, 2H), 7.15 (t, J=8.8 Hz, 2H), 6.77 (br. s, 1H), 3.95-4.07 (m, J=4.2 Hz, 1H), 3.92 (s, 3H), 3.71-3.88 (m, 2H), 3.65 (br. s., 2H), 3.10-3.28 (m, 1H), 2.59 (br, 1H).

Example 131

(R)-1-(4-(4-amino-8-fluoro-6,7-dimethoxyquinazolin-2-yl)piperazin-1-yl)-3-(1,1,2,2,2-$d^5$ ethylamino)-3-(4-fluorophenyl)propan-1-one

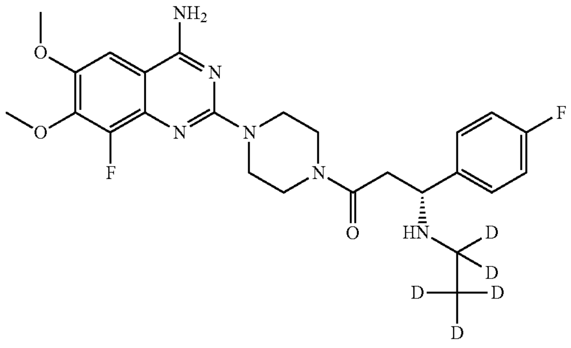 [SMILES: [2H]C([2H])([2H])C([2H])([2H])N[C@H](CC(=O)N1CCN(c2nc(N)c3cc(OC)c(OC)c(F)c3n2)CC1)c1ccc(F)cc1]

At −78° C. trifluoromethanesulfonic anhydride (727 μl, 4.3 mmol) was added dropwise to a solution of ethanol-1,1,2,2,2-$d^5$ (0.25 ml, 3.9 mmol) and triethylamine (0.6 ml, 4.3 mmol) in dichloromethane (8 ml). The reaction mixture was allowed to warm ro RT and stirring was continued for 1 h. Water was added to the reaction mixture and the organic phase was washed with a saturated solution of $NaHCO_3$ and brine. The organic phase was dried ($Na_2SO_4$) and the solvent was evaporated to give 1,1,2,2,2-$d^5$-ethyl trifluoromethanesulfonate which was used without further purification.

At RT a solution of (R)-3-Amino-1-[4-(4-amino-8-fluoro-6,7-dimethoxy-quinazolin-2-yl)-piperazin-1-yl]-3-(4-fluoro-phenyl)-propan-1-one hydrochloride (example 46, 200 mg, 0.42 mmol) in ethyl acetate (1.5 ml) was added dropwise to a solution of 1,1,2,2,2-$d^5$-ethyl trifluoromethanesulfonate (93 mg, 0.51 mmol) and $NaHCO_3$ (178 mg, 2.12 mmol) in ethyl acetate (1.5 ml) and water (3 ml). Stirring at RT was continued for 48 h. Ethyl acetate was added and the mixture was washed with a saturated solution of $NaHCO_3$. The organic phase was dried and concentrated. The crude product was purified by flash chromatography (4 g silica, cyclohexane 100% to cyclohexane/ethyl acetate 1/1 in 20 min, flow=30 ml/min) followed by preparative HPLC (method P11) to give the title compound. LC MS (ESI): 506.4 $[M+H]^+$; =0.60 min (Method A6); $^1H$ NMR (400 MHz, DMSO-$d^6$) δ: 7.35-7.45 (m, 5H), 7.14 (t, 2H), 4.0-4.05 (m, 1H), 3.90 (s, 3H), 3.84 (s, 3H), 3.70-3.80 (m, 2H), 3.25-3.60 (m, 8H).

SUPPLEMENTARY TABLE 1

| | $^1H$-NMR |
|---|---|
| 12b | (600 MHz, DMSO-$d^6$) δ (ppm): 3.78 (m, 1H), 3.74 (m, 1H), 3.37 (m, 1H), 3.17 (m, 1H), 3.11 (m, 1H), 3.03 (m, 1H), 2.71 (m, 1H), 1.41 (s, 9H), 1.19 (d, 3H) |
| 12c | (600 MHz, DMSO-$d^6$) δ (ppm): 3.6-3.8 (m, 2H), 3.35 (m, 2H), 3.2 (m, 1H), 3.1 (m, 1H), 3.0 (m, 1H), 1.5-1.6 (m, 2H), 1.40 (s, 9H), 0.94 (t, 3H) |
| 12d | 400 MHz, DMSO-$d^6$) δ (ppm): 3.15-3.8 (m, 6H), 3.08 (m, 1H), 1.57 (m, 1H), 1.48 (m, 1H), 1.40 (s, 9H), 1.37 (m, 2H), 0.92 (m, 3H) |
| 12e | (600 MHz, DMSO-$d^6$) δ (ppm): 7.44 (m, 5H), 4.24 (dd, 1H), 3.87 (d, 1H), 3.83 (m, 1H), 3.48 (m, 1H), 3.27 (m, 1H), 3.14 (m, 2H) |
| 12g | (400 MHz, $CDCl_3$) δ (ppm): 3.9-4.0 (m, 2H), 3.0-3.1 (m, 2H), 2.4-2.5 (m, 2H), 1.4 (s, 9H), 1.30 (s, 3H), 1.28 (s, 3H) |

SUPPLEMENTARY TABLE 2

| | $^1H$-NMR |
|---|---|
| 21b | (600 MHz, DMSO-$d^6$) δ (ppm): 9.67 (br s, 1H), 9.24 (br s, 1H), 8.54 (br, 2H), 7.67 (s, 1H), 5.05 (m, 1H), 4.61 (m, 1H), 3.97 (s, 3H), 3.89 (s, 3H), 2.9-4.0 (m, 5H), 1.36 (d, 3H) |
| 21c | (600 MHz, DMSO-$d^6$) δ (ppm): 10.54 (br, 1H), 10.2 (br, 1H), 9.42 (br, 1H), 8.55 (s, 1H), 5.69 (m, 1H), 3.7-5.5 (m, 6H), 4.78 (s, 3H), 4.70 (s, 3H), 2.68 (m, 2H), 1.66 (t, 3H) |
| 21d | 600 MHz, DMSO-$d^6$) δ (ppm): 9.95 (br, 1H), 9.52 (br, 1H), 9.39 (br, 1H), 9.0 (br, 1H), 7.89 (s, 1H), 4.99 (m, 1H), 4.54 (m, 1H), 4.00 (s, 3H), 3.93 (s, 3H), 3.0-3.5 (m, 5H), 1.3-1.9 (m, 2H), 1.25 (m, 2H), 0.91 (t, 3H) |
| 21e | (600 MHz, DMSO-$d^6$) δ (ppm): 10.1 (br, 1H), 8.7 (br, 1H), 8.5 (br, 2H), 7.75 (s, 1H), 7.3-7.5 (m, 5H), 6.25 (s, 1H), 4.79 (m, 1H), 3.1-4.2 (m, 5H), 3.98 (s, 3H), 3.91 (s, 3H) |
| 21f | (600 MHz, DMSO-$d^6$) δ (ppm): 9.82 (br, 2H), 8.5-9.5 (br, 2H), 7.87 (s, 1H), 4.3 (m, 2H), 4.06 (m, 4H), 3.92 (s, 3H), 3.6 (m, 2H), 3.27 (s, 3H), 3.21 (m, 4H) |
| 21g | (400 MHz, DMSO-$d^6$) δ (ppm): 9.95 (br, 1H), 9.55 (br, 1H), 8.7-9.5 (br, 2H), 7.85 (s, 1H), 5.05 (m, 1H), 4.55 (m, 1H), 4.3 (m, 2H), 3.9 (s, 3H), 3.27 (s, 3H), 3.0-4.0 (m, 7H), 1.45 (d, 2H) |

SUPPLEMENTARY TABLE 3

| | $^1H$-NMR |
|---|---|
| 45b | (400 MHz, DMSO-$d^6$) δ (ppm): 12.25 (brs, 1H), 7.49-7.21 (m, 5H), 4.65 (m, 1H), 4.17 (m, 1H), 2.90 (m, 1H), 2.27 (m, 1H), 2.06-1.78 (m, 4H), 1.39-1.08 (m, 9H) |
| 45c | (400 MHz, DMSO-$d^6$) δ ppm 12.93 (0 H, br. s), 7.92-8.00 (0 H, m), 7.48-7.57 (0 H, m), 7.24-7.48 (2 H, m), 5.46 (1 H, s), 4.62-4.72 (2 H, m), 3.52-3.73 (2 H, m), 1.41 (9 H, s) |
| 45d | (400 MHz, DMSO-$d^6$) δ (ppm): 6.71 (d, 1H), 3.69 (m, 1H), 2.47-2.38 (m, 1H), 2.33-2.21 (m, 1H), 1.79-1.57 (m, 5H), 1.42 (s, 9H), 1.37-1.31 (m, 1H), 1.20-1.08 (m, 3H), 1.04-0.85 (m, 2H) |

SUPPLEMENTARY TABLE 4

| | $^1$H-NMR |
|---|---|
| 47b | (400 MHz, DMSO-d$^6$) δ ppm 7.46 (1 H, d, J = 8.07 Hz), 6.68 (1 H, d, J = 3.42 Hz), 6.57-6.63 (1 H, m), 4.92-5.09 (1 H, m), 2.68 (2 H, d, J = 7.34 Hz), 2.38 (3 H, s), 1.38 (9 H, s) |
| 47c | (400 MHz, DMSO-d$^6$) δ (ppm): 12.3 (br, 1H), 7.42-7.49 (m, 1H), 7.33-7.40 (m, 2H), 7.14-7.17 (m, 1H), 4.86 (m, 1 H), 2.64-2.70 (m, 2H), 1.36 (s, 9H) |
| 47d | (400 MHz, DMSO-d$^6$) δ (ppm): 12.28 (s, 1H), 7.50 (m, 2H), 7.38 (m, 1H), 7.33 (m, 1H), 4.85 (m, 1H), 2.65 (m, 2H), 1.36 (s, 9H) |
| 47e | (400 MHz, DMSO-d$^6$) δ ppm 7.63 (1 H, br. s), 7.51 (2 H, d), 7.40-7.47 (2 H, m), 6.99 (1 H, t), 4.90 (1 H, q, J = 6.52 Hz), 2.54-2.69 (2 H, m), 1.36 (9 H, s) |
| 47f | (400 MHz, DMSO-d$^6$) δ (ppm): 12.20 (s, 1H), 4.35 (m, 1H), 3.73 (m, 2H), 2.74 (m, 1H), 2.59 (m, 1H), 2.30 (m, 1H), 1.93 (m, 1H), 1.38 (s, 9H) |

SUPPLEMENTARY TABLE 5

| | $^1$H-NMR |
|---|---|
| 51b | (400 MHz, DMSO-d$^6$) δ (ppm): 12.38 (br. s, 1H), 7.87-7.78 (m, 2H), 7.47 (m, 2H), 5.82-5.23 (m, 1H), 3.07 (m, 1H), 2.93-2.84 (m, 1H), 2.65 (br. s, 3H), 1.38 (br. s, 9H) |
| 51c | (400 MHz, DMSO-d$^6$) δ (ppm): 12.05 (br. s, 1H), 3.71-3.54 (m, 1H), 2.61 (s, 3H), 2.42-2.27 (m, 2H), 1.71-1.63 (m, 5H), 1.63-1.55 (m, 1H), 1.37 (s, 9H), 0.84 (m, 5H) |
| 51d | (400 MHz, DMSO-d$^6$) δ (ppm): 12.2 (s, 1H), 7.37 (m, 2H), 7.28 (m, 3H), 5.4-5.65 (m, 1H), 3.0 (m, 1H), 2.7-2.9 (m, 1H), 1.41 (s, 9H) |
| 51e | (400 MHz, DMSO-d$^6$) δ (ppm): 7.33 (m, 2H), 7.20 (m, 2H), 5.4-5.65 (m, 1H), 2.97 (m, 1H), 2.75-2.90 (m, 1H), 1.41 (s, 9H) |

SUPPLEMENTARY TABLE 6

| | $^1$H-NMR |
|---|---|
| 55l | (400 MHz, DMSO-d$^6$) δ (ppm): 7.80 (m, 1H), 7.74 (m, 1H), 7.39 (t, 1H), 3.97 (m, 1H), 2.73 (t, 1H), 2.43-2.28 (m, 1H), 2.16-1.92 (m, 2H), 0.99-0.79 (m, 6H) |
| 55o | (400 MHz, methanol-d$^4$) δ (ppm): 7.45-7.34 (m, 2H), 7.10-6.98 (m, 2H), 4.03 (m, 1H), 3.42 (t, 2H), 3.30 (s, 3H), 2.75-2.54 (m, 1H), 2.54-2.33 (m, 3H), 1.74 (quin, 2H) |

What is claimed is:

1. A compound according to Formula I (I)

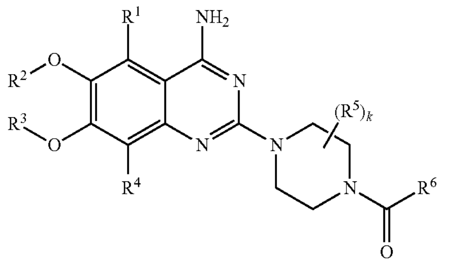

or salt or stereoisomer thereof, wherein $R^1$ is hydrogen or halogen $R^2$ is $C_1$-$C_4$alkyl;

$R^3$ is hydrogen, $C_1$-$C_6$alkyl, $C_1$-$C_4$alkoxy$C_1$-$C_4$alkyl, or halo$C_1$-$C_4$alkyl;

$R^4$ is halogen, cyano or hydrogen, wherein at least one of $R^1$ and $R^4$ is not hydrogen;

$R^5$ is independently selected at each occurrence from hydrogen, $C_1$-$C_6$alkyl, $C_1$-$C_4$alkoxy$C_1$-$C_4$alkyl, phenyl, and $C_3$-$C_6$cycloalkyl;

k is 0-3;

$R^6$ is $CH_2CHR^7R^8$, or $R^6$ is $CH{=}CHR^9$, wherein $R^9$ is $C_3$-$C_6$cycloalkyl or phenyl optionally substituted with 0, 1, or 2 groups independently selected from halogen, $C_1$-$C_4$alkyl, $C_1$-$C_4$alkoxy, halo $C_1$-$C_4$alkyl or cyano; or $R^6$ is bicyclic heteroaryl having 1 or 2 ring heteroatoms independently selected from N, O or S, partially unsaturated carbocycle or partially unsaturated heterocycle having 1 or 2 ring heteroatoms independently selected from N, O or S, each of which is optionally substituted with 0 to 3 substituents independently selected from amino, halogen, cyano, hydroxy, $C_1$-$C_4$alkyl or $C_1$-$C_4$alkoxy; or $R^6$ is $CH_2$heterocycle having 4 to 7 ring atoms and 1 or 2 ring heteroatoms selected from N, O or S, which is optionally substituted with 0, 1, or 2 groups independently selected from phenyl, halogen and $C_1$-$C_6$alkyl, or two substituents, taken in combination form a benzo ring optionally substituted with halogen;

$R^7$ is $(CH_2)_pNR^{10}R^{11}$ or $C(O)NR^A{}_2$, wherein $R^A$ is independently selected at each occurrence from hydrogen and $C_1$-$C_4$alkyl, or $NR^A{}_2$ taken in combination form a 4-6 member azacycle;

p is 0 or 1;

$R^8$ is $C_1$-$C_6$alkyl, $C_3$-$C_6$cycloalkyl; or $R^8$ is phenyl optionally substituted with 0-2 $R^{12}$; or $R^8$ is a 5 or 6 member heteroaryl having 1 or 2 ring heteroatoms selected from N, O and S and optionally substituted with 0-2 $R^{13}$ groups;

$R^{10}$ is hydrogen or $C_1$-$C_4$alkyl;

$R^{11}$ is hydrogen, optionally substituted $C_1$-$C_6$alkyl or $C_1$-$C_6$haloalkyl, wherein the optional substituents are selected from $C_1$-$C_4$alkoxy, $C_3$-$C_6$cycloalkyl and 4-6 member heterocycle having 1-2 ring heteroatoms selected from N, O and S; or $NR^{10}R^{11}$, taken in combination form a 4 to 7 member saturated azacycle optionally substituted with 0, 1, or 2 $C_1$-$C_4$alkyl groups;

$R^{12}$ is independently selected at each occurrence from hydrogen, cyano, hydroxy, halogen, $C_1$-$C_4$alkyl, $C_2$-$C_4$alkenyl, $C_2$-$C_4$alkynyl, $C_1$-$C_4$haloalkyl or $C_1$-$C_4$alkoxy;

$R^{13}$ is independently selected at each occurrence from hydrogen, $C_1$-$C_4$alkyl, or halogen.

2. The compound of claim 1, wherein the compound is represented by formula (II):

(II)

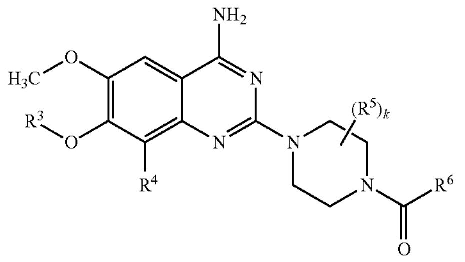

or a salt thereof.

3. A compound of claim 1, wherein the compound is represented by formula III (III)

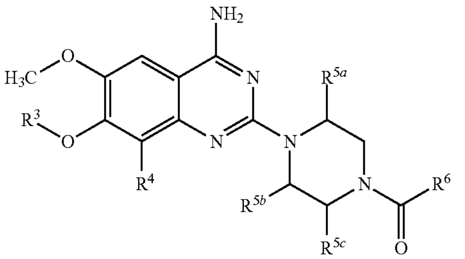

or salt thereof, wherein $R^{5a}$ is hydrogen, phenyl, $C_1$-$C_4$alkyl, methoxy$C_1$-$C_4$alkyl;

$R^{5b}$ is hydrogen or $C_1$-$C_4$alkyl; and $R^{5c}$ is hydrogen or $C_1$-$C_4$alkyl.

4. The compound of claim 1, which compound is a compound of formula (IV):

(IV)

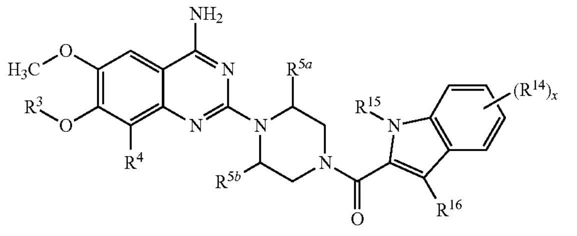

or salt thereof, wherein $R^{5a}$ is hydrogen, methyl, ethyl, propyl or phenyl;

$R^{5b}$ is hydrogen or methyl;

x is 0, 1, or 2;

$R^{14}$ is independently selected at each occurrence from fluoro, chloro, hydroxy, methoxy and cyano;

$R^{15}$ is hydrogen or $C_1$-$C_4$alkyl; and $R^{16}$ is hydrogen or amino.

5. The compound of claim 1, which compound is a compound of formula (V):

(V)

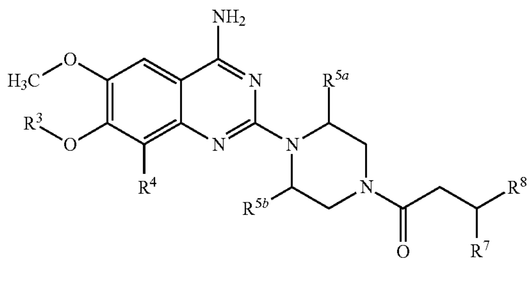

or salt thereof, wherein $R^{5a}$ is hydrogen, methyl, ethyl, propyl or phenyl; and $R^{5b}$ is hydrogen or methyl.

6. The compound of 5, wherein the compound is a compound of formula (V), $R^7$ is $NR^{10}R^{11}$;

$R^9$ is furyl, $C_3$-$C_6$cycloalkyl, $C_1$-$C_4$alkyl, pyridyl optionally substituted by fluoro, thienyl optionally substituted by chloro or $C_1$-$C_4$alkyl, or phenyl optionally substituted by cyano, halogen, mono- di- and trifluoromethyl, $C_1$-$C_4$alkyl, vinyl or ethynyl;

$R^{10}$ is hydrogen or methyl; and $R^{11}$ s hydrogen, $C_1$-$C_6$haloalkyl or $C_1$-$C_6$alkyl optionally substituted with cyclopropyl, $C_1$-$C_4$alkoxy or 4-6 member heterocycle having 1 ring heteroatom selected from N, O and S; or $NR^{10}R^{11}$, taken in combination, form a 4-6 member saturated azacycle.

7. The compound of claim 1, which compound is a compound of formula (VI)

(VI)

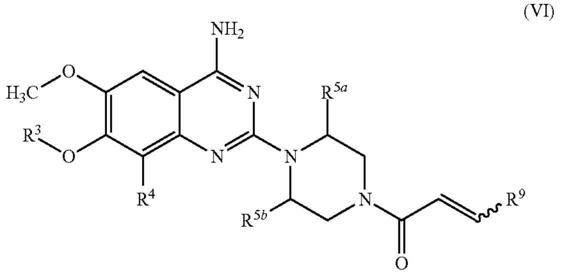

or salt thereof, wherein $R^9$ is selected from $C_3$-$C_6$cycloalkyl or phenyl, wherein the phenyl is unsubstituted or substituted with cyano.

8. The compound of claim 1, which compound is a compound of formula (VII):

(VII)

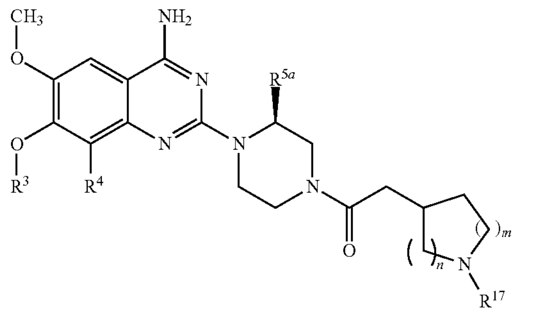

wherein $R^{17}$ is $C_1$-$C_4$alkyl; and n is 0 or 1;

m is 0, 1, or 2, wherein n+m is 1, 2, or 3; or a salt thereof.

9. The compound of claim 1, in which $R^4$ is fluoro.

10. The compound of claim 1, in which $R^3$ is methyl optionally substituted with 0, 1, 2 or 3 fluoro substitutents; or $R^3$ is methoxy$C_1$-$C_4$alkyl.

11. The compound of claim 3, in which $R^{5a}$ is hydrogen, methyl, ethyl, propyl or phenyl; and $R^{5b}$ and $R^{5b}$ are each independently hydrogen or methyl.

12. The compound of claim 1, in which the compound is selected from the group consisting of 1-[4-(4-Amino-8-fluoro-6,7-dimethoxy-quinazolin-2-yl)-piperazin-1-yl]-3-cyclopropyl-propenone;

4-{3-[4-(4-Amino-8-fluoro-6,7-dimethoxy-quinazolin-2-yl)-piperazin-1-yl]-3-oxo-propenyl}-benzonitrile;

(1-[4-(4-Amino-8-fluoro-6,7-dimethoxy-quinazolin-2-yl)-3-methoxymethyl-piperazin-1-yl]-3-cyclopropyl-propenone;

1-[4-(4-Amino-8-fluoro-6,7-dimethoxy-quinazolin-2-yl)-3-(2-methoxy-ethyl)-piperazin-1-yl]-3-cyclopropyl-propenone;

4-Amino-2-[4-(3-cyclopropyl-acryloyl)-piperazin-1-yl]-6,7-dimethoxy-quinazoline-8-carbonitrile;

1-[4-(4-Amino-8-fluoro-6,7-dimethoxy-quinazolin-2-yl)-3-methyl-piperazin-1-yl]-3-cyclobutyl-propenone;

4-{3-[4-(4-Amino-8-fluoro-6,7-dimethoxy-quinazolin-2-yl)-3-methyl-piperazin-1-yl]-3-oxo-propenyl}-benzonitrile;

4-{3-[4-(4-Amino-8-fluoro-6,7-dimethoxy-quinazolin-2-yl)-3-ethyl-piperazin-1-yl]-3-oxo-propenyl}-benzonitrile;

4-{3-[4-(4-Amino-8-fluoro-6,7-dimethoxy-quinazolin-2-yl)-3-propyl-piperazin-1-yl]-3-oxo-propenyl}-benzonitrile;

4-{3-[4-(4-Amino-8-fluoro-6,7-dimethoxy-quinazolin-2-yl)-3-phenyl-piperazin-1-yl]-3-oxo-propenyl}-benzonitrile;

4-(3-{4-[4-Amino-8-fluoro-6-methoxy-7-(2-methoxy-ethoxy)-quinazolin-2-yl]-piperazin-1-yl}-3-oxo-propenyl)-benzonitrile;

1-[4-(4-Amino-5-fluoro-6,7-dimethoxy-quinazolin-2-yl)-piperazin-1-yl]-3-cyclopropyl-propenone;

[4-(4-Amino-8-fluoro-6,7-dimethoxy-quinazolin-2-yl)-piperazin-1-yl]-(1H-indol-2-yl)-methanone;

2-[4-(4-Amino-8-fluoro-6,7-dimethoxy-quinazolin-2-yl)-piperazine-1-carbonyl]-1H-indole-5-carbonitrile;

[4-(4-Amino-8-fluoro-6,7-dimethoxy-quinazolin-2-yl)-piperazin-1-yl]-(5-hydroxy-1H-indol-2-yl)-methanone;

[4-(4-Amino-8-fluoro-6,7-dimethoxy-quinazolin-2-yl)-piperazin-1-yl]-(4-methoxy-1H-indol-2-yl)-methanone;

[4-(4-Amino-8-fluoro-6,7-dimethoxy-quinazolin-2-yl)-piperazin-1-yl]-(5-fluoro-1H-indol-2-yl)-methanone;

[4-(4-Amino-8-fluoro-6,7-dimethoxy-quinazolin-2-yl)-piperazin-1-yl]-(5,7-difluoro-1H-indol-2-yl)-methanone;

2-[4-(4-Amino-8-fluoro-6,7-dimethoxy-quinazolin-2-yl)-3-methyl-piperazine-1-carbonyl]-1H-indole-5-carbonitrile;

[4-(4-Amino-8-fluoro-6,7-dimethoxy-quinazolin-2-yl)-3-methyl-piperazin-1-yl]-(5-fluoro-1H-indol-2-yl)-methanone;

2-[4-(4-Amino-8-fluoro-6,7-dimethoxy-quinazolin-2-yl)-3-ethyl-piperazine-1-carbonyl]-1H-indole-5-carbonitrile;

2-[4-(4-Amino-8-fluoro-6,7-dimethoxy-quinazolin-2-yl)-3-propyl-piperazine-1-carbonyl]-1H-indole-5-carbonitrile;

[4-(4-Amino-8-fluoro-6,7-dimethoxy-quinazolin-2-yl)-3-propyl-piperazin-1-yl]-(5-fluoro-1H-indol-2-yl)-methanone;

2-[4-(4-Amino-8-fluoro-6,7-dimethoxy-quinazolin-2-yl)-3-phenyl-piperazine-1-carbonyl]-1H-indole-5-carbonitrile;

(4-(4-amino-8-fluoro-6,7-dimethoxyquinazolin-2-yl)-3-phenylpiperazin-1-yl)(5-fluoro-1H-indol-2-yl)methanone;

{4-[4-Amino-8-fluoro-6-methoxy-7-(2-methoxy-ethoxy)-quinazolin-2-yl]-3-methyl-piperazin-1-yl}-(5-chloro-1H-indol-2-yl)-methanone;

3-Amino-1-[4-(4-amino-8-fluoro-6,7-dimethoxy-quinazolin-2-yl)-piperazin-1-yl]-hex-5-yn-1-one;

3-Amino-1-[4-(4-amino-8-fluoro-6,7-dimethoxy-quinazolin-2-yl)-piperazin-1-yl]-3-cyclopentyl-propan-1-one;

3-Amino-1-[4-(4-amino-8-fluoro-6,7-dimethoxy-quinazolin-2-yl)-piperazin-1-yl]-5-methyl-hexan-1-one;

3-Amino-1-[4-(4-amino-8-fluoro-6,7-dimethoxy-quinazolin-2-yl)-piperazin-1-yl]-3-furan-2-yl-propan-1-one hydrochloride;

3-Amino-1-[4-(4-amino-8-fluoro-6,7-dimethoxy-quinazolin-2-yl)-piperazin-1-yl]-3-furan-3-yl-propan-1-one;

3-Amino-1-[4-(4-amino-8-fluoro-6,7-dimethoxy-quinazolin-2-yl)-piperazin-1-yl]-3-thiophen-2-yl-propan-1-one;

3-Amino-1-[4-(4-amino-8-fluoro-6,7-dimethoxy-quinazolin-2-yl)-piperazin-1-yl]-3-thiophen-3-yl-propan-1-one;

3-Amino-1-[4-(4-amino-8-fluoro-6,7-dimethoxy-quinazolin-2-yl)-piperazin-1-yl]-3-(5-methyl-thiophen-2-yl)-propan-1-one (R1=H, R2=5-methyl-thiophen-2-yl);

3-Amino-1-[4-(4-amino-8-fluoro-6,7-dimethoxy-quinazolin-2-yl)-piperazin-1-yl]-3-phenyl-propan-1-one;

3-Amino-1-[4-(4-amino-8-fluoro-6,7-dimethoxy-quinazolin-2-yl)-piperazin-1-yl]-3-m-tolyl-propan-1-one;

3-Amino-1-[4-(4-amino-8-fluoro-6,7-dimethoxy-quinazolin-2-yl)-piperazin-1-yl]-3-p-tolyl-propan-1-one;

3-Amino-1-[4-(4-amino-8-fluoro-6,7-dimethoxy-quinazolin-2-yl)-piperazin-1-yl]-3-(4-ethynyl-phenyl)-propan-1-one;

3-{1-Amino-3-[4-(4-amino-8-fluoro-6,7-dimethoxy-quinazolin-2-yl)-piperazin-1-yl]-3-oxo-propyl}-benzonitrile;

4-{1-Amino-3-[4-(4-amino-8-fluoro-6,7-dimethoxy-quinazolin-2-yl)-piperazin-1-yl]-3-oxo-propyl}-benzonitrile;

3-Amino-1-[4-(4-amino-8-fluoro-6,7-dimethoxy-quinazolin-2-yl)-piperazin-1-yl]-3-(3-fluoro-phenyl)-propan-1-one;

3-Amino-1-[4-(4-amino-8-fluoro-6,7-dimethoxy-quinazolin-2-yl)-piperazin-1-yl]-3-(4-fluoro-phenyl)-propan-1-one;

3-Amino-1-[4-(4-amino-8-fluoro-6,7-dimethoxy-quinazolin-2-yl)-piperazin-1-yl]-3-(3-chloro-phenyl)-propan-1-one;

3-Amino-1-[4-(4-amino-8-fluoro-6,7-dimethoxy-quinazolin-2-yl)-piperazin-1-yl]-3-(4-chloro-phenyl)-propan-1-one;

3-Amino-1-[4-(4-amino-8-fluoro-6,7-dimethoxy-quinazolin-2-yl)-piperazin-1-yl]-3-(4-bromo-phenyl)-propan-1-one;

3-Amino-1-[4-(4-amino-8-fluoro-6,7-dimethoxy-quinazolin-2-yl)-piperazin-1-yl]-3-(2,4-difluoro-phenyl)-propan-1-one;

3-Amino-1-[4-(4-amino-8-fluoro-6,7-dimethoxy-quinazolin-2-yl)-piperazin-1-yl]-3-(3-chloro-4-fluoro-phenyl)-propan-1-one;

3-Amino-1-[4-(4-amino-8-fluoro-6,7-dimethoxy-quinazolin-2-yl)-piperazin-1-yl]-3-(4-difluoromethyl-phenyl)-propan-1-one;

3-Amino-1-[4-(4-amino-8-fluoro-6,7-dimethoxy-quinazolin-2-yl)-piperazin-1-yl]-3-(3-trifluoromethyl-phenyl)-propan-1-one;

3-Amino-1-[4-(4-amino-8-fluoro-6,7-dimethoxy-quinazolin-2-yl)-piperazin-1-yl]-3-(4-trifluoromethyl-phenyl)-propan-1-one;

3-Amino-1-[4-(4-amino-8-fluoro-6,7-dimethoxy-quinazolin-2-yl)-3-methyl-piperazin-1-yl]-5-methyl-hexan-1-one;

3-Amino-1-[4-(4-amino-8-fluoro-6,7-dimethoxy-quinazolin-2-yl)-3-methyl-piperazin-1-yl]-3-phenyl-propan-1-one hydrochloride;

4-{1-Amino-3-[4-(4-amino-8-fluoro-6,7-dimethoxy-quinazolin-2-yl)-3-methyl-piperazin-1-yl]-3-oxo-propyl}-benzonitrile;

3-Amino-1-[4-(4-amino-8-fluoro-6,7-dimethoxy-quinazolin-2-yl)-3-methyl-piperazin-1-yl]-3-(2-fluoro-phenyl)-propan-1-one;

3-Amino-1-[4-(4-amino-8-fluoro-6,7-dimethoxy-quinazolin-2-yl)-3-methyl-piperazin-1-yl]-3-(4-fluoro-phenyl)-propan-1-one;

3-Amino-1-[4-(4-amino-8-fluoro-6,7-dimethoxy-quinazolin-2-yl)-3-methyl-piperazin-1-yl]-3-(4-trifluoromethyl-phenyl)-propan-1-one;

3-Amino-1-[4-(4-amino-8-fluoro-6,7-dimethoxy-quinazolin-2-yl)-3-methyl-piperazin-1-yl]-4-phenyl-butan-1-one;

3-Amino-1-[4-(4-amino-8-fluoro-6,7-dimethoxy-quinazolin-2-yl)-3-methyl-piperazin-1-yl]-4-pyridin-4-yl-butan-1-one;

4-{1-Amino-3-[4-(4-amino-8-fluoro-6,7-dimethoxy-quinazolin-2-yl)-3-ethyl-piperazin-1-yl]-3-oxo-propyl}-benzonitrile;

3-Amino-1-[4-(4-amino-8-fluoro-6,7-dimethoxy-quinazolin-2-yl)-3-ethyl-piperazin-1-yl]-3-(4-fluoro-phenyl)-propan-1-one;

3-Amino-1-[4-(4-amino-8-fluoro-6,7-dimethoxy-quinazolin-2-yl)-3-ethyl-piperazin-1-yl]-3-(4-trifluoromethyl-phenyl)-propan-1-one;

4-{1-Amino-3-[4-(4-amino-8-fluoro-6,7-dimethoxy-quinazolin-2-yl)-3-propyl-piperazin-1-yl]-3-oxo-propyl}-benzonitrile;

3-Amino-1-[4-(4-amino-8-fluoro-6,7-dimethoxy-quinazolin-2-yl)-3-propyl-piperazin-1-yl]-3-(4-trifluoromethyl-phenyl)-propan-1-one;

3-Amino-1-[4-(4-amino-8-fluoro-6,7-dimethoxy-quinazolin-2-yl)-3-phenyl-piperazin-1-yl]-3-(4-fluoro-phenyl)-propan-1-one;

4-(1-Amino-3-{4-[4-amino-8-fluoro-6-methoxy-7-(2-methoxy-ethoxy)-quinazolin-2-yl]-piperazin-1-yl}-3-oxo-propyl)-benzonitrile;

4-(1-Amino-3-{4-[4-amino-8-fluoro-6-methoxy-7-(2-methoxy-ethoxy)-quinazolin-2-yl]-3-methyl-piperazin-1-yl}-3-oxo-propyl)-benzonitrile;

1-[4-(4-Amino-8-fluoro-6,7-dimethoxy-quinazolin-2-yl)-piperazin-1-yl]-3-methylamino-3-phenyl-propan-1-one;

3-Amino-1-[4-(4-amino-8-fluoro-6,7-dimethoxy-quinazolin-2-yl)-2,5-dimethyl-piperazin-1-yl]-3-phenyl-propan-1-one;

3-amino-1-[4-(4-amino-8-fluoro-6,7-dimethoxy-quinazolin-2-yl)-2,5-dimethyl-piperazin-1-yl]-3-(4-fluorophenyl)-propan-1-one;

4-Amino-2-[4-(3-amino-3-phenyl-propionyl)-piperazin-1-yl]-6,7-dimethoxy-quinazoline-8-carbonitrile;

4-Amino-2-{4-[3-amino-3-(4-fluoro-phenyl)-propionyl]-piperazin-1-yl}-6,7-dimethoxy-quinazoline-8-carbonitrile;

4-(3-(4-(4-amino-8-fluoro-6,7-dimethoxyquinazolin-2-yl)piperazin-1-yl)-1-(methylamino)-3-oxopropyl)benzonitrile;

1-(4-(4-amino-8-fluoro-6,7-dimethoxyquinazolin-2-yl)piperazin-1-yl)-3-cyclohexyl-3-(methylamino)propan-1-one;

3-Amino-1-[4-(4-amino-5-fluoro-6,7-dimethoxy-quinazolin-2-yl)-piperazin-1-yl]-3-(4-fluoro-phenyl)-propan-1-one;

1-[4-(4-Amino-8-fluoro-6,7-dimethoxy-quinazolin-2-yl)-piperazin-1-yl]-3-ethylamino-3-(4-fluoro-phenyl)-propan-1-one;

1-[4-(4-Amino-8-fluoro-6,7-dimethoxy-quinazolin-2-yl)-piperazin-1-yl]-3-dimethylamino-3-phenyl-propan-1-one;

1-[4-(4-Amino-8-fluoro-6,7-dimethoxy-quinazolin-2-yl)-piperazin-1-yl]-3-dimethylamino-3-phenyl-propan-1-one;

1-(4-(4-amino-8-fluoro-6,7-dimethoxyquinazolin-2-yl) piperazin-1-yl)-3-(1,3-difluoropropan-2-ylamino)-3-(4-fluorophenyl)propan-1-one;

1-[4-(4-Amino-8-fluoro-6,7-dimethoxy-quinazolin-2-yl)-piperazin-1-yl]-3-(4-fluoro-phenyl)-3-(2,2,2-trifluoro-ethylamino)-propan-1-one;

1-[4-(4-Amino-8-fluoro-6,7-dimethoxy-quinazolin-2-yl)-piperazin-1-yl]-3-(4-fluoro-phenyl)-3-isopropylamino-propan-1-one;

4-(3-(4-(4-amino-8-fluoro-6,7-dimethoxyquinazolin-2-yl)piperazin-1-yl)-1-(ethylamino)-3-oxopropyl)benzonitrile;

5-(3-(4-(4-amino-8-fluoro-6,7-dimethoxyquinazolin-2-yl)piperazin-1-yl)-1-(isopropylamino)-3-oxopropyl)-2-fluorobenzonitrile;

1-(4-(4-amino-8-fluoro-6,7-dimethoxyquinazolin-2-yl) piperazin-1-yl)-3-(5-chlorothiophen-2-yl)-3-(propylamino)propan-1-one;

1-(4-(4-amino-8-fluoro-6,7-dimethoxyquinazolin-2-yl) piperazin-1-yl)-3-(cyclopropylmethylamino)-3-(thiophen-3-yl)propan-1-one;

1-(4-(4-amino-8-fluoro-6,7-dimethoxyquinazolin-2-yl) piperazin-1-yl)-3-(4-fluorophenyl)-3-(3-methoxypropylamino)propan-1-one;

4-(3-(4-(4-amino-8-fluoro-6,7-dimethoxyquinazolin-2-yl)piperazin-1-yl)-1-(isopropylamino)-3-oxopropyl) benzonitrile;

1-(4-(4-amino-8-fluoro-6,7-dimethoxyquinazolin-2-yl) piperazin-1-yl)-3-(azetidin-1-yl)-3-(4-fluorophenyl) propan-1-one;

4-(3-(4-(4-amino-8-fluoro-6,7-dimethoxyquinazolin-2-yl)-3,5-dimethylpiperazin-1-yl)-1-(isopropylamino)-3-oxopropyl)benzonitrile;

(1-[4-(4-Amino-8-fluoro-6,7-dimethoxy-quinazolin-2-yl)-piperazin-1-yl]-3-(2-fluoro-ethylamino)-3-(4-fluoro-phenyl)-propan-1-one;

1-[4-(4-Amino-8-fluoro-6,7-dimethoxy-quinazolin-2-yl)-piperazin-1-yl]-3-(4-fluoro-phenyl)-3-piperidin-1-yl-propan-1-one;

1-[4-(4-Amino-8-fluoro-6,7-dimethoxy-quinazolin-2-yl)-piperazin-1-yl]-3-(4-fluoro-phenyl)-3-(2-methoxy-ethylamino)-propan-1-one;

1-[4-(4-Amino-8-fluoro-6,7-dimethoxy-quinazolin-2-yl)-piperazin-1-yl]-3-(5-fluoro-pyridin-2-yl)-3-isopropylamino-propan-1-one;

(4-{3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

(4-{3-[4-(4-Amino-8-fluoro-6,7-dimethoxy-quinazolin-2-yl)-piperazin-1-yl]-1-[(3-methyl-oxetan-3-ylmethyl)-amino]-3-oxo-propyl}-benzonitrile;

[4-(4-Amino-8-fluoro-6,7-dimethoxy-quinazolin-2-yl)-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-methyl-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-ethyl-piperazin-1-yl]-(1-amino-1,2,3,4-tetrahydro-naphthalen-2-yl)-methanone;

[4-(4-Amino-8-fluoro-6,7-dimethoxy-quinazolin-2-yl)-3-phenyl-piperazin-1-yl]-(1-amino-1,2,3,4-tetrahydro-naphthalen-2-yl)-methanone;

1-(4-(4-amino-8-fluoro-6,7-dimethoxyquinazolin-2-yl) piperazin-1-yl)-2-(1-isobutylpyrrolidin-2-yl)ethanone;

1-[4-(4-Amino-8-fluoro-6,7-dimethoxy-quinazolin-2-y)-piperazin-1-yl]-2-azetidin-2-yl-ethanone;

1-[4-(4-Amino-8-fluoro-6,7-dimethoxy-quinazolin-2-yl)-piperazin-1-yl]-2-pyrrolidin-2-yl-ethanone;

1-[4-(4-Amino-8-fluoro-6,7-dimethoxy-quinazolin-2-yl)-piperazin-1-yl]-2-(5-phenyl-pyrrolidin-2-yl)-ethanone;

1-[4-(4-Amino-8-fluoro-6,7-dimethoxy-quinazolin-2-y)-piperazin-1-yl]-2-(2,3-dihydro-1H-isoindol-1-yl)-ethanone;

1-[4-(4-Amino-8-fluoro-6,7-dimethoxy-quinazolin-2-y)-piperazin-1-yl]-2-piperidin-2-yl-ethanone;

1-[4-(4-Amino-8-fluoro-6,7-dimethoxy-quinazolin-2-y)-piperazin-1-yl]-2-piperidin-3-yl-ethanone;

1-[4-(4-Amino-8-fluoro-6,7-dimethoxy-quinazolin-2-yl)-3-methyl-piperazin-1-yl]-2-pyrrolidin-2-yl-ethanone;

1-[4-(4-Amino-8-fluoro-6,7-dimethoxy-quinazolin-2-yl)-3-ethyl-piperazin-1-yl]-2-pyrrolidin-2-yl-ethanone;

1-[4-(4-Amino-8-fluoro-6,7-dimethoxy-quinazolin-2-yl)-3-ethyl-piperazin-1-yl]-2-piperid in-2-yl-ethanone;

1-[4-(4-Amino-8-fluoro-6,7-dimethoxy-quinazolin-2-yl)-3-propyl-piperazin-1-yl]-2-pyrrolidin-2-yl-ethanone;

1-[4-(4-Amino-8-fluoro-6,7-dimethoxy-quinazolin-2-yl)-3-phenyl-piperazin-1-yl]-2-azetidin-2-yl-ethanone hydrochloride;

1-[4-(4-Amino-8-fluoro-6,7-dimethoxy-quinazolin-2-yl)-3-phenyl-piperazin-1-yl]-2-pyrrolidin-2-yl-ethanone;

1-[4-(4-Amino-8-fluoro-6,7-dimethoxy-quinazolin-2-yl)-3-phenyl-piperazin-1-yl]-2-piperidin-2-yl-ethanone;

1-[4-(4-Amino-8-fluoro-6,7-dimethoxy-quinazolin-2-yl)-3-phenyl-piperazin-1-yl]-2-piperidin-3-yl-ethanone;

1-[4-(4-Amino-8-fluoro-6,7-dimethoxy-quinazolin-2-yl)-3-phenyl-piperazin-1-yl]-2-morpholin-2-yl-ethanone;

1-{4-[4-Amino-8-fluoro-6-methoxy-7-(2-methoxy-ethoxy)-quinazolin-2-yl]-piperazin-1-yl}-2-pyrrolidin-2-yl-ethanone;

1-{4-[4-Amino-8-fluoro-6-methoxy-7-(2-methoxy-ethoxy)-quinazolin-2-yl]-piperazin-1-yl}-2-piperidin-2-yl-ethanone;

1-[4-(4-Amino-8-fluoro-6,7-dimethoxy-quinazolin-2-yl)-piperazin-1-yl]-2-1,2,3,4-tetrahydro-isoquinolin-1-yl-ethanone;

1-[4-(4-Amino-8-fluoro-6,7-dimethoxy-quinazolin-2-yl)-piperazin-1-yl]-2-(6-fluoro-1,2,3,4-tetrahydro-isoquinolin-1-yl)-ethanone;

1-[4-(4-Amino-8-fluoro-6,7-dimethoxy-quinazolin-2-yl)-piperazin-1-yl]-3-d-methylamino-3-phenyl-propan-1-one;

1-(4-(4-amino-8-fluoro-6,7-dimethoxyquinazolin-2-yl) piperazin-1-yl)-3-(4-fluorophenyl)-3-($d^3$-methyl-amino)propan-1-one hydrochloride;

1-(4-(4-amino-8-fluoro-6,7-dimethoxyquinazolin-2-yl) piperazin-1-yl)-3-(1,1,2,2,2-$d^5$ ethylamino)-3-(4-fluorophenyl)propan-1-one;

1-(4-(4-Amino-8-chloro-6,7-dimethoxyquinazolin-2-yl) piperazin-1-yl)-3-cyclopropylprop-2-en-1-one;

1-(4-(4-Amino-5-chloro-6,7-dimethoxyquinazolin-2-yl) piperazin-1-yl)-3-cyclopropylprop-2-en-1-one;

1-(4-(4-Amino-8-bromo-6,7-dimethoxyquinazolin-2-yl) piperazin-1-yl)-3-cyclopropylprop-2-en-1-one;

1-(4-(4-Amino-8-chloro-6,7-dimethoxyquinazolin-2-yl) piperazin-1-yl)-3-(4-fluorophenyl)prop-2-en-1-one;

3-amino-1-(4-(4-Amino-8-bromo-6,7-dimethoxyquinazolin-2-yl)piperazin-1-yl)-3-phenylpropan-1-one;

3-Amino-1-(4-(4-amino-8-chloro-6,7-dimethoxyquinazolin-2-yl)piperazin-1-yl)-3-(4-fluorophenyl)propan-1-one;

4-Amino-6,7-dimethoxy-2-(4-(2-(piperidin-2-yl)acetyl)piperazin-1-yl)quinazoline-8-carbonitrile;

4-Amino-1-[4-(4-amino-8-fluoro-6,7-dimethoxy-quinazolin-2-yl)-piperazin-1-yl]-3-phenyl-butan-1-one;

4-[4-(4-Amino-8-fluoro-6,7-dimethoxy-quinazolin-2-yl)-piperazin-1-yl]-2-(4-fluoro-phenyl)-4-oxo-butyramide and salts and stereoisomers thereof.

13. A pharmaceutical composition comprising one or more pharmaceutically acceptable carriers and a therapeutically effective amount of a compound of claim 1.

14. A method of treating a disorder or a disease in a subject mediated by activation of the complement alternative pathway, wherein the method comprises administering to the subject a therapeutically effective amount of the compound according to claim 1 to the subject and in which the disease or disorder is selected from the group consisting of age-related macular degeneration, geographic atrophy, diabetic retinopathy, uveitis, retinitis pigmentosa, macular edema, Behcet's uveitis, and glomerulonephritis.

15. A method of treating age related macular degeneration comprising administering to a subject in need thereof an effective amount of a composition comprising a compound of claim 1.

* * * * *